(12) United States Patent
Quay

(10) Patent No.: US 7,166,575 B2
(45) Date of Patent: *Jan. 23, 2007

(54) COMPOSITIONS AND METHODS FOR ENHANCED MUCOSAL DELIVERY OF PEPTIDE YY AND METHODS FOR TREATING AND PREVENTING OBESITY

(75) Inventor: Steven C Quay, Edmonds, WA (US)

(73) Assignee: Nastech Pharmaceutical Company Inc., Bothell, WA (US)

(*) Notice: Subject to any disclaimer, the term of this patent is extended or adjusted under 35 U.S.C. 154(b) by 659 days.

This patent is subject to a terminal disclaimer.

(21) Appl. No.: 10/322,266

(22) Filed: Dec. 17, 2002

(65) Prior Publication Data

US 2004/0115135 A1    Jun. 17, 2004

(51) Int. Cl.
*A61K 38/17* (2006.01)
*A61K 38/28* (2006.01)
*C07K 14/435* (2006.01)

(52) U.S. Cl. .................. 514/12; 530/324; 530/303
(58) Field of Classification Search .............. 514/12; 530/324, 303
See application file for complete search history.

(56) References Cited

U.S. PATENT DOCUMENTS

| | | | |
|---|---|---|---|
| 5,134,127 A * | 7/1992 | Stella et al. ................. | 514/58 |
| 5,308,620 A | 5/1994 | Yen | |
| 5,574,010 A | 11/1996 | McFadden | |
| 5,604,203 A | 2/1997 | Balasubramaniam | |
| 5,616,311 A | 4/1997 | Yen | |
| 5,696,093 A | 12/1997 | Tseng et al. | |

(Continued)

FOREIGN PATENT DOCUMENTS

EP    1 288 223 A1    3/2003

(Continued)

OTHER PUBLICATIONS

Mei-Huei Chen; Balasubramanian; Murphy; Tabata; Fischer; Chen; Joffe, Sensitive Radioimmunoassay for Measurement of Ci'rculating Peptide YY, Gastroenterology, 1984, pp. 1332-1338, vol. 87, Publisher: American Gastroenterological Association, Published in: Cincinnati, Ohio.

(Continued)

*Primary Examiner*—Jon Weber
*Assistant Examiner*—Rosanne Kosson
(74) *Attorney, Agent, or Firm*—Peter J. Knudsen

(57) ABSTRACT

Pharmaceutical compositions and methods are described comprising at least one peptide YY compound and one or more intranasal delivery-enhancing agents for enhanced nasal mucosal delivery of the peptide YY, for treating a variety of diseases and conditions in mammalian subjects, including obesity. In one aspect, the intranasal delivery formulations and methods provide enhanced delivery of peptide YY to the blood plasma or central nervous system (CNS) tissue or fluid, for example, by yielding a peak concentration ($C_{max}$) of the peptide YY in the blood plasma or CNS tissue or fluid of the subject that is 20% or greater compared to a peak concentration of the peptide YY in the blood plasma or CNS tissue or fluid of the subject following administration to the subject of a same concentration or dose of the peptide YY to the subject by subcutaneous injection.

19 Claims, 1 Drawing Sheet

U.S. PATENT DOCUMENTS

| | | | |
|---|---|---|---|
| 5,716,643 | A | 2/1998 | Yen |
| 5,725,804 | A | 3/1998 | Yen |
| 5,759,656 | A | 6/1998 | Collette et al. |
| 5,912,227 | A | 6/1999 | Croom, Jr. et al. |
| 5,945,033 | A | 8/1999 | Yen |
| 5,968,748 | A | 10/1999 | Bennett et al. |
| 5,977,175 | A | 11/1999 | Lim |
| 5,980,945 | A | 11/1999 | Ruiz |
| 6,013,285 | A | 1/2000 | Yen |
| 6,013,633 | A | 1/2000 | Balasubramanium et al. |
| 6,017,879 | A | 1/2000 | Mutter et al. |
| 6,046,167 | A | 4/2000 | Balasubramaniam |
| 6,103,495 | A * | 8/2000 | Mehta et al. ............... 435/69.1 |
| 6,191,102 | B1 | 2/2001 | DiMarchi et al. |
| 6,264,988 | B1 | 7/2001 | Yen |
| 6,391,855 | B1 * | 5/2002 | Blaschuk et al. ............. 514/17 |
| 2002/0197324 | A1 * | 12/2002 | Watts et al. ................ 424/488 |
| 2004/0228846 | A1 * | 11/2004 | Pang et al. ................ 424/93.7 |
| 2005/0176630 | A1 * | 8/2005 | Cowley et al. ............... 514/12 |

FOREIGN PATENT DOCUMENTS

| | | |
|---|---|---|
| EP | 1 288 224 A1 | 3/2003 |
| EP | 0 678 018 B1 | 4/2003 |
| EP | 1 051 194 B1 | 5/2003 |
| EP | 1 466 610 A1 | 10/2004 |
| WO | PCT WO 94/22467 A1 | 10/1994 |
| WO | PCT WO 98/20885 A1 | 5/1998 |
| WO | PCT WO 99/02135 A1 | 1/1999 |
| WO | PCT/WO 09915516 A1 | 4/1999 |

OTHER PUBLICATIONS

Morley, John E.; Levine, Allen S.; Grace, Martha; Kneip, Julie, "Peptide YY (PYY), a potent orexigenic agent," Brain Research, 1985, vol. 341, pp. 200-203. Elsevier Science Publishers.

John E. Morley and James F. Flood, An Investigation of Tolerance to the actions of Leptogenic and Anorexigenic Drugs in Mice, Life Sciences, Sep. 10, 1987, pp. 22157-22165, vol. 41, Publisher: Pergamon Journals, Published in: Sepulveda, CA, US.

Kazuhiko Tatemoto; Nakano; Makk; Angwin; Mann; Schilling; Go, Isolation and Primary Structure of Human Peptide YY, Biochemical and Biophysical Research Communications, Oct. 31, 1988, pp. 713-717, vol. 157(2), Publisher: Academic Press, Inc., Published in: Los Angeles, California, US.

Balasubramaniam, A.; Servin, A. L.; Rigel, D. F.; Rouyer-Fessard, C. R.; Laburthe, M, Syntheses and receptor affinities of partial sequences of peptide YY (PYY) Peptide.Research., date- 1988, vol. 1, No. 1, pp. 32-35.

John E. Morley, An approach to the development of drugs for appetite disorders, Neuropsychobiology , Date 1989, vol. 21, issue 1, pp. 22-30, Karger AG, Basel.

Eberlein, G. A.;Eysselein, V. E.;Schaeffer, M.; Layer, P.;Grandt, D.;Goebell, H.;Niebel, W.;Davis, M.;Lee, T. D.; Shively,J. E.; Reeve, J. R., Jr.; A new molecular form of PYY: structural characterization of human PYY(3-36) and PYY(1-36) Peptides, DATE-1989, vol. 10, No. 4, pp. 797-803, Pergamon Press, US.

Eysselein, V. E.;Eberlein, G. A.;Grandt, D.;Schaeffer, M.;Zehres, B.; Behn, U.;Schaefer, D.; Goebell, H.;Davis, M.; Lee,T. D.; Shively, J. E.; Meyer, H. E.; Reeve, J. R., Jr, Structural Characterization of canine PYY, Peptides, Jun. 15, 1989, vol. 11 pp. 111-116, Pergamon Press, US.

Hiroyuki Minakata, Takashi Iwashita , Synthesis of analogues of peptide YY with modified N-terminal regions: relationships of amphiphllic secondary structures and activity in rat vas deferens, Journal: Biopolymers, vol. 29, Jan. 29, 1990, pp. 61-67, John Wiley & Sons, Inc.

Ramo, O. J.; Balasubramaniam, A.; Sheriff, S.; Rogers, D. H.; McCullough, P. J.; Bell, R. H., Jr., Neuropeptide Y and peptide YY stimulate the growth of exocrine pancreatic carcinoma cells, Neuropeptides, 1990, vol. 15, pp. 101-106, Longman Group UK.

S.F. Leibowitz, J.T. Alexander, Analysis of Neuropeptide Y-Induced Feeding: Dissociation of Y1 and Y2 Receptor Effects on Natural Meal Patterns, Peptides, Jul. 25, 1991, pp. 1251-1260, vol. 12, Publisher: Pergamon Press, Published in: New York NY, US.

Marc Laburthe, Peptide YY et neuropeptide Y dans L'intesin: disponibilite, effets biologiques et recepteurs epitheliaux, [translated title: Peptide YY and neutopeptide Y in the intestine: availability, biologic effects and epithelial receptors] Arch Int. Physiol Biochim Biophys, Reunion Complementaire de Physiologie, Association des Physiologistes, Toulouse 26-27, Apr. 1991, France.

Inui Akio, Minoru Okita, Masaharu Nakajima, Toru Inoue, Noriaki Sakatani, Manabu Oya, Hideki Morioka, Yasuhiko Okimura, Kazuo Chihara, and Shigeaki Baba, Neuropeptide regulation of feeing in dogs, Neuropeptides and Food Intake, 1991, pp. R5888-R594, 0363-6119, The American Physiological Society.

Grandt, D.; Teyssen, S.; Schimiczek, M.; Reeve, J. R., Jr.; Feth, F.; Rascher, W.; Hirche, H.; Singer, M. V.; Layer, P.; Goebell, H.; Ho, F.J.; Eysselein, V.E.: Novel generation of hormone receptor specificity by amino terminal processing of peptide YY, Biochemical and Biophysical Research Communications, Aug. 14, 1992, vol. 186, No. 3, pp. 1299-1306, Academic Press, Inc.

S. Okada, Ohshima, Mori, K. Tatemoto, Peripherally not Centrally Administered Peptide YY(PYY) Decrease High Fat Diet Intake, Jun. 9, 1993, vol. 520, Publisher: Endocrinology, Published in: Gunmo, Japan.

Grandt, D.; Schimiczek, M.; Struk, K.; Shively, J.; Eysselein, V. E.; Goebell, H.; Reeve, J. R., Jr—Characterization of two forms of peptide YY, PYY(1-36) and PYY(3-36), in the rabbit, Peptides, Jul. 29, 1994, vol. 15, No. 5, pp. 815-820, Pergamon, Elsevier Science Ltd, US.

Dumont, Yvan.; Cadieux, Alain.; Pheng, L.H.; Fournier, A.; St Pierre, S.; Quirion, R., Peptide YY derivatives as selective neuropeptide Y/peptide YY $Y^1$ and $Y^2$ agonists devoided of activity for the $Y^3$ receptor sub-type, Brain Research.Molecular.Brain Research,—Jun. 28, 1994, vol. 26, No. 1-2, pp. 320-324, Elsevier Science B.V.

Margaret Dos Santos Medeiros, M.D.; Anthony J. Turner, Processing and metabolism of peptide-YY: pivotal roles of dipeptidylpeptidase-IV, aminopeptidase-P, and endopeptidase-24. 11, Endocrinology 1994, Vo 134, No. 5, pp. 2088-2094, The Endocrine Society, US.

Grandt, D.; Schimiczek, M.; Beglinger, C.; Layer, P.; Goebell, H.; Eysselein, V. E.; Reeve, J. R., Jr, Two molecular forms of peptide YY (PYY) are abundant in human blood: characterization of a radioimmunoassay recognizing PYY 1-36 and PYY 3-36, Regulatory Peptides, May 5, 1994, vol. 51, No. 2, pp. 151-159, Elsevier Sciences B.V.

Kazuhiko Tatemono, New Developments in Research on digestive tract hormones. Progress in Medicine, vol. 15, No. 9, date Sep. 1995, pp. 1793-1804, 46th Pepsin Research Meeting (translated from Japanese) JP.

Norio Tani, Digestive Tract Hormones, Digestive Tract, 1996, Article Serial No.: 0012 (translated from Japanese) JP.

Gue, M.; Junien, J. L.; Reeve, J. R., Jr.; Rivier, J.; Grandt, D.; Tache, Y, Reversal by NPY, PYY and 3-36 molecular forms of NPY and PYY of intracisternal CRF-induced inhibition of gastric acid secretion in rats, British Journal of Pharmacology, May 1996, pp. 118(2), 237-242, Stockton Press.

Von E. Niebergall-Roth, S. Teyssen K. Rippel Und M.V. Singer, Die wirkungen von peptide yy auf funktionen des gastrointestinaltraktes, Dtsch. Tierarzti, Wschr 104, pp. 85-124, Heft 3, Marz 1997, National Library of Medicine (article in German).

Kazuhiko Tatemoto, Chemical and clinical Applications of Digestive Tract hormones, Digestive hormones, 1994, pp. 38-45, vol. 2, No. 4, G. I. Research (translated Japanese article) JP.

Chen, C. H.; Stephens, R. L., Jr.; Rogers, R. C., PYY and NPY: control of gastric motility via action on Y1 and Y2 receptors in the DVC, Neurogastroenterol.Motil. 1997, pp. 109-116, vol. 9, Blackwell Science, Ltd., US.

Xiao, Q.; Han, X.; Arany, E.; Hill, D.; Challis, J. R.; McDonald, T. J, Human placenta and fetal membranes contain peptide YY1-36 and peptide YY3-36, Journal of Enocrinology, 1998, pp. 485-492, vol. 156, Journal of Endocinology Ltd, UK.

Naruto Yamawaki, Yasuaki Okamoto, Is there a biological case for eating disorders? From the perspective of neurochemistry, Brian Science, 1998, pp. 29-36, Article Serial No. 0003, vol. 20, Special Edition (Eating Disorders and Obesity) Think also presented at conference Apr. 24, 1998 at Showa University, Yokohama, Japan (translated Japanese article) JP.

Noboru Yanaihara, VIP, PYY and Others, All About Hormone Illustrated No. 381, 1998, p. 382-387, Article Serial No. 0033, vol. 46, VI. Gastrointestinal Hormones, (translated Japanese article) JP.

Kazuhiko Tatemoto, Development of Neuropeptide Y Receptor Antagonists, Research on Biologically Active Substances, Research Papers of the Suzuken Memorial Foundation, vol. 14, p. 243-244 (translated Japanese article) JP.

David A. Keire, Mitsuo Kobayashi, Travis E. Solomon, Joseph R. Reeve, Jr., Solution structure of monomeric peptide YY supports the functional significance of the PP-Fold, Biochemistry 2000, pp. 9935-9942, Nov. 8, 1999, American Chemical Society, published on web Jul. 21, 2000, US.

Phillipe Naveilhan, Hessameh Hassani, Josep M. Canals, A. Jonas Ekstrand, ASA Larefalk, Vijay Chhajlani, Ernest Arenas, Karin Gedda, Lennart Svensson, Peter Thoren, and Patrik Ernfors, Normal feeding behavior, body weight and leptin response require the neuropeptide Y Y2 receptor, Nature America Inc. Oct. 1999, pp. 1188-1193, vol. 5, No. 10, Nature Medicine.

Akihiro Asakawa, Akio Inui, Naohiko Ueno, Mineko Fujimiya, Masayuki A. Fujino, Masato Kasuga, Mouse pancreatic polypeptide modulated food intake, while not influencing anxiety in mice, Peptides, 1999, pp. 1445-1448, vol. 20, Elsevier Science Inc.

Keire, D. A.; Mannon P.; Kobayashi, M.; Walsh, J. H.; Solomon, T. E.; Reeve, J. R., Jr., Primary structures of PYY, [Pro$^{34}$]PYY, and PYY-(3-36) confer different conformations and receptor selectivity, Am.J.Physiol Gastrointest.Liver Physiol, Feb. 1, 2000, p. G126-G131, vol. 279.

Rachel, L. Batterham, Michael A. Cowley, Caroline S. Small, Herbert Herzog, Mark A. Cohen, Catherine L. Dakin, Alison M. Wren, Audrey E. Brynes, Malcom J. Low, Mohammad A. Ghatei, Roger D. Cone, Stephen R. Bloom. "Gut hormone PYY3-36 physiologically inhibits food intake," Nature, 2002, vol. 418, pp. 650-654, Nature Publishing Group.

Herbert Herzog, Hypothalamic Y2 Receptors: Central Coordination of Energy Homeostasis and Bone Mass Regulation, Drug News Perspect. Oct. 2002, pp. 506-510, vol. 15 (8), Prous Science.

Batterham, Rachel. L.; Cohen, Mark. A.; Ellis, Sandra. M.; Le Roux, Carel. W.; Withers, Dominic. J.; Frost, Gary. S.; Ghatei, M. A.; Bloom, S. R., Inhibition of food intake in obese subjects by peptide YY3-36, The New.England.Journal of Medicine, DATE-Sep. 4, 2003, pp. 941-948, vol. 349.

Rachel L. Batterham, Stephen R. Bloom,. The gut hormone peptide YY regulates appetite, N.Y.Academy.of Science, 2003, pp. 162-168, vol. 994.

R. L. Batterham, C.W. Le Roux, M.A. Choen, A.J. Park, S.M. Ellis, M. Patterson, G.S. Frost, M.A.Ghatei and S.R. Bloom, Pancreatic polypeptide reduces appetite and food intake in humans, The Journal of Clinical Endocrinology and Metabolism, 2003, pp. 3989-3992, vol. 88(8), the Endocrine Society, US.

ANONYMOUS: "Nastech Begins a Clinical Trial with Intranasal PYY in Overweight Adults" Dailydrugnews.com, Daily Essentials, Jan. 23, 2004, XP001207998.

Cervin, Anders, et al: "Functional Effects of Neuropeptide Y Receptors on Blood Flow and Nitric Oxide Levels in the Human Nose," American Journal of Respiratory and Critical Care Medicine, pp. 1724-1728 v. 160, No. 5, Part I, Nov. 1999, XP002376387; ISSN: 1073-449X.

Suman, Julie D. et al: "Validity of *in Vitro* Tests on Aqueous Spray Pumps as Surrogates for Nasal Deposition," Pharmaceutical Research (New York), pp. 1-6, v. 19, No. 1, Jan. 2002, XP002376388, ISSN: 0724-8741.

* cited by examiner

SEQUENCE LISTING

<160> NUMBER OF SEQ ID NOS: 799

<210> SEQ ID NO 1
<211> LENGTH: 4
<212> TYPE: PRT

```
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa is Ile, Val, or Ala

<400> SEQUENCE: 1

Val Arg Xaa Pro
1

<210> SEQ ID NO 2
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa is Val, Ala or Ile
<220> FEATURE:
<221> NAME/KEY: misc_feature
<222> LOCATION: (4)..(4)
<223> OTHER INFORMATION: Xaa is Ser or Thr

<400> SEQUENCE: 2

Xaa Lys Leu Xaa Cys Ala Tyr
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa is Thr or Ser
<220> FEATURE:
<221> NAME/KEY: misc_feature
<222> LOCATION: (7)..(7)
<223> OTHER INFORMATION: Xaa is Thr or Arg
<220> FEATURE:
<221> NAME/KEY: misc_feature
<222> LOCATION: (9)..(9)
<223> OTHER INFORMATION: Xaa is Met or Glu

<400> SEQUENCE: 3

Glu Asp Xaa Gly Thr Tyr Xaa Cys Xaa
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic construct

<400> SEQUENCE: 4

Val Arg Ile Pro
1

<210> SEQ ID NO 5
<211> LENGTH: 7
<212> TYPE: PRT
<213> ORGANISM: Artificial Sequence
<220> FEATURE:
<223> OTHER INFORMATION: Synthetic construct
```

```
<400> SEQUENCE: 5

Val Lys Leu Ser Cys Ala Tyr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic construct

<400> SEQUENCE: 6

Thr Gly Ile Thr Phe Lys Ser Val Thr
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic construct

<400> SEQUENCE: 7

Ile Thr Ala Ser
1

<210> SEQ ID NO 8
<211> LENGTH: 4
<212> TYPE: PRT
<213> ORGANISM: Artificial Sequence
<220> FEATURE:
<223> OTHER INFORMATION: Synthetic construct

<400> SEQUENCE: 8

Ser Val Thr Arg
1

<210> SEQ ID NO 9
<211> LENGTH: 9
<212> TYPE: PRT
<213> ORGANISM: Artificial Sequence
<220> FEATURE:
<223> OTHER INFORMATION: Synthetic construct

<400> SEQUENCE: 9

Glu Asp Thr Gly Thr Tyr Thr Cys Met
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic construct

<400> SEQUENCE: 10

Gly Phe Ser Ser Pro Arg Val Glu Trp
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic construct
```

```
<400> SEQUENCE: 11

Ser Val Thr Val His Ser Ser Glu Pro Glu
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic construct

<400> SEQUENCE: 12

Val Arg Ile Pro Glu Asn Asn Pro Val Lys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic construct

<400> SEQUENCE: 13

Leu Ser Cys Ala Tyr Ser Gly Phe Ser Ser
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic construct

<400> SEQUENCE: 14

Pro Arg Val Glu Trp Lys Phe Asp Gln Gly
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic construct

<400> SEQUENCE: 15

Asp Thr Thr Arg Leu Val Cys Tyr Asn Asn
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic construct

<400> SEQUENCE: 16

Lys Ile Thr Ala Ser Tyr Glu Asp Arg Val
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic construct

<400> SEQUENCE: 17
```

```
Thr Phe Leu Pro Thr Gly Ile Thr Phe Lys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic construct

<400> SEQUENCE: 18

Ser Val Thr Arg Glu Asp Thr Gly Thr Tyr
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic construct

<400> SEQUENCE: 19

Thr Cys Met Val Ser Glu Glu Gly Gly Asn
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic construct

<400> SEQUENCE: 20

Ser Tyr Gly Glu Val Lys Val Lys Leu Ile
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic construct

<400> SEQUENCE: 21

Val Leu Val Pro Pro Ser Lys Pro Thr Val
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic construct

<400> SEQUENCE: 22

Asn Ile Pro Ser Ser Ala Thr Ile Gly Asn
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic construct

<400> SEQUENCE: 23
```

```
Arg Ala Val Leu Thr Cys Ser Glu Gln Asp
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic construct

<400> SEQUENCE: 24

Gly Ser Pro Pro Ser Glu Tyr Thr Trp Phe
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic construct

<400> SEQUENCE: 25

Lys Asp Gly Ile Val Met Pro Thr Asn Pro
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic construct

<400> SEQUENCE: 26

Lys Ser Thr Arg Ala Phe Ser Asn Ser Ser
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic construct

<400> SEQUENCE: 27

Tyr Val Leu Asn Pro Thr Thr Gly Glu Leu
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic construct

<400> SEQUENCE: 28

Val Phe Asp Pro Leu Ser Ala Ser Asp Thr
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic construct

<400> SEQUENCE: 29

Gly Glu Tyr Ser Cys Glu Ala Arg Asn Gly
```

```
<210> SEQ ID NO 30
<211> LENGTH: 10
<212> TYPE: PRT
<213> ORGANISM: Artificial Sequence
<220> FEATURE:
<223> OTHER INFORMATION: Synthetic construct

<400> SEQUENCE: 30

Tyr Gly Thr Pro Met Thr Ser Asn Ala Val
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic construct

<400> SEQUENCE: 31

Arg Met Glu Ala Val Glu Arg Asn Val Gly
1               5                   10

<210> SEQ ID NO 32
<211> LENGTH: 5
<212> TYPE: PRT
<213> ORGANISM: Artificial Sequence
<220> FEATURE:
<223> OTHER INFORMATION: Synthetic construct

<400> SEQUENCE: 32

Ser Val Thr Val His
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic construct

<400> SEQUENCE: 33

Ser Ser Glu Pro Glu Val Arg Ile Pro Glu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic construct

<400> SEQUENCE: 34

Asn Asn Pro Val Lys Leu Ser Cys Ala Tyr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic construct

<400> SEQUENCE: 35

Ser Gly Phe Ser Ser Pro Arg Val Glu Trp
1               5                   10
```

```
<210> SEQ ID NO 36
<211> LENGTH: 10
<212> TYPE: PRT
<213> ORGANISM: Artificial Sequence
<220> FEATURE:
<223> OTHER INFORMATION: Synthetic construct

<400> SEQUENCE: 36

Lys Phe Asp Gln Gly Asp Thr Thr Arg Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic construct

<400> SEQUENCE: 37

Val Cys Tyr Asn Asn Lys Ile Thr Ala Ser
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic construct

<400> SEQUENCE: 38

Tyr Glu Asp Arg Val Thr Phe Leu Pro Thr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic construct

<400> SEQUENCE: 39

Gly Ile Thr Phe Lys Ser Val Thr Arg Glu
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic construct

<400> SEQUENCE: 40

Asp Thr Gly Thr Tyr Thr Cys Met Val Ser
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic construct

<400> SEQUENCE: 41

Glu Glu Gly Gly Asn Ser Tyr Gly Glu Val
1               5                   10
```

```
<210> SEQ ID NO 42
<211> LENGTH: 10
<212> TYPE: PRT
<213> ORGANISM: Artificial Sequence
<220> FEATURE:
<223> OTHER INFORMATION: Synthetic construct

<400> SEQUENCE: 42

Lys Val Lys Leu Ile Val Leu Val Pro Pro
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic construct

<400> SEQUENCE: 43

Ser Lys Pro Thr Val Asn Ile Pro Ser Ser
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic construct

<400> SEQUENCE: 44

Ala Thr Ile Gly Asn Arg Ala Val Leu Thr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic construct

<400> SEQUENCE: 45

Cys Ser Glu Gln Asp Gly Ser Pro Pro Ser
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic construct

<400> SEQUENCE: 46

Glu Tyr Thr Trp Phe Lys Asp Gly Ile Val
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic construct

<400> SEQUENCE: 47

Met Pro Thr Asn Pro Lys Ser Thr Arg Ala
1               5                   10
```

```
<210> SEQ ID NO 48
<211> LENGTH: 10
<212> TYPE: PRT
<213> ORGANISM: Artificial Sequence
<220> FEATURE:
<223> OTHER INFORMATION: Synthetic construct

<400> SEQUENCE: 48

Phe Ser Asn Ser Ser Tyr Val Leu Asn Pro
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic construct

<400> SEQUENCE: 49

Thr Thr Gly Glu Leu Val Phe Asp Pro Leu
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic construct

<400> SEQUENCE: 50

Ser Ala Ser Asp Thr Gly Glu Tyr Ser Cys
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic construct

<400> SEQUENCE: 51

Glu Ala Arg Asn Gly Tyr Gly Thr Pro Met
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic construct

<400> SEQUENCE: 52

Thr Ser Asn Ala Val Arg Met Glu Ala Val
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Synthetic construct

<400> SEQUENCE: 53

Glu Arg Asn Val Gly Val Ile
1               5

<210> SEQ ID NO 54
```

```
<211> LENGTH: 8
<212> TYPE: PRT
<213> ORGANISM: Artificial Sequence
<220> FEATURE:
<223> OTHER INFORMATION: Synthetic construct

<400> SEQUENCE: 54

Ser Val Thr Val His Ser Ser Glu
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic construct

<400> SEQUENCE: 55

Pro Glu Val Arg Ile Pro Glu Asn
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic construct

<400> SEQUENCE: 56

Asn Pro Val Lys Leu Ser Cys Ala
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic construct

<400> SEQUENCE: 57

Tyr Ser Gly Phe Ser Ser Pro Arg
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic construct

<400> SEQUENCE: 58

Val Glu Trp Lys Phe Asp Gln Gly
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic construct

<400> SEQUENCE: 59

Asp Thr Thr Arg Leu Val Cys Tyr
1               5

<210> SEQ ID NO 60
<211> LENGTH: 8
```

```
<212> TYPE: PRT
<213> ORGANISM: Artificial Sequence
<220> FEATURE:
<223> OTHER INFORMATION: Synthetic construct

<400> SEQUENCE: 60

Asn Asn Lys Ile Thr Ala Ser Tyr
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic construct

<400> SEQUENCE: 61

Glu Asp Arg Val Thr Phe Leu Pro
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic construct

<400> SEQUENCE: 62

Thr Gly Ile Thr Phe Lys Ser Val
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic construct

<400> SEQUENCE: 63

Thr Arg Glu Asp Thr Gly Thr Tyr
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic construct

<400> SEQUENCE: 64

Thr Cys Met Val Ser Glu Glu Gly
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic construct

<400> SEQUENCE: 65

Gly Asn Ser Tyr Gly Glu Val Lys
1               5

<210> SEQ ID NO 66
<211> LENGTH: 8
<212> TYPE: PRT
```

```
<213> ORGANISM: Artificial Sequence
<220> FEATURE:
<223> OTHER INFORMATION: Synthetic construct

<400> SEQUENCE: 66

Val Lys Leu Ile Val Leu Val Pro
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic construct

<400> SEQUENCE: 67

Pro Ser Lys Pro Thr Val Asn Ile
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic construct

<400> SEQUENCE: 68

Pro Ser Ser Ala Thr Ile Gly Asn
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic construct

<400> SEQUENCE: 69

Arg Ala Val Leu Thr Cys Ser Glu
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic construct

<400> SEQUENCE: 70

Gln Asp Gly Ser Pro Pro Ser Glu
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic construct

<400> SEQUENCE: 71

Tyr Thr Trp Phe Lys Asp Gly Ile
1               5

<210> SEQ ID NO 72
<211> LENGTH: 8
<212> TYPE: PRT
<213> ORGANISM: Artificial Sequence
```

```
<220> FEATURE:
<223> OTHER INFORMATION: Synthetic construct

<400> SEQUENCE: 72

Val Met Pro Thr Asn Pro Lys Ser
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic construct

<400> SEQUENCE: 73

Thr Arg Ala Phe Ser Asn Ser Ser
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic construct

<400> SEQUENCE: 74

Tyr Val Leu Asn Pro Thr Thr Gly
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic construct

<400> SEQUENCE: 75

Glu Leu Val Phe Asp Pro Leu Ser
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic construct

<400> SEQUENCE: 76

Ala Ser Asp Thr Gly Glu Tyr Ser
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic construct

<400> SEQUENCE: 77

Cys Glu Ala Arg Asn Gly Tyr Gly
1               5

<210> SEQ ID NO 78
<211> LENGTH: 8
<212> TYPE: PRT
<213> ORGANISM: Artificial Sequence
<220> FEATURE:
```

```
<223> OTHER INFORMATION: Synthetic construct

<400> SEQUENCE: 78

Thr Pro Met Thr Ser Asn Ala Val
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic construct

<400> SEQUENCE: 79

Arg Met Glu Ala Val Glu Arg Asn
1               5

<210> SEQ ID NO 80
<211> LENGTH: 4
<212> TYPE: PRT
<213> ORGANISM: Artificial Sequence
<220> FEATURE:
<223> OTHER INFORMATION: Synthetic construct

<400> SEQUENCE: 80

Val Gly Val Ile
1

<210> SEQ ID NO 81
<211> LENGTH: 4
<212> TYPE: PRT
<213> ORGANISM: Artificial Sequence
<220> FEATURE:
<223> OTHER INFORMATION: Synthetic construct

<400> SEQUENCE: 81

Ser Val Thr Val
1

<210> SEQ ID NO 82
<211> LENGTH: 8
<212> TYPE: PRT
<213> ORGANISM: Artificial Sequence
<220> FEATURE:
<223> OTHER INFORMATION: Synthetic construct

<400> SEQUENCE: 82

His Ser Ser Glu Pro Glu Val Arg
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic construct

<400> SEQUENCE: 83

His Ser Ser Glu Pro Glu Val Arg
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic construct
```

```
<400> SEQUENCE: 84

Leu Ser Cys Ala Tyr Ser Gly
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic construct

<400> SEQUENCE: 85

Ser Ser Pro Arg Val Glu Trp Lys
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic construct

<400> SEQUENCE: 86

Phe Asp Gln Gly Asp Thr Thr Arg
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic construct

<400> SEQUENCE: 87

Leu Val Cys Tyr Asn Asn Lys Ile
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic construct

<400> SEQUENCE: 88

Thr Ala Ser Tyr Glu Asp Arg Val
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic construct

<400> SEQUENCE: 89

Thr Ala Ser Tyr Glu Asp Arg Val
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic construct
```

```
<400> SEQUENCE: 90

Phe Lys Ser Val Thr Arg Glu Asp
1               5

<210> SEQ ID NO 91
<211> LENGTH: 8
<212> TYPE: PRT
<213> ORGANISM: Artificial Sequence
<220> FEATURE:
<223> OTHER INFORMATION: Synthetic construct

<400> SEQUENCE: 91

Thr Gly Thr Tyr Thr Cys Met Val
1               5

<210> SEQ ID NO 92
<211> LENGTH: 8
<212> TYPE: PRT
<213> ORGANISM: Artificial Sequence
<220> FEATURE:
<223> OTHER INFORMATION: Synthetic construct

<400> SEQUENCE: 92

Ser Glu Glu Gly Gly Asn Ser Tyr
1               5

<210> SEQ ID NO 93
<211> LENGTH: 8
<212> TYPE: PRT
<213> ORGANISM: Artificial Sequence
<220> FEATURE:
<223> OTHER INFORMATION: Synthetic construct

<400> SEQUENCE: 93

Gly Glu Val Lys Val Lys Leu Ile
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic construct

<400> SEQUENCE: 94

Val Leu Val Pro Pro Ser Lys Pro
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic construct

<400> SEQUENCE: 95

Thr Val Asn Ile Pro Ser Ser Ala
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic construct

<400> SEQUENCE: 96
```

Thr Ile Gly Asn Arg Ala Val Leu
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic construct

<400> SEQUENCE: 97

Thr Cys Ser Glu Gln Asp Gly Ser
1               5

<210> SEQ ID NO 98
<211> LENGTH: 8
<212> TYPE: PRT
<213> ORGANISM: Artificial Sequence
<220> FEATURE:
<223> OTHER INFORMATION: Synthetic construct

<400> SEQUENCE: 98

Pro Pro Ser Glu Tyr Thr Trp Phe
1               5

<210> SEQ ID NO 99
<211> LENGTH: 8
<212> TYPE: PRT
<213> ORGANISM: Artificial Sequence
<220> FEATURE:
<223> OTHER INFORMATION: Synthetic construct

<400> SEQUENCE: 99

Lys Asp Gly Ile Val Met Pro Thr
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic construct

<400> SEQUENCE: 100

Asn Pro Lys Ser Thr Arg Ala Phe
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic construct

<400> SEQUENCE: 101

Ser Asn Ser Ser Tyr Val Leu Asn
1               5

<210> SEQ ID NO 102
<211> LENGTH: 8
<212> TYPE: PRT
<213> ORGANISM: Artificial Sequence
<220> FEATURE:
<223> OTHER INFORMATION: Synthetic construct

<400> SEQUENCE: 102

```
Pro Thr Thr Gly Glu Leu Val Phe
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic construct

<400> SEQUENCE: 103

Asp Pro Leu Ser Ala Ser Asp Thr
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic construct

<400> SEQUENCE: 104

Gly Glu Tyr Ser Cys Glu Ala Arg
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic construct

<400> SEQUENCE: 105

Asn Gly Tyr Gly Thr Pro Met Thr
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic construct

<400> SEQUENCE: 106

Ser Asn Ala Val Arg Met Glu Ala
1               5

<210> SEQ ID NO 107
<211> LENGTH: 8
<212> TYPE: PRT
<213> ORGANISM: Artificial Sequence
<220> FEATURE:
<223> OTHER INFORMATION: Synthetic construct

<400> SEQUENCE: 107

Val Glu Arg Asn Val Gly Val Ile
1               5

<210> SEQ ID NO 108
<211> LENGTH: 6
<212> TYPE: PRT
<213> ORGANISM: Artificial Sequence
<220> FEATURE:
<223> OTHER INFORMATION: Synthetic construct

<400> SEQUENCE: 108

Pro Val Arg Ile Pro Glu
```

<210> SEQ ID NO 109
<211> LENGTH: 10
<212> TYPE: PRT
<213> ORGANISM: Artificial Sequence
<220> FEATURE:
<223> OTHER INFORMATION: Synthetic construct

<400> SEQUENCE: 109

Glu Pro Glu Val Arg Ile Pro Glu Asn Asn
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Synthetic construct

<400> SEQUENCE: 110

Ser Glu Pro Glu Val Arg Ile Pro Glu Asn Asn Pro
1               5                   10

<210> SEQ ID NO 111
<211> LENGTH: 14
<212> TYPE: PRT
<213> ORGANISM: Artificial Sequence
<220> FEATURE:
<223> OTHER INFORMATION: Synthetic construct

<400> SEQUENCE: 111

Ser Ser Glu Pro Glu Val Arg Ile Pro Glu Asn Asn Pro Val
1               5                   10

<210> SEQ ID NO 112
<211> LENGTH: 16
<212> TYPE: PRT
<213> ORGANISM: Artificial Sequence
<220> FEATURE:
<223> OTHER INFORMATION: Synthetic construct

<400> SEQUENCE: 112

His Ser Ser Glu Pro Glu Val Arg Ile Pro Glu Asn Asn Pro Val Lys
1               5                   10                  15

<210> SEQ ID NO 113
<211> LENGTH: 18
<212> TYPE: PRT
<213> ORGANISM: Artificial Sequence
<220> FEATURE:
<223> OTHER INFORMATION: Synthetic construct

<400> SEQUENCE: 113

Val His Ser Ser Glu Pro Glu Val Arg Ile Pro Glu Asn Asn Pro Val
1               5                   10                  15

Lys Leu

<210> SEQ ID NO 114
<211> LENGTH: 20
<212> TYPE: PRT
<213> ORGANISM: Artificial Sequence
<220> FEATURE:
<223> OTHER INFORMATION: Synthetic construct

<400> SEQUENCE: 114

```
Thr Val His Ser Ser Glu Pro Glu Val Arg Ile Pro Glu Asn Asn Pro
1               5                   10                  15

Val Lys Leu Ser
            20
```

<210> SEQ ID NO 115
<211> LENGTH: 5
<212> TYPE: PRT
<213> ORGANISM: Artificial Sequence
<220> FEATURE:
<223> OTHER INFORMATION: Synthetic construct

<400> SEQUENCE: 115

```
Val Arg Ile Pro Glu
1               5
```

<210> SEQ ID NO 116
<211> LENGTH: 6
<212> TYPE: PRT
<213> ORGANISM: Artificial Sequence
<220> FEATURE:
<223> OTHER INFORMATION: Synthetic construct

<400> SEQUENCE: 116

```
Val Arg Ile Pro Glu Asn
1               5
```

<210> SEQ ID NO 117
<211> LENGTH: 7
<212> TYPE: PRT
<213> ORGANISM: Artificial Sequence
<220> FEATURE:
<223> OTHER INFORMATION: Synthetic construct

<400> SEQUENCE: 117

```
Val Arg Ile Pro Glu Asn Asn
1               5
```

<210> SEQ ID NO 118
<211> LENGTH: 8
<212> TYPE: PRT
<213> ORGANISM: Artificial Sequence
<220> FEATURE:
<223> OTHER INFORMATION: Synthetic construct

<400> SEQUENCE: 118

```
Val Arg Ile Pro Glu Asn Asn Pro
1               5
```

<210> SEQ ID NO 119
<211> LENGTH: 9
<212> TYPE: PRT
<213> ORGANISM: Artificial Sequence
<220> FEATURE:
<223> OTHER INFORMATION: Synthetic construct

<400> SEQUENCE: 119

```
Val Arg Ile Pro Glu Asn Asn Pro Val
1               5
```

<210> SEQ ID NO 120
<211> LENGTH: 10
<212> TYPE: PRT
<213> ORGANISM: Artificial Sequence
<220> FEATURE:
<223> OTHER INFORMATION: Synthetic construct

```
<400> SEQUENCE: 120

Val Arg Ile Pro Glu Asn Asn Pro Val Lys
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Synthetic construct

<400> SEQUENCE: 121

Val Arg Ile Pro Glu Asn Asn Pro Val Lys Leu
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Synthetic construct

<400> SEQUENCE: 122

Val Arg Ile Pro Glu Asn Asn Pro Val Lys Leu Ser
1               5                   10

<210> SEQ ID NO 123
<211> LENGTH: 5
<212> TYPE: PRT
<213> ORGANISM: Artificial Sequence
<220> FEATURE:
<223> OTHER INFORMATION: Synthetic construct

<400> SEQUENCE: 123

Glu Val Arg Ile Pro
1               5

<210> SEQ ID NO 124
<211> LENGTH: 6
<212> TYPE: PRT
<213> ORGANISM: Artificial Sequence
<220> FEATURE:
<223> OTHER INFORMATION: Synthetic construct

<400> SEQUENCE: 124

Pro Glu Val Arg Ile Pro
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic construct

<400> SEQUENCE: 125

Glu Pro Glu Val Arg Ile Pro
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic construct

<400> SEQUENCE: 126
```

```
Ser Glu Pro Glu Val Arg Ile Pro
1               5
```

<210> SEQ ID NO 127
<211> LENGTH: 9
<212> TYPE: PRT
<213> ORGANISM: Artificial Sequence
<220> FEATURE:
<223> OTHER INFORMATION: Synthetic construct

<400> SEQUENCE: 127

```
Ser Ser Glu Pro Glu Val Arg Ile Pro
1               5
```

<210> SEQ ID NO 128
<211> LENGTH: 10
<212> TYPE: PRT
<213> ORGANISM: Artificial Sequence
<220> FEATURE:
<223> OTHER INFORMATION: Synthetic construct

<400> SEQUENCE: 128

```
His Ser Ser Glu Pro Glu Val Arg Ile Pro
1               5                   10
```

<210> SEQ ID NO 129
<211> LENGTH: 11
<212> TYPE: PRT
<213> ORGANISM: Artificial Sequence
<220> FEATURE:
<223> OTHER INFORMATION: Synthetic construct

<400> SEQUENCE: 129

```
Val His Ser Ser Glu Pro Glu Val Arg Ile Pro
1               5                   10
```

<210> SEQ ID NO 130
<211> LENGTH: 12
<212> TYPE: PRT
<213> ORGANISM: Artificial Sequence
<220> FEATURE:
<223> OTHER INFORMATION: Synthetic construct

<400> SEQUENCE: 130

```
Thr Val His Ser Ser Glu Pro Glu Val Arg Ile Pro
1               5                   10
```

<210> SEQ ID NO 131
<211> LENGTH: 4
<212> TYPE: PRT
<213> ORGANISM: Artificial Sequence
<220> FEATURE:
<223> OTHER INFORMATION: Synthetic construct

<400> SEQUENCE: 131

```
Val Arg Val Pro
1
```

<210> SEQ ID NO 132
<211> LENGTH: 6
<212> TYPE: PRT
<213> ORGANISM: Artificial Sequence
<220> FEATURE:
<223> OTHER INFORMATION: Synthetic construct

<400> SEQUENCE: 132

Pro Val Arg Val Pro Glu
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic construct

<400> SEQUENCE: 133

Pro Glu Val Arg Val Pro Glu Asn
1               5

<210> SEQ ID NO 134
<211> LENGTH: 10
<212> TYPE: PRT
<213> ORGANISM: Artificial Sequence
<220> FEATURE:
<223> OTHER INFORMATION: Synthetic construct

<400> SEQUENCE: 134

Glu Pro Glu Val Arg Val Pro Glu Asn Asn
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Synthetic construct

<400> SEQUENCE: 135

Ser Glu Pro Glu Val Arg Val Pro Glu Asn Asn Pro
1               5                   10

<210> SEQ ID NO 136
<211> LENGTH: 14
<212> TYPE: PRT
<213> ORGANISM: Artificial Sequence
<220> FEATURE:
<223> OTHER INFORMATION: Synthetic construct

<400> SEQUENCE: 136

Ser Ser Glu Pro Glu Val Arg Val Pro Glu Asn Asn Pro Val
1               5                   10

<210> SEQ ID NO 137
<211> LENGTH: 16
<212> TYPE: PRT
<213> ORGANISM: Artificial Sequence
<220> FEATURE:
<223> OTHER INFORMATION: Synthetic construct

<400> SEQUENCE: 137

His Ser Ser Glu Pro Glu Val Arg Val Pro Glu Asn Asn Pro Val Lys
1               5                   10                  15

<210> SEQ ID NO 138
<211> LENGTH: 18
<212> TYPE: PRT
<213> ORGANISM: Artificial Sequence
<220> FEATURE:
<223> OTHER INFORMATION: Synthetic construct

<400> SEQUENCE: 138

Val His Ser Ser Glu Pro Glu Val Arg Val Pro Glu Asn Asn Pro Val

```
1               5                   10                  15

Lys Leu

<210> SEQ ID NO 139
<211> LENGTH: 20
<212> TYPE: PRT
<213> ORGANISM: Artificial Sequence
<220> FEATURE:
<223> OTHER INFORMATION: Synthetic construct

<400> SEQUENCE: 139

Thr Val His Ser Ser Glu Pro Glu Val Arg Val Pro Glu Asn Asn Pro
1               5                   10                  15

Val Lys Leu Ser
            20

<210> SEQ ID NO 140
<211> LENGTH: 5
<212> TYPE: PRT
<213> ORGANISM: Artificial Sequence
<220> FEATURE:
<223> OTHER INFORMATION: Synthetic construct

<400> SEQUENCE: 140

Val Arg Val Pro Glu
1               5

<210> SEQ ID NO 141
<211> LENGTH: 6
<212> TYPE: PRT
<213> ORGANISM: Artificial Sequence
<220> FEATURE:
<223> OTHER INFORMATION: Synthetic construct

<400> SEQUENCE: 141

Val Arg Val Pro Glu Asn
1               5

<210> SEQ ID NO 142
<211> LENGTH: 7
<212> TYPE: PRT
<213> ORGANISM: Artificial Sequence
<220> FEATURE:
<223> OTHER INFORMATION: Synthetic construct

<400> SEQUENCE: 142

Val Arg Val Pro Glu Asn Asn
1               5

<210> SEQ ID NO 143
<211> LENGTH: 8
<212> TYPE: PRT
<213> ORGANISM: Artificial Sequence
<220> FEATURE:
<223> OTHER INFORMATION: Synthetic construct

<400> SEQUENCE: 143

Val Arg Val Pro Glu Asn Asn Pro
1               5

<210> SEQ ID NO 144
<211> LENGTH: 9
<212> TYPE: PRT
<213> ORGANISM: Artificial Sequence
<220> FEATURE:
<223> OTHER INFORMATION: Synthetic construct
```

```
<400> SEQUENCE: 144

Val Arg Val Pro Glu Asn Asn Pro Val
1               5

<210> SEQ ID NO 145
<211> LENGTH: 10
<212> TYPE: PRT
<213> ORGANISM: Artificial Sequence
<220> FEATURE:
<223> OTHER INFORMATION: Synthetic construct

<400> SEQUENCE: 145

Val Arg Val Pro Glu Asn Asn Pro Val Lys
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Synthetic construct

<400> SEQUENCE: 146

Val Arg Val Pro Glu Asn Asn Pro Val Lys Leu
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Synthetic construct

<400> SEQUENCE: 147

Val Arg Val Pro Glu Asn Asn Pro Val Lys Leu Ser
1               5                   10

<210> SEQ ID NO 148
<211> LENGTH: 5
<212> TYPE: PRT
<213> ORGANISM: Artificial Sequence
<220> FEATURE:
<223> OTHER INFORMATION: Synthetic construct

<400> SEQUENCE: 148

Glu Val Arg Val Pro
1               5

<210> SEQ ID NO 149
<211> LENGTH: 6
<212> TYPE: PRT
<213> ORGANISM: Artificial Sequence
<220> FEATURE:
<223> OTHER INFORMATION: Synthetic construct

<400> SEQUENCE: 149

Pro Glu Val Arg Val Pro
1               5

<210> SEQ ID NO 150
<211> LENGTH: 7
<212> TYPE: PRT
<213> ORGANISM: Artificial Sequence
<220> FEATURE:
<223> OTHER INFORMATION: Synthetic construct
```

```
<400> SEQUENCE: 150

Glu Pro Glu Val Arg Val Pro
1               5

<210> SEQ ID NO 151
<211> LENGTH: 8
<212> TYPE: PRT
<213> ORGANISM: Artificial Sequence
<220> FEATURE:
<223> OTHER INFORMATION: Synthetic construct

<400> SEQUENCE: 151

Ser Glu Pro Glu Val Arg Val Pro
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic construct

<400> SEQUENCE: 152

Ser Ser Glu Pro Glu Val Arg Val Pro
1               5

<210> SEQ ID NO 153
<211> LENGTH: 10
<212> TYPE: PRT
<213> ORGANISM: Artificial Sequence
<220> FEATURE:
<223> OTHER INFORMATION: Synthetic construct

<400> SEQUENCE: 153

His Ser Ser Glu Pro Glu Val Arg Val Pro
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Synthetic construct

<400> SEQUENCE: 154

Val His Ser Ser Glu Pro Glu Val Arg Val Pro
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Synthetic construct

<400> SEQUENCE: 155

Thr Val His Ser Ser Glu Pro Glu Val Arg Val Pro
1               5                   10

<210> SEQ ID NO 156
<211> LENGTH: 4
<212> TYPE: PRT
<213> ORGANISM: Artificial Sequence
<220> FEATURE:
<223> OTHER INFORMATION: Synthetic construct

<400> SEQUENCE: 156
```

Val Arg Ala Pro
1

<210> SEQ ID NO 157
<211> LENGTH: 6
<212> TYPE: PRT
<213> ORGANISM: Artificial Sequence
<220> FEATURE:
<223> OTHER INFORMATION: Synthetic construct

<400> SEQUENCE: 157

Pro Val Arg Ala Pro Glu
1               5

<210> SEQ ID NO 158
<211> LENGTH: 8
<212> TYPE: PRT
<213> ORGANISM: Artificial Sequence
<220> FEATURE:
<223> OTHER INFORMATION: Synthetic construct

<400> SEQUENCE: 158

Pro Glu Val Arg Ala Pro Glu Asn
1               5

<210> SEQ ID NO 159
<211> LENGTH: 10
<212> TYPE: PRT
<213> ORGANISM: Artificial Sequence
<220> FEATURE:
<223> OTHER INFORMATION: Synthetic construct

<400> SEQUENCE: 159

Glu Pro Glu Val Arg Ala Pro Glu Asn Asn
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Synthetic construct

<400> SEQUENCE: 160

Ser Glu Pro Glu Val Arg Ala Pro Glu Asn Asn Pro
1               5                   10

<210> SEQ ID NO 161
<211> LENGTH: 14
<212> TYPE: PRT
<213> ORGANISM: Artificial Sequence
<220> FEATURE:
<223> OTHER INFORMATION: Synthetic construct

<400> SEQUENCE: 161

Ser Ser Glu Pro Glu Val Arg Ala Pro Glu Asn Asn Pro Val
1               5                   10

<210> SEQ ID NO 162
<211> LENGTH: 16
<212> TYPE: PRT
<213> ORGANISM: Artificial Sequence
<220> FEATURE:
<223> OTHER INFORMATION: Synthetic construct

<400> SEQUENCE: 162

His Ser Ser Glu Pro Glu Val Arg Ala Pro Glu Asn Asn Pro Val Lys
1               5                   10                  15

<210> SEQ ID NO 163
<211> LENGTH: 18
<212> TYPE: PRT
<213> ORGANISM: Artificial Sequence
<220> FEATURE:
<223> OTHER INFORMATION: Synthetic construct

<400> SEQUENCE: 163

Val His Ser Ser Glu Pro Glu Val Arg Ala Pro Glu Asn Asn Pro Val
1               5                   10                  15

Lys Leu

<210> SEQ ID NO 164
<211> LENGTH: 20
<212> TYPE: PRT
<213> ORGANISM: Artificial Sequence
<220> FEATURE:
<223> OTHER INFORMATION: Synthetic construct

<400> SEQUENCE: 164

Thr Val His Ser Ser Glu Pro Glu Val Arg Ala Pro Glu Asn Asn Pro
1               5                   10                  15

Val Lys Leu Ser
            20

<210> SEQ ID NO 165
<211> LENGTH: 5
<212> TYPE: PRT
<213> ORGANISM: Artificial Sequence
<220> FEATURE:
<223> OTHER INFORMATION: Synthetic construct

<400> SEQUENCE: 165

Val Arg Ala Pro Glu
1               5

<210> SEQ ID NO 166
<211> LENGTH: 6
<212> TYPE: PRT
<213> ORGANISM: Artificial Sequence
<220> FEATURE:
<223> OTHER INFORMATION: Synthetic construct

<400> SEQUENCE: 166

Val Arg Ala Pro Glu Asn
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic construct

<400> SEQUENCE: 167

Val Arg Ala Pro Glu Asn Asn
1               5

<210> SEQ ID NO 168
<211> LENGTH: 8
<212> TYPE: PRT
<213> ORGANISM: Artificial Sequence
<220> FEATURE:

<223> OTHER INFORMATION: Synthetic construct

<400> SEQUENCE: 168

Val Arg Ala Pro Glu Asn Asn Pro
1               5

<210> SEQ ID NO 169
<211> LENGTH: 9
<212> TYPE: PRT
<213> ORGANISM: Artificial Sequence
<220> FEATURE:
<223> OTHER INFORMATION: Synthetic construct

<400> SEQUENCE: 169

Val Arg Ala Pro Glu Asn Asn Pro Val
1               5

<210> SEQ ID NO 170
<211> LENGTH: 10
<212> TYPE: PRT
<213> ORGANISM: Artificial Sequence
<220> FEATURE:
<223> OTHER INFORMATION: Synthetic construct

<400> SEQUENCE: 170

Val Arg Ala Pro Glu Asn Asn Pro Val Lys
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Synthetic construct

<400> SEQUENCE: 171

Val Arg Ala Pro Glu Asn Asn Pro Val Lys Leu
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Synthetic construct

<400> SEQUENCE: 172

Val Arg Ala Pro Glu Asn Asn Pro Val Lys Leu Ser
1               5                   10

<210> SEQ ID NO 173
<211> LENGTH: 5
<212> TYPE: PRT
<213> ORGANISM: Artificial Sequence
<220> FEATURE:
<223> OTHER INFORMATION: Synthetic construct

<400> SEQUENCE: 173

Glu Val Arg Ala Pro
1               5

<210> SEQ ID NO 174
<211> LENGTH: 6
<212> TYPE: PRT
<213> ORGANISM: Artificial Sequence
<220> FEATURE:
<223> OTHER INFORMATION: Synthetic construct

```
<400> SEQUENCE: 174

Pro Glu Val Arg Ala Pro
1               5

<210> SEQ ID NO 175
<211> LENGTH: 7
<212> TYPE: PRT
<213> ORGANISM: Artificial Sequence
<220> FEATURE:
<223> OTHER INFORMATION: Synthetic construct

<400> SEQUENCE: 175

Glu Pro Glu Val Arg Ala Pro
1               5

<210> SEQ ID NO 176
<211> LENGTH: 8
<212> TYPE: PRT
<213> ORGANISM: Artificial Sequence
<220> FEATURE:
<223> OTHER INFORMATION: Synthetic construct

<400> SEQUENCE: 176

Ser Glu Pro Glu Val Arg Ala Pro
1               5

<210> SEQ ID NO 177
<211> LENGTH: 9
<212> TYPE: PRT
<213> ORGANISM: Artificial Sequence
<220> FEATURE:
<223> OTHER INFORMATION: Synthetic construct

<400> SEQUENCE: 177

Ser Ser Glu Pro Glu Val Arg Ala Pro
1               5

<210> SEQ ID NO 178
<211> LENGTH: 10
<212> TYPE: PRT
<213> ORGANISM: Artificial Sequence
<220> FEATURE:
<223> OTHER INFORMATION: Synthetic construct

<400> SEQUENCE: 178

His Ser Ser Glu Pro Glu Val Arg Ala Pro
1               5                   10

<210> SEQ ID NO 179
<211> LENGTH: 11
<212> TYPE: PRT
<213> ORGANISM: Artificial Sequence
<220> FEATURE:
<223> OTHER INFORMATION: Synthetic construct

<400> SEQUENCE: 179

Val His Ser Ser Glu Pro Glu Val Arg Ala Pro
1               5                   10

<210> SEQ ID NO 180
<211> LENGTH: 12
<212> TYPE: PRT
<213> ORGANISM: Artificial Sequence
<220> FEATURE:
<223> OTHER INFORMATION: Synthetic construct
```

```
<400> SEQUENCE: 180

Thr Val His Ser Ser Glu Pro Glu Val Arg Ala Pro
1               5                   10

<210> SEQ ID NO 181
<211> LENGTH: 9
<212> TYPE: PRT
<213> ORGANISM: Artificial Sequence
<220> FEATURE:
<223> OTHER INFORMATION: Synthetic construct

<400> SEQUENCE: 181

Pro Val Lys Leu Ser Cys Ala Tyr Ser
1               5

<210> SEQ ID NO 182
<211> LENGTH: 11
<212> TYPE: PRT
<213> ORGANISM: Artificial Sequence
<220> FEATURE:
<223> OTHER INFORMATION: Synthetic construct

<400> SEQUENCE: 182

Asn Pro Val Lys Leu Ser Cys Ala Tyr Ser Gly
1               5                   10

<210> SEQ ID NO 183
<211> LENGTH: 13
<212> TYPE: PRT
<213> ORGANISM: Artificial Sequence
<220> FEATURE:
<223> OTHER INFORMATION: Synthetic construct

<400> SEQUENCE: 183

Asn Asn Pro Val Lys Leu Ser Cys Ala Tyr Ser Gly Phe
1               5                   10

<210> SEQ ID NO 184
<211> LENGTH: 15
<212> TYPE: PRT
<213> ORGANISM: Artificial Sequence
<220> FEATURE:
<223> OTHER INFORMATION: Synthetic construct

<400> SEQUENCE: 184

Glu Asn Asn Pro Val Lys Leu Ser Cys Ala Tyr Ser Gly Phe Ser
1               5                   10                  15

<210> SEQ ID NO 185
<211> LENGTH: 17
<212> TYPE: PRT
<213> ORGANISM: Artificial Sequence
<220> FEATURE:
<223> OTHER INFORMATION: Synthetic construct

<400> SEQUENCE: 185

Pro Glu Asn Asn Pro Val Lys Leu Ser Cys Ala Tyr Ser Gly Phe Ser
1               5                   10                  15

Ser

<210> SEQ ID NO 186
<211> LENGTH: 19
<212> TYPE: PRT
<213> ORGANISM: Artificial Sequence
<220> FEATURE:
<223> OTHER INFORMATION: Synthetic construct
```

<400> SEQUENCE: 186

Ile Pro Glu Asn Asn Pro Val Lys Leu Ser Cys Ala Tyr Ser Gly Phe
1               5                   10                  15
Ser Ser Pro

<210> SEQ ID NO 187
<211> LENGTH: 21
<212> TYPE: PRT
<213> ORGANISM: Artificial Sequence
<220> FEATURE:
<223> OTHER INFORMATION: Synthetic construct

<400> SEQUENCE: 187

Arg Ile Pro Glu Asn Asn Pro Val Lys Leu Ser Cys Ala Tyr Ser Gly
1               5                   10                  15
Phe Ser Ser Pro Arg
            20

<210> SEQ ID NO 188
<211> LENGTH: 8
<212> TYPE: PRT
<213> ORGANISM: Artificial Sequence
<220> FEATURE:
<223> OTHER INFORMATION: Synthetic construct

<400> SEQUENCE: 188

Pro Val Lys Leu Ser Cys Ala Tyr
1               5

<210> SEQ ID NO 189
<211> LENGTH: 9
<212> TYPE: PRT
<213> ORGANISM: Artificial Sequence
<220> FEATURE:
<223> OTHER INFORMATION: Synthetic construct

<400> SEQUENCE: 189

Asn Pro Val Lys Leu Ser Cys Ala Tyr
1               5

<210> SEQ ID NO 190
<211> LENGTH: 10
<212> TYPE: PRT
<213> ORGANISM: Artificial Sequence
<220> FEATURE:
<223> OTHER INFORMATION: Synthetic construct

<400> SEQUENCE: 190

Asn Asn Pro Val Lys Leu Ser Cys Ala Tyr
1               5                   10

<210> SEQ ID NO 191
<211> LENGTH: 11
<212> TYPE: PRT
<213> ORGANISM: Artificial Sequence
<220> FEATURE:
<223> OTHER INFORMATION: Synthetic construct

<400> SEQUENCE: 191

Glu Asn Asn Pro Val Lys Leu Ser Cys Ala Tyr
1               5                   10

<210> SEQ ID NO 192
<211> LENGTH: 12

```
<212> TYPE: PRT
<213> ORGANISM: Artificial Sequence
<220> FEATURE:
<223> OTHER INFORMATION: Synthetic construct

<400> SEQUENCE: 192

Pro Glu Asn Asn Pro Val Lys Leu Ser Cys Ala Tyr
1               5                   10

<210> SEQ ID NO 193
<211> LENGTH: 13
<212> TYPE: PRT
<213> ORGANISM: Artificial Sequence
<220> FEATURE:
<223> OTHER INFORMATION: Synthetic construct

<400> SEQUENCE: 193

Ile Pro Glu Asn Asn Pro Val Lys Leu Ser Cys Ala Tyr
1               5                   10

<210> SEQ ID NO 194
<211> LENGTH: 14
<212> TYPE: PRT
<213> ORGANISM: Artificial Sequence
<220> FEATURE:
<223> OTHER INFORMATION: Synthetic construct

<400> SEQUENCE: 194

Arg Ile Pro Glu Asn Asn Pro Val Lys Leu Ser Cys Ala Tyr
1               5                   10

<210> SEQ ID NO 195
<211> LENGTH: 8
<212> TYPE: PRT
<213> ORGANISM: Artificial Sequence
<220> FEATURE:
<223> OTHER INFORMATION: Synthetic construct

<400> SEQUENCE: 195

Val Lys Leu Ser Cys Ala Tyr Ser
1               5

<210> SEQ ID NO 196
<211> LENGTH: 9
<212> TYPE: PRT
<213> ORGANISM: Artificial Sequence
<220> FEATURE:
<223> OTHER INFORMATION: Synthetic construct

<400> SEQUENCE: 196

Val Lys Leu Ser Cys Ala Tyr Ser Gly
1               5

<210> SEQ ID NO 197
<211> LENGTH: 10
<212> TYPE: PRT
<213> ORGANISM: Artificial Sequence
<220> FEATURE:
<223> OTHER INFORMATION: Synthetic construct

<400> SEQUENCE: 197

Val Lys Leu Ser Cys Ala Tyr Ser Gly Phe
1               5                   10

<210> SEQ ID NO 198
<211> LENGTH: 11
<212> TYPE: PRT
```

```
<213> ORGANISM: Artificial Sequence
<220> FEATURE:
<223> OTHER INFORMATION: Synthetic construct

<400> SEQUENCE: 198

Val Lys Leu Ser Cys Ala Tyr Ser Gly Phe Ser
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Synthetic construct

<400> SEQUENCE: 199

Val Lys Leu Ser Cys Ala Tyr Ser Gly Phe Ser Ser
1               5                   10

<210> SEQ ID NO 200
<211> LENGTH: 13
<212> TYPE: PRT
<213> ORGANISM: Artificial Sequence
<220> FEATURE:
<223> OTHER INFORMATION: Synthetic construct

<400> SEQUENCE: 200

Val Lys Leu Ser Cys Ala Tyr Ser Gly Phe Ser Ser Pro
1               5                   10

<210> SEQ ID NO 201
<211> LENGTH: 14
<212> TYPE: PRT
<213> ORGANISM: Artificial Sequence
<220> FEATURE:
<223> OTHER INFORMATION: Synthetic construct

<400> SEQUENCE: 201

Val Lys Leu Ser Cys Ala Tyr Ser Gly Phe Ser Ser Pro Arg
1               5                   10

<210> SEQ ID NO 202
<211> LENGTH: 7
<212> TYPE: PRT
<213> ORGANISM: Artificial Sequence
<220> FEATURE:
<223> OTHER INFORMATION: Synthetic construct

<400> SEQUENCE: 202

Val Lys Leu Thr Cys Ala Tyr
1               5

<210> SEQ ID NO 203
<211> LENGTH: 7
<212> TYPE: PRT
<213> ORGANISM: Artificial Sequence
<220> FEATURE:
<223> OTHER INFORMATION: Synthetic construct

<400> SEQUENCE: 203

Val Lys Leu Thr Cys Ala Tyr
1               5

<210> SEQ ID NO 204
<211> LENGTH: 9
<212> TYPE: PRT
<213> ORGANISM: Artificial Sequence
```

```
<220> FEATURE:
<223> OTHER INFORMATION: Synthetic construct

<400> SEQUENCE: 204

Pro Val Lys Leu Thr Cys Ala Tyr Ser
1               5

<210> SEQ ID NO 205
<211> LENGTH: 11
<212> TYPE: PRT
<213> ORGANISM: Artificial Sequence
<220> FEATURE:
<223> OTHER INFORMATION: Synthetic construct

<400> SEQUENCE: 205

Asn Pro Val Lys Leu Thr Cys Ala Tyr Ser Gly
1               5                   10

<210> SEQ ID NO 206
<211> LENGTH: 13
<212> TYPE: PRT
<213> ORGANISM: Artificial Sequence
<220> FEATURE:
<223> OTHER INFORMATION: Synthetic construct

<400> SEQUENCE: 206

Asn Asn Pro Val Lys Leu Thr Cys Ala Tyr Ser Gly Phe
1               5                   10

<210> SEQ ID NO 207
<211> LENGTH: 15
<212> TYPE: PRT
<213> ORGANISM: Artificial Sequence
<220> FEATURE:
<223> OTHER INFORMATION: Synthetic construct

<400> SEQUENCE: 207

Glu Asn Asn Pro Val Lys Leu Thr Cys Ala Tyr Ser Gly Phe Ser
1               5                   10                  15

<210> SEQ ID NO 208
<211> LENGTH: 17
<212> TYPE: PRT
<213> ORGANISM: Artificial Sequence
<220> FEATURE:
<223> OTHER INFORMATION: Synthetic construct

<400> SEQUENCE: 208

Pro Glu Asn Asn Pro Val Lys Leu Thr Cys Ala Tyr Ser Gly Phe Ser
1               5                   10                  15

Ser

<210> SEQ ID NO 209
<211> LENGTH: 19
<212> TYPE: PRT
<213> ORGANISM: Artificial Sequence
<220> FEATURE:
<223> OTHER INFORMATION: Synthetic construct

<400> SEQUENCE: 209

Ile Pro Glu Asn Asn Pro Val Lys Leu Thr Cys Ala Tyr Ser Gly Phe
1               5                   10                  15

Ser Ser Pro

<210> SEQ ID NO 210
```

<211> LENGTH: 21
<212> TYPE: PRT
<213> ORGANISM: Artificial Sequence
<220> FEATURE:
<223> OTHER INFORMATION: Synthetic construct

<400> SEQUENCE: 210

Arg Ile Pro Glu Asn Asn Pro Val Lys Leu Thr Cys Ala Tyr Ser Gly
1               5                   10                  15

Phe Ser Ser Pro Arg
            20

<210> SEQ ID NO 211
<211> LENGTH: 8
<212> TYPE: PRT
<213> ORGANISM: Artificial Sequence
<220> FEATURE:
<223> OTHER INFORMATION: Synthetic construct

<400> SEQUENCE: 211

Pro Val Lys Leu Thr Cys Ala Tyr
1               5

<210> SEQ ID NO 212
<211> LENGTH: 9
<212> TYPE: PRT
<213> ORGANISM: Artificial Sequence
<220> FEATURE:
<223> OTHER INFORMATION: Synthetic construct

<400> SEQUENCE: 212

Asn Pro Val Lys Leu Thr Cys Ala Tyr
1               5

<210> SEQ ID NO 213
<211> LENGTH: 10
<212> TYPE: PRT
<213> ORGANISM: Artificial Sequence
<220> FEATURE:
<223> OTHER INFORMATION: Synthetic construct

<400> SEQUENCE: 213

Asn Asn Pro Val Lys Leu Thr Cys Ala Tyr
1               5                   10

<210> SEQ ID NO 214
<211> LENGTH: 11
<212> TYPE: PRT
<213> ORGANISM: Artificial Sequence
<220> FEATURE:
<223> OTHER INFORMATION: Synthetic construct

<400> SEQUENCE: 214

Glu Asn Asn Pro Val Lys Leu Thr Cys Ala Tyr
1               5                   10

<210> SEQ ID NO 215
<211> LENGTH: 12
<212> TYPE: PRT
<213> ORGANISM: Artificial Sequence
<220> FEATURE:
<223> OTHER INFORMATION: Synthetic construct

<400> SEQUENCE: 215

Pro Glu Asn Asn Pro Val Lys Leu Thr Cys Ala Tyr
1               5                   10

```
<210> SEQ ID NO 216
<211> LENGTH: 13
<212> TYPE: PRT
<213> ORGANISM: Artificial Sequence
<220> FEATURE:
<223> OTHER INFORMATION: Synthetic construct

<400> SEQUENCE: 216

Ile Pro Glu Asn Asn Pro Val Lys Leu Thr Cys Ala Tyr
1               5                   10

<210> SEQ ID NO 217
<211> LENGTH: 14
<212> TYPE: PRT
<213> ORGANISM: Artificial Sequence
<220> FEATURE:
<223> OTHER INFORMATION: Synthetic construct

<400> SEQUENCE: 217

Arg Ile Pro Glu Asn Asn Pro Val Lys Leu Thr Cys Ala Tyr
1               5                   10

<210> SEQ ID NO 218
<211> LENGTH: 8
<212> TYPE: PRT
<213> ORGANISM: Artificial Sequence
<220> FEATURE:
<223> OTHER INFORMATION: Synthetic construct

<400> SEQUENCE: 218

Val Lys Leu Thr Cys Ala Tyr Ser
1               5

<210> SEQ ID NO 219
<211> LENGTH: 9
<212> TYPE: PRT
<213> ORGANISM: Artificial Sequence
<220> FEATURE:
<223> OTHER INFORMATION: Synthetic construct

<400> SEQUENCE: 219

Val Lys Leu Thr Cys Ala Tyr Ser Gly
1               5

<210> SEQ ID NO 220
<211> LENGTH: 10
<212> TYPE: PRT
<213> ORGANISM: Artificial Sequence
<220> FEATURE:
<223> OTHER INFORMATION: Synthetic construct

<400> SEQUENCE: 220

Val Lys Leu Thr Cys Ala Tyr Ser Gly Phe
1               5                   10

<210> SEQ ID NO 221
<211> LENGTH: 11
<212> TYPE: PRT
<213> ORGANISM: Artificial Sequence
<220> FEATURE:
<223> OTHER INFORMATION: Synthetic construct

<400> SEQUENCE: 221

Val Lys Leu Thr Cys Ala Tyr Ser Gly Phe Ser
1               5                   10
```

```
<210> SEQ ID NO 222
<211> LENGTH: 12
<212> TYPE: PRT
<213> ORGANISM: Artificial Sequence
<220> FEATURE:
<223> OTHER INFORMATION: Synthetic construct

<400> SEQUENCE: 222

Val Lys Leu Thr Cys Ala Tyr Ser Gly Phe Ser Ser
1               5                   10

<210> SEQ ID NO 223
<211> LENGTH: 13
<212> TYPE: PRT
<213> ORGANISM: Artificial Sequence
<220> FEATURE:
<223> OTHER INFORMATION: Synthetic construct

<400> SEQUENCE: 223

Val Lys Leu Thr Cys Ala Tyr Ser Gly Phe Ser Ser Pro
1               5                   10

<210> SEQ ID NO 224
<211> LENGTH: 14
<212> TYPE: PRT
<213> ORGANISM: Artificial Sequence
<220> FEATURE:
<223> OTHER INFORMATION: Synthetic construct

<400> SEQUENCE: 224

Val Lys Leu Thr Cys Ala Tyr Ser Gly Phe Ser Ser Pro Arg
1               5                   10

<210> SEQ ID NO 225
<211> LENGTH: 7
<212> TYPE: PRT
<213> ORGANISM: Artificial Sequence
<220> FEATURE:
<223> OTHER INFORMATION: Synthetic construct

<400> SEQUENCE: 225

Ala Lys Leu Ser Cys Ala Tyr
1               5

<210> SEQ ID NO 226
<211> LENGTH: 7
<212> TYPE: PRT
<213> ORGANISM: Artificial Sequence
<220> FEATURE:
<223> OTHER INFORMATION: Synthetic construct

<400> SEQUENCE: 226

Ala Lys Leu Ser Cys Ala Tyr
1               5

<210> SEQ ID NO 227
<211> LENGTH: 9
<212> TYPE: PRT
<213> ORGANISM: Artificial Sequence
<220> FEATURE:
<223> OTHER INFORMATION: Synthetic construct

<400> SEQUENCE: 227

Pro Ala Lys Leu Ser Cys Ala Tyr Ser
1               5

<210> SEQ ID NO 228
```

```
<211> LENGTH: 11
<212> TYPE: PRT
<213> ORGANISM: Artificial Sequence
<220> FEATURE:
<223> OTHER INFORMATION: Synthetic construct

<400> SEQUENCE: 228

Asn Pro Ala Lys Leu Ser Cys Ala Tyr Ser Gly
1               5                   10

<210> SEQ ID NO 229
<211> LENGTH: 13
<212> TYPE: PRT
<213> ORGANISM: Artificial Sequence
<220> FEATURE:
<223> OTHER INFORMATION: Synthetic construct

<400> SEQUENCE: 229

Asn Asn Pro Ala Lys Leu Ser Cys Ala Tyr Ser Gly Phe
1               5                   10

<210> SEQ ID NO 230
<211> LENGTH: 15
<212> TYPE: PRT
<213> ORGANISM: Artificial Sequence
<220> FEATURE:
<223> OTHER INFORMATION: Synthetic construct

<400> SEQUENCE: 230

Glu Asn Asn Pro Ala Lys Leu Ser Cys Ala Tyr Ser Gly Phe Ser
1               5                   10                  15

<210> SEQ ID NO 231
<211> LENGTH: 17
<212> TYPE: PRT
<213> ORGANISM: Artificial Sequence
<220> FEATURE:
<223> OTHER INFORMATION: Synthetic construct

<400> SEQUENCE: 231

Pro Glu Asn Asn Pro Ala Lys Leu Ser Cys Ala Tyr Ser Gly Phe Ser
1               5                   10                  15

Ser

<210> SEQ ID NO 232
<211> LENGTH: 19
<212> TYPE: PRT
<213> ORGANISM: Artificial Sequence
<220> FEATURE:
<223> OTHER INFORMATION: Synthetic construct

<400> SEQUENCE: 232

Ile Pro Glu Asn Asn Pro Ala Lys Leu Ser Cys Ala Tyr Ser Gly Phe
1               5                   10                  15

Ser Ser Pro

<210> SEQ ID NO 233
<211> LENGTH: 21
<212> TYPE: PRT
<213> ORGANISM: Artificial Sequence
<220> FEATURE:
<223> OTHER INFORMATION: Synthetic construct

<400> SEQUENCE: 233

Arg Ile Pro Glu Asn Asn Pro Ala Lys Leu Ser Cys Ala Tyr Ser Gly
1               5                   10                  15
```

Phe Ser Ser Pro Arg
            20

<210> SEQ ID NO 234
<211> LENGTH: 8
<212> TYPE: PRT
<213> ORGANISM: Artificial Sequence
<220> FEATURE:
<223> OTHER INFORMATION: Synthetic construct

<400> SEQUENCE: 234

Pro Ala Lys Leu Ser Cys Ala Tyr
1               5

<210> SEQ ID NO 235
<211> LENGTH: 9
<212> TYPE: PRT
<213> ORGANISM: Artificial Sequence
<220> FEATURE:
<223> OTHER INFORMATION: Synthetic construct

<400> SEQUENCE: 235

Asn Pro Ala Lys Leu Ser Cys Ala Tyr
1               5

<210> SEQ ID NO 236
<211> LENGTH: 10
<212> TYPE: PRT
<213> ORGANISM: Artificial Sequence
<220> FEATURE:
<223> OTHER INFORMATION: Synthetic construct

<400> SEQUENCE: 236

Asn Asn Pro Ala Lys Leu Ser Cys Ala Tyr
1               5                   10

<210> SEQ ID NO 237
<211> LENGTH: 11
<212> TYPE: PRT
<213> ORGANISM: Artificial Sequence
<220> FEATURE:
<223> OTHER INFORMATION: Synthetic construct

<400> SEQUENCE: 237

Glu Asn Asn Pro Ala Lys Leu Ser Cys Ala Tyr
1               5                   10

<210> SEQ ID NO 238
<211> LENGTH: 12
<212> TYPE: PRT
<213> ORGANISM: Artificial Sequence
<220> FEATURE:
<223> OTHER INFORMATION: Synthetic construct

<400> SEQUENCE: 238

Pro Glu Asn Asn Pro Ala Lys Leu Ser Cys Ala Tyr
1               5                   10

<210> SEQ ID NO 239
<211> LENGTH: 13
<212> TYPE: PRT
<213> ORGANISM: Artificial Sequence
<220> FEATURE:
<223> OTHER INFORMATION: Synthetic construct

<400> SEQUENCE: 239

```
Ile Pro Glu Asn Asn Pro Ala Lys Leu Ser Cys Ala Tyr
1               5                   10

<210> SEQ ID NO 240
<211> LENGTH: 14
<212> TYPE: PRT
<213> ORGANISM: Artificial Sequence
<220> FEATURE:
<223> OTHER INFORMATION: Synthetic construct

<400> SEQUENCE: 240

Arg Ile Pro Glu Asn Asn Pro Ala Lys Leu Ser Cys Ala Tyr
1               5                   10

<210> SEQ ID NO 241
<211> LENGTH: 8
<212> TYPE: PRT
<213> ORGANISM: Artificial Sequence
<220> FEATURE:
<223> OTHER INFORMATION: Synthetic construct

<400> SEQUENCE: 241

Ala Lys Leu Ser Cys Ala Tyr Ser
1               5

<210> SEQ ID NO 242
<211> LENGTH: 9
<212> TYPE: PRT
<213> ORGANISM: Artificial Sequence
<220> FEATURE:
<223> OTHER INFORMATION: Synthetic construct

<400> SEQUENCE: 242

Ala Lys Leu Ser Cys Ala Tyr Ser Gly
1               5

<210> SEQ ID NO 243
<211> LENGTH: 10
<212> TYPE: PRT
<213> ORGANISM: Artificial Sequence
<220> FEATURE:
<223> OTHER INFORMATION: Synthetic construct

<400> SEQUENCE: 243

Ala Lys Leu Ser Cys Ala Tyr Ser Gly Phe
1               5                   10

<210> SEQ ID NO 244
<211> LENGTH: 11
<212> TYPE: PRT
<213> ORGANISM: Artificial Sequence
<220> FEATURE:
<223> OTHER INFORMATION: Synthetic construct

<400> SEQUENCE: 244

Ala Lys Leu Ser Cys Ala Tyr Ser Gly Phe Ser
1               5                   10

<210> SEQ ID NO 245
<211> LENGTH: 12
<212> TYPE: PRT
<213> ORGANISM: Artificial Sequence
<220> FEATURE:
<223> OTHER INFORMATION: Synthetic construct

<400> SEQUENCE: 245

Ala Lys Leu Ser Cys Ala Tyr Ser Gly Phe Ser Ser
```

```
                   1               5                    10
```

<210> SEQ ID NO 246
<211> LENGTH: 13
<212> TYPE: PRT
<213> ORGANISM: Artificial Sequence
<220> FEATURE:
<223> OTHER INFORMATION: Synthetic construct

<400> SEQUENCE: 246

```
Ala Lys Leu Ser Cys Ala Tyr Ser Gly Phe Ser Ser Pro
1               5                   10
```

<210> SEQ ID NO 247
<211> LENGTH: 14
<212> TYPE: PRT
<213> ORGANISM: Artificial Sequence
<220> FEATURE:
<223> OTHER INFORMATION: Synthetic construct

<400> SEQUENCE: 247

```
Ala Lys Leu Ser Cys Ala Tyr Ser Gly Phe Ser Ser Pro Arg
1               5                   10
```

<210> SEQ ID NO 248
<211> LENGTH: 7
<212> TYPE: PRT
<213> ORGANISM: Artificial Sequence
<220> FEATURE:
<223> OTHER INFORMATION: Synthetic construct

<400> SEQUENCE: 248

```
Ala Lys Leu Thr Cys Ala Tyr
1               5
```

<210> SEQ ID NO 249
<211> LENGTH: 7
<212> TYPE: PRT
<213> ORGANISM: Artificial Sequence
<220> FEATURE:
<223> OTHER INFORMATION: Synthetic construct

<400> SEQUENCE: 249

```
Ala Lys Leu Thr Cys Ala Tyr
1               5
```

<210> SEQ ID NO 250
<211> LENGTH: 9
<212> TYPE: PRT
<213> ORGANISM: Artificial Sequence
<220> FEATURE:
<223> OTHER INFORMATION: Synthetic construct

<400> SEQUENCE: 250

```
Pro Ala Lys Leu Thr Cys Ala Tyr Ser
1               5
```

<210> SEQ ID NO 251
<211> LENGTH: 11
<212> TYPE: PRT
<213> ORGANISM: Artificial Sequence
<220> FEATURE:
<223> OTHER INFORMATION: Synthetic construct

<400> SEQUENCE: 251

```
Asn Pro Ala Lys Leu Thr Cys Ala Tyr Ser Gly
1               5                   10
```

<210> SEQ ID NO 252
<211> LENGTH: 13
<212> TYPE: PRT
<213> ORGANISM: Artificial Sequence
<220> FEATURE:
<223> OTHER INFORMATION: Synthetic construct

<400> SEQUENCE: 252

Asn Asn Pro Ala Lys Leu Thr Cys Ala Tyr Ser Gly Phe
1               5                   10

<210> SEQ ID NO 253
<211> LENGTH: 15
<212> TYPE: PRT
<213> ORGANISM: Artificial Sequence
<220> FEATURE:
<223> OTHER INFORMATION: Synthetic construct

<400> SEQUENCE: 253

Glu Asn Asn Pro Ala Lys Leu Thr Cys Ala Tyr Ser Gly Phe Ser
1               5                   10                  15

<210> SEQ ID NO 254
<211> LENGTH: 17
<212> TYPE: PRT
<213> ORGANISM: Artificial Sequence
<220> FEATURE:
<223> OTHER INFORMATION: Synthetic construct

<400> SEQUENCE: 254

Pro Glu Asn Asn Pro Ala Lys Leu Thr Cys Ala Tyr Ser Gly Phe Ser
1               5                   10                  15

Ser

<210> SEQ ID NO 255
<211> LENGTH: 19
<212> TYPE: PRT
<213> ORGANISM: Artificial Sequence
<220> FEATURE:
<223> OTHER INFORMATION: Synthetic construct

<400> SEQUENCE: 255

Ile Pro Glu Asn Asn Pro Ala Lys Leu Thr Cys Ala Tyr Ser Gly Phe
1               5                   10                  15

Ser Ser Pro

<210> SEQ ID NO 256
<211> LENGTH: 21
<212> TYPE: PRT
<213> ORGANISM: Artificial Sequence
<220> FEATURE:
<223> OTHER INFORMATION: Synthetic construct

<400> SEQUENCE: 256

Arg Ile Pro Glu Asn Asn Pro Ala Lys Leu Thr Cys Ala Tyr Ser Gly
1               5                   10                  15

Phe Ser Ser Pro Arg
            20

<210> SEQ ID NO 257
<211> LENGTH: 8
<212> TYPE: PRT
<213> ORGANISM: Artificial Sequence
<220> FEATURE:

<223> OTHER INFORMATION: Synthetic construct

<400> SEQUENCE: 257

Pro Ala Lys Leu Thr Cys Ala Tyr
1               5

<210> SEQ ID NO 258
<211> LENGTH: 9
<212> TYPE: PRT
<213> ORGANISM: Artificial Sequence
<220> FEATURE:
<223> OTHER INFORMATION: Synthetic construct

<400> SEQUENCE: 258

Asn Pro Ala Lys Leu Thr Cys Ala Tyr
1               5

<210> SEQ ID NO 259
<211> LENGTH: 10
<212> TYPE: PRT
<213> ORGANISM: Artificial Sequence
<220> FEATURE:
<223> OTHER INFORMATION: Synthetic construct

<400> SEQUENCE: 259

Asn Asn Pro Ala Lys Leu Thr Cys Ala Tyr
1               5                   10

<210> SEQ ID NO 260
<211> LENGTH: 11
<212> TYPE: PRT
<213> ORGANISM: Artificial Sequence
<220> FEATURE:
<223> OTHER INFORMATION: Synthetic construct

<400> SEQUENCE: 260

Glu Asn Asn Pro Ala Lys Leu Thr Cys Ala Tyr
1               5                   10

<210> SEQ ID NO 261
<211> LENGTH: 12
<212> TYPE: PRT
<213> ORGANISM: Artificial Sequence
<220> FEATURE:
<223> OTHER INFORMATION: Synthetic construct

<400> SEQUENCE: 261

Pro Glu Asn Asn Pro Ala Lys Leu Thr Cys Ala Tyr
1               5                   10

<210> SEQ ID NO 262
<211> LENGTH: 13
<212> TYPE: PRT
<213> ORGANISM: Artificial Sequence
<220> FEATURE:
<223> OTHER INFORMATION: Synthetic construct

<400> SEQUENCE: 262

Ile Pro Glu Asn Asn Pro Ala Lys Leu Thr Cys Ala Tyr
1               5                   10

<210> SEQ ID NO 263
<211> LENGTH: 14
<212> TYPE: PRT
<213> ORGANISM: Artificial Sequence
<220> FEATURE:
<223> OTHER INFORMATION: Synthetic construct

<400> SEQUENCE: 263

Arg Ile Pro Glu Asn Asn Pro Ala Lys Leu Thr Cys Ala Tyr
1               5                   10

<210> SEQ ID NO 264
<211> LENGTH: 8
<212> TYPE: PRT
<213> ORGANISM: Artificial Sequence
<220> FEATURE:
<223> OTHER INFORMATION: Synthetic construct

<400> SEQUENCE: 264

Ala Lys Leu Thr Cys Ala Tyr Ser
1               5

<210> SEQ ID NO 265
<211> LENGTH: 9
<212> TYPE: PRT
<213> ORGANISM: Artificial Sequence
<220> FEATURE:
<223> OTHER INFORMATION: Synthetic construct

<400> SEQUENCE: 265

Ala Lys Leu Thr Cys Ala Tyr Ser Gly
1               5

<210> SEQ ID NO 266
<211> LENGTH: 10
<212> TYPE: PRT
<213> ORGANISM: Artificial Sequence
<220> FEATURE:
<223> OTHER INFORMATION: Synthetic construct

<400> SEQUENCE: 266

Ala Lys Leu Thr Cys Ala Tyr Ser Gly Phe
1               5                   10

<210> SEQ ID NO 267
<211> LENGTH: 11
<212> TYPE: PRT
<213> ORGANISM: Artificial Sequence
<220> FEATURE:
<223> OTHER INFORMATION: Synthetic construct

<400> SEQUENCE: 267

Ala Lys Leu Thr Cys Ala Tyr Ser Gly Phe Ser
1               5                   10

<210> SEQ ID NO 268
<211> LENGTH: 12
<212> TYPE: PRT
<213> ORGANISM: Artificial Sequence
<220> FEATURE:
<223> OTHER INFORMATION: Synthetic construct

<400> SEQUENCE: 268

Ala Lys Leu Thr Cys Ala Tyr Ser Gly Phe Ser Ser
1               5                   10

<210> SEQ ID NO 269
<211> LENGTH: 13
<212> TYPE: PRT
<213> ORGANISM: Artificial Sequence
<220> FEATURE:
<223> OTHER INFORMATION: Synthetic construct

```
<400> SEQUENCE: 269

Ala Lys Leu Thr Cys Ala Tyr Ser Gly Phe Ser Ser Pro
1               5                   10

<210> SEQ ID NO 270
<211> LENGTH: 14
<212> TYPE: PRT
<213> ORGANISM: Artificial Sequence
<220> FEATURE:
<223> OTHER INFORMATION: Synthetic construct

<400> SEQUENCE: 270

Ala Lys Leu Thr Cys Ala Tyr Ser Gly Phe Ser Ser Pro Arg
1               5                   10

<210> SEQ ID NO 271
<211> LENGTH: 11
<212> TYPE: PRT
<213> ORGANISM: Artificial Sequence
<220> FEATURE:
<223> OTHER INFORMATION: Synthetic construct

<400> SEQUENCE: 271

Arg Glu Asp Thr Gly Thr Tyr Thr Cys Met Val
1               5                   10

<210> SEQ ID NO 272
<211> LENGTH: 13
<212> TYPE: PRT
<213> ORGANISM: Artificial Sequence
<220> FEATURE:
<223> OTHER INFORMATION: Synthetic construct

<400> SEQUENCE: 272

Thr Arg Glu Asp Thr Gly Thr Tyr Thr Cys Met Val Ser
1               5                   10

<210> SEQ ID NO 273
<211> LENGTH: 15
<212> TYPE: PRT
<213> ORGANISM: Artificial Sequence
<220> FEATURE:
<223> OTHER INFORMATION: Synthetic construct

<400> SEQUENCE: 273

Val Thr Arg Glu Asp Thr Gly Thr Tyr Thr Cys Met Val Ser Glu
1               5                   10                  15

<210> SEQ ID NO 274
<211> LENGTH: 17
<212> TYPE: PRT
<213> ORGANISM: Artificial Sequence
<220> FEATURE:
<223> OTHER INFORMATION: Synthetic construct

<400> SEQUENCE: 274

Ser Val Thr Arg Glu Asp Thr Gly Thr Tyr Thr Cys Met Val Ser Glu
1               5                   10                  15

Glu

<210> SEQ ID NO 275
<211> LENGTH: 19
<212> TYPE: PRT
<213> ORGANISM: Artificial Sequence
<220> FEATURE:
<223> OTHER INFORMATION: Synthetic construct
```

```
<400> SEQUENCE: 275

Lys Ser Val Thr Arg Glu Asp Thr Gly Thr Tyr Thr Cys Met Val Ser
1               5                   10                  15
Glu Glu Gly

<210> SEQ ID NO 276
<211> LENGTH: 10
<212> TYPE: PRT
<213> ORGANISM: Artificial Sequence
<220> FEATURE:
<223> OTHER INFORMATION: Synthetic construct

<400> SEQUENCE: 276

Arg Glu Asp Thr Gly Thr Tyr Thr Cys Met
1               5                   10

<210> SEQ ID NO 277
<211> LENGTH: 11
<212> TYPE: PRT
<213> ORGANISM: Artificial Sequence
<220> FEATURE:
<223> OTHER INFORMATION: Synthetic construct

<400> SEQUENCE: 277

Thr Arg Glu Asp Thr Gly Thr Tyr Thr Cys Met
1               5                   10

<210> SEQ ID NO 278
<211> LENGTH: 12
<212> TYPE: PRT
<213> ORGANISM: Artificial Sequence
<220> FEATURE:
<223> OTHER INFORMATION: Synthetic construct

<400> SEQUENCE: 278

Val Thr Arg Glu Asp Thr Gly Thr Tyr Thr Cys Met
1               5                   10

<210> SEQ ID NO 279
<211> LENGTH: 13
<212> TYPE: PRT
<213> ORGANISM: Artificial Sequence
<220> FEATURE:
<223> OTHER INFORMATION: Synthetic construct

<400> SEQUENCE: 279

Ser Val Thr Arg Glu Asp Thr Gly Thr Tyr Thr Cys Met
1               5                   10

<210> SEQ ID NO 280
<211> LENGTH: 14
<212> TYPE: PRT
<213> ORGANISM: Artificial Sequence
<220> FEATURE:
<223> OTHER INFORMATION: Synthetic construct

<400> SEQUENCE: 280

Lys Ser Val Thr Arg Glu Asp Thr Gly Thr Tyr Thr Cys Met
1               5                   10

<210> SEQ ID NO 281
<211> LENGTH: 10
<212> TYPE: PRT
<213> ORGANISM: Artificial Sequence
<220> FEATURE:
```

<223> OTHER INFORMATION: Synthetic construct

<400> SEQUENCE: 281

Glu Asp Thr Gly Thr Tyr Thr Cys Met Val
1               5                   10

<210> SEQ ID NO 282
<211> LENGTH: 11
<212> TYPE: PRT
<213> ORGANISM: Artificial Sequence
<220> FEATURE:
<223> OTHER INFORMATION: Synthetic construct

<400> SEQUENCE: 282

Glu Asp Thr Gly Thr Tyr Thr Cys Met Val Ser
1               5                   10

<210> SEQ ID NO 283
<211> LENGTH: 12
<212> TYPE: PRT
<213> ORGANISM: Artificial Sequence
<220> FEATURE:
<223> OTHER INFORMATION: Synthetic construct

<400> SEQUENCE: 283

Glu Asp Thr Gly Thr Tyr Thr Cys Met Val Ser Glu
1               5                   10

<210> SEQ ID NO 284
<211> LENGTH: 13
<212> TYPE: PRT
<213> ORGANISM: Artificial Sequence
<220> FEATURE:
<223> OTHER INFORMATION: Synthetic construct

<400> SEQUENCE: 284

Glu Asp Thr Gly Thr Tyr Thr Cys Met Val Ser Glu Glu
1               5                   10

<210> SEQ ID NO 285
<211> LENGTH: 14
<212> TYPE: PRT
<213> ORGANISM: Artificial Sequence
<220> FEATURE:
<223> OTHER INFORMATION: Synthetic construct

<400> SEQUENCE: 285

Glu Asp Thr Gly Thr Tyr Thr Cys Met Val Ser Glu Glu Gly
1               5                   10

<210> SEQ ID NO 286
<211> LENGTH: 9
<212> TYPE: PRT
<213> ORGANISM: Artificial Sequence
<220> FEATURE:
<223> OTHER INFORMATION: Synthetic construct

<400> SEQUENCE: 286

Glu Asp Thr Gly Thr Tyr Thr Cys Glu
1               5

<210> SEQ ID NO 287
<211> LENGTH: 11
<212> TYPE: PRT
<213> ORGANISM: Artificial Sequence
<220> FEATURE:
<223> OTHER INFORMATION: Synthetic construct

<400> SEQUENCE: 287

Arg Glu Asp Thr Gly Thr Tyr Thr Cys Glu Val
1               5                   10

<210> SEQ ID NO 288
<211> LENGTH: 13
<212> TYPE: PRT
<213> ORGANISM: Artificial Sequence
<220> FEATURE:
<223> OTHER INFORMATION: Synthetic construct

<400> SEQUENCE: 288

Thr Arg Glu Asp Thr Gly Thr Tyr Thr Cys Glu Val Ser
1               5                   10

<210> SEQ ID NO 289
<211> LENGTH: 15
<212> TYPE: PRT
<213> ORGANISM: Artificial Sequence
<220> FEATURE:
<223> OTHER INFORMATION: Synthetic construct

<400> SEQUENCE: 289

Val Thr Arg Glu Asp Thr Gly Thr Tyr Thr Cys Glu Val Ser Glu
1               5                   10                  15

<210> SEQ ID NO 290
<211> LENGTH: 17
<212> TYPE: PRT
<213> ORGANISM: Artificial Sequence
<220> FEATURE:
<223> OTHER INFORMATION: Synthetic construct

<400> SEQUENCE: 290

Ser Val Thr Arg Glu Asp Thr Gly Thr Tyr Thr Cys Glu Val Ser Glu
1               5                   10                  15

Glu

<210> SEQ ID NO 291
<211> LENGTH: 19
<212> TYPE: PRT
<213> ORGANISM: Artificial Sequence
<220> FEATURE:
<223> OTHER INFORMATION: Synthetic construct

<400> SEQUENCE: 291

Lys Ser Val Thr Arg Glu Asp Thr Gly Thr Tyr Thr Cys Glu Val Ser
1               5                   10                  15

Glu Glu Gly

<210> SEQ ID NO 292
<211> LENGTH: 10
<212> TYPE: PRT
<213> ORGANISM: Artificial Sequence
<220> FEATURE:
<223> OTHER INFORMATION: Synthetic construct

<400> SEQUENCE: 292

Arg Glu Asp Thr Gly Thr Tyr Thr Cys Glu
1               5                   10

<210> SEQ ID NO 293
<211> LENGTH: 11
<212> TYPE: PRT

```
<213> ORGANISM: Artificial Sequence
<220> FEATURE:
<223> OTHER INFORMATION: Synthetic construct

<400> SEQUENCE: 293

Thr Arg Glu Asp Thr Gly Thr Tyr Thr Cys Glu
1               5                   10

<210> SEQ ID NO 294
<211> LENGTH: 12
<212> TYPE: PRT
<213> ORGANISM: Artificial Sequence
<220> FEATURE:
<223> OTHER INFORMATION: Synthetic construct

<400> SEQUENCE: 294

Val Thr Arg Glu Asp Thr Gly Thr Tyr Thr Cys Glu
1               5                   10

<210> SEQ ID NO 295
<211> LENGTH: 13
<212> TYPE: PRT
<213> ORGANISM: Artificial Sequence
<220> FEATURE:
<223> OTHER INFORMATION: Synthetic construct

<400> SEQUENCE: 295

Ser Val Thr Arg Glu Asp Thr Gly Thr Tyr Thr Cys Glu
1               5                   10

<210> SEQ ID NO 296
<211> LENGTH: 14
<212> TYPE: PRT
<213> ORGANISM: Artificial Sequence
<220> FEATURE:
<223> OTHER INFORMATION: Synthetic construct

<400> SEQUENCE: 296

Lys Ser Val Thr Arg Glu Asp Thr Gly Thr Tyr Thr Cys Glu
1               5                   10

<210> SEQ ID NO 297
<211> LENGTH: 10
<212> TYPE: PRT
<213> ORGANISM: Artificial Sequence
<220> FEATURE:
<223> OTHER INFORMATION: Synthetic construct

<400> SEQUENCE: 297

Glu Asp Thr Gly Thr Tyr Thr Cys Glu Val
1               5                   10

<210> SEQ ID NO 298
<211> LENGTH: 11
<212> TYPE: PRT
<213> ORGANISM: Artificial Sequence
<220> FEATURE:
<223> OTHER INFORMATION: Synthetic construct

<400> SEQUENCE: 298

Glu Asp Thr Gly Thr Tyr Thr Cys Glu Val Ser
1               5                   10

<210> SEQ ID NO 299
<211> LENGTH: 12
<212> TYPE: PRT
<213> ORGANISM: Artificial Sequence
```

```
<220> FEATURE:
<223> OTHER INFORMATION: Synthetic construct

<400> SEQUENCE: 299

Glu Asp Thr Gly Thr Tyr Thr Cys Glu Val Ser Glu
1               5                   10

<210> SEQ ID NO 300
<211> LENGTH: 13
<212> TYPE: PRT
<213> ORGANISM: Artificial Sequence
<220> FEATURE:
<223> OTHER INFORMATION: Synthetic construct

<400> SEQUENCE: 300

Glu Asp Thr Gly Thr Tyr Thr Cys Glu Val Ser Glu Glu
1               5                   10

<210> SEQ ID NO 301
<211> LENGTH: 14
<212> TYPE: PRT
<213> ORGANISM: Artificial Sequence
<220> FEATURE:
<223> OTHER INFORMATION: Synthetic construct

<400> SEQUENCE: 301

Glu Asp Thr Gly Thr Tyr Thr Cys Glu Val Ser Glu Glu Gly
1               5                   10

<210> SEQ ID NO 302
<211> LENGTH: 9
<212> TYPE: PRT
<213> ORGANISM: Artificial Sequence
<220> FEATURE:
<223> OTHER INFORMATION: Synthetic construct

<400> SEQUENCE: 302

Glu Asp Thr Gly Thr Tyr Arg Cys Met
1               5

<210> SEQ ID NO 303
<211> LENGTH: 11
<212> TYPE: PRT
<213> ORGANISM: Artificial Sequence
<220> FEATURE:
<223> OTHER INFORMATION: Synthetic construct

<400> SEQUENCE: 303

Arg Glu Asp Thr Gly Thr Tyr Thr Cys Met Val
1               5                   10

<210> SEQ ID NO 304
<211> LENGTH: 13
<212> TYPE: PRT
<213> ORGANISM: Artificial Sequence
<220> FEATURE:
<223> OTHER INFORMATION: Synthetic construct

<400> SEQUENCE: 304

Thr Arg Glu Asp Thr Gly Thr Tyr Thr Cys Met Val Ser
1               5                   10

<210> SEQ ID NO 305
<211> LENGTH: 15
<212> TYPE: PRT
<213> ORGANISM: Artificial Sequence
<220> FEATURE:
```

<223> OTHER INFORMATION: Synthetic construct

<400> SEQUENCE: 305

Val Thr Arg Glu Asp Thr Gly Thr Tyr Thr Cys Met Val Ser Glu
1               5                   10                  15

<210> SEQ ID NO 306
<211> LENGTH: 17
<212> TYPE: PRT
<213> ORGANISM: Artificial Sequence
<220> FEATURE:
<223> OTHER INFORMATION: Synthetic construct

<400> SEQUENCE: 306

Ser Val Thr Arg Glu Asp Thr Gly Thr Tyr Thr Cys Met Val Ser Glu
1               5                   10                  15

Glu

<210> SEQ ID NO 307
<211> LENGTH: 19
<212> TYPE: PRT
<213> ORGANISM: Artificial Sequence
<220> FEATURE:
<223> OTHER INFORMATION: Synthetic construct

<400> SEQUENCE: 307

Lys Ser Val Thr Arg Glu Asp Thr Gly Thr Tyr Thr Cys Met Val Ser
1               5                   10                  15

Glu Glu Gly

<210> SEQ ID NO 308
<211> LENGTH: 10
<212> TYPE: PRT
<213> ORGANISM: Artificial Sequence
<220> FEATURE:
<223> OTHER INFORMATION: Synthetic construct

<400> SEQUENCE: 308

Arg Glu Asp Thr Gly Thr Tyr Thr Cys Met
1               5                   10

<210> SEQ ID NO 309
<211> LENGTH: 11
<212> TYPE: PRT
<213> ORGANISM: Artificial Sequence
<220> FEATURE:
<223> OTHER INFORMATION: Synthetic construct

<400> SEQUENCE: 309

Thr Arg Glu Asp Thr Gly Thr Tyr Thr Cys Met
1               5                   10

<210> SEQ ID NO 310
<211> LENGTH: 12
<212> TYPE: PRT
<213> ORGANISM: Artificial Sequence
<220> FEATURE:
<223> OTHER INFORMATION: Synthetic construct

<400> SEQUENCE: 310

Val Thr Arg Glu Asp Thr Gly Thr Tyr Thr Cys Met
1               5                   10

<210> SEQ ID NO 311
<211> LENGTH: 13

<212> TYPE: PRT
<213> ORGANISM: Artificial Sequence
<220> FEATURE:
<223> OTHER INFORMATION: Synthetic construct

<400> SEQUENCE: 311

Ser Val Thr Arg Glu Asp Thr Gly Thr Tyr Thr Cys Met
1               5                   10

<210> SEQ ID NO 312
<211> LENGTH: 14
<212> TYPE: PRT
<213> ORGANISM: Artificial Sequence
<220> FEATURE:
<223> OTHER INFORMATION: Synthetic construct

<400> SEQUENCE: 312

Lys Ser Val Thr Arg Glu Asp Thr Gly Thr Tyr Thr Cys Met
1               5                   10

<210> SEQ ID NO 313
<211> LENGTH: 10
<212> TYPE: PRT
<213> ORGANISM: Artificial Sequence
<220> FEATURE:
<223> OTHER INFORMATION: Synthetic construct

<400> SEQUENCE: 313

Glu Asp Thr Gly Thr Tyr Thr Cys Met Val
1               5                   10

<210> SEQ ID NO 314
<211> LENGTH: 11
<212> TYPE: PRT
<213> ORGANISM: Artificial Sequence
<220> FEATURE:
<223> OTHER INFORMATION: Synthetic construct

<400> SEQUENCE: 314

Glu Asp Thr Gly Thr Tyr Thr Cys Met Val Ser
1               5                   10

<210> SEQ ID NO 315
<211> LENGTH: 12
<212> TYPE: PRT
<213> ORGANISM: Artificial Sequence
<220> FEATURE:
<223> OTHER INFORMATION: Synthetic construct

<400> SEQUENCE: 315

Glu Asp Thr Gly Thr Tyr Thr Cys Met Val Ser Glu
1               5                   10

<210> SEQ ID NO 316
<211> LENGTH: 13
<212> TYPE: PRT
<213> ORGANISM: Artificial Sequence
<220> FEATURE:
<223> OTHER INFORMATION: Synthetic construct

<400> SEQUENCE: 316

Glu Asp Thr Gly Thr Tyr Thr Cys Met Val Ser Glu Glu
1               5                   10

<210> SEQ ID NO 317
<211> LENGTH: 13
<212> TYPE: PRT

```
<213> ORGANISM: Artificial Sequence
<220> FEATURE:
<223> OTHER INFORMATION: Synthetic construct

<400> SEQUENCE: 317

Glu Asp Thr Gly Thr Tyr Thr Cys Met Val Ser Glu Glu
1               5                   10

<210> SEQ ID NO 318
<211> LENGTH: 9
<212> TYPE: PRT
<213> ORGANISM: Artificial Sequence
<220> FEATURE:
<223> OTHER INFORMATION: Synthetic construct

<400> SEQUENCE: 318

Glu Asp Thr Gly Thr Tyr Arg Cys Glu
1               5

<210> SEQ ID NO 319
<211> LENGTH: 11
<212> TYPE: PRT
<213> ORGANISM: Artificial Sequence
<220> FEATURE:
<223> OTHER INFORMATION: Synthetic construct

<400> SEQUENCE: 319

Arg Glu Asp Thr Gly Thr Tyr Thr Cys Met Val
1               5                   10

<210> SEQ ID NO 320
<211> LENGTH: 13
<212> TYPE: PRT
<213> ORGANISM: Artificial Sequence
<220> FEATURE:
<223> OTHER INFORMATION: Synthetic construct

<400> SEQUENCE: 320

Thr Arg Glu Asp Thr Gly Thr Tyr Thr Cys Met Val Ser
1               5                   10

<210> SEQ ID NO 321
<211> LENGTH: 15
<212> TYPE: PRT
<213> ORGANISM: Artificial Sequence
<220> FEATURE:
<223> OTHER INFORMATION: Synthetic construct

<400> SEQUENCE: 321

Val Thr Arg Glu Asp Thr Gly Thr Tyr Thr Cys Met Val Ser Glu
1               5                   10                  15

<210> SEQ ID NO 322
<211> LENGTH: 17
<212> TYPE: PRT
<213> ORGANISM: Artificial Sequence
<220> FEATURE:
<223> OTHER INFORMATION: Synthetic construct

<400> SEQUENCE: 322

Ser Val Thr Arg Glu Asp Thr Gly Thr Tyr Thr Cys Met Val Ser Glu
1               5                   10                  15
Glu

<210> SEQ ID NO 323
<211> LENGTH: 19
```

```
<212> TYPE: PRT
<213> ORGANISM: Artificial Sequence
<220> FEATURE:
<223> OTHER INFORMATION: Synthetic construct

<400> SEQUENCE: 323

Lys Ser Val Thr Arg Glu Asp Thr Gly Thr Tyr Thr Cys Met Val Ser
1               5                   10                  15
Glu Glu Gly

<210> SEQ ID NO 324
<211> LENGTH: 10
<212> TYPE: PRT
<213> ORGANISM: Artificial Sequence
<220> FEATURE:
<223> OTHER INFORMATION: Synthetic construct

<400> SEQUENCE: 324

Arg Glu Asp Thr Gly Thr Tyr Thr Cys Met
1               5                   10

<210> SEQ ID NO 325
<211> LENGTH: 11
<212> TYPE: PRT
<213> ORGANISM: Artificial Sequence
<220> FEATURE:
<223> OTHER INFORMATION: Synthetic construct

<400> SEQUENCE: 325

Thr Arg Glu Asp Thr Gly Thr Tyr Thr Cys Met
1               5                   10

<210> SEQ ID NO 326
<211> LENGTH: 12
<212> TYPE: PRT
<213> ORGANISM: Artificial Sequence
<220> FEATURE:
<223> OTHER INFORMATION: Synthetic construct

<400> SEQUENCE: 326

Val Thr Arg Glu Asp Thr Gly Thr Tyr Thr Cys Met
1               5                   10

<210> SEQ ID NO 327
<211> LENGTH: 13
<212> TYPE: PRT
<213> ORGANISM: Artificial Sequence
<220> FEATURE:
<223> OTHER INFORMATION: Synthetic construct

<400> SEQUENCE: 327

Ser Val Thr Arg Glu Asp Thr Gly Thr Tyr Thr Cys Met
1               5                   10

<210> SEQ ID NO 328
<211> LENGTH: 14
<212> TYPE: PRT
<213> ORGANISM: Artificial Sequence
<220> FEATURE:
<223> OTHER INFORMATION: Synthetic construct

<400> SEQUENCE: 328

Lys Ser Val Thr Arg Glu Asp Thr Gly Thr Tyr Thr Cys Met
1               5                   10

<210> SEQ ID NO 329
```

<211> LENGTH: 10
<212> TYPE: PRT
<213> ORGANISM: Artificial Sequence
<220> FEATURE:
<223> OTHER INFORMATION: Synthetic construct

<400> SEQUENCE: 329

Glu Asp Thr Gly Thr Tyr Thr Cys Met Val
1               5                   10

<210> SEQ ID NO 330
<211> LENGTH: 11
<212> TYPE: PRT
<213> ORGANISM: Artificial Sequence
<220> FEATURE:
<223> OTHER INFORMATION: Synthetic construct

<400> SEQUENCE: 330

Glu Asp Thr Gly Thr Tyr Thr Cys Met Val Ser
1               5                   10

<210> SEQ ID NO 331
<211> LENGTH: 12
<212> TYPE: PRT
<213> ORGANISM: Artificial Sequence
<220> FEATURE:
<223> OTHER INFORMATION: Synthetic construct

<400> SEQUENCE: 331

Glu Asp Thr Gly Thr Tyr Thr Cys Met Val Ser Glu
1               5                   10

<210> SEQ ID NO 332
<211> LENGTH: 13
<212> TYPE: PRT
<213> ORGANISM: Artificial Sequence
<220> FEATURE:
<223> OTHER INFORMATION: Synthetic construct

<400> SEQUENCE: 332

Glu Asp Thr Gly Thr Tyr Thr Cys Met Val Ser Glu Glu
1               5                   10

<210> SEQ ID NO 333
<211> LENGTH: 14
<212> TYPE: PRT
<213> ORGANISM: Artificial Sequence
<220> FEATURE:
<223> OTHER INFORMATION: Synthetic construct

<400> SEQUENCE: 333

Glu Asp Thr Gly Thr Tyr Thr Cys Met Val Ser Glu Glu Gly
1               5                   10

<210> SEQ ID NO 334
<211> LENGTH: 9
<212> TYPE: PRT
<213> ORGANISM: Artificial Sequence
<220> FEATURE:
<223> OTHER INFORMATION: Synthetic construct

<400> SEQUENCE: 334

Glu Asp Ser Gly Thr Tyr Thr Cys Met
1               5

<210> SEQ ID NO 335
<211> LENGTH: 11

<212> TYPE: PRT
<213> ORGANISM: Artificial Sequence
<220> FEATURE:
<223> OTHER INFORMATION: Synthetic construct

<400> SEQUENCE: 335

Arg Glu Asp Thr Gly Thr Tyr Thr Cys Met Val
1               5                   10

<210> SEQ ID NO 336
<211> LENGTH: 13
<212> TYPE: PRT
<213> ORGANISM: Artificial Sequence
<220> FEATURE:
<223> OTHER INFORMATION: Synthetic construct

<400> SEQUENCE: 336

Thr Arg Glu Asp Thr Gly Thr Tyr Thr Cys Met Val Ser
1               5                   10

<210> SEQ ID NO 337
<211> LENGTH: 15
<212> TYPE: PRT
<213> ORGANISM: Artificial Sequence
<220> FEATURE:
<223> OTHER INFORMATION: Synthetic construct

<400> SEQUENCE: 337

Val Thr Arg Glu Asp Thr Gly Thr Tyr Thr Cys Met Val Ser Glu
1               5                   10                  15

<210> SEQ ID NO 338
<211> LENGTH: 17
<212> TYPE: PRT
<213> ORGANISM: Artificial Sequence
<220> FEATURE:
<223> OTHER INFORMATION: Synthetic construct

<400> SEQUENCE: 338

Ser Val Thr Arg Glu Asp Thr Gly Thr Tyr Thr Cys Met Val Ser Glu
1               5                   10                  15

Glu

<210> SEQ ID NO 339
<211> LENGTH: 19
<212> TYPE: PRT
<213> ORGANISM: Artificial Sequence
<220> FEATURE:
<223> OTHER INFORMATION: Synthetic construct

<400> SEQUENCE: 339

Lys Ser Val Thr Arg Glu Asp Thr Gly Thr Tyr Thr Cys Met Val Ser
1               5                   10                  15

Glu Glu Gly

<210> SEQ ID NO 340
<211> LENGTH: 10
<212> TYPE: PRT
<213> ORGANISM: Artificial Sequence
<220> FEATURE:
<223> OTHER INFORMATION: Synthetic construct

<400> SEQUENCE: 340

Arg Glu Asp Thr Gly Thr Tyr Thr Cys Met
1               5                   10

```
<210> SEQ ID NO 341
<211> LENGTH: 11
<212> TYPE: PRT
<213> ORGANISM: Artificial Sequence
<220> FEATURE:
<223> OTHER INFORMATION: Synthetic construct

<400> SEQUENCE: 341

Thr Arg Glu Asp Thr Gly Thr Tyr Thr Cys Met
1               5                   10

<210> SEQ ID NO 342
<211> LENGTH: 12
<212> TYPE: PRT
<213> ORGANISM: Artificial Sequence
<220> FEATURE:
<223> OTHER INFORMATION: Synthetic construct

<400> SEQUENCE: 342

Val Thr Arg Glu Asp Thr Gly Thr Tyr Thr Cys Met
1               5                   10

<210> SEQ ID NO 343
<211> LENGTH: 13
<212> TYPE: PRT
<213> ORGANISM: Artificial Sequence
<220> FEATURE:
<223> OTHER INFORMATION: Synthetic construct

<400> SEQUENCE: 343

Ser Val Thr Arg Glu Asp Thr Gly Thr Tyr Thr Cys Met
1               5                   10

<210> SEQ ID NO 344
<211> LENGTH: 14
<212> TYPE: PRT
<213> ORGANISM: Artificial Sequence
<220> FEATURE:
<223> OTHER INFORMATION: Synthetic construct

<400> SEQUENCE: 344

Lys Ser Val Thr Arg Glu Asp Thr Gly Thr Tyr Thr Cys Met
1               5                   10

<210> SEQ ID NO 345
<211> LENGTH: 10
<212> TYPE: PRT
<213> ORGANISM: Artificial Sequence
<220> FEATURE:
<223> OTHER INFORMATION: Synthetic construct

<400> SEQUENCE: 345

Glu Asp Thr Gly Thr Tyr Thr Cys Met Val
1               5                   10

<210> SEQ ID NO 346
<211> LENGTH: 11
<212> TYPE: PRT
<213> ORGANISM: Artificial Sequence
<220> FEATURE:
<223> OTHER INFORMATION: Synthetic construct

<400> SEQUENCE: 346

Glu Asp Thr Gly Thr Tyr Thr Cys Met Val Ser
1               5                   10
```

```
<210> SEQ ID NO 347
<211> LENGTH: 12
<212> TYPE: PRT
<213> ORGANISM: Artificial Sequence
<220> FEATURE:
<223> OTHER INFORMATION: Synthetic construct

<400> SEQUENCE: 347

Glu Asp Thr Gly Thr Tyr Thr Cys Met Val Ser Glu
1               5                   10

<210> SEQ ID NO 348
<211> LENGTH: 13
<212> TYPE: PRT
<213> ORGANISM: Artificial Sequence
<220> FEATURE:
<223> OTHER INFORMATION: Synthetic construct

<400> SEQUENCE: 348

Glu Asp Thr Gly Thr Tyr Thr Cys Met Val Ser Glu Glu
1               5                   10

<210> SEQ ID NO 349
<211> LENGTH: 14
<212> TYPE: PRT
<213> ORGANISM: Artificial Sequence
<220> FEATURE:
<223> OTHER INFORMATION: Synthetic construct

<400> SEQUENCE: 349

Glu Asp Thr Gly Thr Tyr Thr Cys Met Val Ser Glu Glu Gly
1               5                   10

<210> SEQ ID NO 350
<211> LENGTH: 9
<212> TYPE: PRT
<213> ORGANISM: Artificial Sequence
<220> FEATURE:
<223> OTHER INFORMATION: Synthetic construct

<400> SEQUENCE: 350

Glu Asp Ser Gly Thr Tyr Thr Cys Glu
1               5

<210> SEQ ID NO 351
<211> LENGTH: 11
<212> TYPE: PRT
<213> ORGANISM: Artificial Sequence
<220> FEATURE:
<223> OTHER INFORMATION: Synthetic construct

<400> SEQUENCE: 351

Arg Glu Asp Ser Gly Thr Tyr Thr Cys Glu Val
1               5                   10

<210> SEQ ID NO 352
<211> LENGTH: 13
<212> TYPE: PRT
<213> ORGANISM: Artificial Sequence
<220> FEATURE:
<223> OTHER INFORMATION: Synthetic construct

<400> SEQUENCE: 352

Thr Arg Glu Asp Ser Gly Thr Tyr Thr Cys Glu Val Ser
1               5                   10

<210> SEQ ID NO 353
```

```
<211> LENGTH: 15
<212> TYPE: PRT
<213> ORGANISM: Artificial Sequence
<220> FEATURE:
<223> OTHER INFORMATION: Synthetic construct

<400> SEQUENCE: 353

Val Thr Arg Glu Asp Ser Gly Thr Tyr Thr Cys Glu Val Ser Glu
1               5                   10                  15

<210> SEQ ID NO 354
<211> LENGTH: 17
<212> TYPE: PRT
<213> ORGANISM: Artificial Sequence
<220> FEATURE:
<223> OTHER INFORMATION: Synthetic construct

<400> SEQUENCE: 354

Ser Val Thr Arg Glu Asp Ser Gly Thr Tyr Thr Cys Glu Val Ser Glu
1               5                   10                  15

Glu

<210> SEQ ID NO 355
<211> LENGTH: 19
<212> TYPE: PRT
<213> ORGANISM: Artificial Sequence
<220> FEATURE:
<223> OTHER INFORMATION: Synthetic construct

<400> SEQUENCE: 355

Lys Ser Val Thr Arg Glu Asp Ser Gly Thr Tyr Thr Cys Glu Val Ser
1               5                   10                  15

Glu Glu Gly

<210> SEQ ID NO 356
<211> LENGTH: 10
<212> TYPE: PRT
<213> ORGANISM: Artificial Sequence
<220> FEATURE:
<223> OTHER INFORMATION: Synthetic construct

<400> SEQUENCE: 356

Arg Glu Asp Ser Gly Thr Tyr Thr Cys Glu
1               5                   10

<210> SEQ ID NO 357
<211> LENGTH: 11
<212> TYPE: PRT
<213> ORGANISM: Artificial Sequence
<220> FEATURE:
<223> OTHER INFORMATION: Synthetic construct

<400> SEQUENCE: 357

Thr Arg Glu Asp Ser Gly Thr Tyr Thr Cys Glu
1               5                   10

<210> SEQ ID NO 358
<211> LENGTH: 12
<212> TYPE: PRT
<213> ORGANISM: Artificial Sequence
<220> FEATURE:
<223> OTHER INFORMATION: Synthetic construct

<400> SEQUENCE: 358

Val Thr Arg Glu Asp Ser Gly Thr Tyr Thr Cys Glu
1               5                   10
```

```
<210> SEQ ID NO 359
<211> LENGTH: 13
<212> TYPE: PRT
<213> ORGANISM: Artificial Sequence
<220> FEATURE:
<223> OTHER INFORMATION: Synthetic construct

<400> SEQUENCE: 359

Ser Val Thr Arg Glu Asp Ser Gly Thr Tyr Thr Cys Glu
1               5                   10

<210> SEQ ID NO 360
<211> LENGTH: 14
<212> TYPE: PRT
<213> ORGANISM: Artificial Sequence
<220> FEATURE:
<223> OTHER INFORMATION: Synthetic construct

<400> SEQUENCE: 360

Lys Ser Val Thr Arg Glu Asp Ser Gly Thr Tyr Thr Cys Glu
1               5                   10

<210> SEQ ID NO 361
<211> LENGTH: 10
<212> TYPE: PRT
<213> ORGANISM: Artificial Sequence
<220> FEATURE:
<223> OTHER INFORMATION: Synthetic construct

<400> SEQUENCE: 361

Glu Asp Ser Gly Thr Tyr Thr Cys Glu Val
1               5                   10

<210> SEQ ID NO 362
<211> LENGTH: 11
<212> TYPE: PRT
<213> ORGANISM: Artificial Sequence
<220> FEATURE:
<223> OTHER INFORMATION: Synthetic construct

<400> SEQUENCE: 362

Glu Asp Ser Gly Thr Tyr Thr Cys Glu Val Ser
1               5                   10

<210> SEQ ID NO 363
<211> LENGTH: 12
<212> TYPE: PRT
<213> ORGANISM: Artificial Sequence
<220> FEATURE:
<223> OTHER INFORMATION: Synthetic construct

<400> SEQUENCE: 363

Glu Asp Ser Gly Thr Tyr Thr Cys Glu Val Ser Glu
1               5                   10

<210> SEQ ID NO 364
<211> LENGTH: 13
<212> TYPE: PRT
<213> ORGANISM: Artificial Sequence
<220> FEATURE:
<223> OTHER INFORMATION: Synthetic construct

<400> SEQUENCE: 364

Glu Asp Ser Gly Thr Tyr Thr Cys Glu Val Ser Glu Glu
1               5                   10
```

```
<210> SEQ ID NO 365
<211> LENGTH: 14
<212> TYPE: PRT
<213> ORGANISM: Artificial Sequence
<220> FEATURE:
<223> OTHER INFORMATION: Synthetic construct

<400> SEQUENCE: 365

Glu Asp Ser Gly Thr Tyr Thr Cys Glu Val Ser Glu Glu Gly
1               5                   10

<210> SEQ ID NO 366
<211> LENGTH: 9
<212> TYPE: PRT
<213> ORGANISM: Artificial Sequence
<220> FEATURE:
<223> OTHER INFORMATION: Synthetic construct

<400> SEQUENCE: 366

Glu Asp Ser Gly Thr Tyr Arg Cys Met
1               5

<210> SEQ ID NO 367
<211> LENGTH: 11
<212> TYPE: PRT
<213> ORGANISM: Artificial Sequence
<220> FEATURE:
<223> OTHER INFORMATION: Synthetic construct

<400> SEQUENCE: 367

Arg Glu Asp Ser Gly Thr Tyr Arg Cys Met Val
1               5                   10

<210> SEQ ID NO 368
<211> LENGTH: 13
<212> TYPE: PRT
<213> ORGANISM: Artificial Sequence
<220> FEATURE:
<223> OTHER INFORMATION: Synthetic construct

<400> SEQUENCE: 368

Thr Arg Glu Asp Ser Gly Thr Tyr Arg Cys Met Val Ser
1               5                   10

<210> SEQ ID NO 369
<211> LENGTH: 15
<212> TYPE: PRT
<213> ORGANISM: Artificial Sequence
<220> FEATURE:
<223> OTHER INFORMATION: Synthetic construct

<400> SEQUENCE: 369

Val Thr Arg Glu Asp Ser Gly Thr Tyr Arg Cys Met Val Ser Glu
1               5                   10                  15

<210> SEQ ID NO 370
<211> LENGTH: 17
<212> TYPE: PRT
<213> ORGANISM: Artificial Sequence
<220> FEATURE:
<223> OTHER INFORMATION: Synthetic construct

<400> SEQUENCE: 370

Ser Val Thr Arg Glu Asp Ser Gly Thr Tyr Arg Cys Met Val Ser Glu
1               5                   10                  15
Glu
```

<210> SEQ ID NO 371
<211> LENGTH: 19
<212> TYPE: PRT
<213> ORGANISM: Artificial Sequence
<220> FEATURE:
<223> OTHER INFORMATION: Synthetic construct

<400> SEQUENCE: 371

Lys Ser Val Thr Arg Glu Asp Ser Gly Thr Tyr Arg Cys Met Val Ser
1               5                  10                  15
Glu Glu Gly

<210> SEQ ID NO 372
<211> LENGTH: 10
<212> TYPE: PRT
<213> ORGANISM: Artificial Sequence
<220> FEATURE:
<223> OTHER INFORMATION: Synthetic construct

<400> SEQUENCE: 372

Arg Glu Asp Ser Gly Thr Tyr Arg Cys Met
1               5                  10

<210> SEQ ID NO 373
<211> LENGTH: 11
<212> TYPE: PRT
<213> ORGANISM: Artificial Sequence
<220> FEATURE:
<223> OTHER INFORMATION: Synthetic construct

<400> SEQUENCE: 373

Thr Arg Glu Asp Ser Gly Thr Tyr Arg Cys Met
1               5                  10

<210> SEQ ID NO 374
<211> LENGTH: 12
<212> TYPE: PRT
<213> ORGANISM: Artificial Sequence
<220> FEATURE:
<223> OTHER INFORMATION: Synthetic construct

<400> SEQUENCE: 374

Val Thr Arg Glu Asp Ser Gly Thr Tyr Arg Cys Met
1               5                  10

<210> SEQ ID NO 375
<211> LENGTH: 13
<212> TYPE: PRT
<213> ORGANISM: Artificial Sequence
<220> FEATURE:
<223> OTHER INFORMATION: Synthetic construct

<400> SEQUENCE: 375

Ser Val Thr Arg Glu Asp Ser Gly Thr Tyr Arg Cys Met
1               5                  10

<210> SEQ ID NO 376
<211> LENGTH: 13
<212> TYPE: PRT
<213> ORGANISM: Artificial Sequence
<220> FEATURE:
<223> OTHER INFORMATION: Synthetic construct

<400> SEQUENCE: 376

Ser Val Thr Arg Glu Asp Ser Gly Thr Tyr Arg Cys Met

<210> SEQ ID NO 377
<211> LENGTH: 10
<212> TYPE: PRT
<213> ORGANISM: Artificial Sequence
<220> FEATURE:
<223> OTHER INFORMATION: Synthetic construct

<400> SEQUENCE: 377

Glu Asp Ser Gly Thr Tyr Arg Cys Met Val
1               5                   10

<210> SEQ ID NO 378
<211> LENGTH: 11
<212> TYPE: PRT
<213> ORGANISM: Artificial Sequence
<220> FEATURE:
<223> OTHER INFORMATION: Synthetic construct

<400> SEQUENCE: 378

Glu Asp Ser Gly Thr Tyr Arg Cys Met Val Ser
1               5                   10

<210> SEQ ID NO 379
<211> LENGTH: 12
<212> TYPE: PRT
<213> ORGANISM: Artificial Sequence
<220> FEATURE:
<223> OTHER INFORMATION: Synthetic construct

<400> SEQUENCE: 379

Glu Asp Ser Gly Thr Tyr Arg Cys Met Val Ser Glu
1               5                   10

<210> SEQ ID NO 380
<211> LENGTH: 13
<212> TYPE: PRT
<213> ORGANISM: Artificial Sequence
<220> FEATURE:
<223> OTHER INFORMATION: Synthetic construct

<400> SEQUENCE: 380

Glu Asp Ser Gly Thr Tyr Arg Cys Met Val Ser Glu Glu
1               5                   10

<210> SEQ ID NO 381
<211> LENGTH: 14
<212> TYPE: PRT
<213> ORGANISM: Artificial Sequence
<220> FEATURE:
<223> OTHER INFORMATION: Synthetic construct

<400> SEQUENCE: 381

Glu Asp Ser Gly Thr Tyr Arg Cys Met Val Ser Glu Glu Gly
1               5                   10

<210> SEQ ID NO 382
<211> LENGTH: 9
<212> TYPE: PRT
<213> ORGANISM: Artificial Sequence
<220> FEATURE:
<223> OTHER INFORMATION: Synthetic construct

<400> SEQUENCE: 382

Glu Asp Ser Gly Thr Tyr Arg Cys Glu
1               5

```
<210> SEQ ID NO 383
<211> LENGTH: 11
<212> TYPE: PRT
<213> ORGANISM: Artificial Sequence
<220> FEATURE:
<223> OTHER INFORMATION: Synthetic construct

<400> SEQUENCE: 383

Arg Glu Asp Ser Gly Thr Tyr Arg Cys Glu Val
1               5                   10

<210> SEQ ID NO 384
<211> LENGTH: 13
<212> TYPE: PRT
<213> ORGANISM: Artificial Sequence
<220> FEATURE:
<223> OTHER INFORMATION: Synthetic construct

<400> SEQUENCE: 384

Thr Arg Glu Asp Ser Gly Thr Tyr Arg Cys Glu Val Ser
1               5                   10

<210> SEQ ID NO 385
<211> LENGTH: 15
<212> TYPE: PRT
<213> ORGANISM: Artificial Sequence
<220> FEATURE:
<223> OTHER INFORMATION: Synthetic construct

<400> SEQUENCE: 385

Val Thr Arg Glu Asp Ser Gly Thr Tyr Arg Cys Glu Val Ser Glu
1               5                   10                  15

<210> SEQ ID NO 386
<211> LENGTH: 17
<212> TYPE: PRT
<213> ORGANISM: Artificial Sequence
<220> FEATURE:
<223> OTHER INFORMATION: Synthetic construct

<400> SEQUENCE: 386

Ser Val Thr Arg Glu Asp Ser Gly Thr Tyr Arg Cys Glu Val Ser Glu
1               5                   10                  15

Glu

<210> SEQ ID NO 387
<211> LENGTH: 19
<212> TYPE: PRT
<213> ORGANISM: Artificial Sequence
<220> FEATURE:
<223> OTHER INFORMATION: Synthetic construct

<400> SEQUENCE: 387

Lys Ser Val Thr Arg Glu Asp Ser Gly Thr Tyr Arg Cys Glu Val Ser
1               5                   10                  15

Glu Glu Gly

<210> SEQ ID NO 388
<211> LENGTH: 10
<212> TYPE: PRT
<213> ORGANISM: Artificial Sequence
<220> FEATURE:
<223> OTHER INFORMATION: Synthetic construct

<400> SEQUENCE: 388
```

```
Arg Glu Asp Ser Gly Thr Tyr Arg Cys Glu
1               5                   10
```

<210> SEQ ID NO 389
<211> LENGTH: 11
<212> TYPE: PRT
<213> ORGANISM: Artificial Sequence
<220> FEATURE:
<223> OTHER INFORMATION: Synthetic construct

<400> SEQUENCE: 389

```
Thr Arg Glu Asp Ser Gly Thr Tyr Arg Cys Glu
1               5                   10
```

<210> SEQ ID NO 390
<211> LENGTH: 12
<212> TYPE: PRT
<213> ORGANISM: Artificial Sequence
<220> FEATURE:
<223> OTHER INFORMATION: Synthetic construct

<400> SEQUENCE: 390

```
Val Thr Arg Glu Asp Ser Gly Thr Tyr Arg Cys Glu
1               5                   10
```

<210> SEQ ID NO 391
<211> LENGTH: 13
<212> TYPE: PRT
<213> ORGANISM: Artificial Sequence
<220> FEATURE:
<223> OTHER INFORMATION: Synthetic construct

<400> SEQUENCE: 391

```
Ser Val Thr Arg Glu Asp Ser Gly Thr Tyr Arg Cys Glu
1               5                   10
```

<210> SEQ ID NO 392
<211> LENGTH: 14
<212> TYPE: PRT
<213> ORGANISM: Artificial Sequence
<220> FEATURE:
<223> OTHER INFORMATION: Synthetic construct

<400> SEQUENCE: 392

```
Lys Ser Val Thr Arg Glu Asp Ser Gly Thr Tyr Arg Cys Glu
1               5                   10
```

<210> SEQ ID NO 393
<211> LENGTH: 10
<212> TYPE: PRT
<213> ORGANISM: Artificial Sequence
<220> FEATURE:
<223> OTHER INFORMATION: Synthetic construct

<400> SEQUENCE: 393

```
Glu Asp Ser Gly Thr Tyr Arg Cys Glu Val
1               5                   10
```

<210> SEQ ID NO 394
<211> LENGTH: 11
<212> TYPE: PRT
<213> ORGANISM: Artificial Sequence
<220> FEATURE:
<223> OTHER INFORMATION: Synthetic construct

<400> SEQUENCE: 394

Glu Asp Ser Gly Thr Tyr Arg Cys Glu Val Ser
1               5                   10

<210> SEQ ID NO 395
<211> LENGTH: 12
<212> TYPE: PRT
<213> ORGANISM: Artificial Sequence
<220> FEATURE:
<223> OTHER INFORMATION: Synthetic construct

<400> SEQUENCE: 395

Glu Asp Ser Gly Thr Tyr Arg Cys Glu Val Ser Glu
1               5                   10

<210> SEQ ID NO 396
<211> LENGTH: 13
<212> TYPE: PRT
<213> ORGANISM: Artificial Sequence
<220> FEATURE:
<223> OTHER INFORMATION: Synthetic construct

<400> SEQUENCE: 396

Glu Asp Ser Gly Thr Tyr Arg Cys Glu Val Ser Glu Glu
1               5                   10

<210> SEQ ID NO 397
<211> LENGTH: 14
<212> TYPE: PRT
<213> ORGANISM: Artificial Sequence
<220> FEATURE:
<223> OTHER INFORMATION: Synthetic construct

<400> SEQUENCE: 397

Glu Asp Ser Gly Thr Tyr Arg Cys Glu Val Ser Glu Glu Gly
1               5                   10

<210> SEQ ID NO 398
<211> LENGTH: 10
<212> TYPE: PRT
<213> ORGANISM: Artificial Sequence
<220> FEATURE:
<223> OTHER INFORMATION: Synthetic construct

<400> SEQUENCE: 398

Ala Val Asn Leu Lys Ser Ser Asn Arg Thr
1               5                   10

<210> SEQ ID NO 399
<211> LENGTH: 10
<212> TYPE: PRT
<213> ORGANISM: Artificial Sequence
<220> FEATURE:
<223> OTHER INFORMATION: Synthetic construct

<400> SEQUENCE: 399

Pro Val Val Gln Glu Phe Glu Ser Val Glu
1               5                   10

<210> SEQ ID NO 400
<211> LENGTH: 10
<212> TYPE: PRT
<213> ORGANISM: Artificial Sequence
<220> FEATURE:
<223> OTHER INFORMATION: Synthetic construct

<400> SEQUENCE: 400

Leu Ser Cys Ile Ile Thr Asp Ser Gln Thr

<210> SEQ ID NO 401
<211> LENGTH: 10
<212> TYPE: PRT
<213> ORGANISM: Artificial Sequence
<220> FEATURE:
<223> OTHER INFORMATION: Synthetic construct

<400> SEQUENCE: 401

Ser Asp Pro Arg Ile Glu Trp Lys Lys Ile
1               5                   10

<210> SEQ ID NO 402
<211> LENGTH: 10
<212> TYPE: PRT
<213> ORGANISM: Artificial Sequence
<220> FEATURE:
<223> OTHER INFORMATION: Synthetic construct

<400> SEQUENCE: 402

Gln Asp Glu Gln Thr Thr Tyr Val Phe Phe
1               5                   10

<210> SEQ ID NO 403
<211> LENGTH: 10
<212> TYPE: PRT
<213> ORGANISM: Artificial Sequence
<220> FEATURE:
<223> OTHER INFORMATION: Synthetic construct

<400> SEQUENCE: 403

Asp Asn Lys Ile Gln Gly Asp Leu Ala Gly
1               5                   10

<210> SEQ ID NO 404
<211> LENGTH: 10
<212> TYPE: PRT
<213> ORGANISM: Artificial Sequence
<220> FEATURE:
<223> OTHER INFORMATION: Synthetic construct

<400> SEQUENCE: 404

Arg Ala Glu Ile Leu Gly Lys Thr Ser Leu
1               5                   10

<210> SEQ ID NO 405
<211> LENGTH: 10
<212> TYPE: PRT
<213> ORGANISM: Artificial Sequence
<220> FEATURE:
<223> OTHER INFORMATION: Synthetic construct

<400> SEQUENCE: 405

Lys Ile Trp Asn Val Thr Arg Arg Asp Ser
1               5                   10

<210> SEQ ID NO 406
<211> LENGTH: 10
<212> TYPE: PRT
<213> ORGANISM: Artificial Sequence
<220> FEATURE:
<223> OTHER INFORMATION: Synthetic construct

<400> SEQUENCE: 406

Ala Leu Tyr Arg Cys Glu Val Val Ala Arg
1               5                   10

```
<210> SEQ ID NO 407
<211> LENGTH: 10
<212> TYPE: PRT
<213> ORGANISM: Artificial Sequence
<220> FEATURE:
<223> OTHER INFORMATION: Synthetic construct

<400> SEQUENCE: 407

Asn Asp Arg Lys Glu Ile Asp Glu Ile Val
1               5                   10

<210> SEQ ID NO 408
<211> LENGTH: 10
<212> TYPE: PRT
<213> ORGANISM: Artificial Sequence
<220> FEATURE:
<223> OTHER INFORMATION: Synthetic construct

<400> SEQUENCE: 408

Ile Glu Leu Thr Val Gln Val Lys Pro Val
1               5                   10

<210> SEQ ID NO 409
<211> LENGTH: 10
<212> TYPE: PRT
<213> ORGANISM: Artificial Sequence
<220> FEATURE:
<223> OTHER INFORMATION: Synthetic construct

<400> SEQUENCE: 409

Thr Pro Val Cys Arg Val Pro Lys Ala Val
1               5                   10

<210> SEQ ID NO 410
<211> LENGTH: 10
<212> TYPE: PRT
<213> ORGANISM: Artificial Sequence
<220> FEATURE:
<223> OTHER INFORMATION: Synthetic construct

<400> SEQUENCE: 410

Pro Val Gly Lys Met Ala Thr Leu His Cys
1               5                   10

<210> SEQ ID NO 411
<211> LENGTH: 10
<212> TYPE: PRT
<213> ORGANISM: Artificial Sequence
<220> FEATURE:
<223> OTHER INFORMATION: Synthetic construct

<400> SEQUENCE: 411

Gln Glu Ser Glu Gly His Pro Arg Pro His
1               5                   10

<210> SEQ ID NO 412
<211> LENGTH: 10
<212> TYPE: PRT
<213> ORGANISM: Artificial Sequence
<220> FEATURE:
<223> OTHER INFORMATION: Synthetic construct

<400> SEQUENCE: 412

Tyr Ser Trp Tyr Arg Asn Asp Val Pro Leu
1               5                   10
```

```
<210> SEQ ID NO 413
<211> LENGTH: 10
<212> TYPE: PRT
<213> ORGANISM: Artificial Sequence
<220> FEATURE:
<223> OTHER INFORMATION: Synthetic construct

<400> SEQUENCE: 413

Pro Thr Asp Ser Arg Ala Asn Pro Arg Phe
1               5                   10

<210> SEQ ID NO 414
<211> LENGTH: 10
<212> TYPE: PRT
<213> ORGANISM: Artificial Sequence
<220> FEATURE:
<223> OTHER INFORMATION: Synthetic construct

<400> SEQUENCE: 414

Arg Asn Ser Ser Phe His Leu Asn Ser Glu
1               5                   10

<210> SEQ ID NO 415
<211> LENGTH: 10
<212> TYPE: PRT
<213> ORGANISM: Artificial Sequence
<220> FEATURE:
<223> OTHER INFORMATION: Synthetic construct

<400> SEQUENCE: 415

Thr Gly Thr Leu Val Phe Thr Ala Val His
1               5                   10

<210> SEQ ID NO 416
<211> LENGTH: 10
<212> TYPE: PRT
<213> ORGANISM: Artificial Sequence
<220> FEATURE:
<223> OTHER INFORMATION: Synthetic construct

<400> SEQUENCE: 416

Lys Asp Asp Ser Gly Gln Tyr Tyr Cys Ile
1               5                   10

<210> SEQ ID NO 417
<211> LENGTH: 10
<212> TYPE: PRT
<213> ORGANISM: Artificial Sequence
<220> FEATURE:
<223> OTHER INFORMATION: Synthetic construct

<400> SEQUENCE: 417

Lys Asp Asp Ser Gly Gln Tyr Tyr Cys Ile
1               5                   10

<210> SEQ ID NO 418
<211> LENGTH: 10
<212> TYPE: PRT
<213> ORGANISM: Artificial Sequence
<220> FEATURE:
<223> OTHER INFORMATION: Synthetic construct

<400> SEQUENCE: 418

Lys Asp Asp Ser Gly Gln Tyr Tyr Cys Ile
1               5                   10
```

```
<210> SEQ ID NO 419
<211> LENGTH: 4
<212> TYPE: PRT
<213> ORGANISM: Artificial Sequence
<220> FEATURE:
<223> OTHER INFORMATION: Synthetic construct

<400> SEQUENCE: 419

Val Asn Leu Lys
1

<210> SEQ ID NO 420
<211> LENGTH: 10
<212> TYPE: PRT
<213> ORGANISM: Artificial Sequence
<220> FEATURE:
<223> OTHER INFORMATION: Synthetic construct

<400> SEQUENCE: 420

Ser Ser Asn Arg Thr Pro Val Val Gln Glu
1               5                   10

<210> SEQ ID NO 421
<211> LENGTH: 10
<212> TYPE: PRT
<213> ORGANISM: Artificial Sequence
<220> FEATURE:
<223> OTHER INFORMATION: Synthetic construct

<400> SEQUENCE: 421

Phe Glu Ser Val Glu Leu Ser Cys Ile Ile
1               5                   10

<210> SEQ ID NO 422
<211> LENGTH: 10
<212> TYPE: PRT
<213> ORGANISM: Artificial Sequence
<220> FEATURE:
<223> OTHER INFORMATION: Synthetic construct

<400> SEQUENCE: 422

Thr Asp Ser Gln Thr Ser Asp Pro Arg Ile
1               5                   10

<210> SEQ ID NO 423
<211> LENGTH: 10
<212> TYPE: PRT
<213> ORGANISM: Artificial Sequence
<220> FEATURE:
<223> OTHER INFORMATION: Synthetic construct

<400> SEQUENCE: 423

Glu Trp Lys Lys Ile Gln Asp Glu Gln Thr
1               5                   10

<210> SEQ ID NO 424
<211> LENGTH: 10
<212> TYPE: PRT
<213> ORGANISM: Artificial Sequence
<220> FEATURE:
<223> OTHER INFORMATION: Synthetic construct

<400> SEQUENCE: 424

Thr Tyr Val Phe Phe Asp Asn Lys Ile Gln
1               5                   10

<210> SEQ ID NO 425
```

```
<211> LENGTH: 10
<212> TYPE: PRT
<213> ORGANISM: Artificial Sequence
<220> FEATURE:
<223> OTHER INFORMATION: Synthetic construct

<400> SEQUENCE: 425

Gly Asp Leu Ala Gly Arg Ala Glu Ile Leu
1               5                   10

<210> SEQ ID NO 426
<211> LENGTH: 10
<212> TYPE: PRT
<213> ORGANISM: Artificial Sequence
<220> FEATURE:
<223> OTHER INFORMATION: Synthetic construct

<400> SEQUENCE: 426

Gly Lys Thr Ser Leu Lys Ile Trp Asn Val
1               5                   10

<210> SEQ ID NO 427
<211> LENGTH: 10
<212> TYPE: PRT
<213> ORGANISM: Artificial Sequence
<220> FEATURE:
<223> OTHER INFORMATION: Synthetic construct

<400> SEQUENCE: 427

Thr Arg Arg Asp Ser Ala Leu Tyr Arg Cys
1               5                   10

<210> SEQ ID NO 428
<211> LENGTH: 10
<212> TYPE: PRT
<213> ORGANISM: Artificial Sequence
<220> FEATURE:
<223> OTHER INFORMATION: Synthetic construct

<400> SEQUENCE: 428

Glu Val Val Ala Arg Asn Asp Arg Lys Glu
1               5                   10

<210> SEQ ID NO 429
<211> LENGTH: 10
<212> TYPE: PRT
<213> ORGANISM: Artificial Sequence
<220> FEATURE:
<223> OTHER INFORMATION: Synthetic construct

<400> SEQUENCE: 429

Ile Asp Glu Ile Val Ile Glu Leu Thr Val
1               5                   10

<210> SEQ ID NO 430
<211> LENGTH: 10
<212> TYPE: PRT
<213> ORGANISM: Artificial Sequence
<220> FEATURE:
<223> OTHER INFORMATION: Synthetic construct

<400> SEQUENCE: 430

Gln Val Lys Pro Val Thr Pro Val Cys Arg
1               5                   10

<210> SEQ ID NO 431
<211> LENGTH: 10
```

<212> TYPE: PRT
<213> ORGANISM: Artificial Sequence
<220> FEATURE:
<223> OTHER INFORMATION: Synthetic construct

<400> SEQUENCE: 431

Val Pro Lys Ala Val Pro Val Gly Lys Met
1               5                   10

<210> SEQ ID NO 432
<211> LENGTH: 10
<212> TYPE: PRT
<213> ORGANISM: Artificial Sequence
<220> FEATURE:
<223> OTHER INFORMATION: Synthetic construct

<400> SEQUENCE: 432

Ala Thr Leu His Cys Gln Glu Ser Glu Gly
1               5                   10

<210> SEQ ID NO 433
<211> LENGTH: 10
<212> TYPE: PRT
<213> ORGANISM: Artificial Sequence
<220> FEATURE:
<223> OTHER INFORMATION: Synthetic construct

<400> SEQUENCE: 433

His Pro Arg Pro His Tyr Ser Trp Tyr Arg
1               5                   10

<210> SEQ ID NO 434
<211> LENGTH: 10
<212> TYPE: PRT
<213> ORGANISM: Artificial Sequence
<220> FEATURE:
<223> OTHER INFORMATION: Synthetic construct

<400> SEQUENCE: 434

Asn Asp Val Pro Leu Pro Thr Asp Ser Arg
1               5                   10

<210> SEQ ID NO 435
<211> LENGTH: 10
<212> TYPE: PRT
<213> ORGANISM: Artificial Sequence
<220> FEATURE:
<223> OTHER INFORMATION: Synthetic construct

<400> SEQUENCE: 435

Ala Asn Pro Arg Phe Arg Asn Ser Ser Phe
1               5                   10

<210> SEQ ID NO 436
<211> LENGTH: 10
<212> TYPE: PRT
<213> ORGANISM: Artificial Sequence
<220> FEATURE:
<223> OTHER INFORMATION: Synthetic construct

<400> SEQUENCE: 436

His Leu Asn Ser Glu Thr Gly Thr Leu Val
1               5                   10

<210> SEQ ID NO 437
<211> LENGTH: 10
<212> TYPE: PRT

```
<213> ORGANISM: Artificial Sequence
<220> FEATURE:
<223> OTHER INFORMATION: Synthetic construct

<400> SEQUENCE: 437

Phe Thr Ala Val His Lys Asp Asp Ser Gly
1               5                   10

<210> SEQ ID NO 438
<211> LENGTH: 10
<212> TYPE: PRT
<213> ORGANISM: Artificial Sequence
<220> FEATURE:
<223> OTHER INFORMATION: Synthetic construct

<400> SEQUENCE: 438

Gln Tyr Tyr Cys Ile Ala Ser Asn Asp Ala
1               5                   10

<210> SEQ ID NO 439
<211> LENGTH: 10
<212> TYPE: PRT
<213> ORGANISM: Artificial Sequence
<220> FEATURE:
<223> OTHER INFORMATION: Synthetic construct

<400> SEQUENCE: 439

Gly Ser Ala Arg Cys Glu Glu Gln Glu Met
1               5                   10

<210> SEQ ID NO 440
<211> LENGTH: 6
<212> TYPE: PRT
<213> ORGANISM: Artificial Sequence
<220> FEATURE:
<223> OTHER INFORMATION: Synthetic construct

<400> SEQUENCE: 440

Glu Val Tyr Asp Leu Asn
1               5

<210> SEQ ID NO 441
<211> LENGTH: 7
<212> TYPE: PRT
<213> ORGANISM: Artificial Sequence
<220> FEATURE:
<223> OTHER INFORMATION: Synthetic construct

<400> SEQUENCE: 441

Val Asn Leu Lys Ser Ser Asn
1               5

<210> SEQ ID NO 442
<211> LENGTH: 8
<212> TYPE: PRT
<213> ORGANISM: Artificial Sequence
<220> FEATURE:
<223> OTHER INFORMATION: Synthetic construct

<400> SEQUENCE: 442

Arg Thr Pro Val Val Gln Glu Phe
1               5

<210> SEQ ID NO 443
<211> LENGTH: 8
<212> TYPE: PRT
<213> ORGANISM: Artificial Sequence
```

<220> FEATURE:
<223> OTHER INFORMATION: Synthetic construct

<400> SEQUENCE: 443

Glu Ser Val Glu Leu Ser Cys Ile
1               5

<210> SEQ ID NO 444
<211> LENGTH: 8
<212> TYPE: PRT
<213> ORGANISM: Artificial Sequence
<220> FEATURE:
<223> OTHER INFORMATION: Synthetic construct

<400> SEQUENCE: 444

Ile Thr Asp Ser Gln Thr Ser Asp
1               5

<210> SEQ ID NO 445
<211> LENGTH: 8
<212> TYPE: PRT
<213> ORGANISM: Artificial Sequence
<220> FEATURE:
<223> OTHER INFORMATION: Synthetic construct

<400> SEQUENCE: 445

Gln Asp Glu Gln Thr Thr Tyr Val
1               5

<210> SEQ ID NO 446
<211> LENGTH: 8
<212> TYPE: PRT
<213> ORGANISM: Artificial Sequence
<220> FEATURE:
<223> OTHER INFORMATION: Synthetic construct

<400> SEQUENCE: 446

Phe Phe Asp Asn Lys Ile Gln Gly
1               5

<210> SEQ ID NO 447
<211> LENGTH: 8
<212> TYPE: PRT
<213> ORGANISM: Artificial Sequence
<220> FEATURE:
<223> OTHER INFORMATION: Synthetic construct

<400> SEQUENCE: 447

Asp Leu Ala Gly Arg Ala Glu Ile
1               5

<210> SEQ ID NO 448
<211> LENGTH: 8
<212> TYPE: PRT
<213> ORGANISM: Artificial Sequence
<220> FEATURE:
<223> OTHER INFORMATION: Synthetic construct

<400> SEQUENCE: 448

Leu Gly Lys Thr Ser Leu Lys Ile
1               5

<210> SEQ ID NO 449
<211> LENGTH: 8
<212> TYPE: PRT
<213> ORGANISM: Artificial Sequence
<220> FEATURE:

```
<223> OTHER INFORMATION: Synthetic construct

<400> SEQUENCE: 449

Trp Asn Val Thr Arg Arg Asp Ser
1               5

<210> SEQ ID NO 450
<211> LENGTH: 8
<212> TYPE: PRT
<213> ORGANISM: Artificial Sequence
<220> FEATURE:
<223> OTHER INFORMATION: Synthetic construct

<400> SEQUENCE: 450

Ala Leu Tyr Arg Cys Glu Val Val
1               5

<210> SEQ ID NO 451
<211> LENGTH: 8
<212> TYPE: PRT
<213> ORGANISM: Artificial Sequence
<220> FEATURE:
<223> OTHER INFORMATION: Synthetic construct

<400> SEQUENCE: 451

Ala Arg Asn Asp Arg Lys Glu Ile
1               5

<210> SEQ ID NO 452
<211> LENGTH: 8
<212> TYPE: PRT
<213> ORGANISM: Artificial Sequence
<220> FEATURE:
<223> OTHER INFORMATION: Synthetic construct

<400> SEQUENCE: 452

Asp Glu Ile Val Ile Glu Leu Thr
1               5

<210> SEQ ID NO 453
<211> LENGTH: 8
<212> TYPE: PRT
<213> ORGANISM: Artificial Sequence
<220> FEATURE:
<223> OTHER INFORMATION: Synthetic construct

<400> SEQUENCE: 453

Val Gln Val Lys Pro Val Thr Pro
1               5

<210> SEQ ID NO 454
<211> LENGTH: 8
<212> TYPE: PRT
<213> ORGANISM: Artificial Sequence
<220> FEATURE:
<223> OTHER INFORMATION: Synthetic construct

<400> SEQUENCE: 454

Val Cys Arg Val Pro Lys Ala Val
1               5

<210> SEQ ID NO 455
<211> LENGTH: 8
<212> TYPE: PRT
<213> ORGANISM: Artificial Sequence
<220> FEATURE:
<223> OTHER INFORMATION: Synthetic construct
```

```
<400> SEQUENCE: 455

Pro Val Gly Lys Met Ala Thr Leu
1               5

<210> SEQ ID NO 456
<211> LENGTH: 8
<212> TYPE: PRT
<213> ORGANISM: Artificial Sequence
<220> FEATURE:
<223> OTHER INFORMATION: Synthetic construct

<400> SEQUENCE: 456

His Cys Gln Glu Ser Glu Gly His
1               5

<210> SEQ ID NO 457
<211> LENGTH: 8
<212> TYPE: PRT
<213> ORGANISM: Artificial Sequence
<220> FEATURE:
<223> OTHER INFORMATION: Synthetic construct

<400> SEQUENCE: 457

Pro Arg Pro His Tyr Ser Trp Tyr
1               5

<210> SEQ ID NO 458
<211> LENGTH: 8
<212> TYPE: PRT
<213> ORGANISM: Artificial Sequence
<220> FEATURE:
<223> OTHER INFORMATION: Synthetic construct

<400> SEQUENCE: 458

Arg Asn Asp Val Pro Leu Pro Thr
1               5

<210> SEQ ID NO 459
<211> LENGTH: 8
<212> TYPE: PRT
<213> ORGANISM: Artificial Sequence
<220> FEATURE:
<223> OTHER INFORMATION: Synthetic construct

<400> SEQUENCE: 459

Asp Ser Arg Ala Asn Pro Arg Phe
1               5

<210> SEQ ID NO 460
<211> LENGTH: 8
<212> TYPE: PRT
<213> ORGANISM: Artificial Sequence
<220> FEATURE:
<223> OTHER INFORMATION: Synthetic construct

<400> SEQUENCE: 460

Arg Asn Ser Ser Phe His Leu Asn
1               5

<210> SEQ ID NO 461
<211> LENGTH: 8
<212> TYPE: PRT
<213> ORGANISM: Artificial Sequence
<220> FEATURE:
<223> OTHER INFORMATION: Synthetic construct
```

```
<400> SEQUENCE: 461

Ser Glu Thr Gly Thr Leu Val Phe
1               5

<210> SEQ ID NO 462
<211> LENGTH: 8
<212> TYPE: PRT
<213> ORGANISM: Artificial Sequence
<220> FEATURE:
<223> OTHER INFORMATION: Synthetic construct

<400> SEQUENCE: 462

Thr Ala Val His Lys Asp Asp Ser
1               5

<210> SEQ ID NO 463
<211> LENGTH: 8
<212> TYPE: PRT
<213> ORGANISM: Artificial Sequence
<220> FEATURE:
<223> OTHER INFORMATION: Synthetic construct

<400> SEQUENCE: 463

Gly Gln Tyr Tyr Cys Ile Ala Ser
1               5

<210> SEQ ID NO 464
<211> LENGTH: 8
<212> TYPE: PRT
<213> ORGANISM: Artificial Sequence
<220> FEATURE:
<223> OTHER INFORMATION: Synthetic construct

<400> SEQUENCE: 464

Asn Asp Ala Gly Ser Ala Arg Cys
1               5

<210> SEQ ID NO 465
<211> LENGTH: 8
<212> TYPE: PRT
<213> ORGANISM: Artificial Sequence
<220> FEATURE:
<223> OTHER INFORMATION: Synthetic construct

<400> SEQUENCE: 465

Glu Glu Gln Glu Met Glu Val Tyr
1               5

<210> SEQ ID NO 466
<211> LENGTH: 3
<212> TYPE: PRT
<213> ORGANISM: Artificial Sequence
<220> FEATURE:
<223> OTHER INFORMATION: Synthetic construct

<400> SEQUENCE: 466

Asp Leu Asn
1

<210> SEQ ID NO 467
<211> LENGTH: 3
<212> TYPE: PRT
<213> ORGANISM: Artificial Sequence
<220> FEATURE:
<223> OTHER INFORMATION: Synthetic construct

<400> SEQUENCE: 467
```

```
Val Asn Leu
1

<210> SEQ ID NO 468
<211> LENGTH: 8
<212> TYPE: PRT
<213> ORGANISM: Artificial Sequence
<220> FEATURE:
<223> OTHER INFORMATION: Synthetic construct

<400> SEQUENCE: 468

Lys Ser Ser Asn Arg Thr Pro Val
1               5

<210> SEQ ID NO 469
<211> LENGTH: 8
<212> TYPE: PRT
<213> ORGANISM: Artificial Sequence
<220> FEATURE:
<223> OTHER INFORMATION: Synthetic construct

<400> SEQUENCE: 469

Val Gln Glu Phe Glu Ser Val Glu
1               5

<210> SEQ ID NO 470
<211> LENGTH: 8
<212> TYPE: PRT
<213> ORGANISM: Artificial Sequence
<220> FEATURE:
<223> OTHER INFORMATION: Synthetic construct

<400> SEQUENCE: 470

Leu Ser Cys Ile Ile Thr Asp Ser
1               5

<210> SEQ ID NO 471
<211> LENGTH: 8
<212> TYPE: PRT
<213> ORGANISM: Artificial Sequence
<220> FEATURE:
<223> OTHER INFORMATION: Synthetic construct

<400> SEQUENCE: 471

Gln Thr Ser Asp Pro Arg Ile Glu
1               5

<210> SEQ ID NO 472
<211> LENGTH: 8
<212> TYPE: PRT
<213> ORGANISM: Artificial Sequence
<220> FEATURE:
<223> OTHER INFORMATION: Synthetic construct

<400> SEQUENCE: 472

Trp Lys Lys Ile Gln Asp Glu Gln
1               5

<210> SEQ ID NO 473
<211> LENGTH: 8
<212> TYPE: PRT
<213> ORGANISM: Artificial Sequence
<220> FEATURE:
<223> OTHER INFORMATION: Synthetic construct

<400> SEQUENCE: 473
```

```
Thr Thr Tyr Val Phe Phe Asp Asn
1               5

<210> SEQ ID NO 474
<211> LENGTH: 8
<212> TYPE: PRT
<213> ORGANISM: Artificial Sequence
<220> FEATURE:
<223> OTHER INFORMATION: Synthetic construct

<400> SEQUENCE: 474

Lys Ile Gln Gly Asp Leu Ala Gly
1               5

<210> SEQ ID NO 475
<211> LENGTH: 8
<212> TYPE: PRT
<213> ORGANISM: Artificial Sequence
<220> FEATURE:
<223> OTHER INFORMATION: Synthetic construct

<400> SEQUENCE: 475

Arg Ala Glu Ile Leu Gly Lys Thr
1               5

<210> SEQ ID NO 476
<211> LENGTH: 8
<212> TYPE: PRT
<213> ORGANISM: Artificial Sequence
<220> FEATURE:
<223> OTHER INFORMATION: Synthetic construct

<400> SEQUENCE: 476

Ser Leu Lys Ile Trp Asn Val Thr
1               5

<210> SEQ ID NO 477
<211> LENGTH: 8
<212> TYPE: PRT
<213> ORGANISM: Artificial Sequence
<220> FEATURE:
<223> OTHER INFORMATION: Synthetic construct

<400> SEQUENCE: 477

Arg Arg Asp Ser Ala Leu Tyr Arg
1               5

<210> SEQ ID NO 478
<211> LENGTH: 8
<212> TYPE: PRT
<213> ORGANISM: Artificial Sequence
<220> FEATURE:
<223> OTHER INFORMATION: Synthetic construct

<400> SEQUENCE: 478

Cys Glu Val Val Ala Arg Asn Asp
1               5

<210> SEQ ID NO 479
<211> LENGTH: 8
<212> TYPE: PRT
<213> ORGANISM: Artificial Sequence
<220> FEATURE:
<223> OTHER INFORMATION: Synthetic construct

<400> SEQUENCE: 479

Arg Lys Glu Ile Asp Glu Ile Val
```

```
1               5

<210> SEQ ID NO 480
<211> LENGTH: 8
<212> TYPE: PRT
<213> ORGANISM: Artificial Sequence
<220> FEATURE:
<223> OTHER INFORMATION: Synthetic construct

<400> SEQUENCE: 480

Ile Glu Leu Thr Val Gln Val Lys
1               5

<210> SEQ ID NO 481
<211> LENGTH: 8
<212> TYPE: PRT
<213> ORGANISM: Artificial Sequence
<220> FEATURE:
<223> OTHER INFORMATION: Synthetic construct

<400> SEQUENCE: 481

Pro Val Thr Pro Val Cys Arg Val
1               5

<210> SEQ ID NO 482
<211> LENGTH: 8
<212> TYPE: PRT
<213> ORGANISM: Artificial Sequence
<220> FEATURE:
<223> OTHER INFORMATION: Synthetic construct

<400> SEQUENCE: 482

Pro Lys Ala Val Pro Val Gly Lys
1               5

<210> SEQ ID NO 483
<211> LENGTH: 8
<212> TYPE: PRT
<213> ORGANISM: Artificial Sequence
<220> FEATURE:
<223> OTHER INFORMATION: Synthetic construct

<400> SEQUENCE: 483

Met Ala Thr Leu His Cys Gln Glu
1               5

<210> SEQ ID NO 484
<211> LENGTH: 8
<212> TYPE: PRT
<213> ORGANISM: Artificial Sequence
<220> FEATURE:
<223> OTHER INFORMATION: Synthetic construct

<400> SEQUENCE: 484

Ser Glu Gly His Pro Arg Pro His
1               5

<210> SEQ ID NO 485
<211> LENGTH: 8
<212> TYPE: PRT
<213> ORGANISM: Artificial Sequence
<220> FEATURE:
<223> OTHER INFORMATION: Synthetic construct

<400> SEQUENCE: 485

Tyr Ser Trp Tyr Arg Asn Asp Val
1               5
```

```
<210> SEQ ID NO 486
<211> LENGTH: 8
<212> TYPE: PRT
<213> ORGANISM: Artificial Sequence
<220> FEATURE:
<223> OTHER INFORMATION: Synthetic construct

<400> SEQUENCE: 486

Pro Leu Pro Thr Asp Ser Arg Ala
1               5

<210> SEQ ID NO 487
<211> LENGTH: 8
<212> TYPE: PRT
<213> ORGANISM: Artificial Sequence
<220> FEATURE:
<223> OTHER INFORMATION: Synthetic construct

<400> SEQUENCE: 487

Asn Pro Arg Phe Arg Asn Ser Ser
1               5

<210> SEQ ID NO 488
<211> LENGTH: 8
<212> TYPE: PRT
<213> ORGANISM: Artificial Sequence
<220> FEATURE:
<223> OTHER INFORMATION: Synthetic construct

<400> SEQUENCE: 488

Phe His Leu Asn Ser Glu Thr Gly
1               5

<210> SEQ ID NO 489
<211> LENGTH: 8
<212> TYPE: PRT
<213> ORGANISM: Artificial Sequence
<220> FEATURE:
<223> OTHER INFORMATION: Synthetic construct

<400> SEQUENCE: 489

Thr Leu Val Phe Thr Ala Val His
1               5

<210> SEQ ID NO 490
<211> LENGTH: 8
<212> TYPE: PRT
<213> ORGANISM: Artificial Sequence
<220> FEATURE:
<223> OTHER INFORMATION: Synthetic construct

<400> SEQUENCE: 490

Lys Asp Asp Ser Gly Gln Tyr Tyr
1               5

<210> SEQ ID NO 491
<211> LENGTH: 8
<212> TYPE: PRT
<213> ORGANISM: Artificial Sequence
<220> FEATURE:
<223> OTHER INFORMATION: Synthetic construct

<400> SEQUENCE: 491

Cys Ile Ala Ser Asn Asp Ala Gly
1               5
```

```
<210> SEQ ID NO 492
<211> LENGTH: 8
<212> TYPE: PRT
<213> ORGANISM: Artificial Sequence
<220> FEATURE:
<223> OTHER INFORMATION: Synthetic construct

<400> SEQUENCE: 492

Ser Ala Arg Cys Glu Glu Gln Glu
1               5

<210> SEQ ID NO 493
<211> LENGTH: 7
<212> TYPE: PRT
<213> ORGANISM: Artificial Sequence
<220> FEATURE:
<223> OTHER INFORMATION: Synthetic construct

<400> SEQUENCE: 493

Met Glu Val Tyr Asp Leu Asn
1               5

<210> SEQ ID NO 494
<211> LENGTH: 10
<212> TYPE: PRT
<213> ORGANISM: Artificial Sequence
<220> FEATURE:
<223> OTHER INFORMATION: Synthetic construct

<400> SEQUENCE: 494

Gly Phe Ser Ala Pro Lys Asp Gln Gln Val
1               5                   10

<210> SEQ ID NO 495
<211> LENGTH: 10
<212> TYPE: PRT
<213> ORGANISM: Artificial Sequence
<220> FEATURE:
<223> OTHER INFORMATION: Synthetic construct

<400> SEQUENCE: 495

Val Thr Ala Val Glu Tyr Gln Glu Ala Ile
1               5                   10

<210> SEQ ID NO 496
<211> LENGTH: 10
<212> TYPE: PRT
<213> ORGANISM: Artificial Sequence
<220> FEATURE:
<223> OTHER INFORMATION: Synthetic construct

<400> SEQUENCE: 496

Leu Ala Cys Lys Thr Pro Lys Lys Thr Val
1               5                   10

<210> SEQ ID NO 497
<211> LENGTH: 10
<212> TYPE: PRT
<213> ORGANISM: Artificial Sequence
<220> FEATURE:
<223> OTHER INFORMATION: Synthetic construct

<400> SEQUENCE: 497

Ser Ser Arg Leu Glu Trp Lys Lys Leu Gly
1               5                   10
```

<210> SEQ ID NO 498
<211> LENGTH: 10
<212> TYPE: PRT
<213> ORGANISM: Artificial Sequence
<220> FEATURE:
<223> OTHER INFORMATION: Synthetic construct

<400> SEQUENCE: 498

Arg Ser Val Ser Phe Val Tyr Tyr Gln Gln
1               5                   10

<210> SEQ ID NO 499
<211> LENGTH: 10
<212> TYPE: PRT
<213> ORGANISM: Artificial Sequence
<220> FEATURE:
<223> OTHER INFORMATION: Synthetic construct

<400> SEQUENCE: 499

Thr Leu Gln Gly Asp Phe Lys Asn Arg Ala
1               5                   10

<210> SEQ ID NO 500
<211> LENGTH: 10
<212> TYPE: PRT
<213> ORGANISM: Artificial Sequence
<220> FEATURE:
<223> OTHER INFORMATION: Synthetic construct

<400> SEQUENCE: 500

Glu Met Ile Asp Phe Asn Ile Arg Ile Lys
1               5                   10

<210> SEQ ID NO 501
<211> LENGTH: 10
<212> TYPE: PRT
<213> ORGANISM: Artificial Sequence
<220> FEATURE:
<223> OTHER INFORMATION: Synthetic construct

<400> SEQUENCE: 501

Asn Val Thr Arg Ser Asp Ala Gly Lys Tyr
1               5                   10

<210> SEQ ID NO 502
<211> LENGTH: 10
<212> TYPE: PRT
<213> ORGANISM: Artificial Sequence
<220> FEATURE:
<223> OTHER INFORMATION: Synthetic construct

<400> SEQUENCE: 502

Arg Cys Glu Val Ser Ala Pro Ser Glu Gln
1               5                   10

<210> SEQ ID NO 503
<211> LENGTH: 10
<212> TYPE: PRT
<213> ORGANISM: Artificial Sequence
<220> FEATURE:
<223> OTHER INFORMATION: Synthetic construct

<400> SEQUENCE: 503

Gly Gln Asn Leu Glu Glu Asp Thr Val Thr
1               5                   10

<210> SEQ ID NO 504

```
<211> LENGTH: 10
<212> TYPE: PRT
<213> ORGANISM: Artificial Sequence
<220> FEATURE:
<223> OTHER INFORMATION: Synthetic construct

<400> SEQUENCE: 504

Leu Glu Val Leu Val Ala Pro Ala Val Pro
1               5                   10

<210> SEQ ID NO 505
<211> LENGTH: 10
<212> TYPE: PRT
<213> ORGANISM: Artificial Sequence
<220> FEATURE:
<223> OTHER INFORMATION: Synthetic construct

<400> SEQUENCE: 505

Ser Cys Glu Val Pro Ser Ser Ala Leu Ser
1               5                   10

<210> SEQ ID NO 506
<211> LENGTH: 10
<212> TYPE: PRT
<213> ORGANISM: Artificial Sequence
<220> FEATURE:
<223> OTHER INFORMATION: Synthetic construct

<400> SEQUENCE: 506

Gly Thr Val Val Glu Leu Arg Cys Gln Asp
1               5                   10

<210> SEQ ID NO 507
<211> LENGTH: 10
<212> TYPE: PRT
<213> ORGANISM: Artificial Sequence
<220> FEATURE:
<223> OTHER INFORMATION: Synthetic construct

<400> SEQUENCE: 507

Lys Glu Gly Asn Pro Ala Pro Glu Tyr Thr
1               5                   10

<210> SEQ ID NO 508
<211> LENGTH: 10
<212> TYPE: PRT
<213> ORGANISM: Artificial Sequence
<220> FEATURE:
<223> OTHER INFORMATION: Synthetic construct

<400> SEQUENCE: 508

Trp Phe Lys Asp Gly Ile Arg Leu Leu Glu
1               5                   10

<210> SEQ ID NO 509
<211> LENGTH: 10
<212> TYPE: PRT
<213> ORGANISM: Artificial Sequence
<220> FEATURE:
<223> OTHER INFORMATION: Synthetic construct

<400> SEQUENCE: 509

Asn Pro Arg Leu Gly Ser Gln Ser Thr Asn
1               5                   10

<210> SEQ ID NO 510
<211> LENGTH: 10
```

```
<212> TYPE: PRT
<213> ORGANISM: Artificial Sequence
<220> FEATURE:
<223> OTHER INFORMATION: Synthetic construct

<400> SEQUENCE: 510

Ser Ser Tyr Thr Met Asn Thr Lys Thr Gly
1               5                   10

<210> SEQ ID NO 511
<211> LENGTH: 10
<212> TYPE: PRT
<213> ORGANISM: Artificial Sequence
<220> FEATURE:
<223> OTHER INFORMATION: Synthetic construct

<400> SEQUENCE: 511

Thr Leu Gln Phe Asn Thr Val Ser Lys Leu
1               5                   10

<210> SEQ ID NO 512
<211> LENGTH: 10
<212> TYPE: PRT
<213> ORGANISM: Artificial Sequence
<220> FEATURE:
<223> OTHER INFORMATION: Synthetic construct

<400> SEQUENCE: 512

Asp Thr Gly Glu Tyr Ser Cys Glu Ala Arg
1               5                   10

<210> SEQ ID NO 513
<211> LENGTH: 10
<212> TYPE: PRT
<213> ORGANISM: Artificial Sequence
<220> FEATURE:
<223> OTHER INFORMATION: Synthetic construct

<400> SEQUENCE: 513

Asn Ser Val Gly Tyr Arg Arg Cys Pro Gly
1               5                   10

<210> SEQ ID NO 514
<211> LENGTH: 9
<212> TYPE: PRT
<213> ORGANISM: Artificial Sequence
<220> FEATURE:
<223> OTHER INFORMATION: Synthetic construct

<400> SEQUENCE: 514

Lys Arg Met Gln Val Asp Asp Leu Asn
1               5

<210> SEQ ID NO 515
<211> LENGTH: 5
<212> TYPE: PRT
<213> ORGANISM: Artificial Sequence
<220> FEATURE:
<223> OTHER INFORMATION: Synthetic construct

<400> SEQUENCE: 515

Gly Phe Ser Ala Pro
1               5

<210> SEQ ID NO 516
<211> LENGTH: 9
<212> TYPE: PRT
```

```
<213> ORGANISM: Artificial Sequence
<220> FEATURE:
<223> OTHER INFORMATION: Synthetic construct

<400> SEQUENCE: 516

Lys Asp Gln Gln Val Val Thr Ala Val
1               5

<210> SEQ ID NO 517
<211> LENGTH: 10
<212> TYPE: PRT
<213> ORGANISM: Artificial Sequence
<220> FEATURE:
<223> OTHER INFORMATION: Synthetic construct

<400> SEQUENCE: 517

Tyr Gln Glu Ala Ile Leu Ala Cys Lys Thr
1               5                   10

<210> SEQ ID NO 518
<211> LENGTH: 10
<212> TYPE: PRT
<213> ORGANISM: Artificial Sequence
<220> FEATURE:
<223> OTHER INFORMATION: Synthetic construct

<400> SEQUENCE: 518

Pro Lys Lys Thr Val Ser Ser Arg Leu Glu
1               5                   10

<210> SEQ ID NO 519
<211> LENGTH: 10
<212> TYPE: PRT
<213> ORGANISM: Artificial Sequence
<220> FEATURE:
<223> OTHER INFORMATION: Synthetic construct

<400> SEQUENCE: 519

Trp Lys Lys Leu Gly Arg Ser Val Ser Phe
1               5                   10

<210> SEQ ID NO 520
<211> LENGTH: 10
<212> TYPE: PRT
<213> ORGANISM: Artificial Sequence
<220> FEATURE:
<223> OTHER INFORMATION: Synthetic construct

<400> SEQUENCE: 520

Val Tyr Tyr Gln Gln Thr Leu Gln Gly Asp
1               5                   10

<210> SEQ ID NO 521
<211> LENGTH: 10
<212> TYPE: PRT
<213> ORGANISM: Artificial Sequence
<220> FEATURE:
<223> OTHER INFORMATION: Synthetic construct

<400> SEQUENCE: 521

Phe Lys Asn Arg Ala Glu Met Ile Asp Phe
1               5                   10

<210> SEQ ID NO 522
<211> LENGTH: 10
<212> TYPE: PRT
<213> ORGANISM: Artificial Sequence
```

<220> FEATURE:
<223> OTHER INFORMATION: Synthetic construct

<400> SEQUENCE: 522

Asn Ile Arg Ile Lys Asn Val Thr Arg Ser
1               5                   10

<210> SEQ ID NO 523
<211> LENGTH: 10
<212> TYPE: PRT
<213> ORGANISM: Artificial Sequence
<220> FEATURE:
<223> OTHER INFORMATION: Synthetic construct

<400> SEQUENCE: 523

Asp Ala Gly Lys Tyr Arg Cys Glu Val Ser
1               5                   10

<210> SEQ ID NO 524
<211> LENGTH: 10
<212> TYPE: PRT
<213> ORGANISM: Artificial Sequence
<220> FEATURE:
<223> OTHER INFORMATION: Synthetic construct

<400> SEQUENCE: 524

Ala Pro Ser Glu Gln Gly Gln Asn Leu Glu
1               5                   10

<210> SEQ ID NO 525
<211> LENGTH: 10
<212> TYPE: PRT
<213> ORGANISM: Artificial Sequence
<220> FEATURE:
<223> OTHER INFORMATION: Synthetic construct

<400> SEQUENCE: 525

Glu Asp Thr Val Thr Leu Glu Val Leu Val
1               5                   10

<210> SEQ ID NO 526
<211> LENGTH: 10
<212> TYPE: PRT
<213> ORGANISM: Artificial Sequence
<220> FEATURE:
<223> OTHER INFORMATION: Synthetic construct

<400> SEQUENCE: 526

Ala Pro Ala Val Pro Ser Cys Glu Val Pro
1               5                   10

<210> SEQ ID NO 527
<211> LENGTH: 10
<212> TYPE: PRT
<213> ORGANISM: Artificial Sequence
<220> FEATURE:
<223> OTHER INFORMATION: Synthetic construct

<400> SEQUENCE: 527

Ser Ser Ala Leu Ser Gly Thr Val Val Glu
1               5                   10

<210> SEQ ID NO 528
<211> LENGTH: 10
<212> TYPE: PRT
<213> ORGANISM: Artificial Sequence
<220> FEATURE:

-continued

<223> OTHER INFORMATION: Synthetic construct

<400> SEQUENCE: 528

Leu Arg Cys Gln Asp Lys Glu Gly Asn Pro
1               5                   10

<210> SEQ ID NO 529
<211> LENGTH: 10
<212> TYPE: PRT
<213> ORGANISM: Artificial Sequence
<220> FEATURE:
<223> OTHER INFORMATION: Synthetic construct

<400> SEQUENCE: 529

Ala Pro Glu Tyr Thr Trp Phe Lys Asp Gly
1               5                   10

<210> SEQ ID NO 530
<211> LENGTH: 10
<212> TYPE: PRT
<213> ORGANISM: Artificial Sequence
<220> FEATURE:
<223> OTHER INFORMATION: Synthetic construct

<400> SEQUENCE: 530

Ile Arg Leu Leu Glu Asn Pro Arg Leu Gly
1               5                   10

<210> SEQ ID NO 531
<211> LENGTH: 10
<212> TYPE: PRT
<213> ORGANISM: Artificial Sequence
<220> FEATURE:
<223> OTHER INFORMATION: Synthetic construct

<400> SEQUENCE: 531

Ser Gln Ser Thr Asn Ser Ser Tyr Thr Met
1               5                   10

<210> SEQ ID NO 532
<211> LENGTH: 10
<212> TYPE: PRT
<213> ORGANISM: Artificial Sequence
<220> FEATURE:
<223> OTHER INFORMATION: Synthetic construct

<400> SEQUENCE: 532

Asn Thr Lys Thr Gly Thr Leu Gln Phe Asn
1               5                   10

<210> SEQ ID NO 533
<211> LENGTH: 10
<212> TYPE: PRT
<213> ORGANISM: Artificial Sequence
<220> FEATURE:
<223> OTHER INFORMATION: Synthetic construct

<400> SEQUENCE: 533

Thr Val Ser Lys Leu Asp Thr Gly Glu Tyr
1               5                   10

<210> SEQ ID NO 534
<211> LENGTH: 10
<212> TYPE: PRT
<213> ORGANISM: Artificial Sequence
<220> FEATURE:
<223> OTHER INFORMATION: Synthetic construct

```
<400> SEQUENCE: 534

Ser Cys Glu Ala Arg Asn Ser Val Gly Tyr
1               5                   10

<210> SEQ ID NO 535
<211> LENGTH: 10
<212> TYPE: PRT
<213> ORGANISM: Artificial Sequence
<220> FEATURE:
<223> OTHER INFORMATION: Synthetic construct

<400> SEQUENCE: 535

Arg Arg Cys Pro Gly Lys Arg Met Gln Val
1               5                   10

<210> SEQ ID NO 536
<211> LENGTH: 4
<212> TYPE: PRT
<213> ORGANISM: Artificial Sequence
<220> FEATURE:
<223> OTHER INFORMATION: Synthetic construct

<400> SEQUENCE: 536

Asp Asp Leu Asn
1

<210> SEQ ID NO 537
<211> LENGTH: 8
<212> TYPE: PRT
<213> ORGANISM: Artificial Sequence
<220> FEATURE:
<223> OTHER INFORMATION: Synthetic construct

<400> SEQUENCE: 537

Gly Phe Ser Ala Pro Lys Asp Gln
1               5

<210> SEQ ID NO 538
<211> LENGTH: 8
<212> TYPE: PRT
<213> ORGANISM: Artificial Sequence
<220> FEATURE:
<223> OTHER INFORMATION: Synthetic construct

<400> SEQUENCE: 538

Gln Val Val Thr Ala Val Glu Tyr
1               5

<210> SEQ ID NO 539
<211> LENGTH: 8
<212> TYPE: PRT
<213> ORGANISM: Artificial Sequence
<220> FEATURE:
<223> OTHER INFORMATION: Synthetic construct

<400> SEQUENCE: 539

Gln Glu Ala Ile Leu Ala Cys Lys
1               5

<210> SEQ ID NO 540
<211> LENGTH: 8
<212> TYPE: PRT
<213> ORGANISM: Artificial Sequence
<220> FEATURE:
<223> OTHER INFORMATION: Synthetic construct
```

```
<400> SEQUENCE: 540

Thr Pro Lys Lys Thr Val Ser Ser
1               5

<210> SEQ ID NO 541
<211> LENGTH: 8
<212> TYPE: PRT
<213> ORGANISM: Artificial Sequence
<220> FEATURE:
<223> OTHER INFORMATION: Synthetic construct

<400> SEQUENCE: 541

Arg Leu Glu Trp Lys Lys Leu Gly
1               5

<210> SEQ ID NO 542
<211> LENGTH: 8
<212> TYPE: PRT
<213> ORGANISM: Artificial Sequence
<220> FEATURE:
<223> OTHER INFORMATION: Synthetic construct

<400> SEQUENCE: 542

Arg Ser Val Ser Phe Val Tyr Tyr
1               5

<210> SEQ ID NO 543
<211> LENGTH: 8
<212> TYPE: PRT
<213> ORGANISM: Artificial Sequence
<220> FEATURE:
<223> OTHER INFORMATION: Synthetic construct

<400> SEQUENCE: 543

Gln Gln Thr Leu Gln Gly Asp Phe
1               5

<210> SEQ ID NO 544
<211> LENGTH: 8
<212> TYPE: PRT
<213> ORGANISM: Artificial Sequence
<220> FEATURE:
<223> OTHER INFORMATION: Synthetic construct

<400> SEQUENCE: 544

Lys Asn Arg Ala Glu Met Ile Asp
1               5

<210> SEQ ID NO 545
<211> LENGTH: 8
<212> TYPE: PRT
<213> ORGANISM: Artificial Sequence
<220> FEATURE:
<223> OTHER INFORMATION: Synthetic construct

<400> SEQUENCE: 545

Phe Asn Ile Arg Ile Lys Asn Val
1               5

<210> SEQ ID NO 546
<211> LENGTH: 8
<212> TYPE: PRT
<213> ORGANISM: Artificial Sequence
<220> FEATURE:
<223> OTHER INFORMATION: Synthetic construct

<400> SEQUENCE: 546
```

Thr Arg Ser Asp Ala Gly Lys Tyr
1               5

<210> SEQ ID NO 547
<211> LENGTH: 8
<212> TYPE: PRT
<213> ORGANISM: Artificial Sequence
<220> FEATURE:
<223> OTHER INFORMATION: Synthetic construct

<400> SEQUENCE: 547

Arg Cys Glu Val Ser Ala Pro Ser
1               5

<210> SEQ ID NO 548
<211> LENGTH: 8
<212> TYPE: PRT
<213> ORGANISM: Artificial Sequence
<220> FEATURE:
<223> OTHER INFORMATION: Synthetic construct

<400> SEQUENCE: 548

Glu Gln Gly Gln Asn Leu Glu Glu
1               5

<210> SEQ ID NO 549
<211> LENGTH: 8
<212> TYPE: PRT
<213> ORGANISM: Artificial Sequence
<220> FEATURE:
<223> OTHER INFORMATION: Synthetic construct

<400> SEQUENCE: 549

Asp Thr Val Thr Leu Glu Val Leu
1               5

<210> SEQ ID NO 550
<211> LENGTH: 8
<212> TYPE: PRT
<213> ORGANISM: Artificial Sequence
<220> FEATURE:
<223> OTHER INFORMATION: Synthetic construct

<400> SEQUENCE: 550

Val Ala Pro Ala Val Pro Ser Cys
1               5

<210> SEQ ID NO 551
<211> LENGTH: 8
<212> TYPE: PRT
<213> ORGANISM: Artificial Sequence
<220> FEATURE:
<223> OTHER INFORMATION: Synthetic construct

<400> SEQUENCE: 551

Glu Val Pro Ser Ser Ala Leu Ser
1               5

<210> SEQ ID NO 552
<211> LENGTH: 8
<212> TYPE: PRT
<213> ORGANISM: Artificial Sequence
<220> FEATURE:
<223> OTHER INFORMATION: Synthetic construct

<400> SEQUENCE: 552

```
Gly Thr Val Val Glu Leu Arg Cys
1               5

<210> SEQ ID NO 553
<211> LENGTH: 8
<212> TYPE: PRT
<213> ORGANISM: Artificial Sequence
<220> FEATURE:
<223> OTHER INFORMATION: Synthetic construct

<400> SEQUENCE: 553

Gln Asp Lys Glu Gly Asn Pro Ala
1               5

<210> SEQ ID NO 554
<211> LENGTH: 8
<212> TYPE: PRT
<213> ORGANISM: Artificial Sequence
<220> FEATURE:
<223> OTHER INFORMATION: Synthetic construct

<400> SEQUENCE: 554

Pro Glu Tyr Thr Trp Phe Lys Asp
1               5

<210> SEQ ID NO 555
<211> LENGTH: 8
<212> TYPE: PRT
<213> ORGANISM: Artificial Sequence
<220> FEATURE:
<223> OTHER INFORMATION: Synthetic construct

<400> SEQUENCE: 555

Gly Ile Arg Leu Leu Glu Asn Pro
1               5

<210> SEQ ID NO 556
<211> LENGTH: 8
<212> TYPE: PRT
<213> ORGANISM: Artificial Sequence
<220> FEATURE:
<223> OTHER INFORMATION: Synthetic construct

<400> SEQUENCE: 556

Gly Ile Arg Leu Leu Glu Asn Pro
1               5

<210> SEQ ID NO 557
<211> LENGTH: 8
<212> TYPE: PRT
<213> ORGANISM: Artificial Sequence
<220> FEATURE:
<223> OTHER INFORMATION: Synthetic construct

<400> SEQUENCE: 557

Ser Ser Tyr Thr Met Asn Thr Lys
1               5

<210> SEQ ID NO 558
<211> LENGTH: 8
<212> TYPE: PRT
<213> ORGANISM: Artificial Sequence
<220> FEATURE:
<223> OTHER INFORMATION: Synthetic construct

<400> SEQUENCE: 558

Thr Gly Thr Leu Gln Phe Asn Thr
```

```
<210> SEQ ID NO 559
<211> LENGTH: 8
<212> TYPE: PRT
<213> ORGANISM: Artificial Sequence
<220> FEATURE:
<223> OTHER INFORMATION: Synthetic construct

<400> SEQUENCE: 559

Val Ser Lys Leu Asp Thr Gly Glu
1               5

<210> SEQ ID NO 560
<211> LENGTH: 8
<212> TYPE: PRT
<213> ORGANISM: Artificial Sequence
<220> FEATURE:
<223> OTHER INFORMATION: Synthetic construct

<400> SEQUENCE: 560

Tyr Ser Cys Glu Ala Arg Asn Ser
1               5

<210> SEQ ID NO 561
<211> LENGTH: 8
<212> TYPE: PRT
<213> ORGANISM: Artificial Sequence
<220> FEATURE:
<223> OTHER INFORMATION: Synthetic construct

<400> SEQUENCE: 561

Val Gly Tyr Arg Arg Cys Pro Gly
1               5

<210> SEQ ID NO 562
<211> LENGTH: 9
<212> TYPE: PRT
<213> ORGANISM: Artificial Sequence
<220> FEATURE:
<223> OTHER INFORMATION: Synthetic construct

<400> SEQUENCE: 562

Lys Arg Met Gln Val Asp Asp Leu Asn
1               5

<210> SEQ ID NO 563
<211> LENGTH: 4
<212> TYPE: PRT
<213> ORGANISM: Artificial Sequence
<220> FEATURE:
<223> OTHER INFORMATION: Synthetic construct

<400> SEQUENCE: 563

Gly Phe Ser Ala
1

<210> SEQ ID NO 564
<211> LENGTH: 8
<212> TYPE: PRT
<213> ORGANISM: Artificial Sequence
<220> FEATURE:
<223> OTHER INFORMATION: Synthetic construct

<400> SEQUENCE: 564

Pro Lys Asp Gln Gln Val Val Thr
1               5
```

<210> SEQ ID NO 565
<211> LENGTH: 8
<212> TYPE: PRT
<213> ORGANISM: Artificial Sequence
<220> FEATURE:
<223> OTHER INFORMATION: Synthetic construct

<400> SEQUENCE: 565

Ala Val Glu Tyr Gln Glu Ala Ile
1               5

<210> SEQ ID NO 566
<211> LENGTH: 8
<212> TYPE: PRT
<213> ORGANISM: Artificial Sequence
<220> FEATURE:
<223> OTHER INFORMATION: Synthetic construct

<400> SEQUENCE: 566

Leu Ala Cys Lys Thr Pro Lys Lys
1               5

<210> SEQ ID NO 567
<211> LENGTH: 8
<212> TYPE: PRT
<213> ORGANISM: Artificial Sequence
<220> FEATURE:
<223> OTHER INFORMATION: Synthetic construct

<400> SEQUENCE: 567

Thr Val Ser Ser Arg Leu Glu Trp
1               5

<210> SEQ ID NO 568
<211> LENGTH: 8
<212> TYPE: PRT
<213> ORGANISM: Artificial Sequence
<220> FEATURE:
<223> OTHER INFORMATION: Synthetic construct

<400> SEQUENCE: 568

Lys Lys Leu Gly Arg Ser Val Ser
1               5

<210> SEQ ID NO 569
<211> LENGTH: 8
<212> TYPE: PRT
<213> ORGANISM: Artificial Sequence
<220> FEATURE:
<223> OTHER INFORMATION: Synthetic construct

<400> SEQUENCE: 569

Phe Val Tyr Tyr Gln Gln Thr Leu
1               5

<210> SEQ ID NO 570
<211> LENGTH: 8
<212> TYPE: PRT
<213> ORGANISM: Artificial Sequence
<220> FEATURE:
<223> OTHER INFORMATION: Synthetic construct

<400> SEQUENCE: 570

Gln Gly Asp Phe Lys Asn Arg Ala
1               5

```
<210> SEQ ID NO 571
<211> LENGTH: 8
<212> TYPE: PRT
<213> ORGANISM: Artificial Sequence
<220> FEATURE:
<223> OTHER INFORMATION: Synthetic construct

<400> SEQUENCE: 571

Glu Met Ile Asp Phe Asn Ile Arg
1               5

<210> SEQ ID NO 572
<211> LENGTH: 8
<212> TYPE: PRT
<213> ORGANISM: Artificial Sequence
<220> FEATURE:
<223> OTHER INFORMATION: Synthetic construct

<400> SEQUENCE: 572

Ile Lys Asn Val Thr Arg Ser Asp
1               5

<210> SEQ ID NO 573
<211> LENGTH: 8
<212> TYPE: PRT
<213> ORGANISM: Artificial Sequence
<220> FEATURE:
<223> OTHER INFORMATION: Synthetic construct

<400> SEQUENCE: 573

Ala Gly Lys Tyr Arg Cys Glu Val
1               5

<210> SEQ ID NO 574
<211> LENGTH: 8
<212> TYPE: PRT
<213> ORGANISM: Artificial Sequence
<220> FEATURE:
<223> OTHER INFORMATION: Synthetic construct

<400> SEQUENCE: 574

Ser Ala Pro Ser Glu Gln Gly Gln
1               5

<210> SEQ ID NO 575
<211> LENGTH: 8
<212> TYPE: PRT
<213> ORGANISM: Artificial Sequence
<220> FEATURE:
<223> OTHER INFORMATION: Synthetic construct

<400> SEQUENCE: 575

Asn Leu Glu Glu Asp Thr Val Thr
1               5

<210> SEQ ID NO 576
<211> LENGTH: 8
<212> TYPE: PRT
<213> ORGANISM: Artificial Sequence
<220> FEATURE:
<223> OTHER INFORMATION: Synthetic construct

<400> SEQUENCE: 576

Leu Glu Val Leu Val Ala Pro Ala
1               5
```

```
<210> SEQ ID NO 577
<211> LENGTH: 8
<212> TYPE: PRT
<213> ORGANISM: Artificial Sequence
<220> FEATURE:
<223> OTHER INFORMATION: Synthetic construct

<400> SEQUENCE: 577

Val Pro Ser Cys Glu Val Pro Ser
1               5

<210> SEQ ID NO 578
<211> LENGTH: 8
<212> TYPE: PRT
<213> ORGANISM: Artificial Sequence
<220> FEATURE:
<223> OTHER INFORMATION: Synthetic construct

<400> SEQUENCE: 578

Ser Ala Leu Ser Gly Thr Val Val
1               5

<210> SEQ ID NO 579
<211> LENGTH: 8
<212> TYPE: PRT
<213> ORGANISM: Artificial Sequence
<220> FEATURE:
<223> OTHER INFORMATION: Synthetic construct

<400> SEQUENCE: 579

Glu Leu Arg Cys Gln Asp Lys Glu
1               5

<210> SEQ ID NO 580
<211> LENGTH: 8
<212> TYPE: PRT
<213> ORGANISM: Artificial Sequence
<220> FEATURE:
<223> OTHER INFORMATION: Synthetic construct

<400> SEQUENCE: 580

Gly Asn Pro Ala Pro Glu Tyr Thr
1               5

<210> SEQ ID NO 581
<211> LENGTH: 8
<212> TYPE: PRT
<213> ORGANISM: Artificial Sequence
<220> FEATURE:
<223> OTHER INFORMATION: Synthetic construct

<400> SEQUENCE: 581

Trp Phe Lys Asp Gly Ile Arg Leu
1               5

<210> SEQ ID NO 582
<211> LENGTH: 8
<212> TYPE: PRT
<213> ORGANISM: Artificial Sequence
<220> FEATURE:
<223> OTHER INFORMATION: Synthetic construct

<400> SEQUENCE: 582

Leu Glu Asn Pro Arg Leu Gly Ser
1               5

<210> SEQ ID NO 583
```

```
<211> LENGTH: 8
<212> TYPE: PRT
<213> ORGANISM: Artificial Sequence
<220> FEATURE:
<223> OTHER INFORMATION: Synthetic construct

<400> SEQUENCE: 583

Gln Ser Thr Asn Ser Ser Tyr Thr
1               5

<210> SEQ ID NO 584
<211> LENGTH: 8
<212> TYPE: PRT
<213> ORGANISM: Artificial Sequence
<220> FEATURE:
<223> OTHER INFORMATION: Synthetic construct

<400> SEQUENCE: 584

Met Asn Thr Lys Thr Gly Thr Leu
1               5

<210> SEQ ID NO 585
<211> LENGTH: 8
<212> TYPE: PRT
<213> ORGANISM: Artificial Sequence
<220> FEATURE:
<223> OTHER INFORMATION: Synthetic construct

<400> SEQUENCE: 585

Gln Phe Asn Thr Val Ser Lys Leu
1               5

<210> SEQ ID NO 586
<211> LENGTH: 8
<212> TYPE: PRT
<213> ORGANISM: Artificial Sequence
<220> FEATURE:
<223> OTHER INFORMATION: Synthetic construct

<400> SEQUENCE: 586

Asp Thr Gly Glu Tyr Ser Cys Glu
1               5

<210> SEQ ID NO 587
<211> LENGTH: 8
<212> TYPE: PRT
<213> ORGANISM: Artificial Sequence
<220> FEATURE:
<223> OTHER INFORMATION: Synthetic construct

<400> SEQUENCE: 587

Ala Arg Asn Ser Val Gly Tyr Arg
1               5

<210> SEQ ID NO 588
<211> LENGTH: 8
<212> TYPE: PRT
<213> ORGANISM: Artificial Sequence
<220> FEATURE:
<223> OTHER INFORMATION: Synthetic construct

<400> SEQUENCE: 588

Arg Cys Pro Gly Lys Arg Met Gln
1               5

<210> SEQ ID NO 589
<211> LENGTH: 5
```

```
<212> TYPE: PRT
<213> ORGANISM: Artificial Sequence
<220> FEATURE:
<223> OTHER INFORMATION: Synthetic construct

<400> SEQUENCE: 589

Val Asp Asp Leu Asn
1               5

<210> SEQ ID NO 590
<211> LENGTH: 10
<212> TYPE: PRT
<213> ORGANISM: Artificial Sequence
<220> FEATURE:
<223> OTHER INFORMATION: Synthetic construct

<400> SEQUENCE: 590

Arg Ile Tyr Ser Tyr Ala Gly Asp Asn Ile
1               5                   10

<210> SEQ ID NO 591
<211> LENGTH: 10
<212> TYPE: PRT
<213> ORGANISM: Artificial Sequence
<220> FEATURE:
<223> OTHER INFORMATION: Synthetic construct

<400> SEQUENCE: 591

Val Thr Ala Gln Ala Met Tyr Glu Gly Leu
1               5                   10

<210> SEQ ID NO 592
<211> LENGTH: 10
<212> TYPE: PRT
<213> ORGANISM: Artificial Sequence
<220> FEATURE:
<223> OTHER INFORMATION: Synthetic construct

<400> SEQUENCE: 592

Trp Met Ser Cys Val Ser Gln Ser Thr Gly
1               5                   10

<210> SEQ ID NO 593
<211> LENGTH: 10
<212> TYPE: PRT
<213> ORGANISM: Artificial Sequence
<220> FEATURE:
<223> OTHER INFORMATION: Synthetic construct

<400> SEQUENCE: 593

Gln Ile Gln Cys Lys Val Phe Asp Ser Leu
1               5                   10

<210> SEQ ID NO 594
<211> LENGTH: 10
<212> TYPE: PRT
<213> ORGANISM: Artificial Sequence
<220> FEATURE:
<223> OTHER INFORMATION: Synthetic construct

<400> SEQUENCE: 594

Gln Ile Gln Cys Lys Val Phe Asp Ser Leu
1               5                   10

<210> SEQ ID NO 595
<211> LENGTH: 5
<212> TYPE: PRT
```

```
<213> ORGANISM: Artificial Sequence
<220> FEATURE:
<223> OTHER INFORMATION: Synthetic construct

<400> SEQUENCE: 595

Arg Ile Tyr Ser Tyr
1               5

<210> SEQ ID NO 596
<211> LENGTH: 10
<212> TYPE: PRT
<213> ORGANISM: Artificial Sequence
<220> FEATURE:
<223> OTHER INFORMATION: Synthetic construct

<400> SEQUENCE: 596

Ala Gly Asp Asn Ile Val Thr Ala Gln Ala
1               5                   10

<210> SEQ ID NO 597
<211> LENGTH: 10
<212> TYPE: PRT
<213> ORGANISM: Artificial Sequence
<220> FEATURE:
<223> OTHER INFORMATION: Synthetic construct

<400> SEQUENCE: 597

Met Tyr Glu Gly Leu Trp Met Ser Cys Val
1               5                   10

<210> SEQ ID NO 598
<211> LENGTH: 10
<212> TYPE: PRT
<213> ORGANISM: Artificial Sequence
<220> FEATURE:
<223> OTHER INFORMATION: Synthetic construct

<400> SEQUENCE: 598

Ser Gln Ser Thr Gly Gln Ile Gln Cys Lys
1               5                   10

<210> SEQ ID NO 599
<211> LENGTH: 10
<212> TYPE: PRT
<213> ORGANISM: Artificial Sequence
<220> FEATURE:
<223> OTHER INFORMATION: Synthetic construct

<400> SEQUENCE: 599

Val Phe Asp Ser Leu Leu Asn Leu Ser Ser
1               5                   10

<210> SEQ ID NO 600
<211> LENGTH: 6
<212> TYPE: PRT
<213> ORGANISM: Artificial Sequence
<220> FEATURE:
<223> OTHER INFORMATION: Synthetic construct

<400> SEQUENCE: 600

Thr Leu Gln Ala Thr Arg
1               5

<210> SEQ ID NO 601
<211> LENGTH: 8
<212> TYPE: PRT
<213> ORGANISM: Artificial Sequence
```

```
<220> FEATURE:
<223> OTHER INFORMATION: Synthetic construct

<400> SEQUENCE: 601

Gln Glu Phe Tyr Asp Pro Met Thr
1               5

<210> SEQ ID NO 602
<211> LENGTH: 7
<212> TYPE: PRT
<213> ORGANISM: Artificial Sequence
<220> FEATURE:
<223> OTHER INFORMATION: Synthetic construct

<400> SEQUENCE: 602

Pro Val Asn Ala Arg Tyr Glu
1               5

<210> SEQ ID NO 603
<211> LENGTH: 11
<212> TYPE: PRT
<213> ORGANISM: Artificial Sequence
<220> FEATURE:
<223> OTHER INFORMATION: Synthetic construct

<400> SEQUENCE: 603

Gln Glu Phe Tyr Asp Pro Met Thr Pro Val Asn
1               5                   10

<210> SEQ ID NO 604
<211> LENGTH: 4
<212> TYPE: PRT
<213> ORGANISM: Artificial Sequence
<220> FEATURE:
<223> OTHER INFORMATION: Synthetic construct

<400> SEQUENCE: 604

Ala Arg Tyr Glu
1

<210> SEQ ID NO 605
<211> LENGTH: 10
<212> TYPE: PRT
<213> ORGANISM: Artificial Sequence
<220> FEATURE:
<223> OTHER INFORMATION: Synthetic construct

<400> SEQUENCE: 605

Lys Thr Ser Ser Tyr Val Gly Ala Ser Ile
1               5                   10

<210> SEQ ID NO 606
<211> LENGTH: 10
<212> TYPE: PRT
<213> ORGANISM: Artificial Sequence
<220> FEATURE:
<223> OTHER INFORMATION: Synthetic construct

<400> SEQUENCE: 606

Val Thr Ala Val Gly Phe Ser Lys Gly Leu
1               5                   10

<210> SEQ ID NO 607
<211> LENGTH: 10
<212> TYPE: PRT
<213> ORGANISM: Artificial Sequence
<220> FEATURE:
```

-continued

<223> OTHER INFORMATION: Synthetic construct

<400> SEQUENCE: 607

Trp Met Glu Cys Ala Thr His Ser Thr Gly
1               5                   10

<210> SEQ ID NO 608
<211> LENGTH: 10
<212> TYPE: PRT
<213> ORGANISM: Artificial Sequence
<220> FEATURE:
<223> OTHER INFORMATION: Synthetic construct

<400> SEQUENCE: 608

Ile Thr Gln Cys Asp Ile Tyr Ser Thr Leu
1               5                   10

<210> SEQ ID NO 609
<211> LENGTH: 11
<212> TYPE: PRT
<213> ORGANISM: Artificial Sequence
<220> FEATURE:
<223> OTHER INFORMATION: Synthetic construct

<400> SEQUENCE: 609

Leu Gly Leu Pro Ala Asp Ile Gln Ala Ala Gln
1               5                   10

<210> SEQ ID NO 610
<211> LENGTH: 5
<212> TYPE: PRT
<213> ORGANISM: Artificial Sequence
<220> FEATURE:
<223> OTHER INFORMATION: Synthetic construct

<400> SEQUENCE: 610

Lys Thr Ser Ser Tyr
1               5

<210> SEQ ID NO 611
<211> LENGTH: 10
<212> TYPE: PRT
<213> ORGANISM: Artificial Sequence
<220> FEATURE:
<223> OTHER INFORMATION: Synthetic construct

<400> SEQUENCE: 611

Val Gly Ala Ser Ile Val Thr Ala Val Gly
1               5                   10

<210> SEQ ID NO 612
<211> LENGTH: 10
<212> TYPE: PRT
<213> ORGANISM: Artificial Sequence
<220> FEATURE:
<223> OTHER INFORMATION: Synthetic construct

<400> SEQUENCE: 612

Phe Ser Lys Gly Leu Trp Met Glu Cys Ala
1               5                   10

<210> SEQ ID NO 613
<211> LENGTH: 10
<212> TYPE: PRT
<213> ORGANISM: Artificial Sequence
<220> FEATURE:
<223> OTHER INFORMATION: Synthetic construct

<400> SEQUENCE: 613

Thr His Ser Thr Gly Ile Thr Gln Cys Asp
1               5                   10

<210> SEQ ID NO 614
<211> LENGTH: 10
<212> TYPE: PRT
<213> ORGANISM: Artificial Sequence
<220> FEATURE:
<223> OTHER INFORMATION: Synthetic construct

<400> SEQUENCE: 614

Ile Tyr Ser Thr Leu Leu Gly Leu Pro Ala
1               5                   10

<210> SEQ ID NO 615
<211> LENGTH: 6
<212> TYPE: PRT
<213> ORGANISM: Artificial Sequence
<220> FEATURE:
<223> OTHER INFORMATION: Synthetic construct

<400> SEQUENCE: 615

Asp Ile Gln Ala Ala Gln
1               5

<210> SEQ ID NO 616
<211> LENGTH: 7
<212> TYPE: PRT
<213> ORGANISM: Artificial Sequence
<220> FEATURE:
<223> OTHER INFORMATION: Synthetic construct

<400> SEQUENCE: 616

Arg Asp Phe Tyr Ser Pro Leu
1               5

<210> SEQ ID NO 617
<211> LENGTH: 10
<212> TYPE: PRT
<213> ORGANISM: Artificial Sequence
<220> FEATURE:
<223> OTHER INFORMATION: Synthetic construct

<400> SEQUENCE: 617

Arg Val Ser Ala Phe Ile Gly Ser Asn Ile
1               5                   10

<210> SEQ ID NO 618
<211> LENGTH: 10
<212> TYPE: PRT
<213> ORGANISM: Artificial Sequence
<220> FEATURE:
<223> OTHER INFORMATION: Synthetic construct

<400> SEQUENCE: 618

Ile Thr Ser Gln Asn Ile Trp Glu Gly Leu
1               5                   10

<210> SEQ ID NO 619
<211> LENGTH: 10
<212> TYPE: PRT
<213> ORGANISM: Artificial Sequence
<220> FEATURE:
<223> OTHER INFORMATION: Synthetic construct

```
<400> SEQUENCE: 619

Trp Met Asn Cys Val Val Gln Ser Thr Gly
1               5                   10

<210> SEQ ID NO 620
<211> LENGTH: 10
<212> TYPE: PRT
<213> ORGANISM: Artificial Sequence
<220> FEATURE:
<223> OTHER INFORMATION: Synthetic construct

<400> SEQUENCE: 620

Gln Met Gln Cys Lys Val Tyr Asp Ser Leu
1               5                   10

<210> SEQ ID NO 621
<211> LENGTH: 11
<212> TYPE: PRT
<213> ORGANISM: Artificial Sequence
<220> FEATURE:
<223> OTHER INFORMATION: Synthetic construct

<400> SEQUENCE: 621

Leu Ala Leu Pro Gln Asp Leu Gln Ala Ala Arg
1               5                   10

<210> SEQ ID NO 622
<211> LENGTH: 5
<212> TYPE: PRT
<213> ORGANISM: Artificial Sequence
<220> FEATURE:
<223> OTHER INFORMATION: Synthetic construct

<400> SEQUENCE: 622

Arg Val Ser Ala Phe
1               5

<210> SEQ ID NO 623
<211> LENGTH: 10
<212> TYPE: PRT
<213> ORGANISM: Artificial Sequence
<220> FEATURE:
<223> OTHER INFORMATION: Synthetic construct

<400> SEQUENCE: 623

Ile Gly Ser Asn Ile Ile Thr Ser Gln Asn
1               5                   10

<210> SEQ ID NO 624
<211> LENGTH: 10
<212> TYPE: PRT
<213> ORGANISM: Artificial Sequence
<220> FEATURE:
<223> OTHER INFORMATION: Synthetic construct

<400> SEQUENCE: 624

Ile Trp Glu Gly Leu Trp Met Asn Cys Val
1               5                   10

<210> SEQ ID NO 625
<211> LENGTH: 10
<212> TYPE: PRT
<213> ORGANISM: Artificial Sequence
<220> FEATURE:
<223> OTHER INFORMATION: Synthetic construct

<400> SEQUENCE: 625
```

Val Gln Ser Thr Gly Gln Met Gln Cys Lys
1               5                   10

<210> SEQ ID NO 626
<211> LENGTH: 10
<212> TYPE: PRT
<213> ORGANISM: Artificial Sequence
<220> FEATURE:
<223> OTHER INFORMATION: Synthetic construct

<400> SEQUENCE: 626

Val Tyr Asp Ser Leu Leu Ala Leu Pro Gln
1               5                   10

<210> SEQ ID NO 627
<211> LENGTH: 6
<212> TYPE: PRT
<213> ORGANISM: Artificial Sequence
<220> FEATURE:
<223> OTHER INFORMATION: Synthetic construct

<400> SEQUENCE: 627

Asp Leu Gln Ala Ala Arg
1               5

<210> SEQ ID NO 628
<211> LENGTH: 8
<212> TYPE: PRT
<213> ORGANISM: Artificial Sequence
<220> FEATURE:
<223> OTHER INFORMATION: Synthetic construct

<400> SEQUENCE: 628

Arg Asp Phe Tyr Asn Pro Val Val
1               5

<210> SEQ ID NO 629
<211> LENGTH: 7
<212> TYPE: PRT
<213> ORGANISM: Artificial Sequence
<220> FEATURE:
<223> OTHER INFORMATION: Synthetic construct

<400> SEQUENCE: 629

Pro Glu Ala Gln Lys Arg Glu
1               5

<210> SEQ ID NO 630
<211> LENGTH: 10
<212> TYPE: PRT
<213> ORGANISM: Artificial Sequence
<220> FEATURE:
<223> OTHER INFORMATION: Synthetic construct

<400> SEQUENCE: 630

Arg Val Thr Ala Phe Ile Gly Ser Asn Ile
1               5                   10

<210> SEQ ID NO 631
<211> LENGTH: 10
<212> TYPE: PRT
<213> ORGANISM: Artificial Sequence
<220> FEATURE:
<223> OTHER INFORMATION: Synthetic construct

<400> SEQUENCE: 631

```
Val Thr Ser Gln Thr Ile Trp Glu Gly Leu
1               5                   10

<210> SEQ ID NO 632
<211> LENGTH: 10
<212> TYPE: PRT
<213> ORGANISM: Artificial Sequence
<220> FEATURE:
<223> OTHER INFORMATION: Synthetic construct

<400> SEQUENCE: 632

Trp Met Asn Cys Val Val Gln Ser Thr Gly
1               5                   10

<210> SEQ ID NO 633
<211> LENGTH: 10
<212> TYPE: PRT
<213> ORGANISM: Artificial Sequence
<220> FEATURE:
<223> OTHER INFORMATION: Synthetic construct

<400> SEQUENCE: 633

Gln Met Gln Cys Lys Val Tyr Asp Ser Leu
1               5                   10

<210> SEQ ID NO 634
<211> LENGTH: 11
<212> TYPE: PRT
<213> ORGANISM: Artificial Sequence
<220> FEATURE:
<223> OTHER INFORMATION: Synthetic construct

<400> SEQUENCE: 634

Leu Ala Leu Pro Gln Asp Leu Gln Ala Ala Arg
1               5                   10

<210> SEQ ID NO 635
<211> LENGTH: 5
<212> TYPE: PRT
<213> ORGANISM: Artificial Sequence
<220> FEATURE:
<223> OTHER INFORMATION: Synthetic construct

<400> SEQUENCE: 635

Arg Val Thr Ala Phe
1               5

<210> SEQ ID NO 636
<211> LENGTH: 10
<212> TYPE: PRT
<213> ORGANISM: Artificial Sequence
<220> FEATURE:
<223> OTHER INFORMATION: Synthetic construct

<400> SEQUENCE: 636

Ile Gly Ser Asn Ile Val Thr Ser Gln Thr
1               5                   10

<210> SEQ ID NO 637
<211> LENGTH: 10
<212> TYPE: PRT
<213> ORGANISM: Artificial Sequence
<220> FEATURE:
<223> OTHER INFORMATION: Synthetic construct

<400> SEQUENCE: 637

Ile Trp Glu Gly Leu Trp Met Asn Cys Val
```

-continued

```
1               5                   10

<210> SEQ ID NO 638
<211> LENGTH: 10
<212> TYPE: PRT
<213> ORGANISM: Artificial Sequence
<220> FEATURE:
<223> OTHER INFORMATION: Synthetic construct

<400> SEQUENCE: 638

Val Gln Ser Thr Gly Gln Met Gln Cys Lys
1               5                   10

<210> SEQ ID NO 639
<211> LENGTH: 10
<212> TYPE: PRT
<213> ORGANISM: Artificial Sequence
<220> FEATURE:
<223> OTHER INFORMATION: Synthetic construct

<400> SEQUENCE: 639

Val Tyr Asp Ser Leu Leu Ala Leu Pro Gln
1               5                   10

<210> SEQ ID NO 640
<211> LENGTH: 6
<212> TYPE: PRT
<213> ORGANISM: Artificial Sequence
<220> FEATURE:
<223> OTHER INFORMATION: Synthetic construct

<400> SEQUENCE: 640

Asp Leu Gln Ala Ala Arg
1               5

<210> SEQ ID NO 641
<211> LENGTH: 8
<212> TYPE: PRT
<213> ORGANISM: Artificial Sequence
<220> FEATURE:
<223> OTHER INFORMATION: Synthetic construct

<400> SEQUENCE: 641

Gln Asp Phe Tyr Asn Pro Leu Val
1               5

<210> SEQ ID NO 642
<211> LENGTH: 7
<212> TYPE: PRT
<213> ORGANISM: Artificial Sequence
<220> FEATURE:
<223> OTHER INFORMATION: Synthetic construct

<400> SEQUENCE: 642

Ala Ser Gly Gln Lys Arg Glu
1               5

<210> SEQ ID NO 643
<211> LENGTH: 10
<212> TYPE: PRT
<213> ORGANISM: Artificial Sequence
<220> FEATURE:
<223> OTHER INFORMATION: Synthetic construct

<400> SEQUENCE: 643

Gln Val Thr Ala Phe Leu Asp His Asn Ile
1               5                   10
```

<210> SEQ ID NO 644
<211> LENGTH: 10
<212> TYPE: PRT
<213> ORGANISM: Artificial Sequence
<220> FEATURE:
<223> OTHER INFORMATION: Synthetic construct

<400> SEQUENCE: 644

Val Thr Ala Gln Thr Thr Trp Lys Gly Leu
1               5                   10

<210> SEQ ID NO 645
<211> LENGTH: 10
<212> TYPE: PRT
<213> ORGANISM: Artificial Sequence
<220> FEATURE:
<223> OTHER INFORMATION: Synthetic construct

<400> SEQUENCE: 645

Trp Met Ser Cys Val Val Gln Ser Thr Gly
1               5                   10

<210> SEQ ID NO 646
<211> LENGTH: 10
<212> TYPE: PRT
<213> ORGANISM: Artificial Sequence
<220> FEATURE:
<223> OTHER INFORMATION: Synthetic construct

<400> SEQUENCE: 646

His Met Gln Cys Lys Val Tyr Asp Ser Val
1               5                   10

<210> SEQ ID NO 647
<211> LENGTH: 11
<212> TYPE: PRT
<213> ORGANISM: Artificial Sequence
<220> FEATURE:
<223> OTHER INFORMATION: Synthetic construct

<400> SEQUENCE: 647

Leu Ala Leu Ser Thr Glu Val Gln Ala Ala Arg
1               5                   10

<210> SEQ ID NO 648
<211> LENGTH: 5
<212> TYPE: PRT
<213> ORGANISM: Artificial Sequence
<220> FEATURE:
<223> OTHER INFORMATION: Synthetic construct

<400> SEQUENCE: 648

Gln Val Thr Ala Phe
1               5

<210> SEQ ID NO 649
<211> LENGTH: 10
<212> TYPE: PRT
<213> ORGANISM: Artificial Sequence
<220> FEATURE:
<223> OTHER INFORMATION: Synthetic construct

<400> SEQUENCE: 649

Leu Asp His Asn Ile Val Thr Ala Gln Thr
1               5                   10

```
<210> SEQ ID NO 650
<211> LENGTH: 10
<212> TYPE: PRT
<213> ORGANISM: Artificial Sequence
<220> FEATURE:
<223> OTHER INFORMATION: Synthetic construct

<400> SEQUENCE: 650

Thr Trp Lys Gly Leu Trp Met Ser Cys Val
1               5                   10

<210> SEQ ID NO 651
<211> LENGTH: 10
<212> TYPE: PRT
<213> ORGANISM: Artificial Sequence
<220> FEATURE:
<223> OTHER INFORMATION: Synthetic construct

<400> SEQUENCE: 651

Val Gln Ser Thr Gly His Met Gln Cys Lys
1               5                   10

<210> SEQ ID NO 652
<211> LENGTH: 10
<212> TYPE: PRT
<213> ORGANISM: Artificial Sequence
<220> FEATURE:
<223> OTHER INFORMATION: Synthetic construct

<400> SEQUENCE: 652

Val Tyr Asp Ser Val Leu Ala Leu Ser Thr
1               5                   10

<210> SEQ ID NO 653
<211> LENGTH: 6
<212> TYPE: PRT
<213> ORGANISM: Artificial Sequence
<220> FEATURE:
<223> OTHER INFORMATION: Synthetic construct

<400> SEQUENCE: 653

Glu Val Gln Ala Ala Arg
1               5

<210> SEQ ID NO 654
<211> LENGTH: 8
<212> TYPE: PRT
<213> ORGANISM: Artificial Sequence
<220> FEATURE:
<223> OTHER INFORMATION: Synthetic construct

<400> SEQUENCE: 654

Arg Glu Phe Tyr Asp Pro Ser Val
1               5

<210> SEQ ID NO 655
<211> LENGTH: 10
<212> TYPE: PRT
<213> ORGANISM: Artificial Sequence
<220> FEATURE:
<223> OTHER INFORMATION: Synthetic construct

<400> SEQUENCE: 655

Lys Val Thr Ala Phe Ile Gly Asn Ser Ile
1               5                   10
```

```
<210> SEQ ID NO 656
<211> LENGTH: 10
<212> TYPE: PRT
<213> ORGANISM: Artificial Sequence
<220> FEATURE:
<223> OTHER INFORMATION: Synthetic construct

<400> SEQUENCE: 656

Val Val Ala Gln Val Val Trp Glu Gly Leu
1               5                   10

<210> SEQ ID NO 657
<211> LENGTH: 10
<212> TYPE: PRT
<213> ORGANISM: Artificial Sequence
<220> FEATURE:
<223> OTHER INFORMATION: Synthetic construct

<400> SEQUENCE: 657

Trp Met Ser Cys Val Val Gln Ser Thr Gly
1               5                   10

<210> SEQ ID NO 658
<211> LENGTH: 10
<212> TYPE: PRT
<213> ORGANISM: Artificial Sequence
<220> FEATURE:
<223> OTHER INFORMATION: Synthetic construct

<400> SEQUENCE: 658

Gln Met Gln Cys Lys Val Tyr Asp Ser Leu
1               5                   10

<210> SEQ ID NO 659
<211> LENGTH: 11
<212> TYPE: PRT
<213> ORGANISM: Artificial Sequence
<220> FEATURE:
<223> OTHER INFORMATION: Synthetic construct

<400> SEQUENCE: 659

Leu Ala Leu Pro Gln Asp Leu Gln Ala Ala Arg
1               5                   10

<210> SEQ ID NO 660
<211> LENGTH: 5
<212> TYPE: PRT
<213> ORGANISM: Artificial Sequence
<220> FEATURE:
<223> OTHER INFORMATION: Synthetic construct

<400> SEQUENCE: 660

Lys Val Thr Ala Phe
1               5

<210> SEQ ID NO 661
<211> LENGTH: 10
<212> TYPE: PRT
<213> ORGANISM: Artificial Sequence
<220> FEATURE:
<223> OTHER INFORMATION: Synthetic construct

<400> SEQUENCE: 661

Ile Gly Asn Ser Ile Val Val Ala Gln Val
1               5                   10

<210> SEQ ID NO 662
```

```
<211> LENGTH: 10
<212> TYPE: PRT
<213> ORGANISM: Artificial Sequence
<220> FEATURE:
<223> OTHER INFORMATION: Synthetic construct

<400> SEQUENCE: 662

Val Trp Glu Gly Leu Trp Met Ser Cys Val
1               5                   10

<210> SEQ ID NO 663
<211> LENGTH: 10
<212> TYPE: PRT
<213> ORGANISM: Artificial Sequence
<220> FEATURE:
<223> OTHER INFORMATION: Synthetic construct

<400> SEQUENCE: 663

Val Gln Ser Thr Gly Gln Met Gln Cys Lys
1               5                   10

<210> SEQ ID NO 664
<211> LENGTH: 10
<212> TYPE: PRT
<213> ORGANISM: Artificial Sequence
<220> FEATURE:
<223> OTHER INFORMATION: Synthetic construct

<400> SEQUENCE: 664

Val Tyr Asp Ser Leu Leu Ala Leu Pro Gln
1               5                   10

<210> SEQ ID NO 665
<211> LENGTH: 6
<212> TYPE: PRT
<213> ORGANISM: Artificial Sequence
<220> FEATURE:
<223> OTHER INFORMATION: Synthetic construct

<400> SEQUENCE: 665

Asp Leu Gln Ala Ala Arg
1               5

<210> SEQ ID NO 666
<211> LENGTH: 8
<212> TYPE: PRT
<213> ORGANISM: Artificial Sequence
<220> FEATURE:
<223> OTHER INFORMATION: Synthetic construct

<400> SEQUENCE: 666

Arg Asp Phe Tyr Asn Pro Leu Val
1               5

<210> SEQ ID NO 667
<211> LENGTH: 7
<212> TYPE: PRT
<213> ORGANISM: Artificial Sequence
<220> FEATURE:
<223> OTHER INFORMATION: Synthetic construct

<400> SEQUENCE: 667

Ala Glu Ala Gln Lys Arg Glu
1               5

<210> SEQ ID NO 668
<211> LENGTH: 10
```

```
<212> TYPE: PRT
<213> ORGANISM: Artificial Sequence
<220> FEATURE:
<223> OTHER INFORMATION: Synthetic construct

<400> SEQUENCE: 668

Gln Met Ser Ser Tyr Ala Gly Asp Asn Ile
1               5                   10

<210> SEQ ID NO 669
<211> LENGTH: 10
<212> TYPE: PRT
<213> ORGANISM: Artificial Sequence
<220> FEATURE:
<223> OTHER INFORMATION: Synthetic construct

<400> SEQUENCE: 669

Ile Thr Ala Gln Ala Met Tyr Lys Gly Leu
1               5                   10

<210> SEQ ID NO 670
<211> LENGTH: 10
<212> TYPE: PRT
<213> ORGANISM: Artificial Sequence
<220> FEATURE:
<223> OTHER INFORMATION: Synthetic construct

<400> SEQUENCE: 670

Trp Met Asp Cys Val Thr Gln Ser Thr Gly
1               5                   10

<210> SEQ ID NO 671
<211> LENGTH: 10
<212> TYPE: PRT
<213> ORGANISM: Artificial Sequence
<220> FEATURE:
<223> OTHER INFORMATION: Synthetic construct

<400> SEQUENCE: 671

Met Met Ser Cys Lys Met Tyr Asp Ser Val
1               5                   10

<210> SEQ ID NO 672
<211> LENGTH: 11
<212> TYPE: PRT
<213> ORGANISM: Artificial Sequence
<220> FEATURE:
<223> OTHER INFORMATION: Synthetic construct

<400> SEQUENCE: 672

Leu Ala Leu Ser Ala Ala Leu Gln Ala Thr Arg
1               5                   10

<210> SEQ ID NO 673
<211> LENGTH: 5
<212> TYPE: PRT
<213> ORGANISM: Artificial Sequence
<220> FEATURE:
<223> OTHER INFORMATION: Synthetic construct

<400> SEQUENCE: 673

Gln Met Ser Ser Tyr
1               5

<210> SEQ ID NO 674
<211> LENGTH: 10
<212> TYPE: PRT
```

```
<213> ORGANISM: Artificial Sequence
<220> FEATURE:
<223> OTHER INFORMATION: Synthetic construct

<400> SEQUENCE: 674

Ala Gly Asp Asn Ile Ile Thr Ala Gln Ala
1               5                   10

<210> SEQ ID NO 675
<211> LENGTH: 10
<212> TYPE: PRT
<213> ORGANISM: Artificial Sequence
<220> FEATURE:
<223> OTHER INFORMATION: Synthetic construct

<400> SEQUENCE: 675

Met Tyr Lys Gly Leu Trp Met Asp Cys Val
1               5                   10

<210> SEQ ID NO 676
<211> LENGTH: 10
<212> TYPE: PRT
<213> ORGANISM: Artificial Sequence
<220> FEATURE:
<223> OTHER INFORMATION: Synthetic construct

<400> SEQUENCE: 676

Thr Gln Ser Thr Gly Met Met Ser Cys Lys
1               5                   10

<210> SEQ ID NO 677
<211> LENGTH: 10
<212> TYPE: PRT
<213> ORGANISM: Artificial Sequence
<220> FEATURE:
<223> OTHER INFORMATION: Synthetic construct

<400> SEQUENCE: 677

Met Tyr Asp Ser Val Leu Ala Leu Ser Ala
1               5                   10

<210> SEQ ID NO 678
<211> LENGTH: 6
<212> TYPE: PRT
<213> ORGANISM: Artificial Sequence
<220> FEATURE:
<223> OTHER INFORMATION: Synthetic construct

<400> SEQUENCE: 678

Ala Leu Gln Ala Thr Arg
1               5

<210> SEQ ID NO 679
<211> LENGTH: 8
<212> TYPE: PRT
<213> ORGANISM: Artificial Sequence
<220> FEATURE:
<223> OTHER INFORMATION: Synthetic construct

<400> SEQUENCE: 679

Thr Asp Phe Tyr Asn Pro Leu Ile
1               5

<210> SEQ ID NO 680
<211> LENGTH: 7
<212> TYPE: PRT
<213> ORGANISM: Artificial Sequence
```

```
<220> FEATURE:
<223> OTHER INFORMATION: Synthetic construct

<400> SEQUENCE: 680

Pro Thr Asn Ile Lys Tyr Glu
1               5

<210> SEQ ID NO 681
<211> LENGTH: 10
<212> TYPE: PRT
<213> ORGANISM: Artificial Sequence
<220> FEATURE:
<223> OTHER INFORMATION: Synthetic construct

<400> SEQUENCE: 681

Arg Val Ser Ala Phe Ile Glu Asn Asn Ile
1               5                   10

<210> SEQ ID NO 682
<211> LENGTH: 10
<212> TYPE: PRT
<213> ORGANISM: Artificial Sequence
<220> FEATURE:
<223> OTHER INFORMATION: Synthetic construct

<400> SEQUENCE: 682

Val Val Phe Glu Asn Phe Trp Glu Gly Leu
1               5                   10

<210> SEQ ID NO 683
<211> LENGTH: 10
<212> TYPE: PRT
<213> ORGANISM: Artificial Sequence
<220> FEATURE:
<223> OTHER INFORMATION: Synthetic construct

<400> SEQUENCE: 683

Trp Met Asn Cys Val Arg Gln Ala Asn Ile
1               5                   10

<210> SEQ ID NO 684
<211> LENGTH: 10
<212> TYPE: PRT
<213> ORGANISM: Artificial Sequence
<220> FEATURE:
<223> OTHER INFORMATION: Synthetic construct

<400> SEQUENCE: 684

Arg Met Gln Cys Lys Ile Tyr Asp Ser Leu
1               5                   10

<210> SEQ ID NO 685
<211> LENGTH: 11
<212> TYPE: PRT
<213> ORGANISM: Artificial Sequence
<220> FEATURE:
<223> OTHER INFORMATION: Synthetic construct

<400> SEQUENCE: 685

Leu Ala Leu Ser Pro Asp Leu Gln Ala Ala Arg
1               5                   10

<210> SEQ ID NO 686
<211> LENGTH: 5
<212> TYPE: PRT
<213> ORGANISM: Artificial Sequence
<220> FEATURE:
```

-continued

<223> OTHER INFORMATION: Synthetic construct

<400> SEQUENCE: 686

Arg Val Ser Ala Phe
1               5

<210> SEQ ID NO 687
<211> LENGTH: 10
<212> TYPE: PRT
<213> ORGANISM: Artificial Sequence
<220> FEATURE:
<223> OTHER INFORMATION: Synthetic construct

<400> SEQUENCE: 687

Ile Glu Asn Asn Ile Val Val Phe Glu Asn
1               5                   10

<210> SEQ ID NO 688
<211> LENGTH: 10
<212> TYPE: PRT
<213> ORGANISM: Artificial Sequence
<220> FEATURE:
<223> OTHER INFORMATION: Synthetic construct

<400> SEQUENCE: 688

Phe Trp Glu Gly Leu Trp Met Asn Cys Val
1               5                   10

<210> SEQ ID NO 689
<211> LENGTH: 10
<212> TYPE: PRT
<213> ORGANISM: Artificial Sequence
<220> FEATURE:
<223> OTHER INFORMATION: Synthetic construct

<400> SEQUENCE: 689

Arg Gln Ala Asn Ile Arg Met Gln Cys Lys
1               5                   10

<210> SEQ ID NO 690
<211> LENGTH: 10
<212> TYPE: PRT
<213> ORGANISM: Artificial Sequence
<220> FEATURE:
<223> OTHER INFORMATION: Synthetic construct

<400> SEQUENCE: 690

Ile Tyr Asp Ser Leu Leu Ala Leu Ser Pro
1               5                   10

<210> SEQ ID NO 691
<211> LENGTH: 6
<212> TYPE: PRT
<213> ORGANISM: Artificial Sequence
<220> FEATURE:
<223> OTHER INFORMATION: Synthetic construct

<400> SEQUENCE: 691

Asp Leu Gln Ala Ala Arg
1               5

<210> SEQ ID NO 692
<211> LENGTH: 8
<212> TYPE: PRT
<213> ORGANISM: Artificial Sequence
<220> FEATURE:
<223> OTHER INFORMATION: Synthetic construct

```
<400> SEQUENCE: 692

Arg Asp Phe Tyr Asn Ser Ile Val
1               5

<210> SEQ ID NO 693
<211> LENGTH: 7
<212> TYPE: PRT
<213> ORGANISM: Artificial Sequence
<220> FEATURE:
<223> OTHER INFORMATION: Synthetic construct

<400> SEQUENCE: 693

Asn Val Ala Gln Lys Arg Glu
1               5

<210> SEQ ID NO 694
<211> LENGTH: 10
<212> TYPE: PRT
<213> ORGANISM: Artificial Sequence
<220> FEATURE:
<223> OTHER INFORMATION: Synthetic construct

<400> SEQUENCE: 694

Lys Val Thr Ala Phe Ile Gly Asn Ser Ile
1               5                   10

<210> SEQ ID NO 695
<211> LENGTH: 10
<212> TYPE: PRT
<213> ORGANISM: Artificial Sequence
<220> FEATURE:
<223> OTHER INFORMATION: Synthetic construct

<400> SEQUENCE: 695

Val Val Ala Gln Val Val Trp Glu Gly Leu
1               5                   10

<210> SEQ ID NO 696
<211> LENGTH: 10
<212> TYPE: PRT
<213> ORGANISM: Artificial Sequence
<220> FEATURE:
<223> OTHER INFORMATION: Synthetic construct

<400> SEQUENCE: 696

Trp Met Ser Cys Val Val Gln Ser Thr Gly
1               5                   10

<210> SEQ ID NO 697
<211> LENGTH: 10
<212> TYPE: PRT
<213> ORGANISM: Artificial Sequence
<220> FEATURE:
<223> OTHER INFORMATION: Synthetic construct

<400> SEQUENCE: 697

Gln Met Gln Cys Lys Val Tyr Asp Ser Leu
1               5                   10

<210> SEQ ID NO 698
<211> LENGTH: 11
<212> TYPE: PRT
<213> ORGANISM: Artificial Sequence
<220> FEATURE:
<223> OTHER INFORMATION: Synthetic construct
```

```
<400> SEQUENCE: 698

Leu Ala Leu Pro Gln Asp Leu Gln Ala Ala Arg
1               5                   10

<210> SEQ ID NO 699
<211> LENGTH: 5
<212> TYPE: PRT
<213> ORGANISM: Artificial Sequence
<220> FEATURE:
<223> OTHER INFORMATION: Synthetic construct

<400> SEQUENCE: 699

Lys Val Thr Ala Phe
1               5

<210> SEQ ID NO 700
<211> LENGTH: 10
<212> TYPE: PRT
<213> ORGANISM: Artificial Sequence
<220> FEATURE:
<223> OTHER INFORMATION: Synthetic construct

<400> SEQUENCE: 700

Ile Gly Asn Ser Ile Val Val Ala Gln Val
1               5                   10

<210> SEQ ID NO 701
<211> LENGTH: 10
<212> TYPE: PRT
<213> ORGANISM: Artificial Sequence
<220> FEATURE:
<223> OTHER INFORMATION: Synthetic construct

<400> SEQUENCE: 701

Val Trp Glu Gly Leu Trp Met Ser Cys Val
1               5                   10

<210> SEQ ID NO 702
<211> LENGTH: 10
<212> TYPE: PRT
<213> ORGANISM: Artificial Sequence
<220> FEATURE:
<223> OTHER INFORMATION: Synthetic construct

<400> SEQUENCE: 702

Val Gln Ser Thr Gly Gln Met Gln Cys Lys
1               5                   10

<210> SEQ ID NO 703
<211> LENGTH: 10
<212> TYPE: PRT
<213> ORGANISM: Artificial Sequence
<220> FEATURE:
<223> OTHER INFORMATION: Synthetic construct

<400> SEQUENCE: 703

Val Tyr Asp Ser Leu Leu Ala Leu Pro Gln
1               5                   10

<210> SEQ ID NO 704
<211> LENGTH: 6
<212> TYPE: PRT
<213> ORGANISM: Artificial Sequence
<220> FEATURE:
<223> OTHER INFORMATION: Synthetic construct

<400> SEQUENCE: 704
```

```
Asp Leu Gln Ala Ala Arg
1               5

<210> SEQ ID NO 705
<211> LENGTH: 8
<212> TYPE: PRT
<213> ORGANISM: Artificial Sequence
<220> FEATURE:
<223> OTHER INFORMATION: Synthetic construct

<400> SEQUENCE: 705

Gln Asp Phe Tyr Asn Pro Leu Val
1               5

<210> SEQ ID NO 706
<211> LENGTH: 7
<212> TYPE: PRT
<213> ORGANISM: Artificial Sequence
<220> FEATURE:
<223> OTHER INFORMATION: Synthetic construct

<400> SEQUENCE: 706

Ala Glu Ala Leu Lys Arg Glu
1               5

<210> SEQ ID NO 707
<211> LENGTH: 10
<212> TYPE: PRT
<213> ORGANISM: Artificial Sequence
<220> FEATURE:
<223> OTHER INFORMATION: Synthetic construct

<400> SEQUENCE: 707

Lys Val Ser Thr Ile Asp Gly Thr Val Ile
1               5                   10

<210> SEQ ID NO 708
<211> LENGTH: 10
<212> TYPE: PRT
<213> ORGANISM: Artificial Sequence
<220> FEATURE:
<223> OTHER INFORMATION: Synthetic construct

<400> SEQUENCE: 708

Thr Thr Ala Thr Tyr Trp Ala Asn Leu Trp
1               5                   10

<210> SEQ ID NO 709
<211> LENGTH: 10
<212> TYPE: PRT
<213> ORGANISM: Artificial Sequence
<220> FEATURE:
<223> OTHER INFORMATION: Synthetic construct

<400> SEQUENCE: 709

Lys Ala Cys Val Thr Asp Ser Thr Gly Val
1               5                   10

<210> SEQ ID NO 710
<211> LENGTH: 10
<212> TYPE: PRT
<213> ORGANISM: Artificial Sequence
<220> FEATURE:
<223> OTHER INFORMATION: Synthetic construct

<400> SEQUENCE: 710
```

```
Ser Asn Cys Lys Asp Phe Pro Ser Met Leu
1               5                   10
```

```
<210> SEQ ID NO 711
<211> LENGTH: 10
<212> TYPE: PRT
<213> ORGANISM: Artificial Sequence
<220> FEATURE:
<223> OTHER INFORMATION: Synthetic construct

<400> SEQUENCE: 711

Ala Leu Asp Gly Tyr Ile Gln Ala Cys Arg
1               5                   10
```

```
<210> SEQ ID NO 712
<211> LENGTH: 5
<212> TYPE: PRT
<213> ORGANISM: Artificial Sequence
<220> FEATURE:
<223> OTHER INFORMATION: Synthetic construct

<400> SEQUENCE: 712

Lys Val Ser Thr Ile
1               5
```

```
<210> SEQ ID NO 713
<211> LENGTH: 10
<212> TYPE: PRT
<213> ORGANISM: Artificial Sequence
<220> FEATURE:
<223> OTHER INFORMATION: Synthetic construct

<400> SEQUENCE: 713

Asp Gly Thr Val Ile Thr Thr Ala Thr Tyr
1               5                   10
```

```
<210> SEQ ID NO 714
<211> LENGTH: 10
<212> TYPE: PRT
<213> ORGANISM: Artificial Sequence
<220> FEATURE:
<223> OTHER INFORMATION: Synthetic construct

<400> SEQUENCE: 714

Trp Ala Asn Leu Trp Lys Ala Cys Val Thr
1               5                   10
```

```
<210> SEQ ID NO 715
<211> LENGTH: 10
<212> TYPE: PRT
<213> ORGANISM: Artificial Sequence
<220> FEATURE:
<223> OTHER INFORMATION: Synthetic construct

<400> SEQUENCE: 715

Asp Ser Thr Gly Val Ser Asn Cys Lys Asp
1               5                   10
```

```
<210> SEQ ID NO 716
<211> LENGTH: 10
<212> TYPE: PRT
<213> ORGANISM: Artificial Sequence
<220> FEATURE:
<223> OTHER INFORMATION: Synthetic construct

<400> SEQUENCE: 716

Phe Pro Ser Met Leu Ala Leu Asp Gly Tyr
```

```
                  1               5                   10

<210> SEQ ID NO 717
<211> LENGTH: 5
<212> TYPE: PRT
<213> ORGANISM: Artificial Sequence
<220> FEATURE:
<223> OTHER INFORMATION: Synthetic construct

<400> SEQUENCE: 717

Ile Gln Ala Cys Arg
1               5

<210> SEQ ID NO 718
<211> LENGTH: 7
<212> TYPE: PRT
<213> ORGANISM: Artificial Sequence
<220> FEATURE:
<223> OTHER INFORMATION: Synthetic construct

<400> SEQUENCE: 718

Glu Phe Phe Asp Pro Leu Phe
1               5

<210> SEQ ID NO 719
<211> LENGTH: 6
<212> TYPE: PRT
<213> ORGANISM: Artificial Sequence
<220> FEATURE:
<223> OTHER INFORMATION: Synthetic construct

<400> SEQUENCE: 719

Val Glu Gln Lys Tyr Glu
1               5

<210> SEQ ID NO 720
<211> LENGTH: 10
<212> TYPE: PRT
<213> ORGANISM: Artificial Sequence
<220> FEATURE:
<223> OTHER INFORMATION: Synthetic construct

<400> SEQUENCE: 720

Asp Arg Gly Tyr Gly Thr Ser Leu Leu Gly
1               5                   10

<210> SEQ ID NO 721
<211> LENGTH: 10
<212> TYPE: PRT
<213> ORGANISM: Artificial Sequence
<220> FEATURE:
<223> OTHER INFORMATION: Synthetic construct

<400> SEQUENCE: 721

Gly Ser Val Gly Tyr Pro Tyr Gly Gly Ser
1               5                   10

<210> SEQ ID NO 722
<211> LENGTH: 10
<212> TYPE: PRT
<213> ORGANISM: Artificial Sequence
<220> FEATURE:
<223> OTHER INFORMATION: Synthetic construct

<400> SEQUENCE: 722

Gly Phe Gly Ser Tyr Gly Ser Gly Tyr Gly
1               5                   10
```

<210> SEQ ID NO 723
<211> LENGTH: 10
<212> TYPE: PRT
<213> ORGANISM: Artificial Sequence
<220> FEATURE:
<223> OTHER INFORMATION: Synthetic construct

<400> SEQUENCE: 723

Tyr Gly Tyr Gly Tyr Gly Tyr Gly Tyr Gly
1               5                   10

<210> SEQ ID NO 724
<211> LENGTH: 6
<212> TYPE: PRT
<213> ORGANISM: Artificial Sequence
<220> FEATURE:
<223> OTHER INFORMATION: Synthetic construct

<400> SEQUENCE: 724

Gly Tyr Thr Asp Pro Arg
1               5

<210> SEQ ID NO 725
<211> LENGTH: 5
<212> TYPE: PRT
<213> ORGANISM: Artificial Sequence
<220> FEATURE:
<223> OTHER INFORMATION: Synthetic construct

<400> SEQUENCE: 725

Asp Arg Gly Tyr Gly
1               5

<210> SEQ ID NO 726
<211> LENGTH: 10
<212> TYPE: PRT
<213> ORGANISM: Artificial Sequence
<220> FEATURE:
<223> OTHER INFORMATION: Synthetic construct

<400> SEQUENCE: 726

Thr Ser Leu Leu Gly Gly Ser Val Gly Tyr
1               5                   10

<210> SEQ ID NO 727
<211> LENGTH: 10
<212> TYPE: PRT
<213> ORGANISM: Artificial Sequence
<220> FEATURE:
<223> OTHER INFORMATION: Synthetic construct

<400> SEQUENCE: 727

Pro Tyr Gly Gly Ser Gly Phe Gly Ser Tyr
1               5                   10

<210> SEQ ID NO 728
<211> LENGTH: 10
<212> TYPE: PRT
<213> ORGANISM: Artificial Sequence
<220> FEATURE:
<223> OTHER INFORMATION: Synthetic construct

<400> SEQUENCE: 728

Gly Ser Gly Tyr Gly Tyr Gly Tyr Gly Tyr
1               5                   10

```
<210> SEQ ID NO 729
<211> LENGTH: 11
<212> TYPE: PRT
<213> ORGANISM: Artificial Sequence
<220> FEATURE:
<223> OTHER INFORMATION: Synthetic construct

<400> SEQUENCE: 729

Gly Tyr Gly Tyr Gly Gly Tyr Thr Asp Pro Arg
1               5                   10

<210> SEQ ID NO 730
<211> LENGTH: 10
<212> TYPE: PRT
<213> ORGANISM: Artificial Sequence
<220> FEATURE:
<223> OTHER INFORMATION: Synthetic construct

<400> SEQUENCE: 730

Gly Val Asn Pro Thr Ala Gln Ser Ser Gly
1               5                   10

<210> SEQ ID NO 731
<211> LENGTH: 10
<212> TYPE: PRT
<213> ORGANISM: Artificial Sequence
<220> FEATURE:
<223> OTHER INFORMATION: Synthetic construct

<400> SEQUENCE: 731

Ser Leu Tyr Gly Ser Gln Ile Tyr Ala Leu
1               5                   10

<210> SEQ ID NO 732
<211> LENGTH: 10
<212> TYPE: PRT
<213> ORGANISM: Artificial Sequence
<220> FEATURE:
<223> OTHER INFORMATION: Synthetic construct

<400> SEQUENCE: 732

Cys Asn Gln Phe Tyr Thr Pro Ala Ala Thr
1               5                   10

<210> SEQ ID NO 733
<211> LENGTH: 10
<212> TYPE: PRT
<213> ORGANISM: Artificial Sequence
<220> FEATURE:
<223> OTHER INFORMATION: Synthetic construct

<400> SEQUENCE: 733

Gly Leu Tyr Val Asp Gln Tyr Leu Tyr His
1               5                   10

<210> SEQ ID NO 734
<211> LENGTH: 8
<212> TYPE: PRT
<213> ORGANISM: Artificial Sequence
<220> FEATURE:
<223> OTHER INFORMATION: Synthetic construct

<400> SEQUENCE: 734

Tyr Cys Val Val Asp Pro Gln Glu
1               5
```

```
<210> SEQ ID NO 735
<211> LENGTH: 5
<212> TYPE: PRT
<213> ORGANISM: Artificial Sequence
<220> FEATURE:
<223> OTHER INFORMATION: Synthetic construct

<400> SEQUENCE: 735

Gly Val Asn Pro Thr
1               5

<210> SEQ ID NO 736
<211> LENGTH: 10
<212> TYPE: PRT
<213> ORGANISM: Artificial Sequence
<220> FEATURE:
<223> OTHER INFORMATION: Synthetic construct

<400> SEQUENCE: 736

Ala Gln Ser Ser Gly Ser Leu Tyr Gly Ser
1               5                   10

<210> SEQ ID NO 737
<211> LENGTH: 10
<212> TYPE: PRT
<213> ORGANISM: Artificial Sequence
<220> FEATURE:
<223> OTHER INFORMATION: Synthetic construct

<400> SEQUENCE: 737

Gln Ile Tyr Ala Leu Cys Asn Gln Phe Tyr
1               5                   10

<210> SEQ ID NO 738
<211> LENGTH: 10
<212> TYPE: PRT
<213> ORGANISM: Artificial Sequence
<220> FEATURE:
<223> OTHER INFORMATION: Synthetic construct

<400> SEQUENCE: 738

Thr Pro Ala Ala Thr Gly Leu Tyr Val Asp
1               5                   10

<210> SEQ ID NO 739
<211> LENGTH: 10
<212> TYPE: PRT
<213> ORGANISM: Artificial Sequence
<220> FEATURE:
<223> OTHER INFORMATION: Synthetic construct

<400> SEQUENCE: 739

Gln Tyr Leu Tyr His Tyr Cys Val Val Asp
1               5                   10

<210> SEQ ID NO 740
<211> LENGTH: 3
<212> TYPE: PRT
<213> ORGANISM: Artificial Sequence
<220> FEATURE:
<223> OTHER INFORMATION: Synthetic construct

<400> SEQUENCE: 740

Pro Gln Glu
1

<210> SEQ ID NO 741
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 741

Ser Val Thr Val His Ser Ser Glu Pro
1               5

<210> SEQ ID NO 742
<211> LENGTH: 9
<212> TYPE: PRT
<213> ORGANISM: Artificial Sequence
<220> FEATURE:
<223> OTHER INFORMATION: Synthetic construct

<400> SEQUENCE: 742

Lys Phe Asp Gln Gly Asp Thr Thr Arg
1               5

<210> SEQ ID NO 743
<211> LENGTH: 9
<212> TYPE: PRT
<213> ORGANISM: Artificial Sequence
<220> FEATURE:
<223> OTHER INFORMATION: Synthetic construct

<400> SEQUENCE: 743

Gly Glu Val Lys Val Lys Leu Ile Val
1               5

<210> SEQ ID NO 744
<211> LENGTH: 9
<212> TYPE: PRT
<213> ORGANISM: Artificial Sequence
<220> FEATURE:
<223> OTHER INFORMATION: Synthetic construct

<400> SEQUENCE: 744

Val Ser Glu Glu Gly Gly Asn Ser Tyr
1               5

<210> SEQ ID NO 745
<211> LENGTH: 9
<212> TYPE: PRT
<213> ORGANISM: Artificial Sequence
<220> FEATURE:
<223> OTHER INFORMATION: Synthetic construct

<400> SEQUENCE: 745

Leu Val Cys Tyr Asn Asn Lys Ile Thr
1               5

<210> SEQ ID NO 746
<211> LENGTH: 5
<212> TYPE: PRT
<213> ORGANISM: Artificial Sequence
<220> FEATURE:
<223> OTHER INFORMATION: Synthetic construct

<400> SEQUENCE: 746

Val Leu Pro Pro Ser
1               5

<210> SEQ ID NO 747
<211> LENGTH: 7
```

```
<212> TYPE: PRT
<213> ORGANISM: Artificial Sequence
<220> FEATURE:
<223> OTHER INFORMATION: Synthetic construct

<400> SEQUENCE: 747

Tyr Glu Asp Arg Val Thr Phe
1               5

<210> SEQ ID NO 748
<211> LENGTH: 5
<212> TYPE: PRT
<213> ORGANISM: Artificial Sequence
<220> FEATURE:
<223> OTHER INFORMATION: Synthetic construct

<400> SEQUENCE: 748

Pro Arg Val Glu Trp
1               5

<210> SEQ ID NO 749
<211> LENGTH: 10
<212> TYPE: PRT
<213> ORGANISM: Artificial Sequence
<220> FEATURE:
<223> OTHER INFORMATION: Synthetic construct

<400> SEQUENCE: 749

Lys Val Phe Asp Ser Leu Leu Asn Leu Ser
1               5                   10

<210> SEQ ID NO 750
<211> LENGTH: 10
<212> TYPE: PRT
<213> ORGANISM: Artificial Sequence
<220> FEATURE:
<223> OTHER INFORMATION: Synthetic construct

<400> SEQUENCE: 750

Asn Arg Ile Val Gln Glu Phe Tyr Asp Pro
1               5                   10

<210> SEQ ID NO 751
<211> LENGTH: 10
<212> TYPE: PRT
<213> ORGANISM: Artificial Sequence
<220> FEATURE:
<223> OTHER INFORMATION: Synthetic construct

<400> SEQUENCE: 751

Tyr Ala Gly Asp Asn Ile Val Thr Ala Gln
1               5                   10

<210> SEQ ID NO 752
<211> LENGTH: 10
<212> TYPE: PRT
<213> ORGANISM: Artificial Sequence
<220> FEATURE:
<223> OTHER INFORMATION: Synthetic construct

<400> SEQUENCE: 752

Val Ser Gln Ser Thr Gly Gln Ile Gln Cys
1               5                   10

<210> SEQ ID NO 753
<211> LENGTH: 10
<212> TYPE: PRT
```

```
<213> ORGANISM: Artificial Sequence
<220> FEATURE:
<223> OTHER INFORMATION: Synthetic construct

<400> SEQUENCE: 753

Met Thr Pro Val Asn Ala Arg Tyr Glu Phe
1               5                   10

<210> SEQ ID NO 754
<211> LENGTH: 10
<212> TYPE: PRT
<213> ORGANISM: Artificial Sequence
<220> FEATURE:
<223> OTHER INFORMATION: Synthetic construct

<400> SEQUENCE: 754

Ala Met Tyr Glu Gly Leu Trp Met Ser Cys
1               5                   10

<210> SEQ ID NO 755
<211> LENGTH: 10
<212> TYPE: PRT
<213> ORGANISM: Artificial Sequence
<220> FEATURE:
<223> OTHER INFORMATION: Synthetic construct

<400> SEQUENCE: 755

Thr Thr Trp Leu Gly Leu Trp Met Ser Cys
1               5                   10

<210> SEQ ID NO 756
<211> LENGTH: 10
<212> TYPE: PRT
<213> ORGANISM: Artificial Sequence
<220> FEATURE:
<223> OTHER INFORMATION: Synthetic construct

<400> SEQUENCE: 756

Tyr Val Gly Ala Ser Ile Val Thr Ala Val
1               5                   10

<210> SEQ ID NO 757
<211> LENGTH: 10
<212> TYPE: PRT
<213> ORGANISM: Artificial Sequence
<220> FEATURE:
<223> OTHER INFORMATION: Synthetic construct

<400> SEQUENCE: 757

Gly Ile Leu Arg Asp Phe Tyr Ser Pro Leu
1               5                   10

<210> SEQ ID NO 758
<211> LENGTH: 10
<212> TYPE: PRT
<213> ORGANISM: Artificial Sequence
<220> FEATURE:
<223> OTHER INFORMATION: Synthetic construct

<400> SEQUENCE: 758

Val Pro Asp Ser Met Lys Phe Glu Ile Gly
1               5                   10

<210> SEQ ID NO 759
<211> LENGTH: 10
<212> TYPE: PRT
<213> ORGANISM: Artificial Sequence
```

```
<220> FEATURE:
<223> OTHER INFORMATION: Synthetic construct

<400> SEQUENCE: 759

Asp Ile Tyr Ser Thr Leu Leu Gly Leu Pro
1               5                   10

<210> SEQ ID NO 760
<211> LENGTH: 10
<212> TYPE: PRT
<213> ORGANISM: Artificial Sequence
<220> FEATURE:
<223> OTHER INFORMATION: Synthetic construct

<400> SEQUENCE: 760

Gly Phe Ser Leu Gly Leu Trp Met Glu Cys
1               5                   10

<210> SEQ ID NO 761
<211> LENGTH: 10
<212> TYPE: PRT
<213> ORGANISM: Artificial Sequence
<220> FEATURE:
<223> OTHER INFORMATION: Synthetic construct

<400> SEQUENCE: 761

Ala Thr His Ser Thr Gly Ile Thr Gln Cys
1               5                   10

<210> SEQ ID NO 762
<211> LENGTH: 10
<212> TYPE: PRT
<213> ORGANISM: Artificial Sequence
<220> FEATURE:
<223> OTHER INFORMATION: Synthetic construct

<400> SEQUENCE: 762

Gly Phe Ser Lys Gly Leu Trp Met Glu Cys
1               5                   10

<210> SEQ ID NO 763
<211> LENGTH: 10
<212> TYPE: PRT
<213> ORGANISM: Artificial Sequence
<220> FEATURE:
<223> OTHER INFORMATION: Synthetic construct

<400> SEQUENCE: 763

Lys Val Tyr Asp Ser Leu Leu Ala Leu Pro
1               5                   10

<210> SEQ ID NO 764
<211> LENGTH: 10
<212> TYPE: PRT
<213> ORGANISM: Artificial Sequence
<220> FEATURE:
<223> OTHER INFORMATION: Synthetic construct

<400> SEQUENCE: 764

Asn Thr Ile Ile Arg Asp Phe Tyr Asn Pro
1               5                   10

<210> SEQ ID NO 765
<211> LENGTH: 10
<212> TYPE: PRT
<213> ORGANISM: Artificial Sequence
<220> FEATURE:
```

<223> OTHER INFORMATION: Synthetic construct

<400> SEQUENCE: 765

Val Val Pro Glu Ala Gln Lys Arg Glu Met
1               5                   10

<210> SEQ ID NO 766
<211> LENGTH: 10
<212> TYPE: PRT
<213> ORGANISM: Artificial Sequence
<220> FEATURE:
<223> OTHER INFORMATION: Synthetic construct

<400> SEQUENCE: 766

Asn Ile Trp Glu Gly Leu Trp Met Asn Cys
1               5                   10

<210> SEQ ID NO 767
<211> LENGTH: 10
<212> TYPE: PRT
<213> ORGANISM: Artificial Sequence
<220> FEATURE:
<223> OTHER INFORMATION: Synthetic construct

<400> SEQUENCE: 767

Val Val Gln Ser Thr Gly Gln Met Gln Cys
1               5                   10

<210> SEQ ID NO 768
<211> LENGTH: 10
<212> TYPE: PRT
<213> ORGANISM: Artificial Sequence
<220> FEATURE:
<223> OTHER INFORMATION: Synthetic construct

<400> SEQUENCE: 768

Phe Ile Gly Ser Asn Ile Ile Thr Ser Gln
1               5                   10

<210> SEQ ID NO 769
<211> LENGTH: 10
<212> TYPE: PRT
<213> ORGANISM: Artificial Sequence
<220> FEATURE:
<223> OTHER INFORMATION: Synthetic construct

<400> SEQUENCE: 769

Val Ala Ser Gly Gln Lys Arg Glu Met Gly
1               5                   10

<210> SEQ ID NO 770
<211> LENGTH: 10
<212> TYPE: PRT
<213> ORGANISM: Artificial Sequence
<220> FEATURE:
<223> OTHER INFORMATION: Synthetic construct

<400> SEQUENCE: 770

Asn Ile Ile Gln Asp Phe Tyr Asn Pro Leu
1               5                   10

<210> SEQ ID NO 771
<211> LENGTH: 10
<212> TYPE: PRT
<213> ORGANISM: Artificial Sequence
<220> FEATURE:
<223> OTHER INFORMATION: Synthetic construct

```
<400> SEQUENCE: 771

Phe Ile Gly Ser Asn Ile Val Thr Ser Gln
1               5                   10

<210> SEQ ID NO 772
<211> LENGTH: 10
<212> TYPE: PRT
<213> ORGANISM: Artificial Sequence
<220> FEATURE:
<223> OTHER INFORMATION: Synthetic construct

<400> SEQUENCE: 772

Thr Ile Trp Glu Gly Leu Trp Met Asn Cys
1               5                   10

<210> SEQ ID NO 773
<211> LENGTH: 10
<212> TYPE: PRT
<213> ORGANISM: Artificial Sequence
<220> FEATURE:
<223> OTHER INFORMATION: Synthetic construct

<400> SEQUENCE: 773

Ile Val Val Arg Glu Phe Tyr Asp Pro Ser
1               5                   10

<210> SEQ ID NO 774
<211> LENGTH: 10
<212> TYPE: PRT
<213> ORGANISM: Artificial Sequence
<220> FEATURE:
<223> OTHER INFORMATION: Synthetic construct

<400> SEQUENCE: 774

Val Val Gln Ser Thr Gly His Met Gln Cys
1               5                   10

<210> SEQ ID NO 775
<211> LENGTH: 10
<212> TYPE: PRT
<213> ORGANISM: Artificial Sequence
<220> FEATURE:
<223> OTHER INFORMATION: Synthetic construct

<400> SEQUENCE: 775

Phe Leu Asp His Asn Ile Val Thr Ala Gln
1               5                   10

<210> SEQ ID NO 776
<211> LENGTH: 10
<212> TYPE: PRT
<213> ORGANISM: Artificial Sequence
<220> FEATURE:
<223> OTHER INFORMATION: Synthetic construct

<400> SEQUENCE: 776

Val Pro Val Ser Gln Lys Tyr Glu Leu Gly
1               5                   10

<210> SEQ ID NO 777
<211> LENGTH: 10
<212> TYPE: PRT
<213> ORGANISM: Artificial Sequence
<220> FEATURE:
<223> OTHER INFORMATION: Synthetic construct
```

-continued

```
<400> SEQUENCE: 777

Lys Val Tyr Asp Ser Val Leu Ala Leu Ser
1               5                   10

<210> SEQ ID NO 778
<211> LENGTH: 10
<212> TYPE: PRT
<213> ORGANISM: Artificial Sequence
<220> FEATURE:
<223> OTHER INFORMATION: Synthetic construct

<400> SEQUENCE: 778

Thr Thr Trp Lys Gly Leu Trp Met Ser Cys
1               5                   10

<210> SEQ ID NO 779
<211> LENGTH: 9
<212> TYPE: PRT
<213> ORGANISM: Artificial Sequence
<220> FEATURE:
<223> OTHER INFORMATION: Synthetic construct

<400> SEQUENCE: 779

Asp Arg Gly Tyr Gly Thr Ser Leu Leu
1               5

<210> SEQ ID NO 780
<211> LENGTH: 9
<212> TYPE: PRT
<213> ORGANISM: Artificial Sequence
<220> FEATURE:
<223> OTHER INFORMATION: Synthetic construct

<400> SEQUENCE: 780

Gly Tyr Gly Tyr Gly Tyr Gly Tyr Gly
1               5

<210> SEQ ID NO 781
<211> LENGTH: 9
<212> TYPE: PRT
<213> ORGANISM: Artificial Sequence
<220> FEATURE:
<223> OTHER INFORMATION: Synthetic construct

<400> SEQUENCE: 781

Gly Tyr Gly Tyr Gly Tyr Gly Tyr Gly
1               5

<210> SEQ ID NO 782
<211> LENGTH: 9
<212> TYPE: PRT
<213> ORGANISM: Artificial Sequence
<220> FEATURE:
<223> OTHER INFORMATION: Synthetic construct

<400> SEQUENCE: 782

Tyr Gly Tyr Gly Gly Tyr Thr Asp Pro
1               5

<210> SEQ ID NO 783
<211> LENGTH: 9
<212> TYPE: PRT
<213> ORGANISM: Artificial Sequence
<220> FEATURE:
<223> OTHER INFORMATION: Synthetic construct

<400> SEQUENCE: 783
```

```
Gly Val Asn Pro Thr Ala Gln Ser Ser
1               5
```

<210> SEQ ID NO 784
<211> LENGTH: 9
<212> TYPE: PRT
<213> ORGANISM: Artificial Sequence
<220> FEATURE:
<223> OTHER INFORMATION: Synthetic construct

<400> SEQUENCE: 784

```
Gly Ser Leu Tyr Gly Ser Gln Ile Tyr
1               5
```

<210> SEQ ID NO 785
<211> LENGTH: 9
<212> TYPE: PRT
<213> ORGANISM: Artificial Sequence
<220> FEATURE:
<223> OTHER INFORMATION: Synthetic construct

<400> SEQUENCE: 785

```
Ala Ala Thr Gly Leu Tyr Val Asp Gln
1               5
```

<210> SEQ ID NO 786
<211> LENGTH: 9
<212> TYPE: PRT
<213> ORGANISM: Artificial Sequence
<220> FEATURE:
<223> OTHER INFORMATION: Synthetic construct

<400> SEQUENCE: 786

```
Ala Leu Cys Asn Gln Phe Tyr Thr Pro
1               5
```

<210> SEQ ID NO 787
<211> LENGTH: 9
<212> TYPE: PRT
<213> ORGANISM: Artificial Sequence
<220> FEATURE:
<223> OTHER INFORMATION: Synthetic construct

<400> SEQUENCE: 787

```
Tyr Leu Tyr His Tyr Cys Val Val Asp
1               5
```

<210> SEQ ID NO 788
<211> LENGTH: 9
<212> TYPE: PRT
<213> ORGANISM: Artificial Sequence
<220> FEATURE:
<223> OTHER INFORMATION: Synthetic construct

<400> SEQUENCE: 788

```
Gly Gly Ser Val Gly Tyr Pro Tyr Gly
1               5
```

<210> SEQ ID NO 789
<211> LENGTH: 13
<212> TYPE: PRT
<213> ORGANISM: Artificial Sequence
<220> FEATURE:
<223> OTHER INFORMATION: Synthetic construct

<400> SEQUENCE: 789

```
Gly Arg Lys Lys Arg Gln Arg Arg Pro Pro Gln
1               5                   10
```

<210> SEQ ID NO 790
<211> LENGTH: 8
<212> TYPE: PRT
<213> ORGANISM: Artificial Sequence
<220> FEATURE:
<223> OTHER INFORMATION: Synthetic construct

<400> SEQUENCE: 790

```
Pro Arg Ile Glu Trp Lys Lys Ile
1               5
```

<210> SEQ ID NO 791
<211> LENGTH: 36
<212> TYPE: PRT
<213> ORGANISM: Artificial Sequence
<220> FEATURE:
<223> OTHER INFORMATION: Synthetic construct

<400> SEQUENCE: 791

```
Tyr Pro Ala Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
            35
```

<210> SEQ ID NO 792
<211> LENGTH: 36
<212> TYPE: PRT
<213> ORGANISM: Artificial Sequence
<220> FEATURE:
<223> OTHER INFORMATION: Synthetic construct

<400> SEQUENCE: 792

```
Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
            35
```

<210> SEQ ID NO 793
<211> LENGTH: 24
<212> TYPE: PRT
<213> ORGANISM: Artificial Sequence
<220> FEATURE:
<223> OTHER INFORMATION: Synthetic construct

<400> SEQUENCE: 793

```
Ser Pro Glu Glu Leu Ser Arg Tyr Tyr Ala Ser Leu Arg His Tyr Leu
1               5                   10                  15

Asn Leu Val Thr Arg Gln Arg Tyr
            20
```

<210> SEQ ID NO 794
<211> LENGTH: 34
<212> TYPE: PRT
<213> ORGANISM: Artificial Sequence
<220> FEATURE:
<223> OTHER INFORMATION: Synthetic construct

<400> SEQUENCE: 794

Ile Lys Pro Glu Ala Pro Gly Gln Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 795
<211> LENGTH: 36
<212> TYPE: PRT
<213> ORGANISM: Artificial Sequence
<220> FEATURE:
<223> OTHER INFORMATION: Synthetic construct

<400> SEQUENCE: 795

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35

<210> SEQ ID NO 796
<211> LENGTH: 36
<212> TYPE: PRT
<213> ORGANISM: Artificial Sequence
<220> FEATURE:
<223> OTHER INFORMATION: Synthetic construct

<400> SEQUENCE: 796

Tyr Pro Ser Lys Pro Asp Asn Pro Gly Glu Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
            35

<210> SEQ ID NO 797
<211> LENGTH: 4
<212> TYPE: PRT
<213> ORGANISM: Artificial Sequence
<220> FEATURE:
<223> OTHER INFORMATION: Synthetic construct

<400> SEQUENCE: 797

Tyr Lys Gly Arg
1

<210> SEQ ID NO 798
<211> LENGTH: 36
<212> TYPE: PRT
<213> ORGANISM: Artificial Sequence
<220> FEATURE:
<223> OTHER INFORMATION: Synthetic construct

<400> SEQUENCE: 798

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Pro Arg Tyr
            35

```
<210> SEQ ID NO 799
<211> LENGTH: 36
<212> TYPE: PRT
<213> ORGANISM: Artificial Sequence
<220> FEATURE:
<223> OTHER INFORMATION: Synthetic construct

<400> SEQUENCE: 799

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Pro Arg Tyr
            35
```

COMPOSITIONS AND METHODS FOR ENHANCED MUCOSAL DELIVERY OF PEPTIDE YY AND METHODS FOR TREATING AND PREVENTING OBESITY

BACKGROUND OF THE INVENTION

A major disadvantage of drug administration by injection is that trained personnel are often required to administer the drug. For self-administered drugs, many patients are reluctant or unable to give themselves injections on a regular basis. Injection is also associated with increased risks of infection. Other disadvantages of drug injection include variability of delivery results between individuals, as well as unpredictable intensity and duration of drug action.

Despite these noted disadvantages, injection remains the only approved delivery mode for a large assemblage of important therapeutic compounds. These include conventional drugs, as well as a rapidly expanding list of peptide and protein biotherapeutics. Delivery of these compounds via alternate routes of administration, for example, oral, nasal and other mucosal routes, often yields variable results and adverse side effects, and fails to provide suitable bioavailability. For macromolecular species in particular, especially peptide and protein therapeutics, alternate routes of administration are limited by susceptibility to inactivation and poor absorption across mucosal barriers.

Mucosal administration of therapeutic compounds may offer certain advantages over injection and other modes of administration, for example in terms of convenience and speed of delivery, as well as by reducing or eliminating compliance problems and side effects that attend delivery by injection. However, mucosal delivery of biologically active agents is limited by mucosal barrier functions and other factors. For these reasons, mucosal drug administration typically requires larger amounts of drug than administration by injection. Other therapeutic compounds, including large molecule drugs, peptides and proteins, are often refractory to mucosal delivery.

The ability of drugs to permeate mucosal surfaces, unassisted by delivery-enhancing agents, appears to be related to a number of factors, including molecular size, lipid solubility, and ionization. Small molecules, less than about 300–1,000 daltons, are often capable of penetrating mucosal barriers, however, as molecular size increases, permeability decreases rapidly. Lipid-soluble compounds are generally more permeable through mucosal surfaces than are non-lipid-soluble molecules. Peptides and proteins are poorly lipid soluble, and hence exhibit poor absorption characteristics across mucosal surfaces.

In addition to their poor intrinsic permeability, large macromolecular drugs, including proteins and peptides, are often subject to limited diffusion, as well as lumenal and cellular enzymatic degradation and rapid clearance at mucosal sites. These mucosal sites generally serve as a first line of host defense against pathogens and other adverse environmental agents that come into contact with the mucosal surface. Mucosal tissues provide a substantial barrier to the free diffusion of macromolecules, while enzymatic activities present in mucosal secretions can severely limit the bioavailability of therapeutic agents, particularly peptides and proteins. At certain mucosal sites, such as the nasal mucosa, the typical residence time of proteins and other macromolecular species delivered is limited, e.g., to about 15–30 minutes or less, due to rapid mucociliary clearance.

Various methods and formulations have been attempted to enhance the absorption of drugs across mucosal surfaces. Penetration enhancing substances that facilitate the transport of solutes across biological membranes are widely reported in the art for facilitating mucosal drug delivery. Mucosal penetration enhancers represented in these reports include (a) chelators (e.g., EDTA, citric acid, salicylates), (b) surfactants (e.g., sodium dodecyl sulfate (SDS)), (c) non-surfactants (e.g., unsaturated cyclic ureas), (d) bile salts (e.g., sodium deoxycholate, sodium taurocholate), and (e) fatty acids (e.g., oleic acid, acylcarnitines, mono- and diglycerides). Numerous additional agents and mechanisms have been proposed for enhancing mucosal penetration of drugs. These include, for example, reducing the viscosity and/or elasticity of mucus layers that cover mucosal surfaces; facilitating transcellular transport by increasing the fluidity of the lipid bilayer of membranes; altering the physicochemical properties (e.g., lipophilicity, stability) of drugs; facilitating paracellular transport by altering tight junctions across the epithelial cell layer; overcoming enzymatic barriers; and increasing the thermodynamic activity of candidate drugs.

While many penetration enhancing methods and additives have been reported to be effective in improving mucosal drug delivery, few penetration enhanced products have been developed and approved for mucosal delivery of drugs. This failure can be attributed to a variety of factors, including poor safety profiles relating to mucosal irritation, and undesirable disruption of mucosal barrier functions.

In view of the foregoing, there remains a substantial unmet need in the art for new methods and tools to facilitate mucosal delivery of biotherapeutic compounds. Related to this need, there is a compelling need in the art for methods and formulations to facilitate mucosal delivery of biotherapeutic compounds that have heretofore proven refractory to delivery via this route, to avail the medical community of the numerous potential advantages of mucosal drug delivery.

One group of therapeutic compounds of interest for mucosal delivery is a therapeutic peptide designated peptide YY. Peptide YY (PYY) as used herein is a class of peptides, peptide analogs, peptide conjugates and peptide mimetics exemplified in base structure and activity by a prototypic, 36 amino acid peptide having tyrosine residues at both C- and N-terminals. The paired terminal tyrosine residues in this well-known prototypic peptide accounts for the "YY" designation used in the art. Structural analyses have demonstrated approximately 70% homology between PYY, neuropeptide Y, and pancreatic polypeptide, suggesting a common evolutionary precursor. These three peptides together form the primary members of the so-called Pancreatic Polypeptide (PP) family believed to play an important role in the normal physiology of the brain-gut axis. PP peptides all exhibit C-terminal amidation, a feature common in many biologically active peptides.

PYY co-localizes with glucagon and glucagon-like products within endocrine L cells of the intestinal mucosa and to a lesser extent in alpha cells of the pancreas. Studies in a number of mammals including humans have shown that PYY expression increases sequentially along the length of the intestines, with peptide levels in the rectum up to 100-fold greater than in the duodenum. This unique distribution makes PYY an ideal candidate for hormonal regulation of upper gastrointestinal function. In fact, PYY causes decreased gastric acid secretion, delays gastric emptying and slows intestinal transit time. PYY is also known to inhibit exocrine and possibly endocrine functions of the pancreas.

Release of PYY occurs following a meal. An alternate molecular form of PYY is $PYY_{3-36}$. Eberlein, et al. *Peptides* 10: 797–803, 1989; Eysselein, et al., *Peptides* 11: 111–116, 1990; Grandt, et al. *Regul Pept* 51: 151–9, 1994, each incorporated herein by reference. This fragment constitutes approximately 40% of total PYY-like immunoreactivity in human and canine intestinal extracts and about 36% of total plasma PYY immunoreactivity in a fasting state to slightly over 50% following a meal. It is apparently a dipeptidyl peptidase-IV (DPP4) cleavage product of PYY. $PYY_{3-36}$ is reportedly a selective ligand at the Y2 and Y5 receptors, which appear pharmacologically unique in preferring N-terminally truncated (i.e. C-terminal fragments of) NPY analogs. Peripheral administration of PYY reportedly reduces gastric acid secretion, gastric motility, exocrine pancreatic secretion, gallbladder contraction and intestinal motility. Yoshinaga, et al. *Am J Physiol* 263: G695–701, 1992; Guan, et al. *Endocrinology* 128: 911–6, 1991; Pappas, et al. *Gastroenterology* 91: 1386–9, 1986; Savage, et al. *Gut* 28: 166–70, 1987, each incorporated herein by reference. The effects of central injection of PYY on gastric emptying, gastric motility and gastric acid secretion, as seen after direct injection in or around the hindbrain/brainstem may differ from those effects observed after peripheral injection. Chen and Rogers. *Am J Physiol* 269: R787-R792, 1995; Chen, et al. *Regul Pept* 61: 95–98, 1996; Yang and Tache, *Am J Physiol* 268: G943–8, 1995; Chen, et al. *Neurogastroenterol Motil* 9: 109–116, 1997, each incorporated herein by reference. For example, centrally administered PYY had some effects opposite to those described herein for peripherally injected $PYY_{3-36}$ in that gastric acid secretion was stimulated, not inhibited. Gastric motility was suppressed only in conjunction with TRH stimulation, but not when administered alone, and was indeed stimulatory at higher doses through presumed interaction with PP receptors. PYY has been shown to stimulate food and water intake after central administration. Morley, et al. *Brain Res* 341: 200–203, 1985; Corp, et al. *Am J Physiol* 259: R317–23, 1990; U.S. application 20020141985, each incorporated herein by reference.

One of the earliest reported central effects of neuropeptide Y (NPY) was to increase food intake, particularly in the hypothalamus. Stanley, et al. Peptides 6: 1205–11, 1985. PYY and PP are reported to mimic these effects, and PYY is more potent or as potent as NPY. Morley, et al., *Brain Res* 341: 200–203, 1985; Kanatani, et al. *Endocrinology* 141: 1011–6, 2000; Nakajima, et al. *J Pharmacol Exp Ther* 268: 1010–4, 1994, U.S. application 20020141985, each incorporated herein by reference.

Receptors for PYY (designated as Y1, Y2, Y5) have been identified throughout the gastrointestinal tract, including both small bowel and colon mucosal epithelium. These findings raise the possibility that PYY may also exhibit additional actions on gastrointestinal tissues, including regulation of cell growth. Dysregulation of cell growth is most critical in the development and progression of cancer. Prospective clinical applications of PYY exist for therapy of malignant disease and cancer. Tseng et al., *Peptides* 23: 389–395 (2002), Michel, et al. *Pharmacol Rev* 50:143–50, 1998; Gehlert, *Proc Soc Exp Biol Med* 218: 7–22, 1998, each incorporated herein by reference.

Additional prospective clinical applications of PYY or neuropeptide Y exist for therapy of controlled food intake or obesity. Food intake is regulated by the hypothalamus, including the melanocortin and neuropeptide Y (NPY) systems in the arcuate nucleus. The orexigenic NPY and the anorectic alpha melanocyte-stimulating hormone (α-MSH) systems of the hypothalamic arcuate nucleus are involved in the central regulation of appetite. However, the potential mechanisms that link signaling associated with meal ingestion with these hypothalamic-feeding circuits are unclear.

From the prototypic PYY peptide, a subpeptide $PYY_{3-36}$ is formed as a cleavage product produced by the action of didpetidyl peptidase-IV. $PYY_{3-36}$ is a major circulating species exhibiting a distinct pharmacology, and showing antidiabetic and antiobesity actions in several animal models. This gut-derived hormone is released postprandially in proportion to calories ingested. $PYY_{3-36}$ shares 70% amino-acid sequence identity with NPY and acts through NPY receptors. The NPY Y2 receptor (Y2R), a putative inhibitory presynaptic receptor, is highly expressed on NPY neurons in the arcuate nucleus, which is accessible to peripheral hormones, although not expressed on the neighboring pro-opiomelanocortin (POMC) neurons. Peptide $PYY_{3-36}$, a high affinity Y2R agonist, is released from the gastrointestinal tract postprandially in proportion to the calorie content of a meal.

Studies have investigated the effects of peripheral administration of $PYY_{3-36}$ on feeding. Experiments show that peripheral injection of $PYY_{3-36}$ in rats inhibits food intake and reduces weight gain. $PYY_{3-36}$ also inhibits food intake in mice but not in Y2r-null mice, which suggests that the anorectic effect requires the Y2R. Peripheral administration of $PYY_{3-36}$ increases c-Fos immunoreactivity in the arcuate nucleus and decreases hypothalamic Npy messenger RNA. Intra-arcuate injection of $PYY_{3-36}$ inhibits food intake. $PYY_{3-36}$ also inhibits electrical activity of NPY nerve terminals, thus activating adjacent pro-opiomelanocortin (POMC) neurons. In humans, infusion of normal postprandial concentrations of $PYY_{3-36}$ significantly decreases appetite and reduces food intake by 33% over 24 h. Thus, postprandial elevation of $PYY_{3-36}$ may act through the arcuate nucleus Y2R to inhibit feeding in a gut-hypothalamic pathway. *Nature* 418: 650–654, 2002, incorporated herein by reference.

Experiments have been performed to investigate whether peripheral $PYY_{3-36}$ might inhibit food intake through the Y2R in the arcuate nucleus, an area that is directly accessible to circulating hormones. To investigate this hypothesis, experiments injected $PYY_{3-36}$ directly into the arcuate nucleus. In rats fasted for 24 h, food intake was significantly decreased by doses as low as 100 fmol, which resulted in a similar inhibition to that seen after intraperitoneal administration. To establish whether these effects occurred through the Y2R, a Y2R selective agonist, Y2A (N-acetyl [Leu, Leu] $NPY_{24-36}$) was used. Its affinity was confirmed using receptor-binding studies on cell lines that expressed the NPY Y1, Y2 and Y5 receptors. Intra-arcuate nucleus injection of Y2A in rats previously fasted for 24 h dose-dependently inhibited (100 fmol to 1 nmol) food intake. To confirm the anatomical specificity of this effect, Y2A (100 fmol to 1 nmol) was injected into the paraventricular nucleus (PVN) of rats fasted for 24 h and found no alteration of food intake. To define further the role of the Y2R in the feeding inhibition caused by peripheral $PYY_{3-36}$, the effect of $PYY_{3-36}$ on Y2r-null mice and littermate controls was examined. $PYY_{3-36}$ inhibited daytime feeding in a dose-responsive manner in fasted male wild-type mice but did not inhibit food intake in fasted male Y2r-null mice. *Nature* 418: 650–654, 2002, incorporated herein by reference.

Results of this experiment suggest that the cells in the arcuate nucleus detect circulating peripheral satiety signals and relay these signals to other brain regions. This is supported by the observation that leptin modifies the activity of both the proopiomelanocortin (POMC) and NPY arcuate neurons. Experiments have shown, through a combination of electrophysiological and hypothalamic explant studies, that the gut hormone, $PYY_{3-36}$, can directly influence hypothalamic circuits, which results in coordinate changes in POMC and NPY action. In addition, $PYY_{3-36}$ administered directly into this brain region reduces food intake. Data show that postprandial concentrations of $PYY_{3-36}$ inhibit food intake in both rodents and man for up to 12 h, which suggests that $PYY_{3-36}$ has a role in longer term regulation of food intake. This contrasts with previously characterized gut-derived short-term satiety signals such as cholecystokinin, the effects of which are relatively short-lived. The failure of $PYY_{3-36}$ to inhibit food intake in the Y2r-null mice provides further evidence that $PYY_{3-36}$ reduces food intake through a Y2R-dependent mechanism. Experimental results suggest that a gut-hypothalamic pathway that involves postprandial $PYY_{3-36}$ acting at the arcuate Y2R has a role in regulating feeding. Thus, the $PYY_{3-36}$ system may provide a therapeutic target for the treatment of obesity. *Nature* 418: 650–654, 2002, incorporated herein by reference.

Leptin is an adiposity hormone that modulates the activity of multiple hypothalamic signaling pathways involved in the control of food intake. Experiments were designed to evaluate whether central administration of leptin or one of its downstream mediators, neuropeptide Y (NPY), could affect food intake by modulating the brain stem neurophysiological response to ascending meal-related feedback signals in the nucleus of the solitary tract (NTS) in anesthetized male Long-Evans rats. NTS neurons at the rostrocaudal level of the area postrema were dose-dependently activated by gastric loads ranging from 2–10 ml, and leptin and NPY had opposite modulatory effects on this load volume/activity relationship: leptin significantly increased NTS responses to gastric loads, whereas NPY reduced the potency and efficacy with which gastric loads activated NTS neurons. These effects were probably not mediated by peripheral effects of centrally administered peptides or by the gastrokinetic effects of central NPY or leptin, because the dose-response relationship between gastric load volume and neurophysiological firing rate was unchanged in gastric load-sensitive vagal afferent fibers. These data suggest a mechanistic framework for considering how feeding behavior occurring in meals is altered by challenges to energy homeostasis, such as fasting and overfeeding. *Endocrinology* 143: 3779–3784, 2002, incorporated herein by reference.

As noted above, the subpeptide $PYY_{3-36}$ exhibits antidiabetic and antiobesity actions in several animal models. Since gastric emptying is an important mediator of post-prandial glycemia, experiments investigated whether $PYY_{3-36}$ affected gastric emptying, and specifically investigated whether such effect was mediated via the area postrema (AP), a circumventricular organ with no blood-brain barrier, that is accessible to circulating peptides and known to be involved in the regulation of gastrointestinal function. While saline injected AP-lesioned animals had a tendency to delay gastric emptying compared to non-operated and sham operated rats, $PYY_{3-36}$ administration had no additional effect on gastric emptying rate in the AP-lesioned animals. $PYY_{3-36}$ has a potent effect to inhibit gastric emptying in normal rats via a pathway that appears to include the area postrema. *American Diabetes Association, 62$^{nd}$ Annual Scientific Sessions*, Jun. 14–18, 2002; Abstract 1661-P, incorporated herein by reference.

To investigate a possible role for peripherally administered $PYY_{3-36}$ in metabolic control, experiments examined the effects of its infusion for 28 days via subcutaneous osmotic pumps (at 0, 30, 100, 300 and 1000 µg/kg/d) to C57BL/6 mice (n=14–22/group) previously fed a high fat diet (HF; 58% fat vs LF, low-fat control diet, with 11% fat) for 47 days. Contrasting with previously reported effects of centrally administered PYY and $PYY_{3-36}$ to increase food intake and body weight, the results of this study indicate that peripherally administered $PYY_{3-36}$ exhibits an anti-obesity and glucose-lowering effect in diet-induced obese mice. *American Diabetes Association, 62$^{nd}$ Annual Scientific Sessions*, Jun. 14–18, 2002; Abstract 1718-P, incorporated herein by reference.

Additional studies examined the effect of 4 weeks of continuous infusion of $PYY_{3-36}$ on 8 week-old male Zucker Diabetic Fatty (ZDF) rats. The results suggest that the improvement in glycemic control following chronic $PYY_{3-36}$ in ZDF rats was unlikely to be due to direct effects on glucoregulatory hormone secretion, and may instead be related to mechanisms such as reduced nutrient availability. The dissociation of food consumption from weight gain in these experiments, despite the presence of glucose-lowering effects, suggests factors such as caloric loss in the urine of diabetic animals. Further studies in Diabetic Fatty Zucker (ZDF) rats demonstrated that continuous infusion of $PYY_{3-36}$ decreased food consumption and improved glycemic control, without decreasing body weight gain, but those observations did not account for caloric redistribution due to treatment-related changes in glycosuria. In contrast to previous data in diabetic animals where caloric losses in the urine may have been a factor and where there was no change in body weight, the results of the present study indicate that in the absence of glycosuria in obese non-diabetic fa/fa rats, $PYY_{3-36}$ treatment decreases food consumption and body weight. *American Diabetes Association, 62$^{nd}$ Annual Scientific Sessions*, Jun. 14–18, 2002; Abstract 1717-P; Abstract 2499, incorporated herein by reference.

Further experiments examined the effect of continuous infusion of $PYY_{3-36}$ in genetically obese mice (ob/ob; B6.V-Lep ob) on food intake and body. Chronic $PYY_{3-36}$ infusion in ob/ob mice was associated with a dose dependent decrease in body weight compared to saline infused animals. This effect appeared to be independent of any effect on food intake. (*American Diabetes Association, 62$^{nd}$ Annual Scientific Sessions*, Jun. 14–18, 2002; Abstract 1716-P, incorporated herein by reference.

As part of an investigation of the potential involvement of the gut in these actions, other experiments examined the dose-response of subcutaneously injected $PYY_{3-36}$ on pentagastrin-stimulated gastric acid secretion. The effect of $PYY_{3-36}$ on ethanol-induced gastritis was evaluated in fasted male Sprague Dawley rats. To study acid secretion, rats chronically implanted with gastric cannulae were injected subcutaneously with 125 µg/kg pentagastrin. Gastric contents obtained by flushing the cannulae every 10 min were titrated to measure acid production. $PYY_{3-36}$ dose-dependently and potently inhibited pentagastrin-stimulated gastric acid secretion, manifest also as a gastroprotective effect, in rats. Endogenously circulating $PYY_{3-36}$ may play a physiologic role in controlling gastric acid secretion and protecting the gastric mucosa. (*American Diabetes Association, 62$^{nd}$ Annual Scientific Sessions*, Jun. 14–18, 2002; Abstract 2444-PO, incorporated herein by reference.

Obesity and its associated disorders are common and very serious public health problems in the United States and throughout the world. Upper body obesity is the strongest risk factor known for type 2 diabetes mellitus, and is a strong risk factor for cardiovascular disease. Obesity is a recognized risk factor for hypertension, arteriosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia. Kopelman. *Nature* 404: 635–43, 2000, incorporated herein by reference. It reduces life-span and carries a serious risk of co-morbidities above, as well disorders such as infections, varicose veins, acanthosis nigricans, eczema, exercise intolerance, insulin resistance, hypertension hypercholesterolemia, cholelithiasis, orthopedic injury, and thromboembolic disease. Rissanen, et al. *BMJ* 301: 835–7, 1990, incorporated herein by reference. Obesity is also a risk factor for the group of conditions called insulin resistance syndrome, or "Syndrome X." Recent estimates for the medical cost of obesity and associated disorders are $150 billion worldwide. The pathogenesis of obesity is believed to be multifactorial but the basic problem is that in obese subjects nutrient availability and energy expenditure do not come into balance until there is excess adipose tissue. Obesity is currently a poorly treatable, chronic, essentially intractable metabolic disorder. A therapeutic drug useful in weight reduction of obese persons could have a profound beneficial effect on their health.

Previous methods have attempted to increase weight gain in healthy subjects by administering peptide YY to the subject. Additional reports propose treatment of metabolic disorders such as obesity, diabetes, and increased cardiovascular risk by administering peptide YY or a peptide YY agonist. See e.g., U.S. Pat. No. 5,912,227; U.S. application 20020141985. These and related reports have attempted to administer peptide YY by various routes. Notably, there are no previous descriptions that demonstrate a therapeutically effective nasal formulation or method for administering peptide YY for any of the foregoing diseases and conditions.

Previous attempts to successfully deliver peptide YY for therapeutic purposes have suffered from a number of important and confounding deficiencies. These deficiencies point to a long-standing unmet need in the art for pharmaceutical formulations and methods of administering peptide YY that are stable and well tolerated and that provide enhanced delivery to target sites, e.g., the serum or other selected cellular or extracellular compartment, in mammalian subjects.

BRIEF SUMMARY OF THE INVENTION

The present invention fulfills the foregoing needs and satisfies additional objects and advantages by providing novel, effective methods and compositions for intranasal delivery of peptide YY yielding improved pharmacokinetic and pharmacodynamic results. In certain aspects of the invention, the peptide YY is delivered to the intranasal mucosa along with one or more intranasal delivery-enhancing agent(s) to yield substantially increased absorption and/or bioavailability of the peptide YY and/or a substantially decreased time to maximal concentration of peptide YY in a tissue or other target site of a mammalian subject as compared to controls (e.g., where the peptide YY is administered to the same intranasal site alone or formulated according to previously disclosed reports).

The enhancement of intranasal delivery of peptide YY according to the methods and compositions of the invention allows for the effective pharmaceutical use of these agents to treat a variety of diseases and conditions in mammalian subjects.

Briefly, the methods and compositions of the invention provide for enhanced delivery of peptide YY across nasal mucosal barriers to reach novel target sites for drug action yielding an enhanced, therapeutically effective rate or concentration of delivery. In certain aspects, employment of one or more intranasal delivery-enhancing agents facilitates the effective delivery of a peptide YY to a targeted, extracellular or cellular compartment, for example the systemic circulation, a selected cell population, tissue or organ. Exemplary targets for enhanced delivery in this context are target physiological compartments, tissues, organs and fluids (e.g., within the blood serum, central nervous system (CNS) or cerebral spinal fluid (CSF) or selected tissues or cells of the liver, bone, muscle, cartilage, pituitary, hypothalamus, kidney, lung, heart, testes, skin, or peripheral nervous system.

In exemplary embodiments, the enhanced delivery methods and compositions of the present invention provide for therapeutically effective mucosal delivery of peptide YY for prevention or treatment of obesity and eating disorders in mammalian subjects. In one aspect of the invention, pharmaceutical formulations suitable for intranasal administration are provided that comprise a therapeutically effective amount of peptide YY and one or more intranasal delivery-enhancing agents as described herein, which formulations are effective in a nasal mucosal delivery method of the invention to prevent the onset or progression of obesity or eating disorders in a mammalian subject. Nasal mucosal delivery of a therapeutically effective amount of peptide YY and one or more intranasal delivery-enhancing agents yields more consistent (normalized) or elevated therapeutic levels of peptide YY in a central nervous system tissue or fluid. In an exemplary embodiment, nasal mucosal delivery of a therapeutically effective amount of peptide YY and one or more intranasal delivery-enhancing agents yields more consistent (normalized) or elevated therapeutic levels of peptide YY in a region of the brain of the mammalian subject, for example, hypothalamus, or arcuate nucleus of the hypothalamus. Nasal mucosal delivery of a therapeutically effective amount of peptide YY and one or more intranasal delivery-enhancing agents yields elevated therapeutic levels of peptide YY in the subject and inhibits food intake in the mammalian subject, reducing symptoms of obesity or an eating disorder.

In other embodiments, the enhanced delivery methods and compositions of the present invention provide for therapeutically effective mucosal delivery of a neuropeptide Y receptor antagonist, for example, a Y1 receptor antagonist, for prevention or treatment of obesity and eating disorders in mammalian subjects. In one aspect of the invention, pharmaceutical formulations suitable for intranasal administration are provided that comprise a therapeutically effective amount of the Y1 receptor antagonist, for example, a dihydropyridine or peptide YY analog, and one or more intranasal delivery-enhancing agents as described herein, which formulations are effective in a nasal mucosal delivery method of the invention to prevent the onset or progression of obesity or eating disorders in a mammalian subject. Nasal mucosal delivery of a therapeutically effective amount of Y1 receptor antagonist and one or more intranasal delivery-enhancing agents yields more consistent, e.g., normalized, or elevated therapeutic levels of peptide YY in a central nervous system tissue or fluid or in a blood serum of the mammalian subject.

The enhanced delivery methods and compositions of the present invention provide for therapeutically effective mucosal delivery of peptide YY for prevention or treatment of a variety of diseases and conditions in mammalian subjects. Peptide YY can be administered via a variety of mucosal routes, for example by contacting peptide YY to a nasal mucosal epithelium, a bronchial or pulmonary mucosal epithelium, an oral, gastric, intestinal or rectal mucosal epithelium, or a vaginal mucosal epithelium. In exemplary embodiments, the methods and compositions are directed to or formulated for intranasal delivery (e.g., nasal mucosal delivery or intranasal mucosal delivery).

In one aspect of the invention, pharmaceutical formulations suitable for intranasal administration are provided that comprise a therapeutically effective amount of peptide YY and one or more intranasal delivery-enhancing agents as described herein, which formulations are effective in a nasal mucosal delivery method of the invention to prevent the onset or progression of obesity, cancer, or malnutrition or wasting related to cancer in a mammalian subject, or to alleviate one or more clinically well-recognized symptoms of obesity, cancer, or malnutrition or wasting related to cancer in a mammalian subject.

In another aspect of the invention, pharmaceutical formulations suitable for intranasal administration are provided that comprise a therapeutically effective amount of peptide YY and one or more intranasal delivery-enhancing agents as described herein, which formulation is effective in a nasal mucosal delivery method of the invention to alleviate symptoms or prevent the onset or lower the incidence or severity of, for example, obesity in children or adult subjects, Alzheimer's disease, colon carcinoma, colon adenocarcinoma, pancreatic carcinoma, pancreatic adenocarcinoma, breast carcinoma, treatment and prevention of malnutrition resulting from iatrogenic causes or cachexia associated with advanced disease, or cancer cachexia.

In another aspect of the invention, pharmaceutical formulations and methods are directed to administration of peptide YY in combination with vitamin E succinate. Peptide YY in combination with vitamin E succinate may be administered to alleviate symptoms or prevent the onset or lower the incidence or severity of cancer, for example, colon adenocarcinoma, pancreatic adenocarcinoma, or breast cancer.

In more detailed aspects of the invention, methods and compositions for intranasal delivery of peptide YY incorporate one or more intranasal delivery enhancing agent(s) combined in a pharmaceutical formulation together with, or administered in a coordinate nasal mucosal delivery protocol with, a therapeutically effective amount of peptide YY. These methods and compositions provide enhanced nasal transmucosal delivery of the peptide YY, often in a pulsatile delivery mode to maintain continued release of peptide YY to yield more consistent (normalized) or elevated therapeutic levels of peptide YY in the blood serum, or in another selected physiological compartment or target tissue or organ for treatment of disease. Peptide YY is produced in the gastrointestinal tract and brain. A major site of action of peptide YY in the brain is the hypothalamic arcuate nucleus. For example, normalized and elevated therapeutic levels of peptide YY may be measured in the central nervous system tissue or cerebral spinal fluid or in the systemic blood serum of the mammalian subject receiving the peptide YY by enhanced nasal transmucosal delivery using methods and compositions of the present invention. Normalized and elevated therapeutic levels of peptide YY are determined, for example, by an increase in bioavailability (e.g., as measured by maximal concentration ($C_{max}$) or the area under concentration vs. time curve (AUC) for an intranasal effective amount of peptide YY) and/or an increase in delivery rate (e.g., as measured by time to maximal concentration ($t_{max}$), $C_{max}$, and or AUC). Normalized and elevated high therapeutic levels of peptide YY in the central nervous system (CNS) tissue or fluid or in the blood serum may be achieved in part by repeated intranasal administration to a subject within a selected dosage period, for example an 8, 12, or 24 hour dosage period.

In an alternative embodiment, normalized and elevated therapeutic levels of peptide YY are determined, for example, by an increase in bioavailability and/or an increase in delivery rate as measured in the hepatic portal vein, (e.g., as measured by $t_{max}$, $C_{max}$, or AUC for an intranasal effective amount of peptide YY in the hepatic portal vein).

To maintain more consistent or normalized therapeutic levels of peptide YY, the pharmaceutical formulations of the present invention are often repeatedly administered to the nasal mucosa of the subject, for example, one, two or more times within a 24 hour period, four or more times within a 24 hour period, six or more times within a 24 hour period, or eight or more times within a 24 hour period. The methods and compositions of the present invention yield improved pulsatile delivery to maintain normalized and/or elevated therapeutic levels of peptide YY, e.g., in the blood serum. The methods and compositions of the invention enhance transnasal mucosal delivery of peptide YY to a selected target tissue or compartment by at least a two- to five- fold increase, more typically a five- to ten-fold increase, and commonly a ten- to twenty-five- up to a fifty-fold increase (e.g., as measured by $t_{max}$ $C_{max}$, and/or AUC, in the central nervous system (CNS) tissue or fluid or the blood serum, or in another selected physiological compartment or target tissue or organ for delivery), compared to the efficacy of delivery of peptide YY administered alone or using a previously-described delivery method, for example a previously-described mucosal delivery, intramuscular delivery, subcutaneous delivery, intravenous delivery, and/or parenteral delivery method.

Nasal mucosal delivery of peptide YY according to the methods and compositions of the invention will often yield effective delivery and bioavailability that approximates dosing achieved by continuous administration methods. In other aspects, the invention provides enhanced nasal mucosal delivery that permits the use of a lower systemic dosage and significantly reduces the incidence of peptide YY-related side effects. Because continuous infusion of peptide YY outside the hospital setting is otherwise impractical, mucosal delivery of peptide YY as provided herein yields unexpected advantages that allow sustained delivery of peptide YY, with the accrued benefits, for example, of improved patient-to-patient dose variability.

In more detailed aspects of the invention, the methods and compositions of the present invention provide improved and/or sustained delivery of peptide YY to the blood serum or central nervous system (CNS). In one exemplary embodiment, an intranasal effective amount of peptide YY and one or more intranasal delivery enhancing agent(s) is contacted with a nasal mucosal surface of a subject to yield enhanced mucosal delivery of peptide YY to the blood serum or CNS of the subject, for example, to effectively treat obesity, cancer, or malnutrition or wasting related to cancer. In certain embodiments, the methods and compositions of the invention provide improved and sustained delivery of peptide YY to blood serum or CNS of peptide YY action, including the central nervous system (CNS) or cerebral spinal fluid (CSF) of the subject, and will effectively treat one or more symptoms of obesity, cancer, or malnutrition or wasting related to cancer, including in cases where conventional peptide YY therapy yields poor results or unacceptable adverse side effects.

In exemplary embodiments, the methods and compositions of the present invention yield a two- to five- fold decrease, more typically a five- to ten-fold decrease, and commonly a ten- to twenty-five- up to a fifty- to one hundred-fold decrease in the time to maximal concentration ($t_{max}$) of the peptide YY in blood serum, gastrointestinal tract, central nervous system, cerebral spinal fluid, and/or in another selected physiological compartment or target tissue or organ for delivery-as compared to delivery rates for peptide YY administered alone or in accordance with previously-described drug delivery methods. Such previously described methods may include, for example, any alternate route of deliver (e.g., intravenous or subcutaneous versus intranasal).

In further exemplary embodiments, the methods and compositions of the invention yield a two- to five- fold increase, more typically a five- to ten-fold increase, and commonly a ten- to twenty-five- up to a fifty- to one hundred-fold increase in the area under concentration vs. time curve, AUC, of the peptide YY in blood serum, gastrointestinal tract, central nervous system, cerebral spinal fluid, or in another selected physiological compartment or target tissue or organ for delivery-as compared to delivery rates for the peptide YY administered alone or in accordance with previously-described administration methods.

In further exemplary embodiments, the methods and compositions of the present invention yield a two- to five-fold increase, more typically a five- to ten-fold increase, and commonly a ten- to twenty-five- up to a fifty- to one hundred-fold increase in the maximal concentration, $C_{max}$, of the peptide YY in blood serum, CNS, gastrointestinal tract, or in another selected physiological compartment or target tissue or organ for delivery-as compared to delivery rates for the peptide YY administered alone or in accordance with previously-described administration methods.

The methods and compositions of the invention will often serve to improve peptide YY dosing schedules and thereby maintain normalized and/or elevated, therapeutic levels of peptide YY in the subject. In certain embodiments, the invention provides compositions and methods for intranasal delivery of peptide YY, wherein peptide YY dosage normalized and sustained by repeated, typically pulsatile, delivery to maintain more consistent, and in some cases elevated, therapeutic levels. In exemplary embodiments, the time to maximum concentration ($t_{max}$) of peptide YY in the blood serum, CNS, or gastrointestinal tract will be from about 0.1 to 4.0 hours, alternatively from about 0.4 to 1.5 hours, and in other embodiments from about 0.7 to 1.5 hours, or from about 1.0 to 1.3 hours. Thus, repeated intranasal dosing with the formulations of the invention, on a schedule ranging from about 0.1 to 2.0 hours between doses, will maintain normalized, sustained therapeutic levels of peptide YY to maximize clinical benefits while minimizing the risks of excessive exposure and side effects.

The methods and compositions of the invention will often serve to improve peptide YY dosing schedules and thereby maintain normalized and/or elevated, therapeutic levels of peptide YY in the subject. In exemplary embodiments, dosage of peptide YY is from about 0.001 pmol to about 100 pmol per kg body weight, from about 0.01 pmol to about 10 pmol per kg body weight, from about 0.1 pmol to about 5 pmol per kg body weight. In further exemplary embodiments, dosage of peptide YY is from about 0.5 pmol to about 1.0 pmol per kg body weight.

In an alternative embodiment, the invention provides compositions and methods for intranasal delivery of peptide YY, wherein the peptide YY compound(s) is/are repeatedly administered through an intranasal effective dosage regimen that involves multiple administrations of the peptide YY compound(s) to the subject during a daily or weekly schedule to maintain a therapeutically effective elevated and lowered pulsatile level of peptide YY during an extended dosing period. The compositions and method provide peptide YY compound(s) that are self-administered by the subject in a nasal formulation between two and six times daily to maintain a therapeutically effective elevated and lowered pulsatile level of peptide YY during an 8 hour to 24 hour extended dosing period.

In alternative embodiments, the invention achieves enhanced delivery of normalized and/or elevated, improved therapeutic levels of peptide YY by combining mucosal administration of one dosage amount of peptide YY formulated with one or more intranasal delivery-enhancing agents, with a separate dosage amount of peptide YY delivered by a non-mucosal route, for example by subcutaneous or intramuscular administration. In one exemplary embodiment, intranasal delivery of peptide YY according to the compositions and methods herein yields normalized and/or elevated, high therapeutic levels of peptide YY in the blood serum, CNS, or gastrointestinal tract of the subject for a time period between approximately 0.1 and 3 hours following intranasal administration. Coordinate administration of peptide YY by a non-mucosal route (before, simultaneous with, or after mucosal administration) provides more consistent, elevated therapeutic levels of peptide YY in the blood serum, CNS, or gastrointestinal tract of the subject for an effective time period of between approximately 2 to 24 hours, more often between about 4 to 16 hours, and in certain embodiments between about 6 to 8 hours. Within these coordinate administration methods, the aims of the treating physician are facilitated by improving clinical benefit while minimizing the risks of excessive exposure.

In other aspects of the invention, the methods and formulations for intranasally administering peptide YY described herein yield a significantly enhanced rate or level of delivery (e.g., decreased $t_{max}$, increased AUC, and/or increased $C_{max}$) of the peptide YY into the serum, or to selected tissues or cells, of the subject. This includes enhanced delivery rates or levels into the blood serum, CNS tissue or fluid, or to selected tissues or cells (e.g., blood serum, CNS, or CSF), compared to delivery rates and levels for the peptide YY administered alone or in accordance with conventional technologies. Thus, in certain aspects of the invention, the foregoing methods and compositions are administered to a mammalian subject to yield enhanced delivery of the peptide YY to a physiological compartment, fluid, tissue or cell within the mammalian subject.

Within more detailed aspects of the invention, bioavailability of peptide YY achieved by the methods and formulations herein (e.g., measured by peak blood plasma levels ($C_{max}$) in blood serum or in another selected physiological compartment or target tissue) will be, for example, from about 0.1 pmol/L to about 1000 pmol/L of blood plasma or CSF, from about 1.0 pmol/L to about 100 pmol/L of blood plasma or CSF, from about 1.0 pmol/L to about 10 pmol/L of blood plasma or CSF, or from about 5.0 pmol/L to about 10 pmol/L of blood plasma or CSF.

Within other detailed aspects of the invention, bioavailability of peptide YY achieved by the methods and formulations herein (e.g., as measured by area under the concentration curve (AUC) in blood plasma, central nervous system (CNS) tissue or fluid, or in another selected physiological compartment or target tissue) will be, for example, from about 0.1 pmol/L to about 1000 pmol/L of blood plasma or CSF, from about 10 pmol/L to about 1000 pmol/L of blood plasma or CSF, from about 10 pmol/L to about 100 pmol/L of blood plasma or CSF, or from about 50 pmol/L to about 100 pmol/L of blood plasma or CSF The procedures for determining the concentrations of peptide YY neuropeptide Y, and pancreatic peptide in blood serum, central nervous system (CNS) tissues or fluids, cerebral spinal fluid (CSF), or other tissues or fluids of a mammalian subject may be determined by immunologic assay for peptide YY neuropeptide Y, and pancreatic peptide. The procedures for determining the concentrations of peptide YY neuropeptide Y, and pancreatic peptide as test materials for evaluating enhanced permeation of active agents in conjunction with coordinate administration of mucosal delivery-enhancing agents or combinatorial formulation of the invention are generally as described above and in accordance with known methods and specific manufacturer instructions for radioimmunoassay (RIA), enzyme immunoassay (EIA), and antibody reagents for immunohistochemistry or immunofluorescence for peptide YY neuropeptide Y, or pancreatic peptide. Bachem AG (King of Prussia, Pa.).

The procedures for determining the concentrations of neuropeptide Y receptors Y1 through Y5 as test materials for evaluating enhanced permeation of active agents in conjunction with coordinate administration of mucosal delivery-enhancing agents or combinatorial formulation of the invention are generally as described above and in accordance with known methods and specific manufacturer instructions for assays to measure neuropeptide Y receptor binding by a neuropeptide Y Scintillation Proximity (SPa.) Binding Assay [Receptors Y 1; Y2]; Amersham Biosciences (Piscataway, N.J.).

Within further detailed aspects of the invention, bioavailability of peptide YY achieved by the methods and formulations herein (e.g., as measured by time to maximal concentration ($t_{max}$) in central nervous system (CNS) tissue or fluid, blood serum, or in another selected physiological compartment or target tissue) will be, for example, about 1.4 hours or less, about 1.0 hours or less, about 0.8 hours or less, about 0.6 hours or less, about 0.4 hours or less, or about 0.2 hours or less.

In exemplary embodiments, administration of one or more peptide YY formulated with one or more intranasal delivery-enhancing agents as described herein yields effective delivery to the central nervous system (CNS) tissue or fluid, or to the blood serum to alleviate a selected disease or condition (e.g., obesity, cancer, or malnutrition or wasting related to cancer, or a symptom thereof) in a mammalian subject. In more detailed aspects, the methods and formulations for intranasally administering peptide YY according to the invention yield a significantly enhanced rate or level of delivery (e.g., decreased $t_{max}$ or increased $C_{max}$) of the peptide YY into the serum or to selected tissues or cells (e.g., gastrointestinal tract or CNS), compared to delivery rates and levels for the peptide YY administered alone or in accordance with previously-described technologies.

The enhanced pharmacokinetics of delivery of peptide YY (e.g., increased rate, normalized, sustained delivery, and elevated levels) according to the methods of the invention, provides improved therapeutic efficacy, e.g., to treat obesity, cancer, or malnutrition or wasting related to cancer in a subject, without unacceptable adverse side effects. Thus, for example, pharmaceutical preparations formulated for nasal mucosal delivery are provided for treating obesity, cancer, or malnutrition or wasting related to cancer in a mammalian subject that comprise a therapeutic intranasal effective amount of peptide YY combined with one or more intranasal delivery-enhancing agents as disclosed herein. These preparations surprisingly yield enhanced mucosal absorption of the peptide YY to produce a therapeutic effective concentration of the drug (e.g., for treating obesity, cancer, or malnutrition or wasting related to cancer in a subject) at a target site or tissue in the subject in about 45 minutes or less, 30 minutes or less, 20 minutes or less, or as little as 15 minutes or less.

Within other detailed embodiments of the invention, the foregoing methods and formulations are administered to a mammalian subject to yield enhanced blood serum, gastrointestinal tract, CNS levels, or other tissue levels of the peptide YY by administering a formulation comprising an intranasal effective amount of peptide YY and one or more intranasal delivery-enhancing agents and one or more sustained release-enhancing agents. The sustained release-enhancing agents, for example, may comprise a polymeric delivery vehicle. In exemplary embodiments, the sustained release-enhancing agent may comprise polyethylene glycol (PEG) coformulated or coordinately delivered with peptide YY and one or more intranasal delivery-enhancing agents. PEG may be covalently bound to peptide YY. The sustained release-enhancing methods and formulations of the present invention will increase residence time (RT) of the peptide YY at a site of administration and will maintain a basal level of the peptide YY over an extended period of time in blood serum, CNS or gastrointestinal tract, or other tissue in the mammalian subject.

Within other detailed embodiments of the invention, the foregoing methods and formulations are administered to a mammalian subject to yield enhanced blood serum, gastrointestinal tract, or CNS levels, or other tissue levels of the peptide YY to maintain basal levels of peptide YY over an extended period of time. Exemplary methods and formulations involve administering a pharmaceutical formulation comprising an intranasal effective amount of peptide YY and one or more intranasal delivery-enhancing agents to a mucosal surface of the subject, in combination with intramuscular or subcutaneous administration of a second pharmaceutical formulation comprising peptide YY. Maintenance of basal levels of peptide YY is particularly useful for treatment and prevention of disease, for example, obesity, cancer, or malnutrition or wasting related to cancer.

The foregoing mucosal drug delivery formulations and preparative and delivery methods of the invention provide improved mucosal delivery of peptide YY to mammalian subjects. These compositions and methods can involve combinatorial formulation or coordinate administration of one or more peptide YY(s) with one or more mucosal (e.g., intranasal) delivery-enhancing agents. Among the mucosal delivery-enhancing agents to be selected from to achieve these formulations and methods are (a) aggregation inhibitory agents; (b) charge modifying agents; (c) pH control agents; (d) degradative enzyme inhibitors; (e) mucolytic or mucus clearing agents; (f) ciliostatic agents; (g) membrane penetration-enhancing agents (e.g., (i) a surfactant, (ii) a bile salt, (ii) a phospholipid or fatty acid additive, mixed micelle, liposome, or carrier, (iii) an alcohol, (iv) an enamine; (v) an NO donor compound, (vi) a long-chain amphipathic molecule (vii) a small hydrophobic penetration enhancer; (viii) sodium or a salicylic acid derivative; (ix) a glycerol ester of acetoacetic acid (x) a cyclodextrin or beta-cyclodextrin derivative, (xi) a medium-chain fatty acid, (xii) a chelating agent, (xiii) an amino acid or salt thereof, (xiv) an N-acetylamino acid or salt thereof, (xv) an enzyme degradative to a selected membrane component, (ix) an inhibitor of fatty acid synthesis, (x) an inhibitor of cholesterol synthesis; or (xi) any combination of the membrane penetration enhancing agents of (i)-(x)); (h) modulatory agents of epithelial junction physiology, such as nitric oxide (NO) stimulators, chitosan, and chitosan derivatives; (i) vasodilator agents; (j) selective transport-enhancing agents; and (k) stabilizing delivery vehicles, carriers, supports or complex-forming species with which the peptide YY(s) is/are effectively combined, associated, contained, encapsulated or bound to stabilize the active agent for enhanced nasal mucosal delivery.

In various embodiments of the invention, peptide YY is combined with one, two, three, four or more of the mucosal (e.g., intranasal) delivery-enhancing agents recited in (a)–(k), above. These mucosal delivery-enhancing agents may be admixed, alone or together, with peptide YY, or otherwise combined therewith in a pharmaceutically acceptable formulation or delivery vehicle. Formulation of peptide YY with one or more of the mucosal delivery-enhancing agents according to the teachings herein (optionally including any combination of two or more mucosal delivery-enhancing agents selected from (a)–(k) above) provides for increased bioavailability of the peptide YY following delivery thereof to a mucosal (e.g., nasal mucosal) surface of a mammalian subject.

In related aspects of the invention, a variety of coordinate administration methods are provided for enhanced mucosal delivery of peptide YY. These methods comprise the step, or steps, of administering to a mammalian subject a mucosally effective amount of at least one peptide YY in a coordinate administration protocol with one or more mucosal delivery-enhancing agents selected from (a) aggregation inhibitory agents; (b) charge modifying agents; (c) pH control agents; (d) degradative enzyme inhibitors; (e) mucolytic or mucus clearing agents; (f) ciliostatic agents; (g) membrane penetration-enhancing agents (e.g., (i) a surfactant, (ii) a bile salt, (ii) a phospholipid or fatty acid additive, mixed micelle, liposome, or carrier, (iii) an alcohol, (iv) an enamine, (v) an NO donor compound, (vi) a long-chain amphipathic molecule (vii) a small hydrophobic penetration enhancer; (viii) sodium or a salicylic acid derivative; (ix) a glycerol ester of acetoacetic acid (x) a cyclodextrin or beta-cyclodextrin derivative, (xi) a medium-chain fatty acid, (xii) a chelating agent, (xiii) an amino acid or salt thereof, (xiv) an N-acetylamino acid or salt thereof, (xv) an enzyme degradative to a selected membrane component, (ix) an inhibitor of fatty acid synthesis, (x) an inhibitor of cholesterol synthesis; or (xi) any combination of the membrane penetration enhancing agents of (i)–(x)); (h) modulatory agents of epithelial junction physiology, such as nitric oxide (NO) stimulators, chitosan, and chitosan derivatives; (i) vasodilator agents; (j) selective transport-enhancing agents; and (k) stabilizing delivery vehicles, carriers, supports or complex-forming species with which the peptide YY(s) is/are effectively combined, associated, contained, encapsulated or bound to stabilize the active agent for enhanced mucosal (e.g., intranasal) delivery.

To practice a coordinate administration method according to the invention, any combination of one, two or more of the mucosal delivery-enhancing agents recited in (a)–(k), above, may be admixed or otherwise combined for simultaneous mucosal (e.g., intranasal) administration. Alternatively, any combination of one, two or more of the mucosal delivery-enhancing agents recited in (a)–(k) can be mucosally administered, collectively or individually, in a predetermined temporal sequence separated from mucosal administration of the peptide YY (e.g., by pre-administering one or more of the delivery-enhancing agent(s)), and via the same or different delivery route as the peptide YY (e.g., to the same or to a different mucosal surface as the peptide YY, or even via a non-mucosal (e.g., intramuscular, subcutaneous, or intravenous route). Coordinate administration of peptide YY with any one, two or more of the mucosal delivery-enhancing agents according to the teachings herein provides for increased bioavailability of the peptide YY following delivery thereof to a mucosal surface of a mammalian subject.

In additional related aspects of the invention, various "multi-processing" or "co-processing" methods are provided for preparing formulations of peptide YY for enhanced nasal mucosal delivery. These methods comprise one or more processing or formulation steps wherein one or more peptide YY(s) is/are serially, or simultaneously, contacted with, reacted with, or formulated with, one, two or more (including any combination of) of the mucosal delivery-enhancing agents as detailed above. To practice the multi-processing or co-processing methods according to the invention, the peptide YY is/are exposed to, reacted with, or combinatorially formulated with any combination of one, two or more of the mucosal delivery-enhancing agents recited in (a)–(k), above, either in a series of processing or formulation steps, or in a simultaneous formulation procedure, that modifies the peptide YY (or other formulation ingredient) in one or more structural or functional aspects, or otherwise enhances mucosal delivery of the active agent in one or more (including multiple, independent) aspect(s) that are each attributed, at least in part, to the contact, modifying action, or presence in a combinatorial formulation, of a specific mucosal delivery-enhancing agent recited in (a)–(k), above.

In certain detailed aspects of the invention, the methods and compositions which comprise a mucosally effective amount of peptide YY and one or more mucosal delivery-enhancing agent(s) (combined in a pharmaceutical formulation together or administered in a coordinate nasal mucosal delivery protocol) provide nasal transmucosal delivery of the peptide YY in a pulsatile delivery mode to maintain more consistent or normalized, and/or elevated levels of peptide YY in the blood serum. In this context, the pulsatile delivery methods and compositions of the invention yield increased bioavailability (e.g., as measured by maximal concentration, ($C_{max}$) or area under concentration curve (AUC) of peptide YY and/or an increased mucosal delivery rate (e.g., as measured by time to maximal concentration ($t_{max}$), $C_{max}$ and/or AUC compared to other mucosal or non-mucosal delivery method-based controls. For example, the invention provides pulsatile delivery methods and formulations comprise peptide YY and one or more mucosal delivery-enhancing agent(s), wherein the formulation administered mucosally (e.g., intranasally) to a mammalian subject, yields an area under the concentration curve (AUC) for peptide YY in the blood serum, CNS or gastrointestinal tract that is about 10% or greater compared to an area under the concentration curve (AUC) for peptide YY in the blood serum, CNS or gastrointestinal tract following subcutaneous injection to the mammalian subject.

Often the formulations of the invention are administered to a nasal mucosal surface of the subject. In certain embodiments, the peptide YY is a human peptide YY, for example, Peptide YY (human: (SEQ ID NO: 792) H-Tyr-Pro-Ile-Lys-Pro-Glu-Ala-Pro-Gly-Glu-Asp-Ala-Ser-Pro -Glu-Glu-Leu-Asn-Arg-Tyr-Tyr-Ala-Ser-Leu-Arg-His-Tyr-Leu-Asn-Leu-Val-Thr-Arg-Gln-Arg-Tyr-NH$_2$); (Leu$^{31}$,Pro$^{34}$)-Peptide YY (human): (SEQ ID NO: 798) H-Tyr-Pro-Ile-Lys-Pro- Glu-Ala-Pro-Gly-Glu-Asp-Ala-Ser-Pro-Glu-Glu-Leu-Asn-Arg-Tyr-Tyr-Ala-Ser-Leu-Arg-His- Tyr-Leu-Asn-Leu-Val-Thr-Arg-Pro-Arg-Tyr-NH$_2$; (Pro$^{34}$)-PYY (human: (SEQ ID NO: 799)  H-Tyr-Pro-Ile-Lys-Pro-Glu-Ala-Pro-Gly-Glu-Asp- Ala-Ser-Pro-Glu-Glu-Leu-Asn-Arg-Tyr-Tyr -Ala-Ser-Leu-Arg-His-Tyr-Leu-Asn-Leu-Val-Thr-Arg-Pro-Arg-Tyr-NH$_2$); PYY$_{3-36}$ (human: (SEQ ID NO: 794) H-Ile-Lys-Pro-Glu-Ala-Pro-Gly-Glu-Asp-Ala-Ser-Pro-Glu-Glu-Leu-Asn -Arg-Tyr-Tyr-Ala-Ser-Leu-Arg-His-Tyr-Leu-Asn-Leu-Val-Thr-Arg-Gln-Arg-Tyr-NH$_2$); Peptide YY$_{13-36}$ (porcine, rat: (SEQ ID NO: 793) H-Ser-Pro-Glu-Glu-Leu-Ser-Arg-Tyr-Tyr-Ala-Ser-Leu -Arg-His-Tyr-Leu-Asn-Leu-Val-Thr-Arg-Gln-Arg-Tyr-NH$_2$); (Bachem AG, King of Prussia, Pa., United States). The PYY peptide has been isolated from human colonic extracts. It is identical in sequence to porcine PYY except for two amino acid replacements. See K. Tatemoto et al., *Biochem. Biophys. Res. Commun.* 157:713, 1988, incorporated herein by reference. PYY$_{3-36}$ form of PYY was found in human intestine and circulating blood. In contrast to PYY, PYY$_{3-36}$ selectively binds to Y$_2$ receptors. Peptide YY$_{13-36}$, the C-terminal fragment, was shown to suppress the noradrenaline release from sympathetic nerve endings. It thereby mimics the effects of PYY and NPY at presynaptic (Y$_2$) receptors. The peptide was also able to compete with NPY for essentially all binding sites in rat brain. A mucosally effective dose of peptide YY within the pharmaceutical formulations of the present invention comprises, for example, between about 0.001 pmol to about 100 pmol per kg body weight, between about 0.01 pmol to about 10 pmol per kg body weight, or between about 0.1 pmol to about 5 pmol per kg body weight. In further exemplary embodiments, dosage of peptide YY is between about 0.5 pmol to about 1.0 pmol per kg body weight. The pharmaceutical formulations of the present invention may be administered one or more times per day (for example, before a meal), or 3 times per week or once per week for between one week and 96 weeks. In certain embodiments, the pharmaceutical formulations of the invention is administered one or more times daily, two times daily, four times daily, six times daily, or eight times daily. In related embodiments, the mucosal (e.g., intranasal) formulations comprising peptide YY(s) and one or more delivery-enhancing agent(s) administered via a repeated dosing regimen yields an area under the concentration curve (AUC) for peptide YY in the blood plasma or CSF following repeated dosing that is about 10% or greater compared to an area under the concentration curve (AUC) for peptide YY in the plasma or CSF following one or more subcutaneous injections of the same or comparable amount of peptide YY. In other embodiments, the mucosal formulations of the invention administered via a repeated dosing regimen yields an area under the concentration curve (AUC) for peptide YY in the blood plasma or CNS following repeated dosing that is about 25% or greater, or about 40%, 80%, 100%, 150%, or greater, compared to the AUC for peptide YY in the blood plasma or CNS following one or more subcutaneous injections of the same or comparable amount of peptide YY.

In a further embodiment, the mucosal (e.g., intranasal) formulations of the present invention comprising peptide YY(s) and one or more delivery-enhancing agent(s) administered via a dosing regimen yield an area under the concentration curve (AUC) for peptide YY in the blood plasma or CSF that is about 110% or greater compared to an area under the concentration curve (AUC) for peptide YY in the plasma or CSF following mucosal delivery of peptide YY in water or saline without enhancers of the same or comparable amount of peptide YY to a mammalian subject. In other embodiments, the mucosal formulations of the invention administered via a dosing regimen yields an area under the concentration curve (AUC) for peptide YY in the blood plasma or CNS that is about 125% or greater, or about 140%, 180%, 200%, 250%, or greater, compared to the AUC for peptide YY in the blood plasma or CNS following mucosal delivery of peptide YY in water or saline without enhancers of the same or comparable amount of peptide YY to a mammalian subject. In a more detailed embodiment, the dosing regimen is, for example, a single dosing regimen or a repeated dosing regimen.

Often the formulations of the invention are administered to a nasal mucosal surface of the subject. In certain embodiments, the formulation comprises neuropeptide Y or pancreatic peptide, having peptide YY-like activity, for example, neuropeptide Y (human, rat), ([$^{125}$I]-Tyr)-neuropeptide Y (human, rat), biotinyl-neuropeptide Y (human, rat), neuropeptide Y (free acid) (human, rat), (Leu$^{31}$,Pro$^{34}$)-neuropeptide Y (human, rat), (D-Trp$^{32}$)-neuropeptide Y (human, rat), (Tyr(Me)$^{21}$)-neuropeptide Y (human, rat), neuropeptide Y (porcine), (Ala$^{31}$,Aib$^{32}$)-neuropeptide Y (porcine), (Leu$^{31}$,Pro$^{34}$)-neuropeptide Y (porcine), (Pro$^{34}$)-neuropeptide Y (porcine), (D-Trp$^{32}$)-neuropeptide Y (porcine), neuropeptide Y$_{1-24}$ amide (human, rat), (Cys$^2$)-neuropeptide Y$_{1-4-8}$-aminooctanoyl-(D-Cys$^{27}$)-neuropeptide Y$_{25-32}$, neuropeptide Y$_{2-36}$ (human, rat), neuropeptide Y$_{2-36}$ (porcine), neuropeptide Y$_{3-36}$ (human, rat), neuropeptide Y$_{3-36}$ (porcine), neuropeptide Y$_{13-36}$ (human, rat), (Leu$^{31}$, Pro$^{34}$)-neuropeptide Y$_{13-36}$ (human, rat), neuropeptide Y$_{13-36}$ (porcine), neuropeptide Y$_{18-36}$, pancreatic polypeptide$_{1-17}$-(Ala$^{31}$,Aib$^{32}$)-neuropeptide Y$_{18-36}$ (human), neuropeptide Y$_{22-36}$, Tyr-Lys-Gly-Arg-(Glu$^{26}$,Lys$^{29}$,Pro$^{34}$)-neuropeptide Y$_{26-36}$, (D-Tyr$^{27,36}$,D-Thr$^{32}$)-neuropeptide Y$_{27-36}$, ((Cys$^{31}$,Nva$^{34}$)-neuropeptide Y$_{27-36}$)$_2$, (Pro$^{30}$,Tyr$^{32}$, Leu$^{34}$)-neuropeptide Y$_{28-36}$, (His$^{32}$,Leu$^{34}$)-neuropeptide Y$_{32-36}$, ([$^{125}$I]-Tyr)-neuropeptide Y (porcine), ([$^{125}$I]-Tyr)-Leu$^{31}$,Pro$^{34}$)-neuropeptide Y (porcine), (Gly$^1$,Ser$^{3,22}$, Gln$^{4,34}$, Thr$^6$,Ala$^9$,Tyr$^{21}$, Ala$^{23,31}$, Aib$^{32}$)-pancreatic polypeptide (human).

In certain detailed aspects of the invention, a stable pharmaceutical formulation is provided which comprises peptide YY and one or more delivery-enhancing agent(s), wherein the formulation administered intranasally to a mammalian subject yields a time to maximal plasma concentration (t$_{max}$) for peptide YY between approximately 0.4 to 2.0 hours in a mammalian subject. Often the formulation is administered to a nasal mucosal surface of the subject.

In certain embodiments of the invention, the intranasal formulation of peptide YY and one or more delivery-enhancing agent(s) yields a time to maximal plasma concentration (t$_{max}$) for peptide YY between approximately 0.4 to 1.5 hours in the mammalian subject. Alternately, the intranasal formulation of the present invention yields a time to maximal plasma concentration (t$_{max}$) for peptide YY between approximately 0.7 to 1.5 hours, or between approximately 1.0 to 1.3 hours in the mammalian subject.

In certain detailed aspects of the invention, a stable pharmaceutical formulation is provided which comprises peptide YY and one or more intranasal delivery-enhancing agent(s), wherein the formulation administered intranasally to a mammalian subject yields a peak concentration of peptide YY in the blood plasma (C$_{max}$) or CNS following intranasal administration to the subject by methods and compositions of the present invention is about 10% or greater compared to a peak concentration of peptide YY in the blood plasma or CNS following subcutaneous injection to the mammalian subject. Within related methods, the formulation is administered to a nasal mucosal surface of the subject.

In other detailed embodiments of the invention, the intranasal formulation of the peptide YY(s) and one or more delivery-enhancing agent(s) yields a peak concentration of peptide YY in blood plasma ($C_{max}$) or CNS following intranasal administration to the subject that is about 25% or greater compared to a peak concentration of peptide YY in the blood plasma or CNS following subcutaneous injection of a comparable dose of peptide YY to the subject. Alternately, the intranasal formulation of the present invention may yield a peak concentration of peptide YY in the blood plasma ($C_{max}$) or CNS that is about 40%, 80%, 100% or 150%, or greater compared to the peak concentration of peptide YY in the blood plasma or CNS following subcutaneous injection to the mammalian subject.

In a further embodiment, the mucosal (e.g., intranasal) formulations of the present invention of the peptide YY(s) and one or more delivery-enhancing agent(s) administered via a dosing regimen yield a peak concentration of peptide YY in blood plasma ($C_{max}$) or CNS following intranasal administration to the subject that is about 110% or greater compared to a peak concentration of peptide YY in the blood plasma or CNS following mucosal delivery of peptide YY in water or saline without enhancers of the same or comparable amount of peptide YY to a mammalian subject. In other embodiments, the mucosal formulations of the present invention administered via a dosing regimen yield a peak concentration of peptide YY in the blood plasma ($C_{max}$) or CNS that is about 125%, 140%, 180%, 200% or 250%, or greater compared to the peak concentration of peptide YY in the blood plasma or CNS following mucosal delivery of peptide YY in water or saline without enhancers of the same or comparable amount of peptide YY to a mammalian subject. In a more detailed embodiment, the dosing regimen is, for example, a single dosing regimen or a repeated dosing regimen.

Intranasal delivery-enhancing agents are employed which enhance delivery of peptide YY into or across a nasal mucosal surface. For passively absorbed drugs, the relative contribution of paracellular and transcellular pathways to drug transport depends upon the pKa, partition coefficient, molecular radius and charge of the drug, the pH of the luminal environment in which the drug is delivered, and the area of the absorbing surface. The intranasal delivery-enhancing agent of the present invention may be a pH control agent. The pH of the pharmaceutical formulation of the present invention is a factor affecting absorption of peptide YY via paracellular and transcellular pathways to drug transport. In one embodiment, the pharmaceutical formulation of the present invention is pH adjusted to between about pH 3.0 to 6.0. In a further embodiment, the pharmaceutical formulation of the present invention is pH adjusted to between about pH 3.0 to 5.0. In a further embodiment, the pharmaceutical formulation of the present invention is pH adjusted to between about pH 4.0 to 5.0. In a further embodiment, the pharmaceutical formulation of the present invention is pH adjusted to between about pH 3.5 to 4.5.

DETAILED DESCRIPTION OF THE INVENTION

Figure 1:
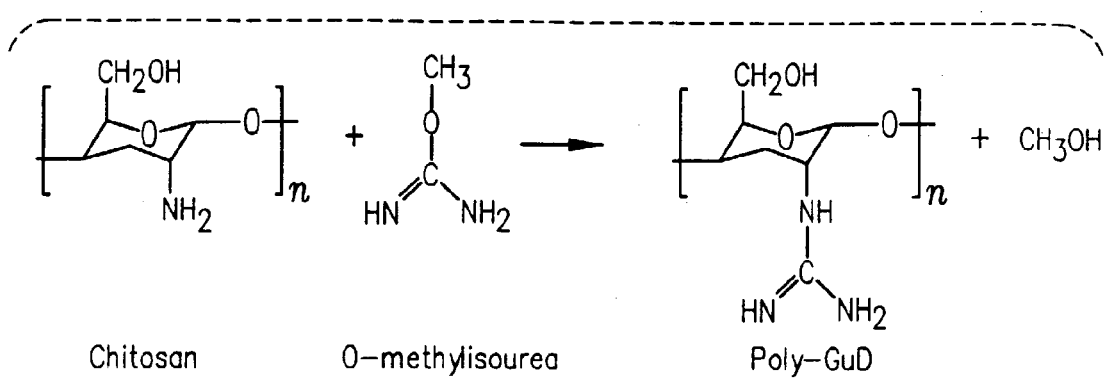
FIG. 1 provides a schematic flow illustration summarizing the synthesis of β-[1→4]-2-guanidino-2-deoxy-D-glucose polymer (poly-GuD), a novel chitosan derivative for use within certain nasal mucosal delivery formulations and methods of the invention.

As noted above, the present invention provides improved methods and compositions for nasal mucosal delivery of peptide YY to mammalian subjects for treatment or prevention of a variety of diseases and conditions. Examples of appropriate mammalian subjects for treatment and prophylaxis according to the methods of the invention include, but are not restricted to, humans and non-human primates, livestock species, such as horses, cattle, sheep, and goats, and research and domestic species, including dogs, cats, mice, rats, guinea pigs, and rabbits.

In order to provide better understanding of the present invention, the following definitions are provided:

Peptide YY

The term, "pancreatic polypeptide family," as used herein, is comprised of three naturally occurring bioactive peptides, "pancreatic polypeptide (PP)", "neuropeptide Y (NPY)", and "peptide YY (PYY)", that are found in the gastrointestinal tract, blood serum, and brain. PYY is released from endocrine L cells of the distal digestive tract by indirect stimulation from the proximal gut through neural and humoral pathways and by direct stimulation of L cells by luminal contents. Two endogenous forms of peptide YY, $PYY_{1-36}$ and $PYY_{3-36}$, are released into the circulation by a meal. Proposed gastrointestinal actions of PYY are inhibition of gastric secretion, inhibition of pancreatic secretion inhibition of intestinal secretion, and inhibition of gastrointestinal motility.

As used herein, "peptide YY" refers to "peptide YY (PYY)" in native-sequence or in variant form, as well as derivatives, fragments, and analogs of peptide YY, and from any source, whether natural, synthetic, or recombinant. Examples include human peptide YY (PYY), which is natural or recombinant peptide YY with the human native sequence, and recombinant peptide YY. U.S. Pat. Nos. 5,604,203 and 5,574,010, each incorporated herein by reference. The term "peptide YY" as used herein, is intended to include recombinant or natural human peptide YY.

As used herein, "pancreatic polypeptide (PP)" or "neuropeptide Y (NPY)" has peptide YY-like activity, or may be a peptide YY agonist binding to a "Y receptor." In certain formulations, "pancreatic polypeptide (PP)" or "neuropeptide Y (NPY)" may be substituted for peptide YY.

The term, "Y receptor", as used herein, refers to PYY binding and activating at least three receptor sub types ($Y_1$, $Y_2$, and $Y_5$) in rats and humans. PYY may interact with a postulated fourth subtype, the peripheral $Y_2$-like receptor. The nomenclature for Y receptors suggested by the International Union of Pharmacology is used. Bjork et al., Scand. J. Gastroenterol. 28: 879–884, 1993, incorporated herein by reference. These Y receptor subtypes display different patterns of affinity and activation for the two endogenous ligands PYY and $PYY_{3-36}$ and for two synthetic analogs, for example, [$Pro^{34}$]PYY and [$D-Trp^{32}$]$PYY_1$ In general, the $Y_1$ receptor subtype has high affinity for PYY and [$Pro^{34}$]PYY, the $Y_2$ has high affinity for PYY and $PYY_{3-36}$, and the $Y_5$ subtype binds PYY, $PYY_{3-36}$, [$Pro^{34}$]PYY, and [$D-Trp^{32}$]PYY with high affinity. These different patterns of receptor selectivity could be caused by differences in primary structure, differences in tertiary structure due to altered conformations of the ligands in solution, or both. Neuropeptide Y1 and Y5 receptor gene variant polymorphisms are associated with reduced serum triglyceride level and elevated HDL cholesterol in severely obese mammalian subjects. Neuropeptide Y1 and Y5 receptor gene variants are likely a gain-in-function polymorphism. Blumenthal, et al., *Clin. Genet.* 62: 196–202, 2002, incorporated herein by reference.

The term, "Y receptor antagonist", as used herein, refers to a small molecule, for example dihydropyridine or a peptide, for example, a peptide YY analog, that binds to the Y receptor and inhibits the normal physiological activity of peptide YY, neuropeptide Y, or pancreatic peptide. Poindexter et al., *Bioorganic & Medicinal Chemistry Letters*, 12: 379–382, 2002, incorporated herein by reference. Methods of treating a feeding disorder may require administration of a compound that is a Y5 receptor antagonist effective to inhibit the subject's Y5 receptor. U.S. application 20020103123, incorporated herein by reference.

The term, "peptide YY agonist" or "Y receptor agonist", as used herein, refers to any compound which elicits an effect of peptide YY (PYY) to reduce nutrient availability leading to weight loss (e.g., $PYY_{3-36}$), or increase nutrient availability leading to weight gain (e.g., $PYY_{1-36}$), for example, a compound (1) having activity in the food intake, gastric emptying, pancreatic secretion, or weight loss assays, and (2) which binds specifically in a Y receptor assay or in a competitive binding assay with labeled PYY or $PYY_{3-36}$ from certain tissues having an abundance of Y receptors, including e.g., area postrema, wherein the PYY agonist is not pancreatic polypeptide. Preferably, PYY agonists would bind in such assays with an affinity of greater than 1 µM, and more preferably with an affinity of greater than 1–5 nM. "Peptide YY agonist" or "Y receptor agonist", as used herein, refers to a small molecule or a peptide, for example, peptide YY, neuropeptide Y, pancreatic peptide, or a peptide YY analog, that binds to the Y receptor and produces the normal physiological activity of peptide YY, neuropeptide Y, or pancreatic peptide.

The term, "peptide YY agonist" or "Y receptor agonist", as used herein, may be a fusion protein containing the PYY peptide sequence or may be formed by modifying the PYY peptide's natural amino acid sequence or modifying the N-terminal amino and/or the C-terminal carboxyl group, and include salts formed with acids and/or bases, particularly physiologically acceptable inorganic and organic acids and bases. Preferred modifications are those which provide a more stable, active peptide which will be less prone to enzymatic degradation in vivo.

In certain embodiments, the peptide YY is a human peptide YY, for example, Peptide YY (human: (SEQ ID NO: 792) H-Tyr-Pro-Ile-Lys-Pro-Glu-Ala-Pro-Gly-Glu-Asp-Ala-Ser-Pro -Glu-Glu-Leu-Asn-Arg-Tyr-Tyr-Ala-Ser-Leu-Arg-His-Tyr-Leu-Asn-Leu-Val-Thr-Arg-Gln-Arg -Tyr-NH$_2$); ($Leu^{31},Pro^{34}$)-Peptide YY (human: (SEQ ID NO: 798) H-Tyr-Pro-Ile-Lys-Pro -Glu-Ala-Pro-Gly-Glu-Asp-Ala-Ser-Pro-Glu-Glu-Leu-Asn-Arg-Tyr-Tyr-Ala-Ser-Leu-Arg-His -Tyr-Leu-Asn-Leu-Val-Thr-Arg-Pro-Arg-Tyr-NH$_2$); ($Pro^{34}$)-Peptide YY (human: (SEQ ID NO: 799) H-Tyr-Pro-Tle-Lys-Pro-Glu-Ala-Pro-Gly-Glu-Asp-Ala-Ser-Pro-Glu-Glu-Leu-Asn-Arg -Tyr-Tyr-Ala-Ser-Leu-Arg-His-Tyr-Leu-Asn-Leu-Val-Thr-Arg-Pro-Arg-Tyr-NH$_2$); Peptide $YY_{3-36}$ (human: (SEQ ID NO: 794) H-Ile-Lys-Pro-Glu-Ala-Pro-Gly-Glu-Asp-Ala-Ser-Pro-Glu-Glu -Leu-Asn-Arg-Tyr-Tyr-Ala-Ser-Leu-Arg-His-Tyr-Leu-Asn-Leu-Val-Thr-Arg-Gln-Arg-Tyr-NH$_2$); Peptide $YY_{13-36}$ (porcine, rat: (SEQ ID NO: 793) H-Ser-Pro-Glu-Glu-Leu-Ser-Arg-Tyr-Tyr-Ala -Ser-Leu-Arg-His-Tyr-Leu-Asn-Leu-Val-Thr-Arg-Gln-Arg-Tyr-NH$_2$); (Bachem A G, King of Prussia, Pa., United States).

The term "endogenous ligand PYY," as used herein, refers to, for example, PYY, a 36 amino acid endogenous polypeptide, and $PYY_{3-36}$, a truncated endogenous polypeptide.

The term "synthetic analogs of PYY," as used herein, refers to polypeptides with natural or synthetic amino acid substitutions replacing the endogenous ligand PYY, for example, [$Pro^{34}$]PYY and [$D-Trp^{32}$]PYY. Synthetic analogs of PYY have biological activity that is comparable or higher than the biological activity of endogenous ligand PYY. See U.S. Pat. Nos. 5,604,203 and 5,574,010, each incorporated herein by reference.

Peptide YY (PYY) is a 36 amino acid residue peptide amide isolated originally from porcine intestine and localized in the endocrine cells of the gastrointestinal tract and the pancreas Tatemotu et al., *Proc. Natl. Acad. Sci.* 79: 2514, 1982, incorporated herein by reference. The amino acid sequences of porcine and human PYY are as follows: porcine PYY—YPAKPEAPGEDASPEELSRYYASL-RHYLNLVTRQRY (SEQ ID NO: 791); human PYY—YPIKPEAPGEDASPEELNRYYASLRHYLNLVTRQRY (SEQ ID NO: 792). The amino acid sequence for canine and rat PYY is the same as porcine PYY. PYY is believed to inhibit gut motility and blood flow, to mediate intestinal secretion, and stimulate net absorption. Laburthe, *Trends Endocrinol. Metab.* 1: 168, 1990; Cox et at., *Br. J. Pharmacol.* 101: 247, 1990; Playford et at., *Cancer* 335: 1555, 1990; MacFayden et at., *Neuropeptides* 7: 219, 1986, each incorporated herein by reference.

Novel analogs have been prepared in order to emulate and preferably enhance the duration of effect, biological activity, and selectivity of the natural peptide. Many of these analogs are derived from biologically active peptide fragments of PYY (e.g., $PYY_{22-36}$ and $PYY_{25-36}$). Such analogs, which inhibit the proliferation of pancreatic tumors, are peptide YY agonists. U.S. Pat. No. 5,574,010, incorporated herein by reference.

Additional peptide YY agonists which can be used to practice the therapeutic method of the present invention include, but are not limited to, those specifically recited in the publications set forth below: U.S. Pat. Nos. 5, 604,203 and 5,574,010; Balasubramaniam, et al., *Peptide Research* 1: 32 (1988); Japanese Patent Application 2,225,497 (1990); Balasubramaniam, et al., *Peptides* 14: 1011, 1993; Grandt, et at., *Reg. Peptides* 51: 151, 1994; and PCT International Application 94/03380, each incorporated herein by reference.

Peptide YY agonists which can be used to practice the therapeutic method of the present invention also include the closely related peptide neuropeptide Y (NPY) as well as derivatives, fragments, and analogs of NPY. The amino acid sequences of porcine and human NPY are as follows: human neuropeptide Y: YPSKPDNPGEDAPAEDMARYYSAL-RHYINLITRQRY (SEQ ID NO: 795); porcine neuropeptide Y: YPSKPDNPGEDAPAEDLARYYSALRHY-INLITRQRY (SEQ ID NO: 796). The amino acid sequence for rat neuropeptide Y, rabbit neuropeptide Y, and guinea pig neuropeptide Y are the same as human neuropeptide Y. See U.S. Pat. Nos. 5,604,203 and 5,574,010, each incorporated herein by reference.

Often the formulations of the invention are administered to a nasal mucosal surface of the subject. In certain embodiments, pancreatic polypeptide (PP)" or "neuropeptide Y (NPY)" has peptide YY-like activity. In certain formulations, "pancreatic polypeptide (PP)" or "neuropeptide Y (NPY)" may be substituted for peptide YY, for example, neuropeptide Y (human, rat), ([$^{125}$I]-Tyr)-neuropeptide Y (human, rat), biotinyl-neuropeptide Y (human, rat), neuropetide Y (free acid) (human, rat), (Leu$^{31}$,Pro$^{34}$)-neuropeptide Y (human, rat), (D-Trp$^{32}$)-neuropeptide Y (human, rat), (Tyr(Me)$^{21}$)-neuropeptide Y (human, rat), neuropeptide Y (porcine), (Ala$^{31}$,Aib$^{32}$)-neuropeptide Y (porcine), (Leu$^{31}$,Pro$^{34}$)-neuropeptide Y (porcine), (Pro$^{34}$)-neuropeptide Y (porcine), (D-Trp$^{32}$)-neuropeptide Y (porcine), neuropeptide Y$_{1-24}$ amide (human, rat), (Cys2)-neuropeptide Y$_{1-4-8}$-aminooctanoyl-(D-Cys$^{27}$)-neuropeptide Y$_{25-32}$, neuropeptide Y$_{2-36}$ (human, rat), neuropeptide Y$_{2-36}$ (porcine), neuropeptide Y$_{3-36}$ (human, rat), neuropeptide Y$_{3-36}$ (porcine), neuropeptide Y$_{13-36}$ (human, rat), (Leu$^{31}$,Pro$^{34}$)-neuropeptide Y$_{13-36}$ (human, rat), neuropeptide Y$_{13-36}$ (porcine), neuropeptide Y$_{18-36}$, pancreatic polypeptide-$_{1-17}$-(Ala$^{31}$,Aib$^{32}$)-neuropeptide Y$_{18-36}$ (human), neuropeptide Y$_{22-36}$, (SEQ ID NO: 797) Tyr-Lys-Gly-Arg-(Glu$^{26}$,Lys$^{29}$,Pro$^{34}$)-neuropeptide Y$_{26-36}$, (D-Tyr$^{27,36}$,D-Thr$^{32}$)-neuropeptide Y$_{27-36}$, ((Cys31,Nva$^{34}$)-neuropeptide Y$_{27-36}$)$_2$, (Pro$^{30}$,Tyr$^{32}$,Leu$^{34}$-neuropeptide Y$_{28-36}$, (His$^{32}$,Leu$^{34}$ )-neuropeptide Y$_{32-36}$, ([$^{125}$I]-Tyr)-neuropeptide Y (porcine), ([$^{125}$I]-Tyr)-(Leu$^{31}$,Pro$^{34}$)-neuropeptide Y (porcine), (Gly$^1$,Ser$^{3,22}$,Gln$^{4,34}$,Thr$^6$,Ala$^{19}$,Tyr$^{21}$,Ala$^{23,31}$,Aib$^{32}$)-pancreatic polypeptide (human).

Examples of neuropeptide Y analogs include but are not limited to, those specifically recited in the publications set forth below. See U.S. Pat. Nos. 5, 604,203 and 5,574,010; German Patent Application DE 3811193A1 (1989); Balasubramaniam et al., *J. Biological Chem.*, 265: 14724–14727, 1990; Cox et al., *Br. J. Pharmacol.*, 101: 247–252, 1990; PCT Application WO 91/08223 (1991); U.S. Pat. No. 5,026, 685 (1991); Balasubramaniam et al., *J. Biological Chem.*, 267: 4680–4685, 1992; European Patent Application 0355793 A3 (1992); Dumont et al., 238 European J. Pharmacol., 37–45 (1993); Kirby et al., *J. Med. Chem.*, 36: 3802–3808, 1993; PCT Application WO 94/00486 (1994); Fournier et al., *Molecular Pharmacol.*, 45: 93–101, 1994. Balasubramaniam et al., 37 *J. Med. Chem.*, 811–815, 1994; Polter et al., *European J. Pharmacol.*, 267: 253–262, 1994; and U.S. Pat. No. 5,328,899, each incorporated herein by reference.

Early descriptions of the structure of avian PP were derived from analysis of X-ray crystallography data which led to modeling of potential structures of mammalian PP, NPY, and PYY by computer analysis. The solution structures of PP and of NPY have been studied by circular dichroism (CD) and nuclear magnetic resonance (NMR). All analyses of PP have consistently found evidence for folded structure (the "PP fold") stabilized by hydrophobic interactions among residues in the NH$_2$- and COOH-terminal portions. A similar structure has been assumed to exist for NPY and PYY because of their high sequence homologies to PP. Such results have led to hypotheses that this stable structure of PP family peptides is critical for binding and activation of PP/NPY/PYY-specific receptors and that receptor selectivity depends in part on differences in solution structure produced by amino acid deletions or substitutions in naturally occurring or synthetic Y receptor agonists.

Further examples of peptide YY, neuropeptide Y, pancreatic polypeptide, neuropeptide Y receptors: Y1, Y2, Y3, Y4, and Y5; neuropeptide Y receptor agonists, and neuropeptide Y antagonists may be found, for example, in U.S. Pat. Nos. 6,368,824; 6,355,478; 6,207,799; 6,075,009; 5,989,920; 5,989,834; 5,976,814; 5,968,819; 5,965,392; 5,696,093; 5,670,482; 5,602,024; 5,621,079; or U.S. Pat. No. 5,571, 695, each incorporated herein by reference.

Peptides and proteins used in the methods and compositions of the invention can be obtained by a variety of means. Many peptides and proteins can be readily obtained in purified form from commercial sources. Smaller peptides (less than 100 amino acids long) can be conveniently synthesized by standard chemical methods familiar to those skilled in the art. Creighton, *Proteins: Structures and Molecular Principles*, W.H. Freeman and Co., N.Y., 1983, incorporated herein by reference. Larger peptides (longer than 100 amino acids) can be produced by a number of methods including recombinant DNA technology. See, for example, the techniques described in Sambrook et al., *Molecular Cloning, A Laboratory Manual*, Cold Spring Harbor Press, N.Y., 1989; and Ausubel et al., eds., *Current Protocols in Molecular Biology*, Green Publishing Associates, Inc., and John Wiley & Sons, Inc., N.Y., 1989, each incorporated herein by reference. Alternatively, RNA encoding the proteins can be chemically synthesized. See, for example, the techniques described in *Oligonucleotide Synthesis*, Gait, M. J., ed., IRL Press, Oxford, 1984, incorporated herein by reference.

Mucosal Delivery Enhancing Agents

"Mucosal delivery enhancing agents" or "intranasal delivery-enhancing agent(s)" are defined as chemicals and other excipients that, when added to a formulation comprising water and peptide YY (the control formulation) produce a formulation that produces a significant increase in transport of peptide YY across the mucosa or nasal mucosa, respectively, as measured by the maximum blood, serum, or cerebral spinal fluid concentration ($C_{max}$) or by the area under the curve, AUC, in a plot of concentration versus time.

Treatment and Prevention of Obesity

As noted above, the instant invention provides improved and useful methods and compositions for nasal mucosal delivery of one or more peptide YY compound(s) to prevent and treat obesity in mammalian subjects. As used herein, prevention and treatment of obesity mean prevention of the onset or lowering the incidence or severity of clinical obesity by reducing food intake during meals. In certain aspects, the pharmaceutical formulations and methods of the invention prevent or alleviate obesity in mammalian subjects. In certain embodiments, the one or more peptide YY compound(s) may be a peptide YY analog, for example, peptide YY$_{3-36}$.

Obesity is a recognized risk factor for hypertension, arteriosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia. Kopelman. *Nature* 404: 635–43, 2000, incorporated herein by reference. It reduces life-span and carries a serious risk of co-morbidities above, as well disorders such as infections, varicose veins, acanthosis nigricans, eczema, exercise intolerance, insulin resistance, hypertension hypercholesterolemia, cholelithiasis, orthopedic injury, and thromboembolic disease. Rissanen, et al. *BMJ* 301: 835–7, 1990, incorporated herein by reference. Obesity is also a risk factor for the group of conditions called insulin resistance syndrome, or "Syndrome X."

The instant invention provides improved and useful methods and compositions for nasal mucosal delivery of peptide YY to regions of the brain, for example, the hypothalamus or the proopiomelanocortin (POMC) and NPY arcuate neurons, to prevent and treat obesity in mammalian subjects. Experimental results support the hypothesis that the cells in the arcuate nucleus detect circulating peripheral satiety signals and relay these signals to other brain regions. This is further supported by the observation that leptin modifies the activity of both the proopiomelanocortin (POMC) and NPY arcuate neurons. Experiments have shown, through a combination of electrophysiological and hypothalamic explant studies, that the gut hormone, $PYY_{3-36}$, can directly influence hypothalamic circuits, which results in coordinate changes in POMC and NPY action. In addition, $PYY_{3-36}$ administered directly into this brain region reduces food intake. Data show that postprandial concentrations of $PYY_{3-36}$ inhibit food intake in both rodents and man for up to 12 h, which suggests that $PYY_{3-36}$ has a role in 'longer term' regulation of food intake. This contrasts with previously characterized gut-derived 'short-term' satiety signals such as cholecystokinin, the effects of which are relatively short-lived. The failure of $PYY_{3-36}$ to inhibit food intake in Y2r-null mice provides further evidence that $PYY_{3-36}$ reduces food intake through a Y2R-dependent mechanism. Experimental results suggest that a gut-hypothalamic pathway that involves postprandial $PYY_{3-36}$ acting at the arcuate Y2R has a role in regulating feeding. Thus, the $PYY_{3-36}$ system provides a therapeutic target for the treatment of obesity. *Nature* 418: 650–654, 2002, incorporated herein by reference.

The instant invention provides improved and useful methods and compositions for nasal mucosal delivery of Y1 receptor antagonists to prevent and treat obesity in mammalian subjects. Y1 receptor antagonists may counter the effect of neuropeptide Y (NPY) on brain stem and central nervous system neurophysiological responses to gastric loads. Y1 receptor antagonists are, for example, dihyropyridine. Poindexter et al., *Bioorganic & Medicinal Chemistry Letters*, 12: 379–382, 2002, incorporated herein by reference. Leptin is an adiposity hormone that modulates the activity of multiple hypothalamic signaling pathways involved in the control of food intake. Experiments demonstrate that central forebrain administration of two feeding modulatory peptides, leptin and NPY, have opposing effects on brain stem; leptin increases the neurophysiological response to ascending meal-related feedback signals in the nucleus of the solitary tract (NTS), and NPY reduces it. The data are consistent with the suggestion that leptin reduces food intake by enhancing the salience of gut negative feedback signals during a meal, whereas NPY may in part increase intake by attenuating the feeding inhibitory potency of these signals. These modulatory effects do not appear to be due to the peptides' downstream effects on gastrointestinal motility or on their ability to directly stimulate primary vagal afferent input to the NTS, because gut vagal afferent responses to the same range of gastric loads were unchanged by central administration of either peptide. Experiments were designed to evaluate whether central administration of leptin or one of its downstream mediators, neuropeptide Y (NPY), could affect food intake by modulating the brain stem neurophysiological response to ascending meal-related feedback signals in the nucleus of the solitary tract (NTS) in anesthetized male Long-Evans rats. NTS neurons at the rostrocaudal level of the area postrema were dose-dependently activated by gastric loads ranging from 2–10 ml, and leptin and NPY had opposite modulatory effects on this load volume/activity relationship: leptin significantly increased NTS responses to gastric loads, whereas NPY reduced the potency and efficacy with which gastric loads activated NTS neurons. These effects were probably not mediated by peripheral effects of centrally administered peptides or by the gastrokinetic effects of central NPY or leptin, because the dose-response relationship between gastric load volume and neurophysiological firing rate was unchanged in gastric load-sensitive vagal afferent fibers. These data suggest a mechanistic framework for considering how feeding behavior occurring in meals is altered by challenges to energy homeostasis, such as fasting and overfeeding. Schwartz et al., *Endocrinology* 143: 3779–3784, 2002, incorporated herein by reference. Nasal mucosal delivery of Y1 receptor antagonists of the present invention are useful to prevent and treat obesity in mammalian subjects. Y1 receptor antagonists may counter the effect of neuropeptide Y (NPY) on brain stem and central nervous system neurophysiological responses to gastric loads.

Treatment and Prevention of Alzheimer's Disease

As noted above, the instant invention provides improved and useful methods and compositions for nasal mucosal delivery of one or more peptide YY compound(s) to prevent and treat Alzheimer's disease in mammalian subjects. It is proposed that aluminum is involved in the initiation and progression of Alzheimer's disease. Young patients with Alzheimer's disease are reported to absorb more aluminum from the intestinal tract than unafflicted controls. Similarly, persons with Down syndrome, a population at high risk for developing Alzheimer's disease, have been reported to absorb orally administered aluminum at an increased rate compared to diploid controls. Experimental administration of supraphysiological doses of human recombinant PYY to both diploid and partially trisomic, Ts65Dn, mice dramatically decreases brain aluminum concentrations suggests the possibility that chelation of aluminum by this peptide may provide new insights into its role and that of aluminum in Alzheimer's disease. *J. Inorg. Biochem.* 87: 51–56, 2001, incorporated herein by reference. In certain embodiments, the one or more peptide YY compound(s) may be a peptide YY analog, agonist or antagonist compound.

Treatment and Prevention of Colon Adenocarcinoma

As noted above, the instant invention provides improved and useful methods and compositions for nasal mucosal delivery of one or more peptide YY compound(s) to prevent and treat colon carcinoma and colon adenocarcinoma in mammalian subjects. If the loss of PYY is correlated with development of adenocarcinoma of the colon, replacement of the peptide has an inhibitory effect on the carcinogenic process or on cancer cells themselves. PYY expression in colon polyps and tumors has been associated with increased differentiation and in fact, PYY-treatment of colon cancer cells may selectively up-regulate expression of brush border enzymes characteristic of the normal colonocytic phenotype. Specific, PYY-preferring Y1 receptors have also been characterized in a human colon adenocarcinoma cells, suggesting the possibility of a unique regulatory pathway for PYY. In certain embodiments, the one or more peptide YY compound(s) may be a peptide YY analog, agonist or antagonist compound.

The few studies directly addressing the potential colon cancer growth regulatory effects of PYY have yielded varying results. For example, in a human colon adenocarcinoma cell line HT-29, PYY demonstrated no effect on cell growth or DNA synthesis. Similarly, at picomolar concentrations, PYY did not alter cell division rates or maintain hyperplastic changes in explants of azoxymethane-treated colon mucosa. In contrast, in a more recent study, micromolar concentrations of PYY were shown to decrease cell viability in Caco-2 and HCT-116 colon cancer cells by 28 and 21% versus control, respectively. The later two studies suggest that growth regulatory effects of PYY may be dose dependent. See Tseng et al., *Peptides* 23: 389–395 (2002), incorporated herein by reference.

Treatment and Prevention of Pancreatic Adenocarcinoma

As noted above, the instant invention provides improved and useful methods and compositions for nasal mucosal delivery of one or more peptide YY compound(s) to prevent and treat pancreatic carcinoma and pancreatic adenocarcinoma in mammalian subjects. In a rat animal model, PYY was shown to inhibit cholecystokinin-mediated growth in the normal pancreas, as determined by pancreatic weight, RNA, and DNA content. Therefore improved and useful methods and compositions for nasal mucosal delivery of peptide YY may exhibit growth regulatory effects in pancreatic cancer cells.

The instant invention provides improved and useful methods and compositions for nasal mucosal delivery of one or more peptide YY compound(s) in combination with vitamin E succinate to prevent and treat pancreatic adenocarcinoma in mammalian subjects. The role of PYY in human pancreatic adenocarcinoma has been examined both in vitro and in vivo. Despite an early in vitro study which suggested a growth stimulatory effect, recent findings support a growth inhibitory effect in several pancreatic cancer cell lines with as little as 2.5 picomoles per liter of peptide. In addition, dramatic additive effects can occur with simultaneous treatment using PYY and vitamin E succinate, an apoptotic inducer. Consistent with these findings, PYY has been shown to reduce pancreatic tumor size by 27% versus control in an orthotopic nude mice model. PYY-mediated growth inhibition has been postulated to occur directly or indirectly from reductions in intracellular cAMP levels. In certain embodiments, the one or more peptide YY compound(s) may be a peptide YY analog, agonist or antagonist compound.

The instant invention provides improved and useful methods and compositions for nasal mucosal delivery of synthetic analogs of peptide YY to prevent and treat pancreatic adenocarcinoma in mammalian subjects. Synthetic analogs of PYY may carry even greater potency alone and as an adjuvant to chemotherapy in pancreatic cancer. For example, BIM-43004-1 is Y2 receptor-specific synthetic analog of PYY corresponding to amino acids 22–36 with a modified N-terminus to increase cell membrane affinity. When compared to PYY, BIM-43004-1 exhibited similar in vitro cytotoxicity in pancreatic cancer cells; however, in vivo data from nude mice demonstrated 2-fold greater decreases in tumor size, seen earlier and lasting longer at the same dosage and route of administration. Moreover, when given in combination with 5-fluorouracil and leucovorin, BIM-43004-1 reduced cell growth and expression of epidermal growth factor receptor slightly more so than PYY. See Tseng et al., *Peptides* 23: 389–395 (2002), incorporated herein by reference.

Treatment and Prevention of Breast Carcinoma

As noted above, the instant invention provides improved and useful methods and compositions for nasal mucosal delivery of one or more peptide YY compound(s) to prevent and treat human breast carcinoma in mammalian subjects. Although normal physiologic actions of peptide YY are largely confined to the brain and gut, studies have also demonstrated a growth regulatory effect in human breast carcinoma. PYY treatment reduced viability by 40% in MCF-7 breast cancer cells versus control and also decreased weight and volume of subcutaneous (s.c.) tumors grown in nude mice. Substantial reduction in intracellular cAMP were observed, implicating a causal role; however, receptors involved are unknown.

The instant invention provides improved and useful methods and compositions for nasal mucosal delivery of one or more peptide YY compound(s) in combination with vitamin E succinate to prevent and treat human breast carcinoma in mammalian subjects. Studies showed that PYY-mediated growth inhibition is independent of estrogen receptor status and can be augmented, as in pancreatic cancer, by combination therapy with vitamin E succinate. See Tseng et al., *Peptides* 23: 389–395 (2002), incorporated herein by reference. In certain embodiments, the one or more peptide YY compound(s) may be a peptide YY analog, agonist or antagonist compound.

Treatment and Prevention of Malnutrition That Results From Iatrogenic Causes or Cachexia Associated with Advanced Disease. Improvement in Malnutrition in Cancer Patients.

As noted above, the instant invention provides improved and useful methods and compositions for nasal mucosal delivery of one or more peptide YY compound(s) to prevent and treat malnutrition in mammalian subjects with cancer. Clinically, chemotherapy and radiation treatment often result in gastrointestinal toxicity, nausea, and vomiting, which limits appetite and predisposes patients to nutritional deficiencies. Total parenteral nutrition (TPN) is often required in patients undergoing treatment or with advanced disease states. Unfortunately, prolonged TPN results in mucosal atrophy which increases risk of infection and other complications; therefore an effective stimulant of mucosal growth is needed in many cancer patients. In certain embodiments, the one or more peptide YY compound(s) may be a peptide YY analog, for example, peptide $YY_{1-36}$.

PYY exhibits properties which render it as a useful clinical tool in the treatment of malnutrition problems associated with cancer. For example, several studies in dogs have demonstrated that PYY, for example, peptide $YY_{1-36}$, carries a potent pro-absorptive effect on both the small bowel and colon. PYY receptors have been characterized in human adipocytes and PYY has been shown to inhibit lipolysis, an essential feature of cancer cachexia. Moreover, PYY has appetite stimulating effects on the central nervous system, which has been speculated to occur due to Y1 receptor binding or possibly a histaminergic receptor.

In an animal model, PYY expression in non-tumor bearing rats has been observed to increase upon administration of cytokines or hormones which stimulate intestinal growth. In an early study, restoration of TPN-induced reduction in gut weight with urogastrone-EGF was selectively paralleled by increases in serum PYY. A subsequent study using keratinocyte growth factor has also demonstrated increased PYY levels in association with gut proliferation. Treatment of mice with IGF-I or transgenic overexpression of growth hormone or TGF-α—all of which are stimulatory toward the gut—lead to increased PYY mRNA and peptide expression.

To better elucidate the role of PYY in promoting normal mucosal proliferation, several studies monitored tissue changes associated with direct exogenous administration of the peptide. An early study concluded that PYY infused i.v. over a period of three days is not trophic to the gastrointestinal tract of rats based on wet weights and mucosal metaphase counts. In contrast, two recent studies have reported the opposite findings. Adult mice given s.c. injections of PYY for ten days demonstrated increased in proximal and distal small bowel weight, DNA content, and protein content that were dose-dependent. Similar findings occurred in TPN-fed rats given i.v. PYY over a seven day course. The direct growth-promoting role of PYY in the gut may thus depend on factors such as route and duration of administration. See Tseng et al., *Peptides* 23: 389–395 (2002), incorporated herein by reference.

Treatment and Prevention of Cancer Cachexia

As noted above, the instant invention provides improved and useful methods and compositions for nasal mucosal delivery of one or more peptide YY compound(s) to prevent and treat cancer cachexia. Up to half of all cancer patients and over 80% of patients with gastrointestinal malignancies will eventually develop cachexia, a debilitating condition of involuntary tissue wasting characterized by protein loss, fat breakdown, and anorexia. The metabolic changes seen in patients are currently believed to result from host and tumor produced factors, which create a state similar to chronic low-grade inflammation. Cancer cachexia has also been shown to be associated with decreased protein synthesis and protein loss in the small bowel. Although PYY may not directly alter the underlying cause of cachexia, PYY does increase small bowel protein content in normal mice and rats, as mentioned. In certain embodiments, the one or more peptide YY compound(s) may be a peptide YY analog, for example, peptide $YY_{1-36}$.

One study has examined the potential therapeutic role of PYY in the context of cancer cachexia. Rats bearing subcutaneous methylcholanthrene sarcomas were given intravenous. PYY, clenbuterol, an anabolic B2 adrenergic agonist, or both agents together. PYY alone increased small bowel weight and protein content, but had no effect on the colon. Combination therapy increased mean protein content in the gastrocnemius muscle; however these effects appear to be mediated by clenbuterol versus PYY. Most significantly no difference in tumor growth was observed between treatment and control groups while tumor bearing rats given PYY alone exhibited higher mean body weights versus control. See Tseng et al., *Peptides* 23: 389–395 (2002), incorporated herein by reference.

Treatment and Prevention of Disease and Reduction of Nasal Mucosal Inflammation by Intranasal Administration of Peptide YY, For Example, Human Peptide YY, in Combination with a Steroid Composition.

The treatment and prevention of disease, for example, obesity, Alzheimer's disease, colon carcinoma, colon adenocarcinoma, pancreatic carcinoma, pancreatic adenocarcinoma, breast carcinoma, treatment and prevention of malnutrition resulting from iatrogenic causes or cachexia associated with advanced disease, or cancer cachexia by therapy with intranasal compositions of peptide YY and corticosteroid, as described herein, results in reduction in disease indications while avoiding side effects of drug delivery. Intranasal compositions of peptide YY and corticosteroid results in reduced nasal irritation, reduced rhinitis and a reduced nasal mucosal allergic response by direct delivery to the nasal mucosal tissue and to the CNS tissue or fluid. Direct intranasal delivery of the compositions to the CNS tissue or fluid avoids delivery to sites of the body other than the CNS and avoids systemic side effects, such as adrenosuppression and weight gain, associated with systemic delivery of corticosteroids to the blood serum and organs, for example, the adrenal gland and kidney.

Mucosal administration of the peptide YY and corticosteroid compositions once or twice per day for 7 to 14 days to the subject yields extended delivery of the peptide YY and corticosteroid compositions. Delivery of the composition is measured by area under the concentration curve (AUC) for peptide YY, the corticosteroid, or for a pharmacokinetic marker for peptide YY. Mucosal administration of the peptide YY and steroid compositions to the subject yields an AUC of corticosteroid or peptide YY in a central nervous system (CNS) tissue or fluid of the subject that is typically about 50%, about 75% or about 100% or greater compared to an AUC of corticosteroid or peptide YY in CNS tissue or fluid following subcutaneous injection of an equivalent concentration or dose of peptide YY to the subject.

A pharmaceutical formulation suitable for intranasal administration comprising peptide YY and a corticosteroid compound for treatment of inflammation, as described herein, provides therapeutic delivery to the CNS while avoiding delivery to the blood serum and organs, for example, adrenal gland and kidneys. Pharmaceutical compositions yield an area under the concentration curve (AUC) of a corticosteroid composition in the CNS that is typically about 2-fold, about 3-fold, about 5-fold, or about 10-fold or greater when compared to an AUC for the composition in a blood plasma or other target tissue (adrenal gland or kidney). Pharmaceutical formulations, as described herein, target corticosteroids to the CNS tissues and fluids thus avoiding adverse steroid side effects, such as adrenosuppression and weight gain caused by prolonged steroid treatment.

Methods and Compositions of Delivery

Improved methods and compositions for mucosal administration of peptide YY to mammalian subjects optimize peptide YY dosing schedules. The present invention provides mucosal delivery of peptide YY formulated with one or more mucosal delivery-enhancing agents wherein peptide YY dosage release is substantially normalized and/or sustained for an effective delivery period of peptide YY release ranges from approximately 0.1 to 2.0 hours; 0.4 to 1.5 hours; 0.7 to 1.5 hours; or 0.8 to 1.0 hours; following mucosal administration. The sustained release of peptide YY is achieved may be facilitated by repeated administration of exogenous peptide YY utilizing methods and compositions of the present invention.

Compositions and Methods of Sustained Release

Improved compositions and methods for mucosal administration of peptide YY to mammalian subjects optimize peptide YY dosing schedules. The present invention provides improved mucosal (e.g., nasal) delivery of a formulation comprising peptide YY in combination with one or more mucosal delivery-enhancing agents and an optional sustained release-enhancing agent or agents. Mucosal delivery-enhancing agents of the present invention yield an effective increase in delivery, e.g., an increase in the maximal plasma concentration ($C_{max}$) to enhance the therapeutic activity of mucosally-administered peptide YY. A second factor affecting therapeutic activity of peptide YY in the blood plasma and CNS is residence time (RT). Sustained release-enhancing agents, in combination with intranasal delivery-enhancing agents, increase $C_{max}$ and increase residence time (RT) of peptide YY. Polymeric delivery vehicles and other agents and methods of the present invention that yield sustained release-enhancing formulations, for example, polyethylene glycol (PEG), are disclosed herein. The present invention provides an improved peptide YY delivery method and dosage form for treatment of symptoms related to obesity, colon cancer, pancreatic cancer, or breast cancer in mammalian subjects.

Maintenance of Basal Levels of Peptide YY

Improved compositions and methods for mucosal administration of peptide YY to mammalian subjects optimize peptide YY dosing schedules. The present invention provides improved nasal mucosal delivery of a formulation comprising peptide YY and intranasal delivery-enhancing agents in combination with intramuscular or subcutaneous administration of peptide YY. Formulations and methods of the present invention maintain relatively consistent basal levels of peptide YY, for example, at a basal level of 15–80 pM when administered by nasal mucosal delivery of a formulation comprising peptide YY and intranasal delivery-enhancing agents of the present invention, alone, or in combination with intramuscular or subcutaneous administration of peptide YY. Basal levels of peptide YY are maintained throughout a 2 to 24 hour, 4–16 hour, or 8–12 hour period following a single dose administration or attended by a multiple dosing regimen of 2–6 sequential administrations. Maintenance of basal levels of peptide YY is particularly useful for treatment and prevention of disease, for example, multiple sclerosis, without unacceptable adverse side effects.

Within the mucosal delivery formulations and methods of the invention, the peptide YY is frequently combined or coordinately administered with a suitable carrier or vehicle for mucosal delivery. As used herein, the term "carrier" means a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, can be found in the *U.S. Pharmacopeia National Formulary*, 1857–1859, 1990, which is incorporated herein by reference. Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other non toxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like. The amount of active ingredient that can be combined with the carrier materials to produce a single dosage form will vary depending upon the particular mode of administration.

The mucosal formulations of the invention are generally sterile, particulate free and stable for pharmaceutical use. As used herein, the term "particulate free" means a formulation that meets the requirements of the USP specification for small volume parenteral solutions. The term "stable" means a formulation that fulfills all chemical and physical specifications with respect to identity, strength, quality, and purity which have been established according to the principles of Good Manufacturing Practice, as set forth by appropriate governmental regulatory bodies.

Within the mucosal delivery compositions and methods of the invention, various delivery-enhancing agents are employed which enhance delivery of peptide YY into or across a mucosal surface. In this regard, delivery of peptide YY across the mucosal epithelium can occur "transcellularly" or "paracellularly". The extent to which these pathways contribute to the overall flux and bioavailability of the peptide YY depends upon the environment of the mucosa, the physico-chemical properties the active agent, and on the properties of the mucosal epithelium. Paracellular transport involves only passive diffusion, whereas transcellular transport can occur by passive, facilitated or active processes. Generally, hydrophilic, passively transported, polar solutes diffuse through the paracellular route, while more lipophilic solutes use the transcellular route. Absorption and bioavailability (e.g., as reflected by a permeability coefficient or physiological assay), for diverse, passively and actively absorbed solutes, can be readily evaluated, in terms of both paracellular and transcellular delivery components, for any selected peptide YY within the invention. These values can be determined and distinguished according to well known methods, such as in vitro epithelial cell culture permeability assays. Hilgers, et al., *Pharm. Res.*, 7: 902–910, 1990; Wilson et al., *J. Controlled Release*, 11: 25–40,1990; Artursson. I., *Pharm. Sci.*, 79: 476–482, 1990; Cogburn et al., *Pharm. Res.*, 8: 210–216, 1991; Pade et al., *Pharmaceutical Research*, 14: 1210–1215, 1997, each incorporated herein by reference.

For passively absorbed drugs, the relative contribution of paracellular and transcellular pathways to drug transport depends upon the pKa, partition coefficient, molecular radius and charge of the drug, the pH of the luminal environment in which the drug is delivered, and the area of the absorbing surface. The paracellular route represents a relatively small fraction of accessible surface area of the nasal mucosal epithelium. In general terms, it has been reported that cell membranes occupy a mucosal surface area that is a thousand times greater than the area occupied by the paracellular spaces. Thus, the smaller accessible area, and the size- and charge-based discrimination against macromolecular permeation would suggest that the paracellular route would be a generally less favorable route than transcellular delivery for drug transport. Surprisingly, the methods and compositions of the invention provide for significantly enhanced transport of biotherapeutics into and across mucosal epithelia via the paracellular route. Therefore, the methods and compositions of the invention successfully target both paracellular and transcellular routes, alternatively or within a single method or composition.

As used herein, "mucosal delivery-enhancing agents" include agents which enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery, or at a selected target site of activity such as the bloodstream or central nervous system) of peptide YY or other biologically active compound(s). Enhancement of mucosal delivery can thus occur by any of a variety of mechanisms, for example by increasing the diffusion, transport, persistence or stability of peptide YY, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, and other mechanisms.

As used herein, an "mucosally effective amount of peptide YY" contemplates effective mucosal delivery of peptide YY to a target site for drug activity in the subject that may involve a variety of delivery or transfer routes. For example, a given active agent may find its way through clearances between cells of the mucosa and reach an adjacent vascular wall, while by another route the agent may, either passively or actively, be taken up into mucosal cells to act within the cells or be discharged or transported out of the cells to reach a secondary target site, such as the systemic circulation. The methods and compositions of the invention may promote the translocation of active agents along one or more such alternate routes, or may act directly on the mucosal tissue or proximal vascular tissue to promote absorption or penetration of the active agent(s). The promotion of absorption or penetration in this context is not limited to these mechanisms.

As used herein "peak concentration ($C_{max}$) of peptide YY in a blood plasma", "area under concentration vs. time curve (AUC) of peptide YY in a blood plasma", "time to maximal plasma concentration ($t_{max}$) of peptide YY in a blood plasma" are pharmacokinetic parameters known to one skilled in the art. Laursen et al., *Eur. J. Endocrinology*, 135: 309–315, 1996, incorporated herein by reference. The "concentration vs. time curve" measures the concentration of peptide YY in a blood serum of a subject vs. time after administration of a dosage of peptide YY to the subject either by intranasal, intramuscular, subcutaneous, or other parenteral route of administration. "$C_{max}$" is the maximum concentration of peptide YY in the blood serum of a subject following a single dosage of peptide YY to the subject. "$t_{max}$" is the time to reach maximum concentration of peptide YY in a blood serum of a subject following administration of a single dosage of peptide YY to the subject.

As used herein, "area under concentration vs. time curve (AUC) of peptide YY in a blood plasma" is calculated according to the linear trapezoidal rule and with addition of the residual areas. A decrease of 23% or an increase of 30% between two dosages would be detected with a probability of 90% (type II error $\beta=10\%$). The "delivery rate" or "rate of absorption" is estimated by comparison of the time ($t_{max}$) to reach the maximum concentration ($C_{max}$). Both $C_{max}$ and $t_{max}$ are analyzed using non-parametric methods. Comparisons of the pharmacokinetics of intramuscular, subcutaneous, intravenous and intranasal peptide YY administrations were performed by analysis of variance (ANOVA). For pairwise comparisons a Bonferroni-Holmes sequential procedure was used to evaluate significance. The dose-response relationship between the three nasal doses was estimated by regression analysis. $P<0.05$ was considered significant. Results are given as mean values +/−SEM. (Laursen et al., 1996.)

Pharmacokinetic parameters and values described herein, including $t_{max}$, $C_{max}$, and AUC may be determined by comparing an intranasal delivery formulation or method of the invention to a previously-described "control" delivery method, for example a previously-described mucosal delivery, intramuscular delivery, subcutaneous delivery, intravenous delivery, and/or parenteral delivery method different formulations or delivery methods involving a common route of delivery. In alternate embodiments, pharmacokinetic and/or pharmacodynamic characteristics or values may be expressed, distinctly from other embodiments, by comparing an intranasal method or formulation of the invention with a different intranasal delivery method or formulation. For example, a method or formulation may be compared with a previously-described "control" method or formulation involving a different administration protocol, or formulation component. Where different different formulations, administration protocols, and/or different pharmacokinetic or pharmacodynamic controls are used herein to determine a comparative pharmacokinetic value or range for one embodiment or aspect of the invention, such values or ranges are not intended to be interchangeable or directly correlated between different embodiments and aspects of the invention. Rather, various embodiments and aspects of the invention are disclosed herein that each may have be characterized by distinct pharmacokinetic and or pharmacodynamic characteristics and/or values, whereby the characteristics and values may not be consistent or comparable among the different embodiments or aspects.

As used herein, "pharmacokinetic markers" include any accepted biological marker that is detectable in an in vitro or in vivo system useful for modeling pharmacokinetics of mucosal delivery of one or more peptide YY compounds, or other biologically active agent(s) disclosed herein, wherein levels of the marker(s) detected at a desired target site following administration of the peptide YY compound(s) according to the methods and formulations herein, provide a reasonably correlative estimate of the level(s) of the peptide YY compound(s) delivered to the target site. Among many art-accepted markers in this context are substances induced at the target site by adminstration of the peptide YY compound(s) or other biologically active agent(s). For example, nasal mucosal delivery of an effective amount of one or more peptide YY compounds according to the invention stimulates an immunologic response in the subject measurable by production of pharmacokinetic markers.

Many known reagents that are reported to enhance mucosal absorption also cause irritation or damage to mucosal tissues. Swenson and Curatolo, *Adv. Drug Delivery Rev.*, 8: 39–92, 1992, incorporated herein by reference. For example, in studies of intestinal absorption enhancing agents, the delivery-enhancing effects of various absorption-promoting agents are reportedly directly related to their membrane toxicity. Uchiyama et al., *Biol. Pharm. Bull.*, 19: 1618–1621, 1996; Yamamoto et al., *J. Pharm. Pharmacol.*, 48: 1285–1289, 1996, each incorporated herein by reference. In this regard, the combinatorial formulation and coordinate administration methods of the present invention incorporate effective, minimally toxic delivery-enhancing agents to enhance mucosal delivery of peptide YY and other biologically active macromolecules useful within the invention.

While the mechanism of absorption promotion may vary with different intranasal delivery-enhancing agents of the invention, useful reagents in this context will not substantially adversely affect the mucosal tissue and will be selected according to the physicochemical characteristics of the particular peptide YY or other active or delivery-enhancing agent. In this context, delivery enhancing agents that increase penetration or permeability of mucosal tissues will often result in some alteration of the protective permeability barrier of the mucosa. For such delivery-enhancing agents to be of value within the invention, it is generally desired that any significant changes in permeability of the mucosa be reversible within a time frame appropriate to the desired duration of drug delivery. Furthermore, there should be no substantial, cumulative toxicity, nor any permanent deleterious changes induced in the barrier properties of the mucosa with long-term use.

Within certain aspects of the invention, absorption-promoting agents for coordinate administration or combinatorial formulation with peptide YY of the invention are selected from small hydrophilic molecules, including but not limited to, dimethyl sulfoxide (DMSO), dimethylformamide, ethanol, propylene glycol, and the 2-pyrrolidones. Alternatively, long-chain amphipathic molecules, for example, deacylmethyl sulfoxide, azone, sodium laurylsulfate, oleic acid, and the bile salts, may be employed to enhance mucosal penetration of the peptide YY. In additional aspects, surfactants (e.g., polysorbates) are employed as adjunct compounds, processing agents, or formulation additives to enhance intranasal delivery of the peptide YY. These penetration enhancing agents typically interact at either the polar head groups or the hydrophilic tail regions of molecules which comprise the lipid bilayer of epithelial cells lining the nasal mucosa. Barry, *Pharmacology of the Skin*, 1:121–137; Shroot et al., Eds., Karger, Basel, 1987; and Barry, *J. controlled Release*, 6: 85–97, 1987, each incorporated herein by reference. Interaction at these sites may have the effect of disrupting the packing of the lipid molecules, increasing the fluidity of the bilayer, and facilitating transport of the peptide YY across the mucosal barrier. Interaction of these penetration enhancers with the polar head groups may also cause or permit the hydrophilic regions of adjacent bilayers to take up more water and move apart, thus opening the paracellular pathway to transport of the peptide YY. In addition to these effects, certain enhancers may have direct effects on the bulk properties of the aqueous regions of the nasal mucosa. Agents such as DMSO, polyethylene glycol, and ethanol can, if present in sufficiently high concentrations in delivery environment (e.g., by pre-administration or incorporation in a therapeutic formulation), enter the aqueous phase of the mucosa and alter its solubilizing properties, thereby enhancing the partitioning of the peptide YY from the vehicle into the mucosa.

Additional mucosal delivery-enhancing agents that are useful within the coordinate administration and processing methods and combinatorial formulations of the invention include, but are not limited to, mixed micelles; enamines; nitric oxide donors (e.g., S-nitroso-N-acetyl-DL-penicillamine, NOR1, NOR4—which are preferably co-administered with an NO scavenger such as carboxy-PITO or doclofenac sodium); sodium salicylate; glycerol esters of acetoacetic acid (e.g., glyceryl-1,3-diacetoacetate or 1,2-isopropylideneglycerine-3-acetoacetate); and other release-diffusion or intra- or trans-epithelial penetration-promoting agents that are physiologically compatible for mucosal delivery. Other absorption-promoting agents are selected from a variety of carriers, bases and excipients that enhance mucosal delivery, stability, activity or trans-epithelial penetration of the peptide YY. These include, inter alia, cyclodextrins and β-cyclodextrin derivatives (e.g., 2-hydroxypropyl-β-cyclodextrin and heptakis(2,6-di-O-methyl-β-cyclodextrin). These compounds, optionally conjugated with one or more of the active ingredients and further optionally formulated in an oleaginous base, enhance bioavailability in the mucosal formulations of the invention. Yet additional absorption-enhancing agents adapted for mucosal delivery include medium-chain fatty acids, including mono- and diglycerides (e.g., sodium caprate—extracts of coconut oil, Capmul), and triglycerides (e.g., amylodextrin, Estaram 299, Miglyol 810).

The mucosal therapeutic and prophylactic compositions of the present invention may be supplemented with any suitable penetration-promoting agent that facilitates absorption, diffusion, or penetration of peptide YY across mucosal barriers. The penetration promoter may be any promoter that is pharmaceutically acceptable. Thus, in more detailed aspects of the invention compositions are provided that incorporate one or more penetration-promoting agents selected from sodium salicylate and salicylic acid derivatives (acetyl salicylate, choline salicylate, salicylamide, etc.); amino acids and salts thereof (e.g. monoaminocarboxlic acids such as glycine, alanine, phenylalanine, proline, hydroxyproline, etc.; hydroxyamino acids such as serine; acidic amino acids such as aspartic acid, glutamic acid, etc; and basic amino acids such as lysine etc—inclusive of their alkali metal or alkaline earth metal salts); and N-acetylamino acids (N-acetylalanine, N-acetylphenylalanine, N-acetylserine, N-acetylglycine, N-acetyllysine, N-acetylglutamic acid, N-acetylproline, N-acetylhydroxyproline, etc.) and their salts (alkali metal salts and alkaline earth metal salts). Also provided as penetration-promoting agents within the methods and compositions of the invention are substances which are generally used as emulsifiers (e.g. sodium oleyl phosphate, sodium lauryl phosphate, sodium lauryl sulfate, sodium myristyl sulfate, polyoxyethylene alkyl ethers, polyoxyethylene alkyl esters, etc.), caproic acid, lactic acid, malic acid and citric acid and alkali metal salts thereof, pyrrolidonecarboxylic acids, alkylpyrrolidonecarboxylic acid esters, N-alkylpyrrolidones, proline acyl esters, and the like.

Within various aspects of the invention, improved nasal mucosal delivery formulations and methods are provided that allow delivery of peptide YY and other therapeutic agents within the invention across mucosal barriers between administration and selected target sites. Certain formulations are specifically adapted for a selected target cell, tissue or organ, or even a particular disease state. In other aspects, formulations and methods provide for efficient, selective endo- or transcytosis of peptide YY specifically routed along a defined intracellular or intercellular pathway. Typically, the peptide YY is efficiently loaded at effective concentration levels in a carrier or other delivery vehicle, and is delivered and maintained in a stabilized form, e.g., at the nasal mucosa and/or during passage through intracellular compartments and membranes to a remote target site for drug action (e.g., the blood stream or a defined tissue, organ, or extracellular compartment). The peptide YY may be provided in a delivery vehicle or otherwise modified (e.g., in the form of a prodrug), wherein release or activation of the peptide YY is triggered by a physiological stimulus (e.g. pH change, lysosomal enzymes, etc.) Often, the peptide YY is pharmacologically inactive until it reaches its target site for activity. In most cases, the peptide YY and other formulation components are non-toxic and non-immunogenic. In this context, carriers and other formulation components are generally selected for their ability to be rapidly degraded and excreted under physiological conditions. At the same time, formulations are chemically and physically stable in dosage form for effective storage.

Biologically Active Agents

The methods and compositions of the present invention are directed toward enhancing mucosal, e.g., intranasal, delivery of peptide YY or other biologically active agents to achieve therapeutic, prophylactic or other desired physiological results in mammalian subjects. As used herein, the term "biologically active agent" encompasses any substance that produces a physiological response when mucosally administered to a mammalian subject according to the methods and compositions herein. Useful biologically active agents in this context include therapeutic or prophylactic agents applied in all major fields of clinical medicine, as well as nutrients, cofactors, enzymes (endogenous or foreign), antioxidants, and the like. Thus, the biologically active agent may be water-soluble or water-insoluble, and may include higher molecular weight proteins, peptides, carbohydrates, glycoproteins, lipids, and/or glycolipids, nucleosides, polynucleotides, and other active agents.

Peptide and Protein Analogs and Mimetics

Included within the definition of biologically active peptides and proteins for use within the invention are natural or synthetic, therapeutically or prophylactically active, peptides (comprised of two or more covalently linked amino acids), proteins, peptide or protein fragments, peptide or protein analogs, and chemically modified derivatives or salts of active peptides or proteins. A wide variety of useful analogs and mimetics of peptide YY are contemplated for use within the invention and can be produced and tested for biological activity according to know methods. Often, the peptides or proteins of peptide YY or other biologically active peptides or proteins for use within the invention are muteins that are readily obtainable by partial substitution, addition, or deletion of amino acids within a naturally occurring or native (e.g., wild-type, naturally occurring mutant, or allelic variant) peptide or protein sequence. Additionally, biologically active fragments of native peptides or proteins are included. Such mutant derivatives and fragments substantially retain the desired biological activity of the native peptide or proteins. In the case of peptides or proteins having carbohydrate chains, biologically active variants marked by alterations in these carbohydrate species are also included within the invention.

"Peptide YY" or "PYY" refers to "peptide YY" in native-sequence or in variant form, and from any source, whether natural, synthetic, or recombinant. Peptide YY is a human peptide YY, for example, Peptide YY (human: (SEQ ID NO: 792) H-Tyr-Pro-Ile-Lys-Pro-Glu-Ala-Pro -Gly-Glu-Asp-Ala-Ser-Pro-Glu-Glu-Leu-Asn-Arg-Tyr-Tyr-Ala-Ser-Leu-Arg-His-Tyr-Leu-Asn -Leu-Val-Thr-Arg-Gln-Arg-Tyr-NH$_2$); (Leu$^{31}$,Pro$^{34}$)-Peptide YY (human: (SEQ ID NO: 798) H-Tyr-Pro-Ile-Lys-Pro-Glu-Ala-Pro-Gly-Glu-Asp-Ala-Ser-Pro-Glu-Glu-Leu-Asn-Arg-Tyr -Tyr-Ala-Ser-Leu-Arg-His-Tyr-Leu-Asn-Leu-Val-Thr-Arg-Pro-Arg-Tyr-NH$_2$); (Pro$^{34}$)-Peptide YY (human: (SEQ ID NO: 799) H-Tyr-Pro-Ile-Lys-Pro-Glu-Ala-Pro-Gly-Glu-Asp-Ala-Ser -Pro-Glu-Glu-Leu-Asn-Arg-Tyr-Tyr-Ala-Ser-Leu-Arg-His-Tyr-Leu-Asn-Leu-Val-Thr-Arg-Pro -Arg-Tyr-NH2); Peptide YY$_{3-36}$ (human: (SEQ ID NO: 794) H-Ile-Lys-Pro-Glu-Ala-Pro-Gly -Glu-Asp-Ala-Ser-Pro-Glu-Glu-Leu-Asn-Arg-Tyr-Tyr-Ala-Ser-Leu-Arg-His-Tyr-Leu-Asn-Leu -Val-Thr-Arg-Gln-Arg-Tyr-NH$_2$); Peptide YY$_{13-36}$ (porcine, rat: (SEQ ID NO: 793) H-Ser-Pro -Glu-Glu-Leu-Ser-Arg-Tyr-Tyr-Ala-Ser-Leu-Arg-His-Tyr-Leu-Asn-Leu-Val-Thr-Arg-Gln-Arg -Tyr-NH$_2$); (Bachem AG, King of Prussia, Pa., United States).

Examples include human peptide YY which is natural or recombinant. Recombinant peptide YY is synthesized in an E. coli bacterial protein synthesis process, or in a protein synthesis process in yeast cells, baculovirus in insect cells, or mammalian cells, for example, CHO or BHK cells.

"Pancreatic polypeptide (PP)" or "neuropeptide Y (NPY)" has peptide YY-like activity, or may be a peptide YY agonist binding to a "Y receptor." In certain formulations, "pancreatic polypeptide (PP)" or "neuropeptide Y (NPY)" may be substituted for peptide YY.

Biologically active peptides and proteins for use within the methods and compositions of the invention thus include native or "wild-type" peptides and proteins and naturally occurring variants of these molecules, e.g., naturally occurring allelic variants and mutant proteins. Also included are synthetic, e.g., chemically or recombinantly engineered, peptides and proteins, as well as peptide and protein "analogs" and chemically modified derivatives, fragments, conjugates, and polymers of naturally occurring peptides and proteins. As used herein, the term peptide or protein "analog" is meant to include modified peptides and proteins incorporating one or more amino acid substitutions, insertions, rearrangements or deletions as compared to a native amino acid sequence of a selected peptide or protein, or of a binding domain, fragment, immunogenic epitope, or structural motif, of a selected peptide or protein. Peptide and protein analogs thus modified exhibit substantially conserved biological activity comparable to that of a corresponding native peptide or protein, which means activity (e.g., specific binding to a peptide YY protein, or to a cell expressing such a protein, specific ligand or receptor binding activity, etc.) levels of at least 50%, typically at least 75%, often 85%–95% or greater, compared to activity levels of a corresponding native protein or peptide.

For purposes of the present invention, the term biologically active peptide or protein "analog" further includes derivatives or synthetic variants of a native peptide or protein, such as amino and/or carboxyl terminal deletions and fusions, as well as intrasequence insertions, substitutions or deletions of single or multiple amino acids. Insertional amino acid sequence variants are those in which one or more amino acid residues are introduced into a predetermined site in the protein. Random insertion is also possible with suitable screening of the resulting product. Deletional variants are characterized by removal of one or more amino acids from the sequence. Substitutional amino acid variants are those in which at least one residue in the sequence has been removed and a different residue inserted in its place.

Where a native peptide or protein is modified by amino acid substitution, amino acids are generally replaced by other amino acids having similar, conservatively related chemical properties such as hydrophobicity, hydrophilicity, electronegativity, small or bulky side chains, and the like. Residue positions which are not identical to the native peptide or protein sequence are thus replaced by amino acids having similar chemical properties, such as charge or polarity, where such changes are not likely to substantially effect the properties of the peptide or protein analog. These and other minor alterations will typically substantially maintain biological properties of the modified peptide or protein, including biological activity (e.g., binding to peptide YY, adhesion molecule, or other ligand or receptor), immunoidentity (e.g., recognition by one or more monoclonal antibodies that recognize a native peptide or protein), and other biological properties of the corresponding native peptide or protein.

As used herein, the term "conservative amino acid substitution" refers to the general interchangeability of amino acid residues having similar side chains. For example, a commonly interchangeable group of amino acids having aliphatic side chains is alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Examples of conservative substitutions include the substitution of a non-polar (hydrophobic) residue such as isoleucine, valine, leucine or methionine for another. Likewise, the present invention contemplates the substitution of a polar (hydrophilic) residue such as between arginine and lysine, between glutamine and asparagine, and between threonine and serine. Additionally, the substitution of a basic residue such as lysine, arginine or histidine for another or the substitution of an acidic residue such as aspartic acid or glutamic acid for another is also contemplated. Exemplary conservative amino acids substitution groups are: valine-leucine-isoleucine, phenylalanine-tyrosine, lysine-arginine, alanine-valine, and asparagine-glutamine.

By aligning a peptide or protein analog optimally with a corresponding native peptide or protein, and by using appropriate assays, e.g., adhesion protein or receptor binding assays, to determine a selected biological activity, one can readily identify operable peptide and protein analogs for use within the methods and compositions of the invention. Operable peptide and protein analogs are typically specifically immunoreactive with antibodies raised to the corresponding native peptide or protein. Likewise, nucleic acids encoding operable peptide and protein analogs will share substantial sequence identity as described above to a nucleic acid encoding the corresponding native peptide or protein, and will typically selectively hybridize to a partial or complete nucleic acid sequence encoding the corresponding native peptide or protein, or fragment thereof, under accepted, moderate or high stringency hybridization conditions. Sambrook et al., *Molecular Cloning: A Laboratory Manual*, Cold Spring Harbor Laboratories, Cold Spring Harbor, N.Y., 1989, incorporated herein by reference. The phrase "selectively hybridizing to" refers to a selective interaction between a nucleic acid probe that hybridizes, duplexes or binds preferentially to a particular target DNA or RNA sequence, for example when the target sequence is present in a heterogenous preparation such as total cellular DNA or RNA. Generally, nucleic acid sequences encoding biologically active peptide and protein analogs, or fragments thereof, will hybridize to nucleic acid sequences encoding the corresponding native peptide or protein under stringent conditions (e.g., selected to be about 5° C. lower than the thermal melting point (Tm) for the subject sequence at a defined ionic strength and pH, where the Tm is the temperature under defined ionic strength and pH at which 50% of the complementary or target sequence hybridizes to a perfectly matched probe). For discussions of nucleic acid probe design and annealing conditions, see, for example, Sambrook et al., *Molecular Cloning: A Laboratory Manual*, 2nd ed., Vols. 1–3, Cold Spring Harbor Laboratory, 1989 or *Current Protocols in Molecular Biology*, F. Ausubel et al, ed., Greene Publishing and Wiley-Interscience, New York, 1987, each of which is incorporated herein by reference. Typically, stringent or selective conditions will be those in which the salt concentration is at least about 0.02 molar at pH 7 and the temperature is at least about 60° C. Less stringent selective hybridization conditions may also be chosen. As other factors may significantly affect the stringency of hybridization, including, among others, base composition and size of the complementary strands, the presence of organic solvents and the extent of base mismatching, the combination of parameters is more important than the specific measure of any one.

Aggregation Inhibitory Agents and Methods

Protein aggregation is of major importance in biotechnology for the in vitro production and in vivo use of recombinant peptides and proteins, including peptide YY and other active peptides and proteins for use within the invention. Aggregation commonly limits the stability, solubility and yields of recombinant proteins for use in pharmaceutical formulations. Under various conditions, therapeutic peptides and proteins for use within the invention may exhibit functionally deleterious aggregation. Commonly, peptides and proteins expressed in large quantities in heterologous expression systems precipitate within the recombinant host cell in dense aggregates. Such insoluble aggregates of expressed polypeptide (inclusion bodies) may reflect improperly folded polypeptides relating to the inability of the host cell to properly process and/or secrete the recombinant polypeptide. The aggregated fraction often constitutes a major fraction of total cell protein in recombinant expression systems. Further details of peptide and protein aggregation are provided in Brems et al., *Biochemistry*, 24: 7662, 1985; Mitraki et al., *Bio/Technology*, 7: 690, 1989; Marston and Hartley, *Meth. Enzymol.* 182:264–276 (1990); Wetzel, Protein Aggregation In vivo: Bacterial Inclusion Bodies and Mammalian Amyloid," in Stability of Protein Pharmaceuticals: In vivo Pathways of Degradation and Strategies for Protein Stabilization, Ahern and Manning (eds.) (Plenum Press, 1991); and Wetzel, "Enhanced Folding and Stabilization of Proteins by Suppression of Aggregation In vitro and In vivo," in Protein Engineering—A Practical Approach, Rees, A. R. et al. (eds.) (IRL Press at Oxford University Press, Oxford, 1991) each of the foregoing publications is incorporated herein by reference.

Recovery of therapeutic peptides and proteins from aggregate forms, e.g., as found in recombinant expression systems, presents numerous problems. In many cases, peptides and proteins recovered from aggregates are predominantly biologically inactive, often because they folded into a three-dimensional-conformation different from that of native protein. Misfolding can occur either in the cell during fermentation or during protein isolation, processing or storage procedures. Methods for preventing aggregation, and for isolating and refolding proteins from aggregated complexes into a correct, biologically active conformation, are therefore important for obtaining functional peptides and proteins for therapeutic use within the invention.

Accordingly, the present invention provides compositions and methods that are effective in producing or maintaining "unaggregated" peptides or proteins in a pharmaceutical formulation for mucosal delivery of the subject peptide(s) or protein(s). The methods involve solubilizing peptides and proteins from aggregates and/or stabilizing peptides and proteins that are prone to aggregation—to provide formulations of soluble, stable, biologically active peptide or protein suitable for mucosal, e.g., intranasal, administration. Such formulations contain a solubilized peptide or protein in a substantially pure, unaggregated and therapeutically useful form.

Typically, the peptide or protein which is solubilized from aggregate or stabilized to reduce aggregation is initially obtained from a recombinant expression system, often from insoluble aggregate form. The latter procedure typically involves disruption of the host cells and separation of the ruptured cell materials from the insolubilized protein (as inclusion bodies). Examples of available means for accomplishing this are procedures involving the use of sonication and homogenization in the presence of one or more detergents and separation of the ruptured cell materials from the aggregated peptide or protein by centrifugation (see, e.g., U.S. Pat. Nos. 4,828,929 and 4,673,641). It should be understood that other well known procedures can be also be used in this context.

Peptides or proteins recovered from recombinant systems in this manner typically comprise a broad spectrum of polypeptides ranging from soluble monomers and multimers to macroscopic insoluble structures in which thousands of such individual polypeptide fragments are bound. Typically, however, those aggregates composed of approximately 10 to 20, or fewer fragments, and having a molecular weight of 200,000 to 400,000 are soluble. Such fragments, which are referred to herein as "soluble aggregate", have relatively low therapeutic utility as measured in in vitro assays. Certain even larger complexes are also soluble, although also of relatively low therapeutic utility.

As used herein, "unaggregated" peptide or protein comprises a peptide or protein composition that is substantially free of aggregate, whether soluble or insoluble. The composition of unaggregated peptide or protein typically comprises a population of monomeric peptide or protein, but may also include noncovalently linked multimeric species. Typically, the amount of "soluble aggregate" present in such samples (e.g., as determined by high performance liquid chromatography (HPLC)) is less than about 15%, often less than about 5%, and commonly less than about 0.5% of the subject peptide or protein species in a preparation. In alternate terms, the compositions of the invention are "substantially free of aggregate", wherein the percent by weight of monomer in a purified peptide or protein preparation is at least about 40% to 65%, more typically about 65% to 80 weight %, often at least 75%–95% or greater.

For some peptides and proteins, the formation of inclusion bodies and other types of insoluble aggregates may be related to the presence of cysteine residues in the subject peptide or protein. It is believed that incorrect disulfide bonds are encouraged to form either within inclusion bodies or during attempts to solubilize the polypeptides there from, as well as under other purification or storage conditions. When such bonds are formed within a polypeptide (an intrachain bond), they may lead to a biologically inactive conformation of the molecule. When disulfide bonds are formed between fragments (an interchain bond), they may lead to insoluble or biologically inactive dimers or aggregates. Illustrative of this phenomenon, misfolded IGF-I possesses different disulfide bond pairs than are found in native IGF-I, and exhibits significantly reduced biological activity (Raschdorf et al., Biomedical and Environmental Mass Spectroscopy, 16:3–8, 1988, incorporated herein by reference). In other cases, proteins isolated from aggregates produce disulfide-linked dimers, trimers, and multimers. Morris et al., Biochem. J., 268:803–806, 1990; Toren et al., Anal. Biochem., 169: 287–299, 1988; Frank et al., in Peptides: synthesis-structure-function, ed. D. H. Rich and E. Gross, pp. 729–738 (Pierce Chemical Company: Rockford, Ill., 1981), each incorporated herein by reference. This association phenomenon is very common during protein refolding, particularly at higher protein concentrations, and appears to often involve association through hydrophobic interaction of partially folded intermediates. Cleland and Wang, Biochemistry, 29:11072–11078, 1990, incorporated herein by reference.

Thus, successful manipulation of mammalian proteins expressed from recombinant bacterial systems has generally required that the cysteine residues thereof be altered so that they cannot react with other cysteine residues. Without this treatment, undesired reaction of the cysteine residues thereof typically occurs, leading to the formation of insoluble or biologically inactive polypeptide aggregates unsuited for effective use as therapeutics.

There are numerous well-known procedures that can be used within the invention to successfully alter cysteine residues of therapeutic peptides and proteins that are prone to aggregation involving disulfide bonding. One such technique involves treatment of cysteine residues with a reducing agent such as; for example, beta-mercaptoethanol or dithiothreitol (DTT) followed by permanent alkylation (for example, with iodoacetamide) of the cysteine residues. Numerous other covalent labels may be attached to the target cysteine residues, so long as they are applied under pH conditions that do not irreversibly denature the target peptide or protein and do not allow chemical reaction with other cysteine residues. Such covalent labeling procedures are generally known in the art and include also, for example, reaction with iodoacetic acid or iodinating agents such as iodofluorescein. Additionally, cysteine residues may be chemically altered such as by sulfitolyzation. Alteration can be accomplished also by site directed mutagenesis of an encoding DNA, replacing cysteine residues with "inert" residues such as, for example, glycine or alanine, or by deletion of sequence positions corresponding to cysteine. A sufficient number of the cysteine residues are altered to avoid the aggregation problems caused by their presence. For additional details regarding methods for preparing cysteine-altered proteins to minimize aggregation, see, e.g., U.S. Pat. No. 5,847,086, incorporated herein by reference.

For methods that do not involve cysteine modification, it is important to note that protein folding is influenced by the nature of the medium containing the protein, and by a combination of weak attractive or repellent intramolecular forces involved in hydrogen bonding, ionic bonding, and hydrophobic interactions. When pairs of cysteine residues are brought into close proximity as the peptide backbone folds, strong covalent disulfide bonds often form between cysteine residues, serving to lock the tertiary conformation in place. Refolding protocols have been designed to break incorrect disulfide bonds, block random disulfide bonding, and allow refolding and correct disulfide bonding under conditions favorable to the formation of an active conformer.

One general method for recovering active protein from aggregates involves solubilizing the aggregated protein in strongly denaturing solutions and then optionally exchanging weakly denaturing solutions for the strongly denaturing solutions (or diluting the strong denaturant), or using molecular sieve or high-speed centrifugation techniques. U.S. Pat. Nos. 4,512,922; 4,518,256; 4,511,502; and 4,511,503, incorporated herein by reference. Such recovery methods are useful within certain methods of the invention to prepare active peptide and protein compositions from aggregated, or aggregation-prone, starting materials. The terms "denaturant" are broadly applied herein to include denaturant and detergent compounds that unfold proteins and/or disrupt disulfide bonds and other interactions between aggregate-prone peptides and proteins. Examples of suitable materials for use as denaturants in this context include, but are not limited to, the denaturants urea and guanidine-hydrochloride, and detergents such as polyoxyethylene p-tert-octylphenol (Nonidet®P40), polyoxyethylene, p-tert-octylphenol (Triton-X-100), and sodium deoxycholate. Often, the formulations and methods of the invention will incorporate urea as the selected denaturant, because it is highly soluble in aqueous solutions and it is capable of being removed rapidly from solution by dialysis. In addition, because urea is a nonionic substance, it does not interfere with ion exchange materials that may be used in the process to remove contaminants of bacterial origin such as DNA and endotoxin. Although numerous procedures are known for solubilizing aggregated inclusion body proteins in the presence of denaturant, clinical use of the resultant product requires that the denaturant contained therein be replaced with clinically acceptable materials which are nontoxic and nonirritating, so that the resultant solution complies with medical standards for injection into humans.

Certain aggregation inhibitory methods for use within the invention seek to eliminate random disulfide bonding prior to coaxing the recombinant protein into its biologically active conformation. The denatured peptide or protein to be refolded is then further purified under reducing conditions that maintain the cysteine moieties of the protein as free sulfhydryl groups. The reducing agent is then diluted into an aqueous solution to enable the refolded protein to form the appropriate disulfide bonds in the presence of air or some other oxidizing agent. This enables refolding to be easily incorporated into the overall purification or formulation process.

In another approach that is useful within the methods and formulations of the invention, refolding of recombinant peptide or protein takes place in the presence of both the reduced (R-SH) and oxidized (R-S-S-R) forms of a sulfhydryl compound. This allows free sulfhydryl groups and disulfides to be formed and reformed constantly throughout the purification process. The reduced and oxidized forms of the sulfhydryl compound are provided in a buffer having sufficient denaturing power that all of the intermediate conformations of the protein remain soluble in the course of the unfolding and refolding. Urea is a suitable buffer medium because of its apparent ability to act both as a sufficiently weak denaturing agent to allow the protein to approximate its correct conformation, and as a sufficiently strong denaturant that the refolding intermediates maintain their solubility.

Yet another alternative purification/preparative technique for use within the methods and compositions of the invention is designed to break any disulfide bonds that may have formed incorrectly during isolation of peptide or protein from aggregated form, and then to derivatize the available free sulfhydryl groups of the recombinant protein. This objective is achieved by sulfonating the protein to block random disulfide pairings, allowing the protein to refold correctly in weak denaturant, and then desulfonating the protein, under conditions that favor correct disulfide bonding. The desulfonation takes place in the presence of a sulfhydryl compound and a small amount of its corresponding oxidized form to ensure that suitable disulfide bonds will remain intact. The pH is raised to a value such that the sulfhydryl compound is at least partially in ionized form to enhance nucleophilic displacement of the sulfonate.

Additional recovery methods useful for providing active peptides and proteins in unaggregated form for mucosal administration according to the invention is provided in WO 88/8003, and Halenbeck et al., *Bio/Technology*, 7: 710–715, 1989 each incorporated herein by reference. These procedures involve initial solubilization of monomers isolated from inclusion bodies under reducing conditions in a chaotropic environment comprising urea or guanidine hydrochloride, followed by refolding by stepwise dilution of the chaotropic agents, and final oxidation of the refolded molecules in the presence of air or a redox-system.

It is also contemplated that certain aggregated peptides and proteins to be processed and mucosally administered according to the methods of the invention will be solubilized and sulphitolysed in denaturant, then precipitated by solvent exchange. U.S. Pat. No. 4,923,967; and EP 361,830, each incorporated herein by reference. According to this technique, the precipitated protein is resolubilized in denaturant and allowed to refold in the presence of reducing agent.

Additional methods useful within the invention for refolding proteins to an active form for mucosal administration involve the use of high concentrations of copper as an oxidant, as employed for interleukin-2 (IL-2). Tsuji et al., *Biochemistry*, 26: 3129–3134, 1987; WO 88/8849, each incorporated herein by reference. According to another technique, a denaturing agent and reducing agent are added to solubilize the protein, followed by removal of the reducing agent, oxidation of the protein, and removal of the denaturant, as employed for growth hormone. U.S. Pat. No. 4,985,544, each incorporated herein by reference. Other methods for refolding are disclosed in George et al., *DNA*, 4: 273–281, 1984; Gill et al., *Bio/Technology*, 3:643–646, 1985; Sekine et al., *Proc. Natl. Acad. Sci. USA*, 82: 4306–4310, 1985, each incorporated herein by reference. Yet additional refolding methods useful within the invention are described in Green et al., *J. Dairy Res.*, 52: 281–286, 1985; Winkler et al., *Bio/Technology*, 3: 990–1000, 1985; U.S. Pat. No. 4,652,630 (urea used for solubilization, followed by a mild oxidizing agent for refolding); EP 360,937; Boss et al., *Nucl. Acids Res.*, 12: 3791–3806, 1984; Cabilly et al., *Proc. Natl. Acad. Sci. USA*, 81: 3273–3277, 1984; Marston et al., *Bio/Technology*, 2: 800–804, 1984; and Marston, *Biochem. J.*, 240: 1–12, 1986, each incorporated herein by reference.

Yet additional techniques for refolding peptides and proteins to active forms for mucosal administration involve the use of SDS for solubilization and $Cu^{+2}$ ions as oxidation promoters of the fully reduced proteins. (e.g., as exemplified for IL-2 and IFN-Beta in U.S. Pat. No. 4,572,798, incorporated herein by reference). Alternative methods for preparing active recombinant proteins from aggregates are described in U.S. Pat. No. 4,620,948, incorporated herein by reference, which involve using strong denaturing agents to solubilize the proteins, reducing conditions to facilitate correct folding, and denaturant replacement in the presence of air or other oxidizing agents to reform the disulfide bonds.

Alternate methods for renaturing unfolded peptides and proteins within the methods and compositions of the invention involve reversibly binding the denatured peptide or protein to a solid matrix and stepwise renaturing it by diluting the denaturant (as exemplified for cytochrome c, ovalbumin, and trypsin inhibitor in WO 86/5809, incorporated herein by reference). Alternatively, peptides and proteins from aggregates can be S-sulfonated during purification to protect thiol moieties and then dimerized in the presence of oxidizing agents to yield an active product as described for a modified monomeric form of human platelet-derived growth factor (PDGF) expressed in *E. coli* by Hoppe et al., *Biochemistry*, 28: 2956–2960, 1989, incorporated herein by reference.

Additionally, EP 433,225, published Jun. 19, 1991, incorporated herein by reference, discloses a process for producing dimeric biologically active transforming growth factor-beta. protein or a salt thereof wherein the denatured monomeric form of the protein is subjected to refolding conditions that include a solubilizing agent such as mild detergent, an organic, water-miscible solvent, and/or a phospholipid. U.S. Pat. No. 4,705,848, incorporated herein by reference, discloses the isolation of monomeric, biologically active growth hormone from inclusion bodies using one denaturing step with a guanidine salt and one renaturing step. Bowden et al., *Bio/Technology* 9:725–730, 1991; Samuelsson et al., *Bio/Technology*, 9: 731, 1991; and Hejnaes et al., *Protein Engineering*, 5: 797–806, 1992, each incorporated herein by reference, describe additional procedures and reagents that are useful to prepare and/or stabilize aggregation-prone peptides and proteins within the methods and compositions of the invention.

Other methods useful within the invention for resolving aggregation problems involve disulfide exchange equilibration of refolding intermediates. For example, the refolding of IGF-I using redox buffers was investigated and the partially oxidized IGF-I forms produced were characterized by Hober et al., *Biochemistry*, 31: 1749–1756, 1992, incorporated herein by reference. Disulfide exchange can also be modulated using the additive agent of peptidyl disulfide isomerase (PDI) or peptidyl prolyl isomerase (PPI). See, for example, JP Patent Application No. 63294796; EP 413,440; and EP 293,793, each incorporated herein by reference.

Enhancement of selected disulfide pairings, e.g., by adding 50% methanol to buffer at low ionic strength, is another useful method for preparing active peptide and protein reagents for intranasal administration according to the invention. Snyder, *J. Biol. Chem.*, 259: 7468–7472, 1984, incorporated herein by reference. This method involves enhancing formation of specific disulfide bonds by adjusting electrostatic factors in the medium to favor the juxtaposition of oppositely charged amino acids that border the selected cysteine residues (see also, Tamura et al., abstract and poster presented at the Eleventh American Peptide Symposium on Jul. 11, 1989, incorporated herein by reference, which discloses addition of acetonitrile, DMSO, methanol, or ethanol to improve processing of correctly folded IGF-I).

Related methods that are useful within the invention involve changing the redox potential of a subject peptide or protein by dialysis against a buffer containing from 20–40% v/v ethanol over a period of up to five hours and acidifying the mixture, e.g., as disclosed for AlaGlu-IGF-I in WO 92/03477, incorporated herein by reference. Alternatively, methanol can be used at certain concentrations in the denaturation of active peptides and proteins. Lustig et al., *Biochim. Biophys. Acta.*, 1119: 205–210, 1992, incorporated herein by reference. Yet additional methods involve the use of moderate concentrations of alcohol or other methods of modulating solution polarity to reduce association of peptides under conditions that promote structure destabilization. Bryant et al., *Biochemistry*, 31: 5692–5698, 1992; Hua et al., *Biochim. Biophys. Acta*, 1078: 101–110, 1991; Brems et al., *Biochemistry*, 29: 9289–9293, 1990; JP 62–190199, Jackson et al., *Biochim Biophys. Acta*, 1118: 139–143, 1992; Shibata et al., *Biochemistry*, 31: 5728–5733, 1992; Zhong et al., *Proc. Natl. Acad. Sci. USA*, 89: 4462–4465, 1992, each incorporated herein by reference.

In additional methods useful within the invention, low copper or manganese concentrations are used to facilitate disulfide oxidation of polypeptides. U.S. Pat. No. 5,756,672, incorporated herein by reference. The peptide or protein is first maintained in an alkaline buffer comprising a chaotropic agent and a reducing agent in amounts sufficient for solubilization. During the refolding or processing step the subject peptide or protein is incubated at a concentration of about 0.1 to 15 mg/mL in a buffer of pH 7–12 comprising about 5–40% (v/v) of an alcoholic or polar aprotic solvent, about 0.2 to 3M of an alkaline earth, alkali metal, or ammonium salt, about 0.1 to 9M of a chaotropic agent, and about 0.01 to 15 µM of a copper or manganese salt. An oxygen source is introduced, so that refolding of the peptide or protein occurs during the incubation. The essence of this method involves the use of a special buffer containing a minimal concentration of copper or manganese salt to enhance refolding of misfolded polypeptides. The use of manganese or copper salts as oxidation catalysts avoids the necessity of more expensive disulfide-exchange agents such as glutathione. Furthermore, the method avoids the possibility of producing polypeptide containing disulfide adducts that can result when disulfide-exchange agents are employed.

Additional techniques useful within the methods and compositions of invention involve the use of a pro-sequence of a naturally occurring polypeptide to promote folding of a biologically inactive polypeptide to its active form, (e.g., as exemplified for subtilisin in U.S. Pat. No. 5,191,063, incorporated herein by reference).

The foregoing recovery, purification and preparative methods and compositions are generally useful to prepare formulations of aggregation-prone peptides and proteins for mucosal administration. These methods and compositions of the invention further reduce aggregation problems that occur during storage, delivery, and even after delivery when pharmaceutical formulations comprising aggregation-prone biologically active agents are delivered to, or absorbed into or across, a mucosal tissue. By determining the molecular pathways that contribute to aggregation of solid peptides and proteins, rational approaches for stabilization in accordance with the foregoing teachings are readily determined. These approaches specifically target the particular mechanisms involved in aggregation of a selected biologically active peptide or protein within the invention. In conjunction with these strategies, the methods and compositions of the invention, e.g., which involve admixtures or complexes of peptides or proteins with carriers, such as polymeric matrices, maintain the level of moisture activity within the formulation at optimal levels to reduce peptide or protein aggregation. This can be achieved, for example, selecting a carrier or delivery vehicle that provides for reduced water activities. The pH of the microenvironment for storage and/or delivery is also controlled to minimize peptide or protein aggregation, following the application of physicochemical principles set forth herein.

Another approach for stabilizing solid protein formulations of the invention is to increase the physical stability of purified, e.g., lyophilized, protein. This will inhibit aggregation via hydrophobic interactions as well as via covalent pathways that may increase as proteins unfold. Stabilizing formulations in this context often include polymer-based formulations, for example a biodegradable hydrogel formulation/delivery system. As noted above, the critical role of water in protein structure, function, and stability is well known. Typically, proteins are relatively stable in the solid state with bulk water removed. However, solid therapeutic protein formulations may become hydrated upon storage at elevated humidities or during delivery from a sustained release composition or device. The stability of proteins generally drops with increasing hydration. Water can also play a significant role in solid protein aggregation, for example, by increasing protein flexibility resulting in enhanced accessibility of reactive groups, by providing a mobile phase for reactants, and by serving as a reactant in several deleterious processes such as beta-elimination and hydrolysis.

Protein preparations containing between about 6% to 28% water are the most unstable. Below this level, the mobility of bound water and protein internal motions are low. Above this level, water mobility and protein motions approach those of full hydration. Up to a point, increased susceptibility toward solid-phase aggregation with increasing hydration has been observed in several systems. However, at higher water content, less aggregation is observed because of the dilution effect.

In accordance with these principles, an effective method for stabilizing peptides and proteins against solid-state aggregation for mucosal delivery is to control the water content in a solid formulation and maintain the water activity in the formulation at optimal levels. This level depends on the nature of the protein, but in general, proteins maintained below their "monolayer" water coverage will exhibit superior solid-state stability. According to current FDA requirements, an acceptable protein drug containing pharmaceutical product should exhibit less than about 10% deterioration after 2 years. Cleland, J. L. and Langer, R. In formulation and delivery of proteins and peptides, ACS books, 1994, incorporated herein by reference.

A variety of additives, diluents, bases and delivery vehicles are provided within the invention that effectively control water content to enhance protein stability. These reagents and carrier materials effective as anti-aggregation agents in this sense include, for example, polymers of various functionalities, such as polyethylene glycol, dextran, diethylaminoethyl dextran, and carboxymethyl cellulose, which significantly increase the stability and reduce the solid-phase aggregation of peptides and proteins admixed therewith or linked thereto. In some instances, the activity or physical stability of proteins can also be enhanced by various additives to aqueous solutions of the peptide or protein drugs. For example, additives, such as polyols (including sugars), amino acids, proteins such as collagen and gelatin, and various salts may be used.

Certain additives, in particular sugars and other polyols, also impart significant physical stability to dry, e.g., lyophilized proteins. These additives can also be used within the invention to protect the proteins against aggregation not only during lyophilization but also during storage in the dry state. For example sucrose and Ficoll 70 (a polymer with sucrose units) exhibit significant protection against peptide or protein aggregation during solid-phase incubation under various conditions. These additives may also enhance the stability of solid proteins embedded within polymer matrices.

Yet additional additives, for example sucrose, stabilize proteins against solid-state aggregation in humid atmospheres at elevated temperatures, as may occur in certain sustained-release formulations of the invention. Proteins such as gelatin and collagen also serve as stabilizing or bulking agents to reduce denaturation and aggregation of unstable proteins in this context. These additives can be incorporated into polymeric melt processes and compositions within the invention. For example, polypeptide microparticles can be prepared by simply lyophilizing or spray drying a solution containing various stabilizing additives described above. Sustained release of unaggregated peptides and proteins can thereby be obtained over an extended period of time.

Various additional preparative components and methods, as well as specific formulation additives, are provided herein which yield formulations for mucosal delivery of aggregation-prone peptides and proteins, wherein the peptide or protein is stabilized in a substantially pure, unaggregated form. A range of components and additives are contemplated for use within these methods and formulations. Exemplary of these anti-aggregation agents are linked dimers of cyclodextrins (CDs), which selectively bind hydrophobic side chains of polypeptides. Breslow, et al., *J. Am. Chem. Soc.*, 120: 3536–3537; Maletic, et al., *Angew. Chem. Int. Ed. Engl.*, 35: 1490–1492; each incorporated herein by reference. These CD dimers have been found to bind to hydrophobic patches of proteins in a manner that significantly inhibits aggregation. Leung et al., *Proc. Nat.l Acad. Sci. USA*, 97: 5050–5053, 2000, incorporated herein by reference. This inhibition is selective with respect to both the CD dimer and the protein involved. Such selective inhibition of protein aggregation provides additional advantages within the intranasal delivery methods and compositions of the invention. Additional agents for use in this context include CD trimers and tetramers with varying geometries controlled by the linkers that specifically block aggregation of peptides and protein. Breslow et al., *J. Am. Chem. Soc.*, 118: 11678–11681, 1996; Breslow et al., *PNAS USA*, 94: 11156–11158, 1997; Breslow et al., *Tetrahedron Lett.*, 2887–2890, 1998, each incorporated herein by reference.

Yet additional anti-aggregation agents and methods for incorporation within the invention involve the use of peptides and peptide mimetics to selectively block protein-protein interactions. In one aspect, the specific binding of hydrophobic side chains reported for CD multimers is extended to proteins via the use of peptides and peptide mimetics that similarly block protein aggregation. A wide range of suitable methods and anti-aggregation agents are available for incorporation within the compositions and procedures of the invention. Zutshi et al., *Curr. Opin. Chem. Biol.*, 2: 62–66, 1998; Daugherty et al., *J. Am. Chem. Soc.*, 121: 4325–4333, 1999: Zutshi et al., *J. Am. Chem. Soc.*, 119: 4841–4845, 1997; Ghosh et al, *Chem. Biol.*, 5: 439–445, 1997; Hamuro et al., *Angew. Chem. Int. Ed. Engl.*, 36: 2680–2683, 1997; Alberg et al., *Science*, 262: 248–250, 1993; Tauton et al., *J. Am. Chem. Soc.*, 118: 10412–10422, 1996; Park et al., *J. Am. Chem. Soc.*, 121: 8–13, 1999; Prasanna et al., *Biochemistry*, 37: 6883–6893, 1998; Tiley et al., *J. Am. Chem. Soc.*, 119: 7589–7590, 1997; Judice et al., *PNAS, USA*, 94: 13426–13430, 1997; Fan et al., *J. Am. Chem. Soc.*, 120: 8893–8894, 1998; Gamboni et al., *Biochemistry*, 37: 12189–12194, 1998, each incorporated herein by reference. Briefly, these methods involve rational design and selection of peptides and mimetics that effectively block interactions between selected biologically active peptides or proteins, whereby the selected peptides and mimetics significantly reduce aggregation of the active peptides or proteins in a mucosal formulation. Anti-aggregation peptides and mimetics thus identified are coordinately administered with, or admixed or conjugated in a combinatorial formulation with, a biologically active peptide or protein to effectively inhibit aggregation of the active peptide or protein in a manner that significantly enhances absorption and/or bioavailability of the active peptide or protein.

Other anti-aggregation agents for use within the invention include chaperonins and analogs and mimetics of such molecules, as well as antibodies and antibody fragments that function in a similar, but often more specific, manner as chaperonins to bind peptide and protein domains and thereby block associative interactions there between. These molecular chaperones were initially recognized as stress proteins produced in cells requiring repair. In particular, studies of heat shock on enzymes showed that molecular chaperones function not only during cellular stress but also to chaperone the process of normal protein folding. Chaperonins comprise a ubiquitous family of proteins that mediate post-translational folding and assembly of other proteins into oligomeric structures. They prevent the formation of incorrect structures, and also act to disrupt incorrect structures that form during these processes. The chaperones non-covalently bind to the interactive surface of a target protein. This binding is reversed under circumstances that favor the formation of the correct structure by folding. Chaperones have not been shown to be specific for only one protein, but rather act on families of proteins that have similar stoichiometric requirements (e.g., specific structural domains that are recognized by the chaperones). Various publications describe the selection and use of chaperoning, antibodies and antibody fragments as aggregation-blocking agents for use within the invention (see, e.g., WO 93/11248; WO 93/13200; WO 94/08012; WO; WO 94/11513; WO 94/08012; and U.S. Pat. No. 5,688,651, each incorporated herein by reference).

Additional methods for inhibiting aggregation within the invention include the use of fusion proteins, as disclosed for example for IGF-I EP 130,166; U.S. Pat. No. 5,019,500; and EP 219,814, each incorporated herein by reference. These incorporated references disclose expression of fusion peptides of IGF-I with a protective polypeptide in bacteria. EP 264,074 discloses a two-cistronic met-IGF-I expression vector with a protective peptide of 500–50,000 molecular weight. U.S. Pat. No. 5,028,531; and Saito et al., *J. Biochem.*, 101: 1281–1288, 1987, each incorporated herein by reference. Other fusion techniques include fusion of IGF-I with a protective peptide from which a rop gene is cut off, EP 219,814, incorporated herein by reference, in which IGF-I is multimerized, Schulz et al., *J. Bacteriol.*, 169: 5385–5392, 1987, incorporated herein by reference, in which IGF-I is fused with luteinizing hormone (LH) through a chemically cleavable methionyl or tryptophan residue at the linking site, Saito et al., *J. Biochem.*, 101: 123–134, 1987, incorporated herein by reference, and in which IGF-I is fused with superoxide dismutase. EP 196,056; Niwa et al., *Ann. NY Acad. Sci.*, 469: 31–52, 1986, incorporated herein by reference. These disclosures, which teach chemical synthesis, cloning, and successful expression of genes for IGF-I fused to another polypeptide, are generally applicable to prepare a range of fusion polypeptides with other therapeutic peptides and proteins for use within the invention.

Yet additional methods for use within the methods and formulations of the invention involve addition of a leader sequence to the subject therapeutic peptide or protein to improve the fidelity of folding after recombinant expression. In this context, U.S. Pat. No. 5,158,875, incorporated herein by reference, describes a method for refolding recombinant IGF-I that involves cloning the IGF-I gene with a positively charged leader sequence prior to transfecting the DNA into the host cell. The additional positive charge on the amino terminus of the recombinant IGF-I promotes correct refolding when the solubilized protein is stirred for 2–16 hours in denaturant solution. Following refolding, the leader sequence is cleaved and the active recombinant protein is purified.

Another method for facilitating in vitro refolding of recombinant polypeptides involves using a solubilized affinity fusion partner, for example comprising two IgG-binding domains derived from staphylococcal protein A. Samuelsson et al., *Bio/Technology*, 9: 731, 1991, incorporated herein by reference. This method uses the protein A domain as a solubilizer of misfolded and multimeric IGF-I. While this method does not use denaturing agents or redox chemicals, it involves the added steps of fusing onto the IGF-I gene a separate gene and removing the polypeptide encoded by that gene after expression of the fusion gene.

Other techniques in peptide and protein engineering disclosed herein will further reduce the extent of protein aggregation and instability in mucosal delivery methods and formulations of the invention. One example of a useful method for peptide or protein modification in this context is PEGylation. The stability and aggregation problems of polypeptide drugs can be significantly improved by covalently conjugating water-soluble polymers such as PEG with the polypeptide. Another example is modification of a peptide or protein amino acid sequence in terms of the identity or location of one or more residues, e.g., by terminal or internal addition, deletion or substitution (e.g., deletion of cysteine residues or replacement by alanine or serine) to reduce aggregation potential. The improvements in terms of stability and aggregation potential that are achieved by these methods enables effective mucosal delivery of a therapeutically effective polypeptide or protein composition within the methods of the invention.

Charge Modifying and pH Control Agents and Methods

To improve the transport characteristics of biologically active agents (including peptide YY, other active peptides and proteins, and macromolecular and small molecule drugs) for enhanced delivery across hydrophobic mucosal membrane barriers, the invention also provides techniques and reagents for charge modification of selected biologically active agents or delivery-enhancing agents described herein. In this regard, the relative permeabilities of macromolecules is generally be related to their partition coefficients. The degree of ionization of molecules, which is dependent on the $pK_a$ of the molecule and the pH at the mucosal membrane surface, also affects permeability of the molecules. Permeation and partitioning of biologically active agents, including peptide YY and analogs of the invention, for mucosal delivery may be facilitated by charge alteration or charge spreading of the active agent or permeabilizing agent, which is achieved, for example, by alteration of charged functional groups, by modifying the pH of the delivery vehicle or solution in which the active agent is delivered, or by coordinate administration of a charge- or pH-altering reagent with the active agent.

A model compound for evaluating charge- and pH-modification methods for use within the mucosal delivery formulations and methods of the inventions is nicotine. The charge status of this model therapeutic as a function of pH has been investigated at various delivery sites of skin and absorptive mucosae. Nair et al., *J. Pharm. Sci.*, 86: 257–262, 1997, incorporated herein by reference. Nicotine is a diacidic base with well-separated $pK_a$ values (3.04 and 7.84) that allow the study of particular species by pH control. The dissociation of nicotine follows the pH-partition hypothesis, so the theoretical relative proportions of the different charged species at any particular pH can be determined. As an ionizable compound ($pK_a$ values of 3.04 and 7.84), nicotine in solutions of different pH values provides a model for determining the influence of the charge status of a molecule on permeation.

The permeation of nicotine across certain mucosal and skin surfaces follows zero-order kinetics. The rate of permeation is dependent on donor solution pH and increases exponentially as the pH of the delivery solution is increased.

As expected with a majority of charged macromolecular species for use within the invention, the permeability of nicotine across various skin and mucosal surfaces is reportedly higher un-ionized species (NN) than for ionized species (NNH$^+$, NH$^+$NH$^+$). It is also reported that un-ionized nicotine molecules are more permeable through absorptive mucosae (nasal, buccal, sublingual, and gingival) than through skin (abdominal, dorsal, thigh, and ear pinna). Partition studies confirm that biomembrane permeation of nicotine follows the pH-partition theory.

Consistent with these general teachings, mucosal delivery of charged macromolecular species, including peptide YY and other biologically active peptides and proteins, within the methods and compositions of the invention is substantially improved when the active agent is delivered to the mucosal surface in a substantially un-ionized, or neutral, electrical charge state.

Calculation of the isoelectric points of peptide YY and other biologically active peptides, proteins, and peptide analogs and mimetics is readily undertaken to guide the selection of pH and other values for mucosal formulations within the invention, which optionally deliver charged macromolecules in a substantially un-ionized state to the mucosal surface or, alternatively, following mucosal delivery at a target site of drug action. The pI of an amphoteric molecule is defined as the pH at which the net charge is zero. The variation of net charge with pH is of importance in charge-dependent separation methods like electrophoresis, isoelectric focusing, chromatofocusing and ion-exchange chromatography. Thus, methods for estimating isoelectric points (pI) for native peptides and proteins are well known and readily implemented within the methods and compositions of the invention. Cameselle, et al., *Biochem. Educ.*, 14: 131–136, 1986; Skoog, et al., *Trends Anal. Chem.*, 5: 82–83, 1986; Sillero et al., *Anal. Biochem.*, 179: 319–25, 1989; Englund, et al., *Biochim. Biophys. Acta.*, 1065: 185–194, 1991; Bjellquist et al., *Electrophoresis.*, 14: 1023–1031, 1993; Mosher et al., *J. Chromatogr.*, 638: 155–164, 1993; Bjellqvist et al., *Electrophoresis*, 15: 529–539, 1994; Watts, et al., *Electrophoresis*, 16: 22–27, 1995, each incorporated herein by reference.

For determining pI values of peptides and proteins for use within the invention, net charge can be estimated, for example, by the well-known Henderson-Hasselbalch equation. These determinations are based in part on the amino acid composition of the subject peptide or protein, yielding component pI values for specific amino acid side chains and for the N- and C-terminal groups. The individual ionizable side chains of each type of amino acid are typically assumed to have pKa values distributed around the projected pKa, value, simulating the situation in polypeptides and proteins where a given type of ionizable amino acid side chain often appears in several positions in the amino acid sequence and with various individual ionization constants, depending both on the adjacent side chains and on the three-dimensional environment in the protein. Bjellqvist et al., *Electrophoresis*, 15: 529–539, 1994; Matthew, *Annu. Rev. Biophys. Chem.*, 14: 387–417, 1985, each incorporated herein by reference. By assuming a distribution of pKa values, the calculated titration curves will be smoothed out. The presence of other charged groups is also taken into account. These analyses yield a set of pKa values, including values for amino acid residues with ionizable side chains. Each particular type of ionizable group is assumed to have pKa values distributed around the chosen value, thereby simulating the situation in intact proteins and polypeptides. According to these known calculation methods, accurate estimates of pI values for peptides and proteins show sufficient agreement with experimental values determined for native proteins, over a wide pH range (3.4–11), particularly when more refined analyses, including such factors as charge contributions of heme groups, sialic acid residues, etc., are taken into account. Henriksson et al., *Electrophoresis.*, 16: 1377–1380, 1995, incorporated herein by reference.

Thus, for polypeptides of known amino acid composition, a sufficient pI value estimate can be calculated by use of the ionization constant pKa for amino acid side chain groups. Where other types of ionizable groups occur, the charge for each such group at any given pH can also be readily estimated. The total net charge at a selected pH is obtained by summing up the charge for each type of ionizable group times the number of groups. In the present study, suitable average pKa, values were selected for the ionizable amino acid side chains, and for the terminal groups. Additional guidance for determining pI values for polypeptides useful within the invention is provided, for example, by Englund, et al., *Biochim. Biophys. Acta*, 1065: 185–194, 1991; Englund et al., *Electrophoresis*, 14: 1307–1311, 1993; Uzcategui et al., *J. Biotechnol.*, 19: 271–286, 1991; Sims et al., *Gene*, 74: 411–422, 1988; Cameselle, et al., *Biochem. Educ.*, 14: 131–136, 1986; Skoog, et al., *Trends Anal. Chem.*, 5: 82–83, 1986; Sillero et al., *Anal. Biochem.*, 179: 319–25, 1989; Bjellquist et al., *Electrophoresis*, 14: 1023–1031, 1993; Mosher et al., *J. Chromatogr.*, 638: 155–164, 1993; Bjellqvist et al., *Electrophoresis*, 15: 529–539, 1994; Watts, et al., *Electrophoresis*, 16: 22–27, 1995; and Oda et al., *Biochemistry*, 33: 5275–5284, 1994, each incorporated herein by reference. These and other teachings in the art allow for sufficiently accurate determination of charge values for peptides and proteins, and ready determination of appropriate pH values and other modifications to mucosal formulations within the invention to facilitate delivery of peptide and protein therapeutics in a substantially unionized form. Naturally, pH adjustments and other modifications to alter the charge status of a given peptide or protein therapeutic are determined in such a manner as to preserve substantial biological activity of the subject peptide or protein within the formulation or after delivery at a target site of action.

Certain peptide YY and other biologically active peptide and protein components of mucosal formulations for use within the invention will be charge modified to yield an increase in the positive charge density of the peptide or protein. These modifications extend also to cationization of peptide and protein conjugates, carriers and other delivery forms disclosed herein. Cationization offers a convenient means of altering the biodistribution and transport properties of proteins and macromolecules within the invention. Cationization is undertaken in a manner that substantially preserves the biological activity of the active agent and limits potentially adverse side effects, including tissue damage and toxicity. In many cases, cationized molecules have higher organ uptake and penetration compared with non-cationized forms. Ekrami et al., *Journal of Pharmaceutical Sciences*, 84:456–461, 1995; Bergman et al., *Clin. Sci.*, 67:35–43, 1984; Triguero et al., *J. Pharm. Exp. Ther.*, 258:186–192, 1991. In some cases, cationized proteins can penetrate physiological barriers considered impenetrable by the native proteins. For example, cationized albumin, Pardridge et al., *J. Pharm. Exp. Ther.*, 255:893–899, 1991, incorporated herein by reference, and cationized IgG, Triguero et al., *Proc. Nat. Acad. Sci. U.S.A.*, 86:4761–4765, 1989, incorporated herein by reference, have been demonstrated to bind to the brain capillary endothelium in vitro and cross the blood-brain barrier in vivo to a much greater extent than native albumin and native IgG. Cationized proteins are also generally taken up by the lungs to a greater extent than native proteins. Bergman et al., *Clin. Sci.*, 67:35–43, 1984; Triguero et al., *J. Pharm. Exp. Ther.*, 258:186–192, 1991; Pardridge et al., *J. Pharm. Exp. Ther.*, 251:821–826, 1989, each incorporated herein by reference. At the tissue level, it has been demonstrated that cationized ferritin (CF) binds to and is transcytosed across the pulmonary endothelium, Pietra et al., *Lab Invest.*, 49:54–61, 1983; Pietra et al., *Lab Invest.*, 59:683–691, 1988, in isolated, perfused rat lungs, whereas native ferritin does not bind to the pulmonary endothelium and is only transcytosed across this barrier to a small degree. Bergman et al. *Clin. Sci.*, 67:35–43, 1984, incorporated herein by reference, demonstrated that by increasing the level of cationization and the charge density of human serum albumin (as measured by the change in the pI value of native albumin), the uptake of cationized albumins by the lungs following iv administration in rats can be increased. Pardridge et al. have also demonstrated that cationized IgG and physiologically cationic histone. Pardridge et al., *J. Pharm. Exp. Ther.*, 251:821–826, 1989, incorporated herein by reference, have higher uptakes in the lungs compared with native IgG and bovine albumin, respectively. However, some studies have failed to demonstrate higher lung uptake for cationized proteins compared with native proteins. For instance, Pardridge et al., *J. Pharm. Exp. Ther.*, 255:893–899, 1991, incorporated herein by reference, and Takakura et al., *Pharm. Res.*, 7:339–346, 1990, incorporated herein by reference, report lower lung uptake for cationized albumin compared with native albumin following iv biodistribution studies in animals.

Degradative Enzyme Inhibitory Agents and Methods

A major drawback to effective mucosal delivery of biologically active agents, including peptide YY, is that they may be subject to degradation by mucosal enzymes. The oral route of administration of therapeutic compounds is particularly problematic, because in addition to proteolysis in the stomach, the high acidity of the stomach destroys many active and inactive components of mucosal delivery formulations before they reach an intended target site of drug action. Further impairment of activity occurs by the action of gastric and pancreatic enzymes, and exo and endopeptidases in the intestinal brush border membrane, and by metabolism in the intestinal mucosa where a penetration barrier substantially blocks passage of the active agent across the mucosa.

In addition to their susceptibility to enzymatic degradation, many therapeutic compounds, particularly relatively low molecular weight proteins, and peptides, introduced into the circulation, are cleared quickly from mammalian subjects by the kidneys. This problem may be partially overcome by administering large amounts of the therapeutic compound through repeated administration. However, higher doses of therapeutic formulations containing protein or peptide components can elicit antibodies that can bind and inactivate the protein and/or facilitate the clearance of the protein from the subject's body. Repeated administration of the formulation containing the therapeutic protein or peptide is essentially ineffective and can be dangerous as it can elicit an allergic or autoimmune response.

The problem of metabolic lability of therapeutic peptides, proteins and other compounds may be addressed in part through rational drug design. However, medicinal chemists have had less success in manipulating the structures of peptides and proteins to achieve high cell membrane permeability while still retaining pharmacological activity. Unfortunately, many of the structural features of peptides and proteins (e.g., free N-terminal amino and C-terminal carboxyl groups, and side chain carboxyl (e.g., Asp, Glu), amino (e.g., Lys, Arg) and hydroxyl (e.g. Ser, Thr, Tyr) groups) that bestow upon the molecule affinity and specificity for its pharmacological binding partner also bestow upon the molecule undesirable physicochemical properties (e.g., charge, hydrogen bonding potential) which limit their cell membrane permeability. Therefore, alternative strategies need to be considered for intranasal formulation and delivery of peptide and protein therapeutics.

Attempts to overcome the so-called enzymatic barrier to drug delivery include the use of liposomes, Takeuchi et al., *Pharm. Res.*, 13:896–901, 1996, incorporated herein by reference, and nanoparticles, Mathiowitz et al., *Nature*, 386:410–4, 1997, incorporated herein by reference, that reportedly provide protection for incorporated insulin towards an enzymatic attack and the development of delivery systems targeting to the colon, where the enzymatic activity is comparatively low. Rubenstein et al., *J. Control Rel.*, 46:59–73, 1997, incorporated herein by reference. In addition, co-administration of protease inhibitors has been reported in various studies to improve the oral bioavailability of insulin. Fujii et al, *J. Pharm Pharmacol.*, 37:545–9, 1985; Yamamoto et al., *Pharm Res.*, 11:1496–600, 1994; Moroshita et al., *Int. J. Pharm.*, 78:9–16, 1992, incorporated herein by reference.

More recent research efforts in the area of protease inhibition for enhanced delivery of biotherapeutic compounds, including peptide and protein therapeutics, has focused on covalent immobilization of enzyme inhibitors on mucoadhesive polymers used as drug carrier matrices. Bernkop-Schnurch et al., *Drug Dev. Ind. Pharm.*, 23:733–40, 1997; Bernkop-Schnurch et al., *J. Control. Rel.*, 47:113–21, 1997; Bernkop-Schnurch et al., *J. Drug Targ.*, 7:55–63, 1999, each incorporated herein by reference. In conjunction with these teachings, the invention provides in more detailed aspects an enzyme inhibitor formulated with a common carrier or vehicle for mucosal delivery of peptide YY and other biologically active peptides, analogs and mimetics, optionally to be administered coordinately one or more additional biologically active or delivery-enhancing agents. Optionally, the enzyme inhibitor is covalently linked to the carrier or vehicle. In certain embodiments, the carrier or vehicle is a biodegradable polymer, for example, a bioadhesive polymer. Thus, for example, a protease inhibitor, such as Bowman-Birk inhibitor (BBI), displaying an inhibitory effect towards trypsin and α-chymotrypsin, Birk Y. *Int. J. Pept. Protein Res.*, 25:113–31, 1985, incorporated herein by reference, or elastatinal, an elastase-specific inhibitor of low molecular size, may be covalently linked to a mucoadhesive polymer as described herein. The resulting polymer-inhibitor conjugate exhibits substantial utility as a mucosal delivery vehicle for peptides and other biologically active agents formulated or delivered alone or in combination with other biologically active agents or additional delivery-enhancing agents.

Exemplary mucoadhesive polymer-enzyme inhibitor complexes that are useful within the mucosal delivery formulations and methods of the invention include, but are not limited to: Carboxymethylcellulose-pepstatin (with anti-pepsin activity); Poly(acrylic acid)-Bowman-Birk inhibitor (anti-chymotrypsin); Poly(acrylic acid)-chymostatin (anti-chymotrypsin); Poly(acrylic acid)-elastatinal (anti-elastase); Carboxymethylcellulose-elastatinal (anti-elastase); Polycarbophil—elastatinal (anti-elastase); Chitosan—antipain (anti-trypsin); Poly(acrylic acid)—bacitracin (anti-aminopeptidase N); Chitosan—EDTA (anti-aminopeptidase N, anti-carboxypeptidase A); Chitosan—EDTA—antipain (anti-trypsin, anti-chymotrypsin, anti-elastase). Bernkop-Schnürch, *J. Control. Rel.,* 52:1–16, 1998, incorporated herein by reference. As described in further detail below, certain embodiments of the invention will optionally incorporate a novel chitosan derivative or chemically modified form of chitosan. One such novel derivative for use within the invention is denoted as a β-[1→4]-2-guanidino-2-deoxy-D-glucose polymer (poly-GuD) (see, FIG. 1).

In recent years the use of enzyme inhibitors to overcome the enzymatic barrier to perorally administered therapeutic peptides and proteins has gained considerable interest. For a detailed review see Bernkop-Schnuirch, A. *J. Control. Rel.,* 52:1–16, 1998, incorporated herein by reference. However, especially for peptide and protein drugs that are used in long-term therapy, the co-administration of enzyme inhibitors has remained questionable because of side effects caused by these agents. Several side effects, such as systemic intoxications, a disturbed digestion of nutritive proteins, and hypertrophy as well as hyperplasia of the pancreas based on a feedback regulation, may accompany enzyme inhibitor co-administration by oral delivery methods. Even if systemic toxic side effects and an intestinal mucosal damage can be excluded, enzyme inhibitors of pancreatic proteases still have a toxic potential caused by the inhibition of these digestive enzymes themselves. Besides a disturbed digestion of nutritive proteins, an inhibitor-induced stimulation of protease secretion caused by a feed-back regulation may be expected. Reseland et al., *Hum. Clin. Nutr.,* 126:634–642, 1996, incorporated herein by reference. Numerous studies have investigated this feed-back regulation with inhibitors, such as Bowman-Birk inhibitor, soybean trypsin inhibitor (Kunitz trypsin inhibitor) and camostat, in rats and mice. They demonstrate that this feed-back regulation rapidly leads to both hypertrophy and hyperplasia of the pancreas. Moreover, a prolonged oral administration of the Bowman-Birk inhibitor and soybean trypsin inhibitor leads to the development of numerous neoplastic foci, frequently progressing to invasive carcinoma. Otsuki et al., *Pancreas,* 2:164–169, 1987; Melmed et al., *Biochim. Biophys. Acta,* 421:280–288, 1976; McGuinness et al. *Scand. J. Gastroneterol.,* 17:273–277, 1982; Ge et al., *Br. J. Nutr.,* 70:333–345, 1993, each incorporated herein by reference. A reduction or even exclusion of this feed-back regulation might be possible by the development of drug delivery systems which keep inhibitor(s) concentrated on a restricted area of the intestine, where drug liberation and subsequent absorption takes place. For a general review of more recent enzyme inhibitor strategies in the context of oral peptide drug delivery, see, e.g., Marschütz et al., *Biomaterials,* 21:1499–1507, 2000, incorporated herein by reference.

The present invention provides coordinate administration methods and/or combinatorial formulations directed toward coordinate administration of a biologically active agent, including one or more peptide YY proteins, analogs and mimetics, with an enzyme inhibitor. Since a variety of degradative enzymes are present in the mucosal environment, the prophylactic and therapeutic compositions and methods of the invention are readily modified to incorporate the addition or coadministration of an enzyme inhibitor, such as a protease inhibitor, with the biologically active agent (e.g., a physiologically active peptide or protein), to thereby improve bioavailability of the active agent. For example, in the case of therapeutically active peptides and proteins, one or more protease inhibiting agent(s) is/are optionally combined or coordinately administered in a formulation or method of the invention with one or more inhibitors of a proteolytic enzyme. In certain embodiments, the enzyme inhibitor is admixed with or bound to a common carrier with the biologically active agent. For example, an inhibitor of proteolytic enzymes may be incorporated in a therapeutic or prophylactic formulation of the invention to protect a biologically active protein or peptide from proteolysis, and thereby enhance bioavailability of the active protein or peptide.

Any inhibitor that inhibits the activity of an enzyme to protect the biologically active agent(s) may be usefully employed in the compositions and methods of the invention. Useful enzyme inhibitors for the protection of biologically active proteins and peptides include, for example, soybean trypsin inhibitor, pancreatic trypsin inhibitor, chymotrypsin inhibitor and trypsin and chrymotrypsin inhibitor isolated from potato (solanum tuberosum L.) tubers. A combination or mixtures of inhibitors may be employed. Additional inhibitors of proteolytic enzymes for use within the invention include ovomucoid-enzyme, gabaxate mesylate, alpha1-antitrypsin, aprotinin, amastatin, bestatin, puromycin, bacitracin, leupepsin, alpha2-macroglobulin, pepstatin and egg white or soybean trypsin inhibitor. These and other inhibitors can be used alone or in combination. The inhibitor(s) may be incorporated in or bound to a carrier, e.g., a hydrophilic polymer, coated on the surface of the dosage form which is to contact the nasal mucosa, or incorporated in the superficial phase of the surface, in combination with the biologically active agent or in a separately administered (e.g., pre-administered) formulation.

The amount of the inhibitor, e.g., of a proteolytic enzyme inhibitor that is optionally incorporated in the compositions of the invention will vary depending on (a) the properties of the specific inhibitor, (b) the number of functional groups present in the molecule (which may be reacted to introduce ethylenic unsaturation necessary for copolymerization with hydrogel forming monomers), and (c) the number of lectin groups, such as glycosides, which are present in the inhibitor molecule. It may also depend on the specific therapeutic agent that is intended to be administered. Generally speaking, a useful amount of an enzyme inhibitor is from about 0.1 mg/ml to about 50 mg/ml, often from about 0.2 mg/ml to about 25 mg/ml, and more commonly from about 0.5 mg/ml to 5 mg/ml of the of the formulation (i.e., a separate protease inhibitor formulation or combined formulation with the inhibitor and biologically active agent).

With the necessary caveat of determining and considering possible toxic and other deleterious side effects, various inhibitors of proteases may be evaluated for use within the mucosal delivery methods and compositions of the invention. In the case of trypsin inhibition, suitable inhibitors may be selected from, e.g., aprotinin, BBI, soybean trypsin inhibitor, chicken ovomucoid, chicken ovoinhibitor, human pancreatic trypsin inhibitor, camostat mesilate, flavonoid inhibitors, antipain, leupeptin , p-aminobenzamidine, AEBSF, TLCK (tosyllysine chloromethylketone), APMSF, DFP, PMSF, and poly(acrylate) derivatives. In the case of chymotrypsin inhibition, suitable inhibitors may be selected from, e.g., aprotinin, BBI, soybean trypsin inhibitor, chymostatin, benzyloxycarbonyl-Pro-Phe-CHO, FK-448, chicken ovoinhibitor, sugar biphenylboronic acids complexes, DFP, PMSF, β-phenylpropionate, and poly(acrylate) derivatives. In the case of elastase inhibition, suitable inhibitors may be selected from, e.g., elastatinal, methoxysuccinyl-Ala-Ala-Pro-Val-chloromethylketone (MPCMK), BBI, soybean trypsin inhibitor, chicken ovoinhibitor, DFP, and PMSF. Other naturally occurring, endogenous enzyme inhibitors for additional known degradative enzymes present in the intranasal environment, or alternatively present in preparative materials for production of intranasal formulations, will be readily ascertained by those skilled in the art for incorporation within the methods and compositions of the invention.

Additional enzyme inhibitors for use within the invention are selected from a wide range of non-protein inhibitors that vary in their degree of potency and toxicity L. Stryer, *Biochemistry*, WH Freeman and Company, NY, N.Y., 1988, incorporated herein by reference. As described in further detail below, immobilization of these adjunct agents to matrices or other delivery vehicles, or development of chemically modified analogues, may be readily implemented to reduce or even eliminate toxic effects, when they are encountered. Among this broad group of candidate enzyme inhibitors for use within the invention are organo-phosphorous inhibitors, such as diisopropylfluorophosphate (DFP) and phenylmethylsulfonyl fluoride (PMSF), which are potent, irreversible inhibitors of serine proteases (e.g., trypsin and chymotrypsin). The additional inhibition of acetylcholinesterase by these compounds makes them highly toxic in uncontrolled delivery settings. L. Stryer, *Biochemistry*, WH Freeman and Company, NY, N.Y., 1988, incorporated herein by reference. Another candidate inhibitor, 4-(2-Aminoethyl)-benzenesulfonyl fluoride (AEBSF), has an inhibitory activity comparable to DFP and PMSF, but it is markedly less toxic. (4-Aminophenyl)-methanesulfonyl fluoride hydrochloride (APMSF) is another potent inhibitor of trypsin, but is toxic in uncontrolled settings. In contrast to these inhibitors, 4-(4-isopropylpiperadinocarbonyl)phenyl 1,2,3,4,-tetrahydro-1-naphthoate methanesulphonate (FK-448) is a low toxic substance, representing a potent and specific inhibitor of chymotrypsin. The co-administration of this compound led to an enhanced intestinal absorption of insulin in rats and dogs, resulting in a decrease in blood glucose level. This increased bioavailability of insulin was found to be related to the inhibition of digestive enzymes, especially chymotrypsin. Fujii et al., *J. Pharm. Pharmacol.*, 37:545–549, 1985, each incorporated herein by reference. Further representatives of this non-protein group of inhibitor candidates, and also exhibiting low toxic risk, are camostat mesilate (N,N'-dimethyl carbamoylmethyl-p-(p'-guanidinobenzoyloxy)phenylacetate methane-sulphonate), Yamamoto et al., *Pharm. Res.*, 11:1496–1500, 1994, incorporated herein by reference, and Na-glycocholate, Yamamoto et al., *Pharm. Res.*, 11: 1496–1500, 1994; Okagava et al., *Life Sci.*, 55:677–683, 1994, incorporated herein by reference.

Solution or powder formulations of IFN-β administered intranasally without surfactants were not absorbed in rabbits. However, absorption occurred after the addition of surfactants (non-ionic, anionic and amphoteric). Maximum concentrations of WN in plasma were dependent on the surfactant used, sodium glycocholate being the most effective. Total absorption of IFN following nasal administration with sodium glycocholate was 2.2% of that following intravenous administration. Maitani, et al., *Drug Design and Delivery*, 4:109–119, 1989, incorporated herein by reference.

Yet another type of enzyme inhibitory agent for use within the methods and compositions of the invention are amino acids and modified amino acids that interfere with enzymatic degradation of specific therapeutic compounds. For use in this context, amino acids and modified amino acids are substantially non-toxic and can be produced at a low cost. However, due to their low molecular size and good solubility, they are readily diluted and absorbed in mucosal environments. Nevertheless, under proper conditions, amino acids can act as reversible, competitive inhibitors of protease enzymes. McClellan et al., *Biochim. Biophys. Acta.,* 613:160–167, 1980, incorporated herein by reference. Certain modified amino acids can display a much stronger inhibitory activity. A desired modified amino acid in this context is known as a 'transition-state' inhibitor. The strong inhibitory activity of these compounds is based on their structural similarity to a substrate in its transition-state geometry, while they are generally selected to have a much higher affinity for the active site of an enzyme than the substrate itself. Transition-state inhibitors are reversible, competitive inhibitors. Examples of this type of inhibitor are cc-aminoboronic acid derivatives, such as boro-leucine, boro-valine and boro-alanine. The boron atom in these derivatives can form a tetrahedral boronate ion that is believed to resemble the transition state of peptides during their hydrolysis by aminopeptidases. These amino acid derivatives are potent and reversible inhibitors of aminopeptidases and it is reported that boro-leucine is more than 100-times more effective in enzyme inhibition than bestatin and more than 1000-times more effective than puromycin. Hussain et al., *Pharm. Res.,* 6:186–189, 1989, incorporated herein by reference. Another modified amino acid for which a strong protease inhibitory activity has been reported is N-acetylcysteine, which inhibits enzymatic activity of aminopeptidase N. Bernkop-Schnurch et al., *Pharm. Res.,* 14:181–185, 1997, incorporated herein by reference. This adjunct agent also displays mucolytic properties that can be employed within the methods and compositions of the invention to reduce the effects of the mucus diffusion barrier. Bemkop-Schnurch et al., *Pharm. Sci.,* 2:361–363, 1996, incorporated herein by reference.

Still other useful enzyme inhibitors for use within the coordinate administration methods and combinatorial formulations of the invention may be selected from peptides and modified peptide enzyme inhibitors. An important representative of this class of inhibitors is the cyclic dodecapeptide, bacitracin, obtained from *Bacillus lichenformis*. Bacitracin A has a molecular mass of 1423 Da and shows remarkable resistance against the action of proteolytic enzymes like trypsin and pepsin. Hickey, R. J., *Prog. Ind. Microbiol.,* 5:93–150, 1964, incorporated herein by reference. It has several biological properties inhibiting bacterial peptidoglycan synthesis, mammalian transglutaminase activity, and proteolytic enzymes such as aminopeptidase N. Because of its protease inhibitory activity, it has been used to inhibit the degradation of various therapeutic (poly) peptides, such as insulin, metkephamid, LH-RH, and buserelin. Yamamoto et al., *Pharm. Res.,* 11:1496–1500, 1994; Langguth et al., *J. Pharm. Pharmacol.,* 46:34–40, 1994; Raehs, et al., *Pharm. Res.,* 5:689–693, 1988, each incorporated herein by reference. Besides its inhibitory activity, bacitracin also displays absorption-enhancing effects without leading to a serious intestinal mucosal damage. Gotoh et al., *Biol. Pharm. Bull.,* 18:794–796, 1995, incorporated herein by reference.

Nevertheless, bacitracin may not be useful in certain uncontrolled delivery settings due to its established nephrotoxicity. To date, it has almost exclusively been used in veterinary medicine and as a topical antibiotic in the treatment of infections in man. Covalent linkage of bacitracin to a mucoadhesive polymer (carbomer) has been shown to conserve the inhibitory activity of the compound within the carrier matrix. Bernkop-Schnurch et al., *Pharm. Res.*, 14:181–185, 1997, incorporated herein by reference.

In addition to these types of peptides, certain dipeptides and tripeptides display weak, non-specific inhibitory activity towards some proteases. Langguth et al., *J. Pharm. Pharmacol.*, 46:34–40, 1994, incorporated herein by reference. By analogy with amino acids, their inhibitory activity can be improved by chemical modifications. For example, phosphinic acid dipeptide analogues are also 'transition-state' inhibitors with a strong inhibitory activity towards aminopeptidases. They have reportedly been used to stabilize nasally administered leucine enkephalin Hussain et al., *Pharm. Res.*, 9:626–628, 1992, each incorporated herein by reference. Another example of a transition-state analogue is the modified pentapeptide pepstatin, McConnell et al., *J. Med. Chem.*, 34:2298–2300, 1991, incorporated herein by reference, which is a very potent inhibitor of pepsin. Structural analysis of pepstatin, by testing the inhibitory activity of several synthetic analogues, demonstrated the major structure-function characteristics of the molecule responsible for the inhibitory activity. McConnell et al., *J. Med. Chem.*, 34:2298–2300, 1991, incorporated herein by reference. Similar analytic methods can be readily applied to prepare modified amino acid and peptide analogs for blockade of selected, intranasal degradative enzymes.

Another special type of modified peptide includes inhibitors with a terminally located aldehyde function in their structure. For example, the sequence benzyloxycarbonyl-Pro-Phe-CHO, which fulfill the known primary and secondary specificity requirements of chymotrypsin, has been found to be a potent reversible inhibitor of this target proteinase. Walker et al., *Biochem. J.*, 321–323, 1993, incorporated herein by reference. The chemical structures of further inhibitors with a terminally located aldehyde function, e.g. antipain, leupeptin, chymostatin and elastatinal, are also known in the art, as are the structures of other known, reversible, modified peptide inhibitors, such as phosphoramidon, bestatin, puromycin and amastatin Due to their comparably high molecular mass, polypeptide protease inhibitors are more amenable than smaller compounds to concentrated delivery in a drug-carrier matrix. The advantages of a slow release carrier system for delivery of enzyme inhibitors have been discussed by Kimura et al., *Biol. Pharm. Bull.*, 19:897–900, 1996, incorporated herein by reference. In this study a mucoadhesive delivery system exhibited a desired release rate of the protease inhibitor aprotinin of approximately 10% per hour, which was almost synchronous with the release rate of a polypeptide drug. In vivo studies with this delivery system showed an improved bioavailability of the drug (id.) For this reason, and due to their low toxicity and strong inhibitory activity, polypeptide protease inhibitors will often be selected for use within the methods and compositions of the invention.

Additional agents for protease inhibition within the formulations and methods of the invention involve the use of complexing agents. These agents mediate enzyme inhibition by depriving the intranasal environment (or preparative or therapeutic composition) of divalent cations which are cofactors for many proteases. For instance, the complexing agents EDTA and DTPA as coordinately administered or combinatorially formulated adjunct agents, in suitable concentration, will be sufficient to inhibit selected proteases to thereby enhance intranasal delivery of biologically active agents according to the invention. Further representatives of this class of inhibitory agents are EGTA, 1,10-phenanthroline and hydroxychinoline. Ikesue et al., *Int. J. Pharm.* 95:171–9, 1993; Garner et al., *Biochemistry*, 13:3227–3233, 1974; Sangadala et al., *J. Biol. Chem.*, 269:10088–10092, 1994; Mizuma et al., *Biochim. Biophys. Acta.*, 1335:111–119, 1997, each incorporated herein by reference. In addition, due to their propensity to chelate divalent cations, these and other complexing agents are useful within the invention as direct, absorption-promoting agents. Lee, V. H. L., *J. Control Release*, 13:213–334, 1990, incorporated herein by reference.

As noted in more detail elsewhere herein, it is also contemplated to use various polymers, particularly mucoadhesive polymers, as enzyme inhibiting agents within the coordinate administration, multi-processing and/or combinatorial formulation methods and compositions of the invention. For example, poly(acrylate) derivatives, such as poly (acrylic acid) and polycarbophil, can affect the activity of various proteases, including trypsin, chymotrypsin. The inhibitory effect of these polymers may also be based on the complexation of divalent cations such as $Ca^{2+}$ and $Zn^{2+}$. Luepen et al., *Pharm. Res.*, 12:1293–1298, 1995, incorporated herein by reference. It is further contemplated that these polymers may serve as conjugate partners or carriers for additional enzyme inhibitory agents, as described above. For example, a chitosan-EDTA conjugate has been developed and is useful within the invention that exhibits a strong inhibitory effect towards the enzymatic activity of zinc-dependent proteases. The mucoadhesive properties of polymers following covalent attachment of other enzyme inhibitors in this context are not expected to be substantially compromised, nor is the general utility of such polymers as a delivery vehicle for biologically active agents within the invention expected to be diminished. On the contrary, the reduced distance between the delivery vehicle and mucosal surface afforded by the mucoadhesive mechanism will minimize presystemic metabolism of the active agent, while the covalently bound enzyme inhibitors remain concentrated at the site of drug delivery, minimizing undesired dilution effects of inhibitors as well as toxic and other side effects caused thereby. In this manner, the effective amount of a coordinately administered enzyme inhibitor can be reduced due to the exclusion of dilution effects.

More recent research efforts in the area of protease inhibition for enhanced delivery of peptide and protein therapeutics has focused on covalent immobilization of protease inhibitors on mucoadhesive polymers used as drug carrier matrices. Bernkop-Schnurch et al., *Drug Dev. Ind. Pharm.* 23:733–40, 1997; Bernkop-Schnurch et al., *J. Control. Rel.* 47:113–21, 1997; Bernkop-Schnurch et al., *J. Drug Targ.* 7:55–63, 1999, each incorporated herein by reference. In conjunction with these teachings, the invention provides in more detailed aspects an enzyme inhibitor formulated with a common carrier or vehicle for intranasal delivery of a biologically active agent. Optionally, the enzyme inhibitor is covalently linked to the carrier or vehicle. In certain embodiments, the carrier or vehicle is a biodegradable polymer, for example, a bioadhesive polymer. Thus, for example, a protease inhibitor, such as Bowman-Birk inhibitor (BBI), displaying an inhibitory effect towards trypsin and α-chymotrypsin, Birk Y. *Int. J. Pept. Protein Res.*, 25:113–31, 1985, incorporated herein by reference, or elastatinal, an elastase-specific inhibitor of low molecular size, may be covalently linked to a mucoadhesive polymer as described herein. The resulting polymer-inhibitor conjugate exhibits substantial utility as an intranasal delivery vehicle for biologically active agents according to the methods and compositions of the invention.

Exemplary mucoadhesive polymer-enzyme inhibitor complexes that are useful within the mucosal formulations and methods of the invention include, but are not limited to: Carboxymethylcellulose-pepstatin (with anti-pepsin activity); Poly(acrylic acid)-Bowman-Birk inhibitor (anti-chymotrypsin); Poly(acrylic acid)-chymostatin (anti-chymotrypsin); Poly(acrylic acid)-elastatinal (anti-elastase); Carboxymethylcellulose-elastatinal (anti-elastase); Polycarbophil—elastatinal (anti-elastase); Chitosan—antipain (anti-trypsin); Poly(acrylic acid)—bacitracin (anti-aminopeptidase N); Chitosan—EDTA (anti-aminopeptidase N, anti-carboxypeptidase A); Chitosan—EDTA—antipain (anti-trypsin, anti-chymotrypsin, anti-elastase). Bernkop-Schnürch, *J. Control. Rel.*, 52:1–16, 1998, incorporated herein by reference.

Mucolytic and Mucus-Clearing Agents and Methods

Effective delivery of biotherapeutic agents via intranasal administration must take into account the decreased drug transport rate across the protective mucus lining of the nasal mucosa, in addition to drug loss due to binding to glycoproteins of the mucus layer. Normal mucus is a viscoelastic, gel-like substance consisting of water, electrolytes, mucins, macromolecules, and sloughed epithelial cells. It serves primarily as a cytoprotective and lubricative covering for the underlying mucosal tissues. Mucus is secreted by randomly distributed secretory cells located in the nasal epithelium and in other mucosal epithelia. The structural unit of mucus is mucin. This glycoprotein is mainly responsible for the viscoelastic nature of mucus, although other macromolecules may also contribute to this property. In airway mucus, such macromolecules include locally produced secretory IgA, IgM, IgE, lysozyme, and bronchotransferrin, which also play an important role in host defense mechanisms.

The thickness of mucus varies from organ to organ and between species. However, mucin glycoproteins obtained from different sources have similar overall amino acid and protein/carbohydrate compositions, although the molecular weight may vary over a wide. Mucin consists of a large protein core with oligosaccharide side-chains attached through the O-glycosidic linkage of galactose or N-acetyl glucosamine to hydroxyl groups of serine and threonine residues. Either sialic acid or L-fucose forms the terminal group of the side chain oligosaccharides with sialic acid (negatively charged at pH greater than 2.8) forming 50 to 60% of the terminal groups. The presence of cysteine in the end regions of the mucin core facilitates cross-linking of mucin molecules via disulfide bridge formation.

The presence of a mucus layer that coats all epithelial surfaces has been largely overlooked in the elucidation of epithelial penetration enhancement mechanisms to date. This is partly because the role of mucus in the absorption of peptide and protein drugs has not yet been well established. However, for these and other drugs exhibiting a comparatively high molecular mass, the mucus layer covering the nasal mucosal surfaces may represent an almost insurmountable barrier. According to the conventional formula for calculation of the diffusion coefficient, in which the radius of the molecule indirectly correlates with the diffusion coefficient, the mucus barrier increases tremendously for polypeptide drugs. Studies focusing on this so called 'diffusion barrier' have demonstrated that proteins of a molecular mass greater than approximately 5 kDa exhibit minimal or no permeation into mucus layers. Allen, et al., 'Mucus Medicine and Biology', E. N. Elder, J. B. Elstein (eds.) p. 115, Vol. 144, Plenum Press, New York, 1982; Bernkop-Schnürch., *Pharm. Sci.*, 2:361, 1996, each incorporated herein by reference.

The coordinate administration methods of the instant invention optionally incorporate effective mucolytic or mucus-clearing agents, which serve to degrade, thin or clear mucus from intranasal mucosal surfaces to facilitate absorption of intranasally administered biotherapeutic agents. Within these methods, a mucolytic or mucus-clearing agent is coordinately administered as an adjunct compound to enhance intranasal delivery of the biologically active agent. Alternatively, an effective amount of a mucolytic or mucus-clearing agent is incorporated as a processing agent within a multi-processing method of the invention, or as an additive within a combinatorial formulation of the invention, to provide an improved formulation that enhances intranasal delivery of biotherapeutic compounds by reducing the barrier effects of intranasal mucus.

A variety of mucolytic or mucus-clearing agents are available for incorporation within the methods and compositions of the invention. Lee, et al., *Crit. Rev. Ther. Drug Carrier Syst.*, 8:91–192, 1991; Bernkop-Schnurch et al., *Arzneimittelforschung*, 49:799–803, 1999, each incorporated herein by reference. Based on their mechanisms of action, mucolytic and mucus clearing agents can often be classified into the following groups: proteases (e.g., pronase, papain) that cleave the protein core of mucin glycoproteins; sulfhydryl compounds that split mucoprotein disulfide linkages; and detergents (e.g., Triton X-100, Tween 20) that break non-covalent bonds within the mucus (see, e.g., Allen, A. in 'Physiology of the Gastrointestinal Tract. L. R. Johnson (ed.), p. 617, Raven Press, New York, 1981, incorporated herein by reference). Additional compounds in this context include, but are not limited to, bile salts and surfactants, for example, sodium deoxycholate, sodium taurodeoxycholate, sodium glycocholate, and lysophosphatidylcholine.

The effectiveness of bile salts in causing structural breakdown of mucus is in the order deoxycholate>taurocholate>glycocholate. Other effective agents that reduce mucus viscosity or adhesion to enhance intranasal delivery according to the methods of the invention include, e.g., short-chain fatty acids, and mucolytic agents that work by chelation, such as N-acylcollagen peptides, bile acids, and saponins (the latter function in part by chelating $Ca^{2+}$ and/or $Mg^{2+}$ which play an important role in maintaining mucus layer structure).

Additional mucolytic agents for use within the methods and compositions of the invention include N-acetyl-L-cysteine (ACS), a potent mucolytic agent that reduces both the viscosity and adherence of bronchopulmonary mucus and is reported to modestly increase nasal bioavailability of human growth hormone in anesthetized rats (from 7.5 to 12.2%). O'Hagen et al., *Pharm. Res.*, 7:772, 1990, incorporated herein by reference. These and other mucolytic or mucus-clearing agents are contacted with the nasal mucosa, typically in a concentration range of about 0.2 to 20 mM, coordinately with administration of the biologically active agent, to reduce the polar viscosity and/or elasticity of intranasal mucus.

Still other mucolytic or mucus-clearing agents may be selected from a range of glycosidase enzymes, which are able to cleave glycosidic bonds within the mucus glycoprotein. α-amylase and β-amylase are representative of this class of enzymes, although their mucolytic effect may be limited. Leiberman, J., *Am. Rev. Respir. Dis.*, 97:662, 1967, incorporated herein by reference. In contrast, bacterial glycosidases which allow these microorganisms to permeate mucus layers of their hosts, Corfield et al, *Glycoconjugate J.*, 10:72, 1993, incorporated herein by reference, are highly mucolytic active.

For selecting mucolytic agents for use within the methods and compositions of the invention, it is important to consider the chemical nature of both the mucolytic (or mucus-clearing) and biologically active agents. For example, the proteolytic enzyme pronase exhibits a very strong mucolytic activity at pH 5.0, as well as at pH 7.2. In contrast, the protease papain exhibited substantial mucolytic activity at pH 5.0, but no detectable mucolytic activity at pH 7.2. The reason for these differences in activity are explained in part by the distinct pH-optimum for papain, reported to be pH 5. Karlson, P., *Biochemie*, Thieme, Verlag, Stuttgart, New York, 1984, incorporated herein by reference. Thus, mucolytic and other enzymes for use within the invention are typically delivered in formulations having a pH at or near the pH optimum of the subject enzyme.

With respect to chemical characterization of the biologically active agent, one notable concern is the vulnerability of peptide and protein molecules to the degradative activities of proteases and sulfhydryl. In particular, peptide and protein drugs can be attacked by different types of mucolytic agents. In one study, the mucolytic proteases pronase and papain (which each are endopeptidases that cleave at a high number of bonds) were shown to completely degrade insulin within 2–3h at pH 7.2. Bernkop-Schnurch et al., *Arzneimittelforschung*, 49:799–803, 1999, incorporated herein by reference. In contrast, at pH 2.5 insulin was not at all, or only slightly, degraded by pronase and papain, which can be explained by the pH optimum of both enzymes being far away from pH 2.5. Whereas pronase represents an unusually non-specific protease, papain cleaves after Arg, Lys, Leu, and Gly, Karlson, P., *Biochemie*, Thieme, Verlag, Stuttgart, New York, 1984, incorporated herein by reference, which are all included in the primary structure of insulin and serve as an additional guide to selection of mucolytic and mucus-clearing agents within the invention.

The presence and number of cysteine residues and disulfide bonds in peptide and protein therapeutics are also important factors to consider in selecting mucolytic or mucus-clearing agents within the invention. When insulin, which displays three disulfide bonds within its molecular structure, is incubated with di-thiothreitol or N-acetylcysteine, there is a rapid degradation of the insulin polypeptide at pH 7.2. A substantially lower degree of degradation at pH 2.5 is attributed to the relatively low amount of reactive thiolate anions (responsible for nucleophilic attack on disulfide bonds) at this pH value. Bernkop-Schnurch et al., *Arzneimittelforschung*, 49:799–803, 1999, incorporated herein by reference.

Whereas it is generally contraindicated to use general proteases such as pronase or papain in combination with peptide or protein drugs, the practical use of more specific proteases can be undertaken according to the above principals, as can the use of sulfhydryl compounds. For therapeutic polypeptides that exhibit no cysteine moieties within their primary structure (e.g. cyclosporin), the use of sulfhydryl compounds is not problematic. Moreover, even for protein drugs bearing disulfide bonds the use of sulfhydryl compounds can be achieved, particularly where the disulfide bonds are not accessible for thiol attack due to the conformation of the protein, they should remain stable in the presence of this type of mucolytic agents.

For combinatorial use with most biologically active agents within the invention, including peptide and protein therapeutics, non-ionogenic detergents are generally also useful as mucolytic or mucus-clearing agents. These agents typically will not modify or substantially impair the activity of therapeutic polypeptides.

Ciliostatic Agents and Methods

Because the self-cleaning capacity of certain mucosal tissues (e.g., nasal mucosal tissues) by mucociliary clearance is necessary as a protective function (e.g., to remove dust, allergens, and bacteria), it has been generally considered that this function should not be substantially impaired by mucosal medications. Mucociliary transport in the respiratory tract is a particularly important defense mechanism against infections. Wasserman., *J. Allergy Clin. Immunol.*, 73:17–19, 1984, incorporated herein by reference. To achieve this function, ciliary beating in the nasal and airway passages moves a layer of mucus along the mucosa to removing inhaled particles and microorganisms. During chronic bronchitis and chronic sinusitis, tracheal and nasal mucociliary clearance are often impaired. Wanner., *Am. Rev. Respir. Dis.*, 116:73–125, 1977, incorporated herein by reference. This is presumably due to either excess secretion, Dulfano, et al., *Am. Rev. Respir. Dis.*, 104:88–98, 1971, increased viscosity of mucus, Chen, et al., *J. Lab. Clin. Med.*, 91:423–431, 1978, incorporated herein by reference, alterations in ciliary activity caused by decreased beat frequency, Puchelle et al., *Biorheology*, 21:265–272, 1984, incorporated herein by reference), loss of portions of the ciliated epithelium, Chodosh et al., *Am. Rev. Respir. Dis.*, 104:888–898, 1971, incorporated herein by reference, or to a combination of these factors. Decreased clearance presumably favors bacterial colonization of respiratory mucosal surfaces, predisposing the subject to infection. The ability to interfere with this host defense system may contribute significantly to a pathological organism's virulence.

Various reports show that mucociliary clearance can be impaired by mucosally administered drugs, as well as by a wide range of formulation additives including penetration enhancers and preservatives. For example, ethanol at concentrations greater than 2% has been shown to reduce the in vitro ciliary beating frequency. This may be mediated in part by an increase in membrane permeability that indirectly enhances flux of calcium ion which, at high concentration, is ciliostatic, or by a direct effect on the ciliary axoneme or actuation of regulatory proteins involved in a ciliary arrest response. Exemplary preservatives (methyl-p-hydroxybenzoate (0.02% and 0.15%), propyl-p-hydroxybenzoate (0.02%), and chlorobutanol (0.5%)) reversibly inhibit ciliary activity in a frog palate model. Other common additives (EDTA (0.1%), benzalkoniuin chloride (0.01%), chlorhexidine (0.01%), phenylinercuric nitrate (0.002%), and phenylmercuric borate (0.002%), have been reported to inhibit mucociliary transport irreversibly. In addition, several penetration enhancers including STDHF, laureth-9, deoxycholate, deoxycholic acid, taurocholic acid, and glycocholic acid have been reported to inhibit ciliary activity in model systems.

Despite the potential for adverse effects on mucociliary clearance attributed to ciliostatic factors, ciliostatic agents nonetheless find use within the methods and compositions of the invention to increase the residence time of mucosally (e.g., intranasally) administered peptide YY proteins, analogs and mimetics, and other biologically active agents disclosed herein. In particular, the delivery these agents within the methods and compositions of the invention is significantly enhanced in certain aspects by the coordinate administration or combinatorial formulation of one or more ciliostatic agents that function to reversibly inhibit ciliary activity of mucosal cells, to provide for a temporary, reversible increase in the residence time of the mucosally administered active agent(s). For use within these aspects of the invention, the foregoing ciliostatic factors, either specific or indirect in their activity, are all candidates for successful employment as ciliostatic agents in appropriate amounts (depending on concentration, duration and mode of delivery) such that they yield a transient (i.e., reversible) reduction or cessation of mucociliary clearance at a mucosal site of administration to enhance delivery of peptide YY proteins, analogs and mimetics, and other biologically active agents disclosed herein, without unacceptable adverse side effects.

Within more detailed aspects, a specific ciliostatic factor is employed in a combined formulation or coordinate administration protocol with one or more peptide YY proteins, analogs and mimetics, and/or other biologically active agents disclosed herein. Various bacterial ciliostatic factors isolated and characterized in the literature may be employed within these embodiments of the invention. For example, Hingley, et al. *Infection and Immunity.*, 51:254–262, 1986, incorporated herein by reference, have recently identified ciliostatic factors from the bacterium *Pseudomonas aeruginosa*. These are heat-stable factors released by *Pseudomonas aeruginosa* in culture supernatants that have been shown to inhibit ciliary function in epithelial cell cultures. Exemplary among these cilioinhibitory components are a phenazine derivative, a pyo compound (2-alkyl-4-hydroxyquinolines), and a rhamnolipid (also known as a hemolysin). Inhibitory concentrations of these and other active components were established by quantitative measures of ciliary motility and beat frequency. The pyo compound produced ciliostasis at concentrations of 50 µg/ml and without obvious ultrastructural lesions. The phenazine derivative also inhibited ciliary motility but caused some membrane disruption, although at substantially greater concentrations of 400 µg/ml. Limited exposure of tracheal explants to the rhamnolipid resulted in ciliostasis which was associated with altered ciliary membranes. More extensive exposure to rhamnolipid was associated with removal of dynein arms from axonemes. It is proposed that these and other bacterial ciliostatic factors have evolved to enable *P. aeruginosa* to more easily and successfully colonize the respiratory tract of mammalian hosts. On this basis, respiratory bacteria are useful pathogens for identification of suitable, specific ciliostatic factors for use within the methods and compositions of the invention.

Several methods are available to measure mucociliary clearance for evaluating the effects and uses of ciliostatic agents within the methods and compositions of the invention. Nasal mucociliary clearance can be measured by monitoring the disappearance of visible tracers such as India ink, edicol orange powder, and edicol supra orange. These tracers are followed either by direct observation or with the aid of posterior rhinoscopy or a binocular operating microscope. This method simply measures the time taken by a tracer to travel a definite distance. In more modern techniques, radiolabeled tracers are administered as an aerosol and traced by suitably collimated detectors. Alternatively, particles with a strong taste like saccharin can be placed in the nasal passage and assayed to determine the time before the subject first perceives the taste is used as an indicator of mucociliary clearance.

Additional assays are known in the art for measuring ciliary beat activity. For example, a laser light scattering technique to measure tracheobronchial mucociliary activity is based on mono-chromaticity, coherence, and directionality of laser light. Ciliary motion is measured as intensity fluctuations due to the interference of Doppler-shifted scattered light. The scattered light from moving cilia is detected by a photomultiplier tube and its frequency content analyzed by a signal correlator yielding an autocorrelation function of the detected photocurrents. In this way, both the frequency and synchrony of beating cilia can be measured continuously. Through fiberoptic rhinoscopy, this method also allows the measurement of ciliary activity in the peripheral parts of the nasal passages.

In vitro assays for evaluating ciliostatic activity of formulations within the invention are also available. For example, a commonly used and accepted assay in this context is a rabbit tracheal explant system. Gabridge et al., *Pediatr. Res.*, 1:31–35, 1979; Chandler et al., *Infect. Immun.*, 29:1111–1116, 1980, each incorporated herein by reference. Other assay systems measure the ciliary beat frequency of a single cell or a small number of cells. Kennedy et al., *Exp. Cell Res.*, 135:147–156, 1981; Rutland et al., *Lancet*, ii:564–565, 1980; Verdugo, et al., *Pediatr. Res.*, 13:131–135, 1979, each incorporated herein by reference.

Surface Active Agents and Methods

Within more detailed aspects of the invention, one or more membrane penetration-enhancing agents may be employed within a mucosal delivery method or formulation of the invention to enhance mucosal delivery of peptide YY proteins, analogs and mimetics, and other biologically active agents disclosed herein. Membrane penetration enhancing agents in this context can be selected from: (i) a surfactant, (ii) a bile salt, (ii) a phospholipid additive, mixed micelle, liposome, or carrier, (iii) an alcohol, (iv) an enamine, (v) an NO donor compound, (vi) a long-chain amphipathic molecule (vii) a small hydrophobic penetration enhancer; (viii) sodium or a salicylic acid derivative; (ix) a glycerol ester of acetoacetic acid (x) a clyclodextrin or beta-cyclodextrin derivative, (xi) a medium-chain fatty acid, (xii) a chelating agent, (xiii) an amino acid or salt thereof, (xiv) an N-acetylamino acid or salt thereof, (xv) an enzyme degradative to a selected membrane component, (ix) an inhibitor of fatty acid synthesis, or (x) an inhibitor of cholesterol synthesis; or (xi) any combination of the membrane penetration enhancing agents recited in (i)–(x)

Certain surface-active agents are readily incorporated within the mucosal delivery formulations and methods of the invention as mucosal absorption enhancing agents. These agents, which may be coordinately administered or combinatorially formulated with peptide YY proteins, analogs and mimetics, and other biologically active agents disclosed herein, may be selected from a broad assemblage of known surfactants. Surfactants, which generally fall into three classes: (1) nonionic polyoxyethylene ethers; (2) bile salts such as sodium glycocholate (SGC) and deoxycholate (DOC); and (3) derivatives of fusidic acid such as sodium taurodihydrofusidate (STDHF). The mechanisms of action of these various classes of surface active agents typically include solubilization of the biologically active agent. For proteins and peptides which often form aggregates, the surface active properties of these absorption promoters can allow interactions with proteins such that smaller units such as surfactant coated monomers may be more readily maintained in solution. These monomers are presumably more transportable units than aggregates. A second potential mechanism is the protection of the peptide or protein from proteolytic degradation by proteases in the mucosal environment. Both bile salts and some fusidic acid derivatives reportedly inhibit proteolytic degradation of proteins by nasal homogenates at concentrations less than or equivalent to those required to enhance protein absorption. This protease inhibition may be especially important for peptides with short biological half-lives.

Degradation Enzymes and Inhibitors of Fatty Acid and Cholesterol Synthesis

In related aspects of the invention, peptide YY proteins, analogs and mimetics, and other biologically active agents for mucosal administration are formulated or coordinately administered with a penetration enhancing agent selected from a degradation enzyme, or a metabolic stimulatory agent or inhibitor of synthesis of fatty acids, sterols or other selected epithelial barrier components. U.S. Pat. No. 6,190,894, incorporated herein by reference. In one embodiment, known enzymes that act on mucosal tissue components to enhance permeability are incorporated in a combinatorial formulation or coordinate administration method of instant invention, as processing agents within the multi-processing methods of the invention. For example, degradative enzymes such as phospholipase, hyaluronidase, neuraminidase, and chondroitinase may be employed to enhance mucosal penetration of peptide YY proteins, analogs and mimetics, and other biologically active agents, Squier *Brit. J. Dermatol.*, 111:253–264, 1984; Aungst and Rogers *Int. J. Pharm.*, 53:227–235, 1989, incorporated herein by reference, without causing irreversible damage to the mucosal barrier. In one embodiment, chondroitinase is employed within a method or composition as provided herein to alter glycoprotein or glycolipid constituents of the permeability barrier of the mucosa, thereby enhancing mucosal absorption of peptide YY proteins, analogs and mimetics, and other biologically active agents disclosed herein.

With regard to inhibitors of synthesis of mucosal barrier constituents, it is noted that free fatty acids account for 20–25% of epithelial lipids by weight. Two rate limiting enzymes in the biosynthesis of free fatty acids are acetyl CoA carboxylase and fatty acid synthetase. Through a series of steps, free fatty acids are metabolized into phospholipids. Thus, inhibitors of free fatty acid synthesis and metabolism for use within the methods and compositions of the invention include, but are not limited to, inhibitors of acetyl CoA carboxylase such as 5-tetradecyloxy-2-furancarboxylic acid (TOFA); inhibitors of fatty acid synthetase; inhibitors of phospholipase A such as gomisin A, 2-(p-amylcinnamyl) amino-4-chlorobenzoic acid, bromophenacyl bromide, monoalide, 7,7-dimethyl-5,8-eicosadienoic acid, nicergoline, cepharanthine, nicardipine, quercetin, dibutyryl-cyclic AMP, R-24571, N-oleoylethanolamine, N-(7-nitro-2,1,3-benzoxadiazol-4-yl) phosphostidyl serine, cyclosporine A, topical anesthetics, including dibucaine, prenylamine, retinoids, such as all-trans and 13-cis-retinoic acid, W-7, trifluoperazine, R-24571 (calmidazolium), 1-hexadocyl-3-trifluoroethyl glycero-sn-2-phosphomenthol (MJ33); calcium channel blockers including nicardipine, verapamil, diltiazem, nifedipine, and nimodipine; antimalarials including quinacrine, mepacrine, chloroquine and hydroxychloroquine; beta blockers including propanalol and labetalol; calmodulin antagonists; EGTA; thimersol; glucocorticosteroids including dexamethasone and prednisolone; and non-steroidal antiinflammatory agents including indomethacin and naproxen.

Free sterols, primarily cholesterol, account for 20–25% of the epithelial lipids by weight. The rate limiting enzyme in the biosynthesis of cholesterol is 3-hydroxy-3-methylglutaryl (HMG) CoA reductase. Inhibitors of cholesterol synthesis for use within the methods and compositions of the invention include, but are not limited to, competitive inhibitors of (HMG) CoA reductase, such as simvastatin, lovastatin, fluindostatin (fluvastatin), pravastatin, mevastatin, as well as other HMG CoA reductase inhibitors, such as cholesterol oleate, cholesterol sulfate and phosphate, and oxygenated sterols, such as 25-OH— and 26-OH— cholesterol; inhibitors of squalene synthetase; inhibitors of squalene epoxidase; inhibitors of DELTA7 or DELTA24 reductases such as 22,25-diazacholesterol, 20,25-diazacholestenol, AY9944, and triparanol.

Each of the inhibitors of fatty acid synthesis or the sterol synthesis inhibitors may be coordinately administered or combinatorially formulated with one or more peptide YY proteins, analogs and mimetics, and other biologically active agents disclosed herein to achieve enhanced epithelial penetration of the active agent(s). An effective concentration range for the sterol inhibitor in a therapeutic or adjunct formulation for mucosal delivery is generally from about 0.0001% to about 20% by weight of the total, more typically from about 0.01% to about 5%.

Nitric Oxide Donor Agents and Methods

Within other related aspects of the invention, a nitric oxide (NO) donor is selected as a membrane penetration-enhancing agent to enhance mucosal delivery of one or more peptide YY proteins, analogs and mimetics, and other biologically active agents disclosed herein. Recently, Salzman et al. *Am. J. Physiol.*, 268:G361–G373, 1995, incorporated herein by reference, reported that NO donors increase the permeability of water-soluble compounds across Caco-2 cell monolayers with neither loss of cell viability nor lactate dehydrogenase (LDH) release. In addition, Utoguchi et al. *Pharm. Res.*, 15:870–876, 1998, incorporated herein by reference, demonstrated that the rectal absorption of insulin was remarkably enhanced in the presence of NO donors, with attendant low cytotoxicity as evaluated by the cell detachment and LDH release studies in Caco-2 cells.

Various NO donors are known in the art and are useful in effective concentrations within the methods and formulations of the invention. Exemplary NO donors include, but are not limited to, nitroglycerine, nitropruside, NOC5 [3-(2-hydroxy-1-(methyl-ethyl)-2-nitrosohydrazino)-1-propanamine], NOC12 [N-ethyl-2-(1-ethyl-hydroxy-2-nitrosohydrazino)-ethanamine], SNAP [S-nitroso-N-acetyl-DL-penicillamine], NORI and NOR4. Efficacy of these and other NO donors, as well as other mucosal delivery-enhancing agents disclosed herein, for enhancing mucosal delivery of peptide YY proteins, analogs and mimetics, and other biologically active agents can be evaluated routinely according to known efficacy and cytotoxicity assay methods (e.g., involving control coadministration of an NO scavenger, such as carboxy-PIIO) as described by Utoguchi et al., *Pharm. Res.*, 15:870–876, 1998, incorporated herein by reference.

Within the methods and compositions of the invention, an effective amount of a selected NO donor is coordinately administered or combinatorially formulated with one or more peptide YY proteins, analogs and mimetics, and/or other biologically active agents disclosed herein, into or through the mucosal epithelium.

Agents for Modulating Epithelial Junction Structure and/or Physiology

The present invention provides novel pharmaceutical compositions that include a biologically active agent and a permeabilizing agent effective to enhance mucosal delivery of the biologically active agent in a mammalian subject. The permeabilizing agent reversibly enhances mucosal epithelial paracellular transport, typically by modulating epithelial junctional structure and/or physiology at a mucosal epithelial surface in the subject. This effect typically involves inhibition by the permeabilizing agent of homotypic or heterotypic binding between epithelial membrane adhesive proteins of neighboring epithelial cells. Target proteins for this blockade of homotypic or heterotypic binding can be selected from various related junctional adhesion molecules (JAMs), occludins, or claudins.

In more detailed embodiments of the invention, the permeabilizing agent is a peptide or peptide analog or mimetic. Exemplary permeabilizing peptides comprise from about 4–25 contiguous amino acids of an extracellular domain of a mammalian JAM-1, JAM-2, or JAM-3 protein. Alternatively, the permeabilizing peptide may comprise from about 6–15 contiguous amino acids of an extracellular domain of a mammalian JAM-1, JAM-2, or JAM-3 protein. In additional embodiments, the permeabilizing peptide comprises from about 4–25 contiguous amino acids of an extracellular domain of a mammalian JAM-1, JAM-2, or JAM-3 protein, or a sequence of amino acids that exhibits at least 85% amino acid identity with a corresponding reference sequence of 4–25 contiguous amino acids of an extracellular domain of a mammalian JAM-1, JAM-2, or JAM-3 protein. In certain embodiments, the amino acid sequence of the permeabilizing peptide exhibits one or more amino acid substitutions, insertions, or deletions compared to the corresponding reference sequence of the mammalian JAM-1, JAM-2, or JAM-3 protein. For example, the permeabilizing peptide may exhibit one or more conservative amino acid substitutions compared to a corresponding reference sequence of a mammalian JAM-1, JAM-2, or JAM-3 protein. Such functional peptide analogs or variants may, for instance, have one or more amino acid mutations in comparison to a corresponding wild-type sequence of the same human JAM protein (e.g., human JAM-1), wherein the mutation(s) correspond to a divergent amino acid residue or sequence identified in a different human JAM protein (e.g., human JAM-2 or JAM-3) or in a homologous JAM protein found in a different species (e.g. murine, rat, or bovine JAM-1, JAM-2 or JAM-3 protein).

In more detailed embodiments, the methods and compositions of the invention incorporate a permeabilizing peptide that is between about 4–25 amino acids in length, and includes one or more contiguous sequence elements selected from: V R (I, V, A) P, (SEQ ID NO: 1); (V, A, I) K L (S, T) C A Y, (SEQ ID NO: 2); or E D (T, S) G T Y (T, R) C (M, E), (SEQ ID NO: 3). In one such embodiment, the peptide will include a conservative sequence motif V R (I, V, A) P, (SEQ ID NO: 1), wherein the third position of the motif may be represented by one of the alternative amino acid residues I, V, or A. In another such embodiment, the peptide will include a conservative sequence motif (V, A, I) K L (S, T) C A Y, (SEQ ID NO: 2), wherein the first position of the motif may be represented by one of the alternative amino acid residues V, A, or I, and the fourth position of the motif may be represented by one of the alternative amino acid residues S or T. In yet another such embodiment, the peptide will include a conservative sequence motif E D (T, S) G T Y (T, R) C (M, E), (SEQ ID NO: 3), wherein the third position of the motif may be represented by one of the alternative amino acid residues T or S, the seventh position of the motif may be represented by one of the alternative amino acid residues T or R, and the ninth position of the motif may be represented by one of the alternative residues M or E. In exemplary embodiments, the permeabilizing peptide is between about 4–25 amino acids in length and includes one or more contiguous sequence elements selected from wild-type human JAM-1 peptide sequences VRIP, (SEQ ID NO: 4), VKLSCAY, (SEQ ID NO: 5), TGITFKSVT, (SEQ ID NO: 6), ITAS, (SEQ ID NO: 7), SVTR, (SEQ ID NO: 8), EDTGTYTCM, (SEQ ID NO: 9), and/or GFSSPRVEW, (SEQ ID NO: 10).

Within additional aspects of the invention, pharmaceutical compositions and methods are provided which employ a permeabilizing peptide comprising from about 4–25 contiguous amino acids of an extracellular domain of a mammalian occludin protein. In alternate embodiments, the permeabilizing peptide comprises from about 6–15 contiguous amino acids of an extracellular domain of a mammalian occludin protein. In certain aspects, the permeabilizing peptide comprises from about 4–25 contiguous amino acids of an extracellular domain of a mammalian occludin protein or comprises an amino acid sequence that exhibits at least 85% amino acid identity with a corresponding reference sequence of 4–25 contiguous amino acids of an extracellular domain of a mammalian occludin protein. In exemplary embodiments, the permeabilizing peptide exhibits one or more amino acid substitutions, insertions, or deletions compared to a corresponding reference sequence of the mammalian occludin protein. Often, such peptide "analogs" will exhibit one or more conservative amino acid substitutions compared to the corresponding reference sequence of the mammalian occludin protein. In related embodiments, the permeabilizing peptide is a human occludin peptide and the amino acid sequence of the permeabilizing peptide exhibits one or more amino acid mutations in comparison to a corresponding wild-type sequence of the same human occludin protein, wherein the mutation(s) correspond to a structural feature (e.g., a divergent, aligned residue or sequence of residues) identified in a different human occludin protein or a homologous occludin protein found in a different species.

Within other aspects of the invention, pharmaceutical compositions and methods are provided which employ a permeabilizing peptide comprising from about 4–25 contiguous amino acids of an extracellular domain of a mammalian claudin protein. In alternate embodiments, the permeabilizing peptide comprises from about 6–15 contiguous amino acids of an extracellular domain of a mammalian claudin protein. In certain aspects, the permeabilizing peptide comprises from about 4–25 contiguous amino acids of an extracellular domain of a mammalian claudin protein or comprises an amino acid sequence that exhibits at least 85% amino acid identity with a corresponding reference sequence of 4–25 contiguous amino acids of an extracellular domain of a mammalian claudin protein. In exemplary embodiments, the permeabilizing peptide exhibits one or more amino acid substitutions, insertions, or deletions compared to a corresponding reference sequence of the mammalian claudin protein. Often, such peptide "analogs" will exhibit one or more conservative amino acid substitutions compared to the corresponding reference sequence of the mammalian claudin protein. In related embodiments, the permeabilizing peptide is a human claudin peptide and the amino acid sequence of the permeabilizing peptide exhibits one or more amino acid mutations in comparison to a corresponding wild-type sequence of the same human claudin protein, wherein the mutation(s) correspond to a structural feature (e.g., a divergent, aligned residue or sequence of residues) identified in a different human claudin protein or a homologous claudin protein found in a different species.

In yet additional embodiments, the invention provides methods and pharmaceutical compositions which employ a permeabilizing agent as described above, such as a permeabilizing peptide, and one or more therapeutic protein(s) or peptide(s) that is/are effective as a hematopoietic agent, cytokine agent, antiinfective agent, antidementia agent, antiviral agent, antitumoral agent, antipyretic agent, analgesic agent, antiinflammatory agent, antiulcer agent, antiallergic agent, antidepressant agent, psychotropic agent, cardiotonic agent, antiarrythmic agent, vasodilator agent, antihypertensive agent, antidiabetic agent, anticoagulant agent, cholesterol-lowering agent, hormone agent, anti-osteoporosis agent, antibiotic agent, vaccine agent, and/or bacterial toxoid.

In certain embodiments of the invention, a biologically active agent and a permeabilizing agent as described above are administered in combination with one or more mucosal delivery-enhancing agent(s). In more detailed embodiments of the inventions, the pharmaceutical compositions noted above are formulated for intranasal administration. In exemplary embodiments, the formulations are provided as an intranasal spray or powder. To enhance intranasal administration, these formulations may combine the biologically active agent and permeabilizing agent with one or more intranasal delivery-enhancing agents selected from:

(a) an aggregation inhibitory agent;
(b) a charge modifying agent;
(c) a pH control agent;
(d) a degradative enzyme inhibitory agent;
(e) a mucolytic or mucus clearing agent;
(f) a ciliostatic agent;
(g) a membrane penetration-enhancing agent selected from (i) a surfactant, (ii) a bile salt, (ii) a phospholipid additive, mixed micelle, liposome, or carrier, (iii) an alcohol, (iv) an enamine, (v) an NO donor compound, (vi) a long-chain amphipathic molecule (vii) a small hydrophobic penetration enhancer; (viii) sodium or a salicylic acid derivative; (ix) a glycerol ester of acetoacetic acid (x) a cyclodextrin or beta-cyclodextrin derivative, (xi) a medium-chain fatty acid, (xii) a chelating agent, (xiii) an amino acid or salt thereof, (xiv) an N-acetylamino acid or salt thereof, (xv) an enzyme degradative to a selected membrane component, (ix) an inhibitor of fatty acid synthesis, or (x) an inhibitor of cholesterol synthesis; or (xi) any combination of the membrane penetration enhancing agents recited in (i)–(x);
(h) a second modulatory agent of epithelial junction physiology;
(i) a vasodilator agent;
(j) a selective transport-enhancing agent; and
(k) a stabilizing delivery vehicle, carrier, support or complex-forming species with which the biologically active agent is effectively combined, associated, contained, encapsulated or bound resulting in stabilization of the active agent for enhanced intranasal delivery, wherein the one or more intranasal delivery-enhancing agents comprises any one or combination of two or more of the intranasal delivery-enhancing agents recited in (a)–(k), and wherein the formulation of the biologically active agent with the one or more intranasal delivery-enhancing agents provides for increased bioavailability of the biologically active agent delivered to a nasal mucosal surface of a mammalian subject.

In other related aspects of the invention, the pharmaceutical compositions comprising a permeabilizing agent, e.g., a permeabilizing peptide, and a biologically active agent are effective following mucosal administration to a mammalian subject to yield enhanced bioavailability of the therapeutic compound, for example by yielding a peak concentration ($C_{max}$) of the biologically active agent in a blood plasma or cerebral spinal fluid (CNS) of the subject that is about 25% or greater as compared to a peak concentration of the biologically active agent following intramuscular injection of an equivalent concentration or dose of the active agent to the subject. In certain embodiments, the pharmaceutical composition following mucosal administration yields a peak concentration ($C_{max}$) of the biologically active agent in the blood plasma or CNS of the subject that is about 50% or greater than the peak concentration of the biologically active agent in the blood plasma or CNS following intramuscular injection of an equivalent concentration or dose of the active agent.

In alternate embodiments of the invention, the pharmaceutical compositions comprising a permeabilizing agent and a biologically active agent are effective following mucosal administration to yield enhanced bioavailability by yielding an area under concentration curve (AUC) of the biologically active agent in a blood plasma CNS tissue or fluid of the subject that is about 25% or greater compared to an AUC of the biologically active agent in a blood plasma CNS tissue or fluid following intramuscular injection of an equivalent concentration or dose of the active agent to the subject. In certain embodiments, the pharmaceutical compositions yield an area under concentration curve (AUC) of the biologically active agent in a blood plasma or CNS tissue or fluid of the subject that is about 50% or greater compared to an AUC of the biologically active agent in a blood plasma or CNS tissue or fluid following intramuscular injection of an equivalent concentration or dose of the active agent to the subject.

In additional embodiments of the invention, the pharmaceutical compositions comprising a permeabilizing agent and a biologically active agent are effective following mucosal administration to yield enhanced bioavailability by yielding a time to maximal plasma concentration ($t_{max}$) of the biologically active agent in a blood plasma or CNS tissue or fluid of the subject between about 0.1 to 1.0 hours. In certain embodiments, the compositions yield a time to maximal plasma concentration ($t_{max}$) of the biologically active agent in a blood plasma or CNS tissue or fluid of the subject between about 0.2 to 0.5 hours.

In other embodiments of the invention, the pharmaceutical compositions comprising a permeabilizing agent and a biologically active agent are effective following mucosal administration to yield enhanced bioavailability of the active agent in the CNS, for example by yielding a peak concentration of the biologically active agent in a CNS tissue or fluid of the subject that is 10% or greater compared to a peak concentration of the biologically active agent in a blood plasma of the subject (e.g., wherein the CNS and plasma concentration is measured contemporaneously in the same subject following the mucosal administration). In certain embodiments, compositions of the invention yield a peak concentration of the biologically active agent in a CNS tissue or fluid of the subject that is 20%, 40%, or greater compared to a peak concentration of the active agent in a blood plasma of the subject.

The methods of the invention for treating or preventing a disease or condition in a mammalian subject amenable to treatment by therapeutic administration of one or more of the biologically active agents identified herein generally comprise coordinately, mucosally administering to the subject a pharmaceutical formulation comprising a biologically active agent (e.g., peptide YY) and an effective amount of a permeabilizing agent (e.g., a permeabilizing peptide), as described above, to enhance mucosal delivery of the biologically active agent. Coordinate administration of the permeabilizing agent reversibly enhances mucosal epithelial paracellular transport by modulating epithelial junctional structure and/or physiology in a target mucosal epithelium of the subject. Typically, the permeabilizing agent effectively inhibits homotypic or heterotypic binding of an epithelial membrane adhesive protein selected from a junctional adhesion molecule (JAM), occludin, or claudin. In certain embodiments, the step(s) of coordinate mucosal administration involves delivery of the permeabilizing agent before, after, or simultaneous with (e.g., in a combinatorial formulation) delivery of the biologically active agent to a mucosal surface of the subject. In more detailed embodiments, the permeabilizing agent is coordinately administered with the biologically active agent to a nasal mucosal surface of the subject, for example in a combinatorial or separate nasal spray, gel or powder formulation(s). In exemplary embodiments, the permeabilizing agent is a permeabilizing peptide administered coordinately with the biologically active agent to yield enhanced mucosal epithelial paracellular transport of the biologically active agent. In certain exemplary embodiments, the permeabilizing peptide comprises from about 4–25, or about 6–15, contiguous amino acids of an extracellular domain of a mammalian JAM, occludin or claudin protein as described above, or a comparable length peptide that exhibits at least 85% amino acid identity with a corresponding reference sequence of an extracellular domain of a mammalian JAM, occludin or claudin protein.

In related aspects of the invention, coordinate administration of the permeabilizing agent and biologically active agent yields a peak concentration ($C_{max}$) of the biologically active agent in a blood plasma or CNS tissue or fluid of the subject that is 25% or greater as compared to a peak concentration of the biologically active agent following intramuscular injection of an equivalent concentration or dose of the active agent to the subject. In additional embodiments, coordinate administration of the permeabilizing agent and biologically active agent yields an area under concentration curve (AUC) of the biologically active agent in a blood plasma or CNS tissue or fluid of the subject that is 25% or greater compared to an AUC of the biologically active agent in a blood plasma or CNS tissue or fluid following intramuscular injection of an equivalent concentration or dose of the active agent to the subject. In other embodiments, coordinate administration of the permeabilizing agent and biologically active agent yields a time to maximal plasma concentration ($t_{max}$) of the biologically active agent in a blood plasma or CNS tissue or fluid of the subject between 0.2 to 0.5 hours. In still other embodiments, coordinate administration of the permeabilizing agent and biologically active agent yields a peak concentration of the biologically active agent in a central nervous system (CNS) tissue or fluid of the subject that is 10% or greater compared to a peak concentration of the biologically active agent in a blood plasma of the subject.

In yet additional detailed embodiments, the invention provides permeabilizing peptides and peptide analogs and mimetics for enhancing mucosal epithelial paracellular transport. The subject peptides and peptide analogs and mimetics typically work within the compositions and methods of the invention by modulating epithelial junctional structure and/or physiology in a mammalian subject. In certain embodiments, the peptides and peptide analogs and mimetics effectively inhibit homotypic and/or heterotypic binding of an epithelial membrane adhesive protein selected from a junctional adhesion molecule (JAM), occludin, or claudin. In more detailed embodiments, the permeabilizing peptide or peptide analog comprises from about 4–25 contiguous amino acids of a wild-type sequence of an extracellular domain of a mammalian JAM-1, JAM-2, JAM-3, occludin or claudin protein, or an amino acid sequence that exhibits at least 85% amino acid identity with a corresponding reference sequence of about 4–25 contiguous amino acids of a wild-type sequence of an extracellular domain of a mammalian JAM-1, JAM-2, JAM-3, occludin or claudin protein. In exemplary embodiments, the permeabilizing peptide or peptide analog is a human JAM peptide (e.g., human JAM-1) having a wild-type amino acid sequence or exhibiting one or more amino acid mutations in comparison to a corresponding wild-type sequence of the same human JAM protein, wherein the mutation(s) correspond to a structural feature identified in a different human JAM protein or a homologous JAM protein found in a different species.

In more detailed embodiments, (see, e.g., U.S. patent application entitled COMPOSITIONS AND METHODS FOR MODULATING PHYSIOLOGY OF EPITHELIAL JUNCTIONAL ADHESION MOLECULES FOR ENHANCED MUCOSAL DELIVERY OF THERAPEUTIC COMPOUNDS, filed by Quay on Jun. 28$^{th}$, 2002 and assigned Attorney Docket Number NPCI-0156, incorporated herein by reference) the permeabilizing peptide is between about 4–25 amino acids in length, and includes one or more contiguous sequence elements selected from: V R (I, V, A) P, (SEQ ID NO: 1); (V, A, I) K L (S, T) C A Y, (SEQ ID NO: 2); or E D (T, S) G T Y (T,R) C (M, E), (SEQ ID NO: 3). In one such embodiment, the peptide will include a conservative sequence motif V R (I, V, A) P, (SEQ ID NO: 1), wherein the third position of the motif may be represented by one of the alternative amino acid residues I, V, or A. In another such embodiment, the peptide will include a conservative sequence motif (V, A, I) K L (S, T) C A Y, (SEQ ID NO: 2), wherein the first position of the motif may be represented by one of the alternative amino acid residues V, A, or I, and the fourth position of the motif may be represented by one of the alternative amino acid residues S or T. In yet another such embodiment, the peptide will include a conservative sequence motif E D (T, S) G T Y (T,R) C (M, E), (SEQ ID NO: 3), wherein the third position of the motif may be represented by one of the alternative amino acid residues T or S, the seventh position of the motif may be represented by one of the alternative amino acid residues T or R, and the ninth position of the motif may be represented by one of the alternative residues M or E. In exemplary embodiments, the permeabilizing peptide is between about 4–25 amino acids in length and includes one or more contiguous sequence elements selected from wild-type human JAM-1 peptide sequences VRIP, (SEQ ID NO: 4), VKLSCAY, (SEQ ID NO: 5), and/or EDTGTYTCM, (SEQ ID NO: 9).

Candidate permeabilizing peptides of human JAM-1 include, but are not limited to, SVTVHSSEPE, (SEQ ID NO: 11), VRIPENNPVK, (SEQ ID NO: 12), LSCAYSGFSS, (SEQ ID NO: 13), PRVEWKFDQG, (SEQ ID NO: 14), DTTRLVCYNN, (SEQ ID NO: 15), KITASYEDRV, (SEQ ID NO: 16), TFLPTGITFK, (SEQ ID NO: 17), SVTREDTGTY, (SEQ ID NO: 18), TCMVSEEGGN, (SEQ ID NO: 19), SYGEVKVKLI, (SEQ ID NO: 20), VLVPPSKPTV, (SEQ ID NO: 21), NIPSSATIGN, (SEQ ID NO: 22), RAVLTCSEQD, (SEQ ID NO: 23), GSPPSEYTWF, (SEQ ID NO: 24), KDGIVMPTNP, (SEQ ID NO: 25), KSTRAFSNSS, (SEQ ID NO: 26), YVLNPTTGEL, (SEQ ID NO: 27), VFDPLSASDT, (SEQ ID NO: 28), GEYSCEARNG, (SEQ ID NO: 29), YGTPMTSNAV, (SEQ ID NO: 30), RMEAVERNVG, (SEQ ID NO: 31). Human JAM-1 peptides further include, SVTVH, (SEQ ID NO: 32), SSEPEVRIPE, (SEQ ID NO: 33), KNPVKLSCAY, (SEQ ID NO: 34), SGFSSPRVEW, (SEQ ID NO: 35), KFDQGDTTRL, (SEQ ID NO: 36), VCYNNKITAS, (SEQ ID NO: 37), YEDRVTFLPT, (SEQ ID NO: 38), GITFKSVTRE, (SEQ ID NO: 39), DTGTYTCMVS, (SEQ ID NO: 40), EEGGNSYGEV, (SEQ ID NO: 41), KVKLIVLVPP, (SEQ ID NO: 42), SKLPTVNIPSS, (SEQ ID NO: 43), ATIGNRAVLT, (SEQ ID NO: 44), CSEQDGSPPS, (SEQ ID NO: 45), EYTWFKDGIV, (SEQ ID NO: 46), MPTNPKSTRA, (SEQ ID NO: 47), FSNSSYVLNP, (SEQ ID NO: 48), TTGELVFDPL, (SEQ ID NO: 49), SASDTGEYSC, (SEQ ID NO: 50), EARNGYGTPM, (SEQ ID NO: 51), TSNAVRMEAV, (SEQ ID NO: 52), ERNVGVI, (SEQ ID NO: 53). Human JAM-1 peptides further include, SVTVHSSE, (SEQ ID NO: 54), PEVRIPEN, (SEQ ID NO: 55), NPVKLSCA, (SEQ ID NO: 56), YSGFSSPR, (SEQ ID NO: 57), VEWKFDQG, (SEQ ID NO: 58), DTTRLVCY, (SEQ ID NO: 59), NNKITASY, (SEQ ID NO: 60), EDRVTFLP, (SEQ ID NO: 61), TGITFKSV, (SEQ ID NO: 62), TREDTGTY, (SEQ ID NO: 63), TCMVSEEG, (SEQ ID NO: 64), GNSYGEVK, (SEQ ID NO: 65), VKLIVLVP, (SEQ ID NO: 66), PSKPTVNI, (SEQ ID NO: 67), PSSATIGN, (SEQ ID NO: 68), RAVLTCSE, (SEQ ID NO: 69), QDGSPPSE, (SEQ ID NO: 70), YTWFKDGI, (SEQ ID NO: 71), VMPTNPKS, (SEQ ID NO: 72), TRAFSNSS, (SEQ ID NO: 73), YVLNPTTG, (SEQ ID NO: 74), ELVFDPLS, (SEQ ID NO: 75), ASDTGEYS, (SEQ ID NO: 76), CEARNGYG, (SEQ ID NO: 77), TPMTSNAV, (SEQ ID NO: 78), RMEAVERN, (SEQ ID NO: 79), VGVI, (SEQ ID NO: 80). Human JAM-1 peptides further include, SVTV, (SEQ ID NO: 81), HSSEPEVR, (SEQ ID NO: 82), IPENNPVK, (SEQ ID NO: 83), LSCAYSGF, (SEQ ID NO: 84), SSPRVEWK, (SEQ ID NO: 85), FDQGDTTR, (SEQ ID NO: 86), LVCYNNKI, (SEQ ID NO: 87), TASYEDRV, (SEQ ID NO: 88), TFLPTGIT, (SEQ ID NO: 89), FKSVTRED, (SEQ ID NO: 90), TGTYTCMV, (SEQ ID NO: 91), SEEGGNSY, (SEQ ID NO: 92), GEVKVKLI, (SEQ ID NO: 93), VLVPPSKP, (SEQ ID NO: 94), TVNIPSSA, (SEQ ID NO: 95), TIGNRAVL, (SEQ ID NO: 96), TCSEQDGS, (SEQ ID NO: 97), PPSEYTWF, (SEQ ID NO: 98), KDGIVMPT, (SEQ ID NO: 99), NPKSTRAF, (SEQ ID NO: 100), SNSSYVLN, (SEQ ID NO: 101), PTTGELVF, (SEQ ID NO: 102), DPLSASDT, (SEQ ID NO: 103), GEYSCEAR, (SEQ ID NO: 104), NGYGTPMT, (SEQ ID NO: 105), SNAVRMEA, (SEQ ID NO: 106), VERNVGVI, (SEQ ID NO: 107).

Exemplary permeabilizing peptides of human JAM-1 include but are not limited to VR(I,V,A)P, (SEQ ID NO: 1), VR(I)P, (SEQ ID NO: 4), PVR(I)PE, (SEQ ID NO: 108), PEVR(I)PEN, (SEQ ID NO: 108), EPEVR(I)PENN, (SEQ ID NO: 109), SEPEVR(I)PENNP, (SEQ ID NO: 110), SSEPEVR(I)PENNPV, (SEQ ID NO: 111), HSSEPEVR(I)PENNPVK, (SEQ ID NO: 112), VHSSEPEVR(I)PENNPVKL, (SEQ ID NO: 113), TVHSSEPEVR(I)PENNPVKLS, (SEQ ID NO: 114), VR(I)PE, (SEQ ID NO: 115), VR(I)PEN, (SEQ ID NO: 116), VR(I)PENN, (SEQ ID NO: 117), VR(I)PENNP, (SEQ ID NO: 118), VR(I)PENNPV, (SEQ ID NO: 119), VR(I)PENNPVK, (SEQ ID NO: 120), VR(I)PENNPVKL, (SEQ ID NO: 121), VR(I)PENNPVKLS, (SEQ ID NO: 122), EVR(I)P, (SEQ ID NO: 123), PEVR(I)P, (SEQ ID NO: 124), EPEVR(I)P, (SEQ ID NO: 125), SEPEVR(I)P, (SEQ ID NO: 126), SSEPEVR(I)P, (SEQ ID NO: 127), HSSEPEVR(I)P, (SEQ ID NO: 128), VHSSEPEVR(I)P, (SEQ ID NO: 129), TVHSSEPEVR(I)P, (SEQ ID NO: 130).

Exemplary permeabilizing human JAM-1 peptides further include, VR(V)P, (SEQ ID NO: 131), PVR(V)PE, (SEQ ID NO: 132), PEVR(V)PEN, (SEQ ID NO: 133), EPEVR(V)PENN, (SEQ ID NO: 134), SEPEVR(V)PENNP, (SEQ ID NO: 135), SSEPEVR(V)PENNPV, (SEQ ID NO: 136), HSSEPEVR(V)PENNPVK, (SEQ ID NO: 137), VHSSEPEVR(V)PENNPVKL, (SEQ ID NO: 138), TVHSSEPEVR(V)PENNPVKLS, (SEQ ID NO: 139), VR(V)PE, (SEQ ID NO: 140), VR(V)PEN, (SEQ ID NO: 141), VR(V)PENN, (SEQ ID NO: 142), VR(V)PENNP, (SEQ ID NO: 143), VR(V)PENNPV, (SEQ ID NO: 144), VR(V)PENNPVK, (SEQ ID NO: 145), VR(V)PENNPVKL, (SEQ ID NO: 146), VR(V)PENNPVKLS, (SEQ ID NO: 147), EVR(V)P, (SEQ ID NO: 148), PEVR(V)P, (SEQ ID NO: 149), EPEVR(V)P, (SEQ ID NO: 150), SEPEVR(V)P, (SEQ ID NO: 151), SSEPEVR(V)P, (SEQ ID NO: 152), HSSEPEVR(V)P, (SEQ ID NO: 153), VHSSEPEVR(V)P, (SEQ ID NO: 154), TVHSSEPEVR(V)P, (SEQ ID NO: 155), VR(A)P, (SEQ ID NO: 156), PVR(A)PE, (SEQ ID NO: 157), PEVR(A)PEN, (SEQ ID NO: 158), EPEVR(A)PENN, (SEQ ID NO: 159), SEPEVR(A)PENNP, (SEQ ID NO: 160), SSEPEVR(A)PENNPV, (SEQ ID NO: 161), HSSEPEVR(A)PENNPVK, (SEQ ID NO: 162), VHSSEPEVR(A)PENNPVKL, (SEQ ID NO: 163), TVHSSEPEVR(A)PENNPVKLS, (SEQ ID NO: 164), VR(A)PE, (SEQ ID NO: 165), VR(A)PEN, (SEQ ID NO: 166), VR(A)PENN, (SEQ ID NO: 167), VR(A)PENNP, (SEQ ID NO: 168), VR(A)PENNPV, (SEQ ID NO: 169), VR(A)PENNPVK, (SEQ ID NO: 170), VR(A)PENNPVKL, (SEQ ID NO: 171), VR(A)PENNPVKLS, (SEQ ID NO: 172), EVR(A)P, (SEQ ID NO: 173), PEVR(A)P, (SEQ ID NO: 174), EPEVR(A)P, (SEQ ID NO: 175), SEPEVR(A)P, (SEQ ID NO: 176), SSEPEVR(A)P, (SEQ ID NO: 177), HSSEPEVR(A)P, (SEQ ID NO: 178), VHSSEPEVR(A)P, (SEQ ID NO: 179), TVHSSEPEVR(A)P, (SEQ ID NO: 180).

Exemplary permeabilizing human JAM-1 peptides further include, (V,A,I)KL(S,T)CAY, (SEQ ID NO: 2), (V)KL(S)CAY, (SEQ ID NO: 6), P(V)KL(S)CAYS, (SEQ ID NO: 181), NP(V)KL(S)CAYSG, (SEQ ID NO: 182), NNP(V)KL(S)CAYSGF, (SEQ ID NO: 183), ENNP(V)KL(S)CAYSGFS, (SEQ ID NO: 184), PENNP(V)KL(S)CAYSGFSS, (SEQ ID NO: 185), IPENNP(V)KL(S)CAYSGFSSP, (SEQ ID NO: 186), RIPENNP(V)KL(S)CAYSGFSSPR, (SEQ ID NO: 187), P(V)KL(S)CAY, (SEQ ID NO: 188), NP(V)KL(S)CAY, (SEQ ID NO: 189), NNP(V)KL(S)CAY, (SEQ ID NO: 190), ENNP(V)KL(S)CAY, (SEQ ID NO: 191), PENNP(V)KL(S)CAY, (SEQ ID NO: 192), IPENNP(V)KL(S)CAY, (SEQ ID NO: 193), RIPENNP(V)KL(S)CAY, (SEQ ID NO: 194), (V)KL(S)CAYS, (SEQ ID NO: 195), (V)KL(S)CAYSG, (SEQ ID NO: 196), (V)KL(S)CAYSGF, (SEQ ID NO: 197), (V)KL(S)CAYSGFS, (SEQ ID NO: 198), (V)KL(S)CAYSGFSS, (SEQ ID NO: 199), (V)KL(S)CAYSGFSSP, (SEQ ID NO: 200), (V)KL(S)CAYSGFSSPR, (SEQ ID NO: 201), (V)KL(T)CAY, (SEQ ID NO: 202), (V)KL(T)CAY, (SEQ ID NO: 203), P(V)KL(T)CAYS, (SEQ ID NO: 204), NP(V)KL(T)CAYSG, (SEQ ID NO: 205), NNP(V)KL(T)CAYSGF, (SEQ ID NO: 206), ENNP(V)KL(T)CAYSGFS, (SEQ ID NO: 207), PENNP(V)KL(T)CAYSGFSS, (SEQ ID NO: 208), IPENNP(V)KL(T)CAYSGFSSP, (SEQ ID NO: 209), RIPENNP(V)KL(T)CAYSGFSSPR, (SEQ ID NO: 210), P(V)KL(T)CAY, (SEQ ID NO: 211), NP(V)KL(T)CAY, (SEQ ID NO: 212), NNP(V)KL(T)CAY, (SEQ ID NO: 213), ENNP(V)KL(T)CAY, (SEQ ID NO: 214), PENNP(V)KL(T)CAY, (SEQ ID NO:

215), IPENNP(V)KL(T)CAY, (SEQ ID NO: 216), RIPENNP(V)KL(T)CAY, (SEQ ID NO: 217), (V)KL(T)CAYS, (SEQ ID NO: 218), (V)KL(T)CAYSG, (SEQ ID NO: 219), (V)KL(T)CAYSGF, (SEQ ID NO: 220), (V)KL(T)CAYSGFS, (SEQ ID NO: 221), (V)KL(T)CAYSGFSS, (SEQ ID NO: 222), (V)KL(T)CAYSGFSSP, (SEQ ID NO: 223), (V)KL(T)CAYSGFSSPR, (SEQ ID NO: 224).

Exemplary permeabilizing human JAM-1 peptides further include, (A)KL(S)CAY, (SEQ ID NO: 225), (A)KL(S)CAY, (SEQ ID NO: 226), P(A)KL(S)CAYS, (SEQ ID NO: 227), NP(A)KL(S)CAYSG, (SEQ ID NO: 228), NNP(A)KL(S)CAYSGF, (SEQ ID NO: 229), ENNP(A)KL(S)CAYSGFS, (SEQ ID NO: 230), PENNP(A)KL(S)CAYSGFSS, (SEQ ID NO: 231), IPENNP(A)KL(S)CAYSGFSSP, (SEQ ID NO: 232), RIPENNP(A)KL(S)CAYSGFSSPR, (SEQ ID NO: 233), P(A)KL(S)CAY, (SEQ ID NO: 234), NP(A)KL(S)CAY, (SEQ ID NO: 235), NNP(A)KL(S)CAY, (SEQ ID NO: 236), ENNP(A)KL(S)CAY, (SEQ ID NO: 237), PENNP(A)KL(S)CAY, (SEQ ID NO: 238), IPENNP(A)KL(S)CAY, (SEQ ID NO: 239), RIPENNP(A)KL(S)CAY, (SEQ ID NO: 240), (A)KL(S)CAYS, (SEQ ID NO: 241), (A)KL(S)CAYSG, (SEQ ID NO: 242), (A)KL(S)CAYSGF, (SEQ ID NO: 243), (A)KL(S)CAYSGFS, (SEQ ID NO: 244), (A)KL(S)CAYSGFSS, (SEQ ID NO: 245), (A)KL(S)CAYSGFSSP, (SEQ ID NO: 246), (A)KL(S)CAYSGFSSPR, (SEQ ID NO: 247), (A)KL(T)CAY, (SEQ ID NO: 248), (A)KL(T)CAY, (SEQ ID NO: 249), P(A)KL(T)CAYS, (SEQ ID NO: 250), NP(A)KL(T)CAYSG, (SEQ ID NO: 251), NNP(A)KL(T)CAYSGF, (SEQ ID NO: 252), ENNP(A)KL(T)CAYSGFS, (SEQ ID NO: 253), PENNP(A)KL(T)CAYSGFSS, (SEQ ID NO: 254), IPENNP(A)KL(T)CAYSGFSSP, (SEQ ID NO: 255), RIPENNP(A)KL(T)CAYSGFSSPR, (SEQ ID NO: 256), P(A)KL(T)CAY, (SEQ ID NO: 257), NP(A)KL(T)CAY, (SEQ ID NO: 258), NNP(A)KL(T)CAY, (SEQ ID NO: 259), ENNP(A)KL(T)CAY, (SEQ ID NO: 260), PENNP(A)KL(T)CAY, (SEQ ID NO: 261), IPENNP(A)KL(T)CAY, (SEQ ID NO: 262), RIPENNP(A)KL(T)CAY, (SEQ ID NO: 263), (A)KL(T)CAYS, (SEQ ID NO: 264), (A)KL(T)CAYSG, (SEQ ID NO: 265), (A)KL(T)CAYSGF, (SEQ ID NO: 266), (A)KL(T)CAYSGFS, (SEQ ID NO: 267), (A)KL(T)CAYSGFSS, (SEQ ID NO: 268), (A)KL(T)CAYSGFSSP, (SEQ ID NO: 269), (A)KL(T)CAYSGFSSPR, (SEQ ID NO: 270).

Exemplary permeabilizing human JAM-1 peptides further include, ED(T,S)GTY(T,R)C(M,E), (SEQ ID NO: 3), ED(T)GTY(T)C(M), (SEQ ID NO: 9), RED(T)GTY(T)C(M)V, (SEQ ID NO: 271), TRED(T)GTY(T)C(M)VS, (SEQ ID NO: 272), VTRED(T)GTY(T)C(M)VSE, (SEQ ID NO: 273), SVTRED(T)GTY(T)C(M)VSEE, (SEQ ID NO: 274), KSVTRED(T)GTY(T)C(M)VSEEG, (SEQ ID NO: 275), RED(T)GTY(T)C(M), (SEQ ID NO: 276), TRED(T)GTY(T)C(M), (SEQ ID NO: 277), VTRED(T)GTY(T)C(M), (SEQ ID NO: 278), SVTRED(T)GTY(T)C(M), (SEQ ID NO: 279), KSVTRED(T)GTY(T)C(M), (SEQ ID NO: 280), ED(T)GTY(T)C(M)V, (SEQ ID NO: 281), ED(T)GTY(T)C(M)VS, (SEQ ID NO: 282), ED(T)GTY(T)C(M)VSE, (SEQ ID NO: 283), ED(T)GTY(T)C(M)VSEE, (SEQ ID NO: 284), ED(T)GTY(T)C(M)VSEEG, (SEQ ID NO: 285), ED(T)GTY(T)C(E), (SEQ ID NO: 286), RED(T)GTY(T)C(E)V, (SEQ ID NO: 287), TRED(T)GTY(T)C(E)VS, (SEQ ID NO: 288), VTRED(T)GTY(T)C(E)VSE, (SEQ ID NO: 289), SVTRED(T)GTY(T)C(E)VSEE, (SEQ ID NO: 290), KSVTRED(T)GTY(T)C(E)VSEEG, (SEQ ID NO: 291), RED(T)GTY(T)C(E), (SEQ ID NO: 292), TRED(T)GTY(T)C(E), (SEQ ID NO: 293), VTRED(T)GTY(T)C(E), (SEQ ID NO: 294), SVTRED(T)GTY(T)C(E), (SEQ ID NO: 295), KSVTRED(T)GTY(T)C(E), (SEQ ID NO: 296), ED(T)GTY(T)C(E)V, (SEQ ID NO: 297), ED(T)GTY(T)C(E)VS, (SEQ ID NO: 298), ED(T)GTY(T)C(E)VSE, (SEQ ID NO: 299), ED(T)GTY(T)C(E)VSEE, (SEQ ID NO: 300), ED(T)GTY(T)C(E)VSEEG, (SEQ ID NO: 301), ED(T)GTY(R)C(M), (SEQ ID NO: 302), RED(T)GTY(T)C(M)V, (SEQ ID NO: 303), TRED(T)GTY(T)C(M)VS, (SEQ ID NO: 304), VTRED(T)GTY(T)C(M)VSE, (SEQ ID NO: 305), SVTRED(T)GTY(T)C(M)VSEE, (SEQ ID NO: 306), KSVTRED(T)GTY(T)C(M)VSEEG, (SEQ ID NO: 307), RED(T)GTY(T)C(M), (SEQ ID NO: 308), TRED(T)GTY(T)C(M), (SEQ ID NO: 309), VTRED(T)GTY(T)C(M), (SEQ ID NO: 310), SVTRED(T)GTY(T)C(M), (SEQ ID NO: 311), KSVTRED(T)GTY(T)C(M), (SEQ ID NO: 312), ED(T)GTY(T)C(M)V, (SEQ ID NO: 313), ED(T)GTY(T)C(M)VS, (SEQ ID NO: 314), ED(T)GTY(T)C(M)VSE, (SEQ ID NO: 315), ED(T)GTY(T)C(M)VSEE, (SEQ ID NO: 316), ED(T)GTY(T)C(M)VSEEG, (SEQ ID NO: 317).

Exemplary permeabilizing human JAM-1 peptides further include, ED(T)GTY(R)C(E), (SEQ ID NO: 318), RED(T)GTY(T)C(M)V, (SEQ ID NO: 319), TRED(T)GTY(T)C(M)VS, (SEQ ID NO: 320), VTRED(T)GTY(T)C(M)VSE, (SEQ ID NO: 321), SVTRED(T)GTY(T)C(M)VSEE, (SEQ ID NO: 322), KSVTRED(T)GTY(T)C(M)VSEEG, (SEQ ID NO: 323), RED(T)GTY(T)C(M), (SEQ ID NO: 324), TRED(T)GTY(T)C(M), (SEQ ID NO: 325), VTRED(T)GTY(T)C(M), (SEQ ID NO: 326), SVTRED(T)GTY(T)C(M), (SEQ ID NO: 327), KSVTRED(T)GTY(T)C(M), (SEQ ID NO: 328), ED(T)GTY(T)C(M)V, (SEQ ID NO: 329), ED(T)GTY(T)C(M)VS, (SEQ ID NO: 330), ED(T)GTY(T)C(M)VSE, (SEQ ID NO: 331), ED(T)GTY(T)C(M)VSEE, (SEQ ID NO: 332), ED(T)GTY(T)C(M)VSEEG, (SEQ ID NO: 333), ED(S)GTY(T)C(M), (SEQ ID NO: 334), RED(T)GTY(T)C(M)V, (SEQ ID NO: 335), TRED(T)GTY(T)C(M)VS, (SEQ ID NO: 336), VTRED(T)GTY(T)C(M)VSE, (SEQ ID NO: 337), SVTRED(T)GTY(T)C(M)VSEE, (SEQ ID NO: 338), KSVTRED(T)GTY(T)C(M)VSEEG, (SEQ ID NO: 339), RED(T)GTY(T)C(M), (SEQ ID NO: 340), TRED(T)GTY(T)C(M), (SEQ ID NO: 341), VTRED(T)GTY(T)C(M), (SEQ ID NO: 342), SVTRED(T)GTY(T)C(M), (SEQ ID NO: 343), KSVTRED(T)GTY(T)C(M), (SEQ ID NO: 344), ED(T)GTY(T)C(M)V, (SEQ ID NO: 345), ED(T)GTY(T)C(M)VS, (SEQ ID NO: 346), ED(T)GTY(T)C(M)VSE, (SEQ ID NO: 347), ED(T)GTY(T)C(M)VSEE, (SEQ ID NO: 348), ED(T)GTY(T)C(M)VSEEG, (SEQ ID NO: 349), ED(S)GTY(T)C(E), (SEQ ID NO: 350), RED(S)GTY(T)C(E)V, (SEQ ID NO: 351), TRED(S)GTY(T)C(E)VS, (SEQ ID NO: 352), VTRED(S)GTY(T)C(E)VSE, (SEQ ID NO: 353), SVTRED(S)GTY(T)C(E)VSEE, (SEQ ID NO: 354), KSVTRED(S)GTY(T)C(E)VSEEG, (SEQ ID NO: 355), RED(S)GTY(T)C(E), (SEQ ID NO: 356), TRED(S)GTY(T)C(E), (SEQ ID NO: 357), VTRED(S)GTY(T)C(E), (SEQ ID NO: 358), SVTRED(S)GTY(T)C(E), (SEQ ID NO: 359), KSVTRED(S)GTY(T)C(E), (SEQ ID NO: 360), ED(S)GTY(T)C(E)V, (SEQ ID NO: 361), ED(S)GTY(T)C(E)VS, (SEQ ID NO: 362), ED(S)GTY(T)C(E)VSE, (SEQ ID NO: 363), ED(S)GTY(T)C(E)VSEE, (SEQ ID NO: 364), ED(S)GTY(T)C(E)VSEEG, (SEQ ID NO: 365).

Exemplary permeabilizing human JAM-1 peptides further include, ED(S)GTY(R)C(M), (SEQ ID NO: 366), RED(S)GTY(R)C(M)V, (SEQ ID NO: 367), TRED(S)GTY(R)C(M)VS, (SEQ ID NO: 368), VTRED(S)GTY(R)C(M)VSE, (SEQ ID NO: 369), SVTRED(S)GTY(R)C(M)VSEE, (SEQ ID NO: 370), KSVTRED(S)GTY(R)C(M)VSEEG, (SEQ ID NO: 371), RED(S)GTY(R)C(M), (SEQ ID NO: 372), TRED(S)GTY(R)C(M), (SEQ ID NO: 373), VTRED(S)GTY(R)C(M), (SEQ ID NO: 374), SVTRED(S)GTY(R)C (M), (SEQ ID NO: 375), KSVTRED(S)GTY(R)C(M), (SEQ ID NO: 376), ED(S)GTY(R)C(M)V, (SEQ ID NO: 377), ED(S)GTY(R)C(M)VS, (SEQ ID NO: 378), ED(S)GTY(R)C(M)VSE, (SEQ ID NO: 379), ED(S)GTY(R)C(M)VSEE, (SEQ ID NO: 380), ED(S)GTY(R)C(M)VSEEG, (SEQ ID NO: 381).

Exemplary permeabilizing human JAM-1 peptides further include, ED(S)GTY(R)C(E), (SEQ ID NO: 382), RED(S)GTY(R)C(E)V, (SEQ ID NO: 383), TRED(S)GTY(R)C(E)VS, (SEQ ID NO: 384), VTRED(S)GTY(R)C(E)VSE, (SEQ ID NO: 385), SVTRED(S)GTY(R)C(E)VSEE, (SEQ ID NO: 386), KSVTRED(S)GTY(R)C(E)VSEEG, (SEQ ID NO: 387), RED(S)GTY(R)C(E), (SEQ ID NO: 388), TRED(S)GTY(k)C(E), (SEQ ID NO: 389), VTRED(S)GTY(R)C(E), (SEQ ID NO: 390), SVTRED(S)GTY(R)C(E), (SEQ ID NO: 391), KSVTRED(S)GTY(R)C(E), (SEQ ID NO: 392), ED(S)GTY(R)C(E)V, (SEQ ID NO: 393), ED(S)GTY(R)C(E)VS, (SEQ ID NO: 394), ED(S)GTY(R)C(E)VSE, (SEQ ID NO: 395), ED(S)GTY(R)C(E)VSEE, (SEQ ED NO: 396), ED(S)GTY(R)C(E)VSEEG, (SEQ ID NO: 397).

Candidate permeabilizing peptides of human JAM-2 include, but are not limited to AVNLKSSNRT, (SEQ ID NO: 398), PVVQEFESVE, (SEQ ID NO: 399), LSCIITDSQT, (SEQ ID NO: 400), SDPRIEWKKI, (SEQ ID NO: 401), QDEQTTYVFF, (SEQ ID NO: 402), DNKIQGDLAG, (SEQ ID NO: 403), RAEILGKTSL, (SEQ ID NO: 404), KIWNVTRRDS, (SEQ ID NO: 405), ALYRCEVVAR, (SEQ ID NO: 406), NDRKEIDEIV, (SEQ ID NO: 407), IELTVQVKPV, (SEQ ID NO: 408), TPVCRVPKAV, (SEQ ID NO: 409), PVGKMATLHC, (SEQ ID NO: 410), QESEGHPRPH, (SEQ ID NO: 411), YSWYRNDVPL, (SEQ ID NO: 412), PTDSRANPRF, (SEQ ID NO: 413), RNSSFHLNSE, (SEQ ID NO: 414), TGTLVFTAVH, (SEQ ID NO: 415), KDDSGQYYCI, (SEQ ID NO: 416), ASNDAGSARC, (SEQ ID NO: 417), EEQEMEVYDLN, (SEQ ID NO: 418).

Candidate permeabilizing peptides of human JAM-2 further include AVNLK, (SEQ ID NO: 419), SSNRTPVVQE, (SEQ ID NO: 420), FESVELSCII, (SEQ ID NO: 421), TDSQTSDPRI, (SEQ ID NO: 422), EWKKIQDEQT, (SEQ ID NO: 423), TYVFFDNKIQ, (SEQ ID NO: 424), GDLAGRAEIL, (SEQ ID NO: 425), GKTSLKIWNV, (SEQ ID NO: 426), TRRDSALYRC, (SEQ ID NO: 427), EVVARNDRKE, (SEQ ID NO: 428), IDEIVIELTV, (SEQ ID NO: 429), QVKPVTPVCR, (SEQ ID NO: 430), VPKAVPVGKM, (SEQ ID NO: 431), ATLHCQESEG, (SEQ ID NO: 432), HPRPHYSWYR, (SEQ ID NO: 433), NDVPLPTDSR, (SEQ ID NO: 434), ANPRFRNSSF, (SEQ ID NO: 435), HLNSETGTLV, (SEQ ID NO: 436), FTAVHKDDSG, (SEQ ID NO: 437), QYYCIASNDA, (SEQ ID NO: 438), GSARCEEQEM, (SEQ ID NO: 439), EVYDLN, (SEQ ID NO: 440).

Candidate permeabilizing peptides of human JAM-2 further include AVNLKSSN, (SEQ ID NO: 441), RTPVVQEF, (SEQ ID NO: 442), ESVELSCI, (SEQ ID NO: 443), ITDSQTSD, (SEQ ID NO: 444), PRIEWKKI, (SEQ ID NO: 790), QDEQTTYV, (SEQ ID NO: 445), FFDNKIQG, (SEQ ID NO: 446), DLAGRAEI, (SEQ ID NO: 447), LGKTSLKI, (SEQ ID NO: 448), WNVTRRDS, (SEQ ID NO: 449), ALYRCEVV, (SEQ ID NO: 450), ARNDRKEI, (SEQ ID NO: 451), DEIVIELT, (SEQ ID NO: 452), VQVKPVTP, (SEQ ID NO: 453), VCRVPKAV, (SEQ ID NO: 454), PVGKMATL, (SEQ ID NO: 455), HCQESEGH, (SEQ ID NO: 456), PRPHYSWY, (SEQ ID NO: 457), RNDVPLPT, (SEQ ID NO: 458), DSRANPRF, (SEQ ID NO: 459), RNSSFHLN, (SEQ ID NO: 460), SETGTLVF, (SEQ ID NO: 461), TAVHKDDS, (SEQ ID NO: 462), GQYYCIAS, (SEQ ID NO: 463), NDAGSARC, (SEQ ID NO: 464), EEQEMEVY, (SEQ ID NO: 465), DLN, (SEQ ID NO: 466).

Candidate permeabilizing peptides of human JAM-2 further include AVNL, (SEQ ID NO: 467), KSSNRTPV, (SEQ ID NO: 468), VQEFESVE, (SEQ ID NO: 469), LSCIITDS, (SEQ ID NO: 470), QTSDPRIE, (SEQ ID NO: 471), WKKIQDEQ, (SEQ ID NO: 472), TTYVFFDN, (SEQ ID NO: 473), KIQGDLAG, (SEQ ID NO: 474), RAEILGKT, (SEQ ID NO: 475), SLKIWNVT, (SEQ ID NO: 476), RRDSALYR, (SEQ ID NO: 477), CEVVARND, (SEQ ID NO: 478), RKEIDEIV, (SEQ ID NO: 479), IELTVQVK, (SEQ ID NO: 480), PVTPVCRV, (SEQ ID NO: 481), PKAVPVGK, (SEQ ID NO: 482), MATLHCQE, (SEQ ID NO: 483), SEGHPRPH, (SEQ ID NO: 484), YSWYRNDV, (SEQ ID NO: 485), PLPTDSRA, (SEQ ID NO: 486), NPRFRNSS, (SEQ ID NO: 487), FHLNSETG, (SEQ ID NO: 488), TLVFTAVH, (SEQ ID NO: 489), KDDSGQYY, (SEQ ID NO: 490), CIASNDAG, (SEQ ID NO: 491), SARCEEQE, (SEQ ID NO: 492), MEVYDLN, (SEQ ID NO: 493).

Exemplary permeabilizing peptides of human JAM-3 include, but are not limited to, GFSAPKDQQV, (SEQ ID NO: 494), VTAVEYQEAI, (SEQ ID NO: 495), LACKTPKKTV, (SEQ ID NO: 496), SSRLEWKKLG, (SEQ ID NO: 497), RSVSFVYYQQ, (SEQ ID NO: 498), TLQGDFKNRA, (SEQ ID NO: 499), EMIDFNIRIK, (SEQ ID NO: 500), NVTRSDAGKY, (SEQ ID NO: 501), RCEVSAPSEQ, (SEQ ID NO: 502), GQNLEEDTVT, (SEQ ID NO: 503), LEVLVAPAVP, (SEQ ID NO: 504), SCEVPSSALS, (SEQ ID NO: 505), GTVVELRCQD, (SEQ ID NO: 506), KEGNPAPEYT, (SEQ ID NO: 507), WFKDGIRLLE, (SEQ ID NO: 508), NPRLGSQSTN, (SEQ ID NO: 509), SSYTMNTKTG, (SEQ ID NO: 510), TLQFNTVSKL, (SEQ ID NO: 511), DTGEYSCEAR, (SEQ ID NO: 512), NSVGYRRCPG, (SEQ ID NO: 513), KRMQVDDLN, (SEQ ID NO: 514).

Exemplary permeabilizing peptides of human JAM-3 further include GFSAP, (SEQ ID NO: 515), KDQQVVTAVE, (SEQ ID NO: 516), YQEAILACKT, (SEQ ID NO: 517), PKKTVSSRLE, (SEQ ID NO: 518), WKKLGRSVSF, (SEQ ID NO: 519), VYYQQTLQGD, (SEQ ID NO: 520), FKNRAEMIDF, (SEQ ID NO: 521), NIRIKNVTRS, (SEQ ID NO: 522), DAGKYRCEVS, (SEQ ID NO: 523), APSEQGQNLE, (SEQ ID NO: 524), EDTVTLEVLV, (SEQ ID NO: 525), APAVPSCEVP, (SEQ ID NO: 526), SSALSGTVVE, (SEQ ID NO: 527), LRCQDKEGNP, (SEQ ID NO: 528), APEYTWFKDG, (SEQ ID NO: 529), IRLLENPRLG, (SEQ ID NO: 530), SQSTNSSYTM, (SEQ ID NO: 531), NTKTGTLQFN, (SEQ ID NO: 532), TVSKLDTGEY, (SEQ ID NO: 533), SCEARNSVGY, (SEQ ID NO: 534), RRCPGKRMQV, (SEQ ID NO: 535), DDLN, (SEQ ID NO: 536).

Exemplary permeabilizing peptides of human JAM-3 further include GFSAPKDQ, (SEQ ID NO: 537), QVVTAVEY, (SEQ ID NO: 538), QEAILACK, (SEQ ID NO: 539), TPKKTVSS, (SEQ ID NO: 540), RLEWKKLG, (SEQ ID NO: 541), RSVSFVYY, (SEQ ID NO: 542), QQTLQGDF, (SEQ ID NO: 543), KNRAEMID, (SEQ ID NO: 544), FNIRIKNV, (SEQ ID NO: 545), TRSDAGKY, (SEQ ID NO: 546), RCEVSAPS, (SEQ ID NO: 547), EQGQNLEE, (SEQ ID NO: 548), DTVTLEVL, (SEQ ID NO: 549), VAPAVPSC, (SEQ ID NO: 550), EVPSSALS, (SEQ ID NO: 551), GTVVELRC, (SEQ ID NO: 552), QDKEGNPA, (SEQ ID NO: 553), PEYTWFKD, (SEQ ID NO: 554), GIRLLENP, (SEQ ID NO: 555), RLGSQSTN, (SEQ ID NO: 556), SSYTMNTK, (SEQ ID NO: 557), TGTLQFNT, (SEQ ID NO: 558), VSKLDTGE, (SEQ ID NO: 559), YSCEARNS, (SEQ ID NO: 560), VGYRRCPG, (SEQ ID NO: 561), KRMQVDDLN, (SEQ ID NO: 562).

Exemplary permeabilizing peptides of human JAM-3 further include GFSA, (SEQ ID NO: 563), PKDQQVVT, (SEQ ID NO: 564), AVEYQEAI, (SEQ,ID NO: 565), LACKTPKK, (SEQ ID NO: 566), TVSSRLEW, (SEQ ID NO: 567), KKLGRSVS, (SEQ ID NO: 568), FVYYQQTL, (SEQ ID NO: 569), QGDFKNRA, (SEQ ID NO: 570), EMIDFNIR, (SEQ ID NO: 571), IKNVTRSD, (SEQ ID NO: 572), AGKYRCEV, (SEQ ID NO: 573), SAPSEQGQ, (SEQ ID NO: 574), NLEEDTVT, (SEQ ID NO: 575), LEVLVAPA, (SEQ ID NO: 576), VPSCEVPS, (SEQ ID NO: 577), SALSGTVV, (SEQ ID NO: 578), ELRCQDKE, (SEQ ID NO: 579), GNPAPEYT, (SEQ ID NO: 580), WFKDGIRL, (SEQ ID NO: 581), LENPRLGS, (SEQ ID NO: 582), QSTNSSYT, (SEQ ID NO: 583), MNTKTGTL, (SEQ ID NO: 584), QFNTVSKL, (SEQ ID NO: 585), DTGEYSCE, (SEQ ID NO: 586), ARNSVGYR, (SEQ ID NO: 587), RCPGKRMQ, (SEQ ID NO: 588), VDDLN, (SEQ ID NO: 589).

Exemplary permeabilizing peptides of human claudin 1 extracellular domain include, but are not limited to, RIYSYAGDNI, (SEQ ID NO: 590), VTAQAMYEGL, (SEQ ID NO: 591), WMSCVSQSTG, (SEQ ID NO: 592), QIQCKVFDSL, (SEQ ID NO: 593), LNLSSTLQATR, (SEQ ID NO: 594), RIYSY, (SEQ ID NO: 595), AGDNIVTAQA, (SEQ ID NO: 596), MYEGLWMSCV, (SEQ ID NO: 597), SQSTGQIQCK, (SEQ ID NO: 598), VFDSLLNLSS, (SEQ ID NO: 599), TLQATR, (SEQ ID NO: 600), QEFYDPMT, (SEQ ID NO: 601), PVNARYE, (SEQ ID NO: 602), QEFYDPMTPVN, (SEQ ID NO: 603), ARYE, (SEQ ID NO: 604).

Exemplary permeabilizing peptides of human claudin 2 extracellular domain include, but are not limited to, KTSSYVGASI, (SEQ ID NO: 605), VTAVGFSKGL, (SEQ ID NO: 606), WMECATHSTG, (SEQ ID NO: 607), ITQCDIYSTL, (SEQ ID NO: 608), LGLPADIQAAQ, (SEQ ID NO: 609), KTSSY, (SEQ ID NO: 610), VGASIVTAVG, (SEQ ID NO: 611), FSKGLWMECA, (SEQ ID NO: 612), THSTGITQCD, (SEQ ID NO: 613), IYSTLLGLPA, (SEQ ID NO: 614), DIQAAQ, (SEQ ID NO: 615), RDFYSPL, (SEQ ID NO: 616).

Exemplary permeabilizing peptides of human claudin 3 extracellular domain include, but are not limited to, RVSAFIGSNI, (SEQ ID NO: 617), ITSQNIWEGL, (SEQ ID NO: 618), WMNCVVQSTG, (SEQ ID NO: 619), QMQCKVYDSL, (SEQ ID NO: 620), LALPQDLQAAR, (SEQ ID NO: 621), RVSAF, (SEQ ID NO: 622), IGSNIITSQN, (SEQ ID NO: 623), IWEGLWMNCV, (SEQ ID NO: 624), VQSTGQMQCK, (SEQ ID NO: 625), VYDSLLALPQ, (SEQ ID NO: 626), DLQAAR, (SEQ ID NO: 627), RDFYNPVV, (SEQ ID NO: 628), PEAQKRE, (SEQ ID NO: 629).

Exemplary permeabilizing peptides of human claudin 4 extracellular domain include, but are not limited to, RVTAFIGSNI, (SEQ ID NO: 630), VTSQTIWEGL, (SEQ ID NO: 631), WMNCVVQSTG, (SEQ ID NO: 632), QMQCKVYDSL, (SEQ ID NO: 633), LALPQDLQAAR, (SEQ ID NO: 634), RVTAF, (SEQ ID NO: 635), IGSNIVTSQT, (SEQ ID NO: 636), IWEGLWMNCV, (SEQ ID NO: 637), VQSTGQMQCK, (SEQ ID NO: 638), VYDSLLALPQ, (SEQ ID NO: 639), DLQAAR, (SEQ ID NO: 640), QDFYNPLV, (SEQ ID NO: 641), ASGQKRE, (SEQ ID NO: 642).

Exemplary permeabilizing peptides of human claudin 5 extracellular domain include, but are not limited to, QVTAFLDHNI, (SEQ ID NO: 643), VTAQTTWKGL, (SEQ ID NO: 644), WMSCVVQSTG, (SEQ ID NO: 645), HMQCKVYDSV, (SEQ ID NO: 646), LALSTEVQAAR, (SEQ ID NO: 647), QVTAF, (SEQ ID NO: 648), LDHNIVTAQT, (SEQ ID NO: 649), TWKGLWMSCV, (SEQ ID NO: 650), VQSTGHMQCK, (SEQ ID NO: 651), VYDSVLALST, (SEQ ID NO: 652), EVQAAR, (SEQ ID NO: 653), REFYDPSV, (SEQ ID NO: 654).

Exemplary permeabilizing peptides of human claudin 6 extracellular domain include, but are not limited to, KVTAFIGNSI, (SEQ ID NO: 655), VVAQVVWEGL, (SEQ ID NO: 656), WMSCVVQSTG, (SEQ ID NO: 657), QMQCKVYDSL, (SEQ ID NO: 658), LALPQDLQAAR, (SEQ ID NO: 659), KVTAF, (SEQ ID NO: 660), IGNSIVAQV, (SEQ ID NO: 661), VWEGLWMSCV, (SEQ ID NO: 662), VQSTGQMQCK, (SEQ ID NO: 663), VYDSLLALPQ, (SEQ ID NO: 664), DLQAAR, (SEQ ID NO: 665), RDFYNPLV, (SEQ ID NO: 666), AEAQKRE, (SEQ ID NO: 667).

Exemplary permeabilizing peptides of human claudin 7 extracellular domain include, but are not limited to, QMSSYAGDNI, (SEQ ID NO: 668), ITAQAMYKGL, (SEQ ID NO: 669), WMDCVTQSTG, (SEQ ID NO: 670), MMSCKMYDSV, (SEQ ID NO: 671), LALSAALQATR, (SEQ ID NO: 672), QMSSY, (SEQ ID NO: 673), AGDNIITAQA, (SEQ ID NO: 674), MYKGLWMDCV, (SEQ ID NO: 675), TQSTGMMSCK, (SEQ ID NO: 676), MYDSVLALSA, (SEQ ID NO: 677), ALQATR, (SEQ ID NO: 678), TDFYNPLI, (SEQ ID NO: 679), PTNIKYE, (SEQ ID NO: 680).

Exemplary permeabilizing peptides of human claudin 8 extracellular domain include, but are not limited to, RVSAFIENNI, (SEQ ID NO: 681), VVFENFWEGL, (SEQ ID NO: 682), WMNCVRQANI, (SEQ ID NO: 683), RMQCKIYDSL, (SEQ ID NO: 684), LALSPDLQAAR, (SEQ ID NO: 685), RVSAF, (SEQ ID NO: 686), IENNIVFEN, (SEQ ID NO: 687), FWEGLWMNCV, (SEQ ID NO: 688), RQANIRMQCK, (SEQ ID NO: 689), IYDSLLALSP, (SEQ ID NO: 690), DLQAAR, (SEQ ID NO: 691), RDFYNSIV, (SEQ ID NO:-692), NVAQKRE, (SEQ ID NO: 693).

Exemplary permeabilizing -peptides of human claudin 9 extracellular domain include, but are not limited to, KVTAFIGNSI, (SEQ ID NO: 694), VVAQVVWEGL, (SEQ ID NO: 695), WMSCVVQSTG, (SEQ ID NO: 696), QMQCKVYDSL, (SEQ ID NO: 697), LALPQDLQAAR, (SEQ ID NO: 698), KVTAF, (SEQ ID NO: 699), IGNSIVAQV, (SEQ ID NO: 700), VWEGLWMSCV, (SEQ ID NO: 701), VQSTGQMQCK, (SEQ ID NO: 702), VYDSLLALPQ, (SEQ ID NO: 703), DLQAAR, (SEQ ID NO: 704), QDFYNPLV, (SEQ ID NO: 705), AEALKRE, (SEQ ID NO: 706).

Exemplary permeabilizing peptides of human claudin 10 extracellular domain include, but are not limited to, KVSTIDGTVI, (SEQ ID NO: 707), TTATYWANLW, (SEQ ID NO: 708), KACVTDSTGV, (SEQ ID NO: 709), SNCKDFPSMIL, (SEQ ID NO: 710), ALDGYIQACR, (SEQ ID NO: 711), KVSTI, (SEQ ID NO: 712), DGTVITTATY, (SEQ ID NO: 713), WANLWKACVT, (SEQ ID NO: 714), DSTGVSNCKD, (SEQ ID NO: 715), FPSMLALDGY, (SEQ ID NO: 716), IQACR, (SEQ ID NO: 717), EFFDPLF, (SEQ ID NO: 718), VEQKYE, (SEQ ID NO: 719).

Exemplary permeabilizing peptides of human occludin extracellular domain include, but are not limited to, DRGYGTSLLG, (SEQ ID NO: 720), GSVGYPYGGS, (SEQ ID NO: 721), GFGSYGSGYG, (SEQ ID NO: 722), YGYGYGYGYG, (SEQ ID NO: 723), GYTDPR, (SEQ ID NO: 724), DRGYG, (SEQ ID NO: 725), TSLLGGSVGY, (SEQ ID NO: 726), PYGGSGFGSY, (SEQ ID NO: 727), GSGYGYGYGY, (SEQ ID NO: 728), GYGYGGYTDPR, (SEQ ID NO: 729), GVNPTAQSSG, (SEQ ID NO: 730), SLYGSQIYAL, (SEQ ID NO: 731), CNQFYTPAAT, (SEQ ID NO: 732), GLYVDQYLYH, (SEQ ID NO: 733), YCV-VDPQE, (SEQ ID NO: 734), GVNPT, (SEQ ID NO: 735), AQSSGSLYGS, (SEQ ID NO: 736), QIYALCNQFY, (SEQ ID NO: 737), TPAATGLYVD, (SEQ ID NO: 738), QYLY-HYCVVD, (SEQ ID NO: 739), PQE, (SEQ ID NO: 740).

Further candidate permeabilizing peptides of human JAM-1 include, but are not limited to, VRIP, (SEQ ID NO: 4), VKLSCAY, (SEQ ID NO: 5), TGITFKSVT, (SEQ ID NO: 6), ITAS, (SEQ ID NO: 7), SVTR, (SEQ ID NO: 8), SVTVHSSEP, (SEQ ID NO: 741), KFDQGDTTR, (SEQ ID NO: 742), EDTGTYTCM, (SEQ ID NO: 9), GEVKVKLIV, (SEQ ID NO: 743), VSEEGGNSY, (SEQ ID NO: 744), LVCYNNKIT, (SEQ ID NO: 745), GFSSPRVEW, (SEQ ID NO: 10), VLPPS, (SEQ ID NO: 746), YEDRVTF, (SEQ ID NO: 747), PRVEW, (SEQ ID NO: 748).

Further candidate permeabilizing peptides of human claudin-1 include, but are not limited to, KVFDSLLNLS, (SEQ ID NO: 749), NRIVQEFYDP, (SEQ ID NO: 750), YAGD-NIVTAQ, (SEQ ID NO: 751), VSQSTGQIQC, (SEQ ID NO: 752), MTPVNARYEF, (SEQ ID NO: 753), AMYEGL-WMSC, (SEQ ID NO: 754), TTWLGLWMSC, (SEQ ID NO: 755).

Further candidate permeabilizing peptides of human claudin-2 include, but are not limited to, YVGASIVTAV, (SEQ ID NO: 756), GILRDFYSPL, (SEQ ID NO: 757), VPDSMKFEIG, (SEQ ID NO: 758), DIYSTLLGLP, (SEQ ID NO: 759), GFSLGLWMEC, (SEQ ID NO: 760), ATH-STGITQC, (SEQ ID NO: 761), GFSKGLWMEC, (SEQ ID NO: 762).

Further candidate permeabilizing peptides of human claudin-3 include, but are not limited to, KVYDSLLALP, (SEQ ID NO: 763), NTIIRDFYNP, (SEQ ID NO: 764), VVPEAQKREM, (SEQ ID NO: 765), NIWEGLWMNC, (SEQ ID NO: 766), VVQSTGQMQC, (SEQ ID NO: 767), FIGSNIITSQ, (SEQ ID NO: 768).

Further candidate permeabilizing peptides of human claudin-4 include, but are not limited to, VASGQKREMG, (SEQ ID NO: 769), NIIQDFYNPL, (SEQ ID NO: 770), FIGSNIV-TSQ, (SEQ ID NO: 771), TIWEGLWMNC, (SEQ ID NO: 772).

Further candidate permeabilizing peptides of human claudin-5 include, but are not limited to, IVVREFYDPS, (SEQ ID NO: 773), VVQSTGHMQC, (SEQ ID NO: 774), FLDH-NIVTAQ, (SEQ ID NO: 775), VPVSQKYELG, (SEQ ID NO: 776), KVYDSVLALS, (SEQ ID NO: 777), TTWKGL-WMSC, (SEQ ID NO: 778).

Further candidate permeabilizing peptides of human occludin include, but are not limited to, DRGYGTSLL, (SEQ ID NO: 779), GYGYGYGYG, (SEQ ID NO: 780), GSGFGSYGS, (SEQ ID NO: 781), YGYGGYTDP, (SEQ ID NO: 782), GVNPTAQSS, (SEQ ID NO: 783), GSLYG-SQIY, (SEQ ID NO: 784), AATGLYVDQ, (SEQ ID NO: 785), ALCNQFYTP, (SEQ ID NO: 786), YLYHYCVVD, (SEQ ID NO: 787), GGSVGYPYG, (SEQ ID NO: 788).

In addition to JAM, occludin and claudin peptides, proteins, analogs and mimetics, additional agents for modulating epithelial junctional physiology and/or structure are contemplated for use within the methods and formulations of the invention. Epithelial tight junctions are generally impermeable to molecules with radii of approximately 15 angstroms, unless treated with junctional physiological control agents that stimulate substantial junctional opening as provided within the instant invention. Among the "secondary" tight junctional regulatory components that will serve as useful targets for secondary physiological modulation within the methods and compositions of the invention, the ZO1-ZO2 heterodimeric complex has shown itself amenable to physiological regulation by exogenous agents that can readily and effectively alter paracellular permeability in mucosal epithelia. On such agent that has been extensively studied is the bacterial toxin from *Vibrio cholerae* known as the "zonula occludens toxin" (ZOT). This toxin mediates increased intestinal mucosal permeability and causes disease symptoms including diarrhea in infected subjects. Fasano et al, *Proc. Nat. Acad. Sci., U.S.A.,* 8:5242–5246, 1991; Johnson et al, *J. Clin. Microb.,* 31/3:732–733, 1993; and Karasawa et al, *FEBS Let.,* 106:143–146, 1993, each incorporated herein by reference. When tested on rabbit ileal mucosa, ZOT increased the intestinal permeability by modulating the structure of intercellular tight junctions. More recently, it has been found that ZOT is capable of reversibly opening tight junctions in the intestinal mucosa. WO 96/37196; U.S. Pat. Nos. 5,945,510; 5,948,629; 5,912,323; 5,864,014; 5,827,534; 5,665,389, each incorporated herein by reference. It has also been reported that ZOT is capable of reversibly opening tight junctions in the nasal mucosa. U.S. Pat No. 5,908,825, incorporated herein by reference. Thus, ZOT and other agents that modulate the ZO1-ZO2 complex will be combinatorially formulated or coordinately administered with one or more JAM, occludin and claudin peptides, proteins, analogs and mimetics, and/or other biologically active agents disclosed herein.

Within the methods and compositions of the invention, ZOT, as well as various analogs and mimetics of ZOT that function as agonists or antagonists of ZOT activity, are useful for enhancing intranasal delivery of biologically active agents—by increasing paracellular absorption into and across the nasal mucosa. In this context, ZOT typically acts by causing a structural reorganization of tight junctions marked by altered localization of the junctional protein ZO1. Within these aspects of the invention, ZOT is coordinately administered or combinatorially formulated with the biologically active agent in an effective amount to yield significantly enhanced absorption of the active agent, by reversibly increasing nasal mucosal permeability without substantial adverse side effects Suitable methods for determining ZOT biological activity may be selected from a variety of known assays, e.g., involving assaying for a decrease of tissue or cell culture resistance (Rt) using Ussing chambers (e.g., as described by Fasano et al, Proc. Natl. Acad. Sci., USA, 8:5242–5246, 1991, incorporated herein by reference), assaying for a decrease of tissue resistance (Rt) of intestinal epithelial cell monolayers in Ussing chambers; or directly assaying enhancement of absorption of a therapeutic agent across a mucosal surface in vivo.

In addition to ZOT, various other tight junction modulatory agents can be employed within the methods and compositions of the invention that mimic the activity of ZOT by reversibly increasing mucosal epithelial paracellular permeability. These include specific binding or blocking agents, such as antibodies, antibody fragments, peptides, peptide mimetics, bacterial toxins and other agents that serve as agonists or antagonists of ZOT activity, or which otherwise alter physiology of the ZO1-ZO2complex (e.g., by blocking dimerization). Naturally, these additional regulatory agents include peptide analogs, including site-directed mutant variants, of the native ZOT protein, as well as truncated active forms of the protein and peptide mimetics that model functional domains or active sites of the native protein. In addition, these agents include a native mammalian protein "zonulin", which has been proposed to be an endogenous regulator of tight junctional physiology similar in both structural and functional aspects to ZOT (see, e.g., WO 96/37196; WO 00/07609; U.S. Pat. Nos. 5,945,510; 5,948,629; 5,912,323; 5,864,014; 5,827,534; 5,665,389, each incorporated herein by reference), which therefore suggests that ZOT is a convergent evolutionary development of *Vibrio cholerae* patterned after the endogenous mammalian zonulin regulatory mechanism to facilitate host entry. Both zonulin and ZOT are proposed to bind a specific membrane receptor, designated "ZOT receptor" (see, e.g., U.S. Pat. Nos. 5,864,014; 5,912,323; and 5,948,629, each incorporated herein by reference), which can be used within the invention to screen for additional agonists and antagonists to ZOT and zonulin activity for regulation of tight junctional physiology. In this context, structure-function analysis of the ZOT receptor, and comparisons between ZOT and zonulin, will guide production and selection of specific binding or blocking agents, (e.g., antibodies, antibody fragments, peptides, peptide mimetics, additional bacterial toxins and other agents) to serve as ZOT or zonulin agonists or antagonists, for example with respect to ZOT or zonulin binding or activation of the ZOT receptor, to regulate tight junctional physiology within the methods and compositions of the invention.

Vasodilator Agents and Methods

Yet another class of absorption-promoting agents that shows beneficial utility within the coordinate administration and combinatorial formulation methods and compositions of the invention are vasoactive compounds, more specifically vasodilators. These compounds function within the invention to modulate the structure and physiology of the submucosal vasculature, increasing the transport rate of peptide YY proteins, analogs and mimetics, and other biologically active agents into or through the mucosal epithelium and/or to specific target tissues or compartments (e.g., the systemic circulation or central nervous system.).

Vasodilator agents for use within the invention typically cause submucosal blood vessel relaxation by either a decrease in cytoplasmic calcium, an increase in nitric oxide (NO) or by inhibiting myosin light chain kinase. They are generally divided into 9 classes: calcium antagonists, potassium channel openers, ACE inhibitors, angiotensin-II receptor antagonists, α-adrenergic and imidazole receptor antagonists, β1-adrenergic agonists, phosphodiesterase inhibitors, eicosanoids and NO donors.

Despite chemical differences, the pharmacokinetic properties of calcium antagonists are similar. Absorption into the systemic circulation is high, and these agents therefore undergo considerable first-pass metabolism by the liver, resulting in individual variation in pharmacokinetics. Except for the newer drugs of the dihydropyridine type (amlodipine, felodipine, isradipine, nilvadipine, nisoldipine and nitrendipine), the half-life of calcium antagonists is short. Therefore, to maintain an effective drug concentration for many of these may require delivery by multiple dosing, or controlled release formulations, as described elsewhere herein. Treatment with the potassium channel opener minoxidil may also be limited in manner and level of administration due to potential adverse side effects.

ACE inhibitors prevent conversion of angiotensin-I to angiotensin-II, and are most effective when renin production is increased. Since ACE is identical to kininase-II, which inactivates the potent endogenous vasodilator bradykinin, ACE inhibition causes a reduction in bradykinin degradation. ACE inhibitors provide the added advantage of cardioprotective and cardioreparative effects, by preventing and reversing cardiac fibrosis and ventricular hypertrophy in animal models. The predominant elimination pathway of most ACE inhibitors is via renal excretion. Therefore, renal impairment is associated with reduced elimination and a dosage reduction of 25 to 50% is recommended in patients with moderate to severe renal impairment.

With regard to NO donors, these compounds are particularly useful within the invention for their additional effects on mucosal permeability. In addition to the above-noted NO donors, complexes of NO with nucleophiles called NO/nucleophiles, or NONOates, spontaneously and nonenzymatically release NO when dissolved in aqueous solution at physiologic pH. Cornfield et al., *J. Lab. Clin. Med.*, 134: 419–425, 1999, incorporated herein by reference. In contrast, nitro vasodilators such as nitroglycerin require specific enzyme activity for NO release. NONOates release NO with a defined stoichiometry and at predictable rates ranging from <3 minutes for diethylamine/NO to approximately 20 hours for diethylenetriamine/NO (DETANO).

Within certain methods and compositions of the invention, a selected vasodilator agent is coordinately administered (e.g., systemically or intranasally, simultaneously or in combinatorially effective temporal association) or combinatorially formulated with one or more peptide YY proteins, analogs and mimetics, and other biologically active agent(s) in an amount effective to enhance the mucosal absorption of the active agent(s) to reach a target tissue or compartment in the subject (e.g., the liver, hepatic portal vein, CNS tissue or fluid, or blood plasma).

Selective Transport-Enhancing Agents and Methods

Within certain aspects of the invention, mucosal delivery of biologically active agents is enhanced by methods and agents that target selective transport mechanisms and promote endo- or transcytocis of macromoloecular drugs. In this regard, the compositions and delivery methods of the invention optionally incorporate a selective transport-enhancing agent that facilitates transport of one or more biologically active agents. These transport-enhancing agents may be employed in a combinatorial formulation or coordinate administration protocol with one or more of the peptide YY proteins, analogs and mimetics disclosed herein, to coordinately enhance delivery of one or more additional biologically active agent(s) across mucosal transport barriers, to enhance mucosal delivery of the active agent(s) to reach a target tissue or compartment in the subject (e.g., the mucosal epithelium, liver, CNS tissue or fluid, or blood plasma). Alternatively, the transport-enhancing agents may be employed in a combinatorial formulation or coordinate administration protocol to directly enhance mucosal delivery of one or more of the peptide YY proteins, analogs and mimetics, with or without enhanced delivery of an additional biologically active agent.

Exemplary selective transport-enhancing agents for use within this aspect of the invention include, but are not limited to, glycosides, sugar-containing molecules, and binding agents such as lectin binding agents, which are known to interact specifically with epithelial transport barrier components. Goldstein et al., *Annu. Rev. Cell. Biol.* 1: 1–39, 1985, incorporated herein by reference. For example, specific "bioadhesive" ligands, including various plant and bacterial lectins, which bind to cell surface sugar moieties by receptor-mediated interactions can be employed as carriers or conjugated transport mediators for enhancing mucosal, e.g., nasal delivery of biologically active agents within the invention. Certain bioadhesive ligands for use within the invention will mediate transmission of biological signals to epithelial target cells that trigger selective uptake of the adhesive ligand by specialized cellular transport processes (endocytosis or transcytosis). These transport mediators can therefore be employed as a "carrier system" to stimulate or direct selective uptake of one or more peptide YY proteins, analogs and mimetics, and other biologically active agent(s) into and/or through mucosal epithelia. These and other selective transport-enhancing agents significantly enhance mucosal delivery of macromolecular biopharmaceuticals (particularly peptides, proteins, oligonucleotides and polynucleotide vectors) within the invention. To utilize these transport-enhancing agents, general carrier formulation and/or conjugation methods as described elsewhere herein are used to coordinately administer a selective transport enhancer (e.g., a receptor-specific ligand) and a biologically active agent to a mucosal surface, whereby the transport-enhancing agent is effective to trigger or mediate enhanced endo- or transcytosis of the active agent into or across the mucosal epithelium and/or to additional target cell(s), tissue(s) or compartment(s).

Lectins are plant proteins that bind to specific sugars found on the surface of glycoproteins and glycolipids of eukaryotic cells. Concentrated solutions of lectins have a 'mucotractive' effect, and various studies have demonstrated rapid receptor mediated endocytocis (RME) of lectins and lectin conjugates (e.g., concanavalin A conjugated with colloidal gold particles) across mucosal surfaces. Additional studies have reported that the uptake mechanisms for lectins can be utilized for intestinal drug targeting in vivo. In certain of these studies, polystyrene nanoparticles (500 nm) were covalently coupled to tomato lectin and reported yielded improved systemic uptake after oral administration to rats.

In addition to plant lectins, microbial adhesion and invasion factors provide a rich source of candidates for use as adhesive/selective transport carriers within the mucosal delivery methods and compositions of the invention. Lehr, *Crit. Rev. Therap. Drug Carrier Syst.,* 11:177–218, 1995; Swann, Pa., *Pharmaceutical Research,* 15:826–832, 1998, each incorporated herein by reference. Two components are necessary for bacterial adherence processes, a bacterial 'adhesin' (adherence or colonization factor) and a receptor on the host cell surface. Bacteria causing mucosal infections need to penetrate the mucus layer before attaching themselves to the epithelial surface. This attachment is usually mediated by bacterial fimbriae or pilus structures, although other cell surface components may also take part in the process. Adherent bacteria colonize mucosal epithelia by multiplication and initiation of a series of biochemical reactions inside the target cell through signal transduction mechanisms (with or without the help of toxins). Associated with these invasive mechanisms, a wide diversity of bioadhesive proteins (e.g., invasin, intemalin) originally produced by various bacteria and viruses are known. These allow for extracellular attachment of such microorganisms with an impressive selectivity for host species and even particular target tissues. Signals transmitted by such receptor-ligand interactions trigger the transport of intact, living microorganisms into, and eventually through, epithelial cells by endo- and transcytotic processes. Such naturally occurring phenomena may be harnessed (e.g., by complexing biologically active agents such as peptide YY with an adhesin) according to the teachings herein for enhanced delivery of biologically active compounds into or across mucosal epithelia and/or to other designated target sites of drug action. One advantage of this strategy is that the selective carrier partners thus employed are substrate-specific, leaving the natural barrier function of epithelial tissues intact against other solutes. Lehr, *Drug Absorption Enhancement,* 325–362, de Boer, Ed., Harwood Academic Publishers, 1994, incorporated herein by reference.

Various bacterial and plant toxins that bind epithelial surfaces in a specific, lectin-like manner are also useful within the methods and compositions of the invention. For example, diptheria toxin (DT) enters host cells rapidly by RME. Likewise, the B subunit of the *E. coli* heat labile toxin binds to the brush border of intestinal epithelial cells in a highly specific, lectin-like manner. Uptake of this toxin and transcytosis to the basolateral side of the enterocytes has been reported in vivo and in vitro. Other researches have expressed the transmembrane domain of diphtheria toxin in *E. coli* as a maltose-binding fusion protein and coupled it chemically to high-Mw poly-L-lysine. The resulting complex was successfully used to mediate internalization of a reporter gene in vitro. In addition to these examples, *Staphylococcus aureus* produces a set of proteins (e.g., staphylococcal enterotoxin A (SEA), SEB, toxic shock syndrome toxin 1 (TSST-1) which act both as superantigens and toxins. Studies relating to these proteins have reported dose-dependent, facilitated transcytosis of SEB and TSST-I in Caco-2 cells.

Various plant toxins, mostly ribosome-inactivating proteins (RIPs), have been identified that bind to any mammalian cell surface expressing galactose units and are subsequently internalized by RME. Toxins such as nigrin b, α-sarcin, ricin and saporin, viscumin, and modeccin are highly toxic upon oral administration (i.e., are rapidly internalized). Therefore, modified, less toxic subunits of these compound will be useful within the invention to facilitate the uptake of biologically active agents, including peptide YY proteins, analogs and mimetics.

Viral haemagglutinins comprise another type of transport agent to facilitate mucosal delivery of biologically active agents within the methods and compositions of the invention. The initial step in many viral infections is the binding of surface proteins (haemagglutinins) to mucosal cells. These binding proteins have been identified for most viruses, including rotaviruses, varicella zoster virus, semliki forest virus, adenoviruses, potato leafroll virus, and reovirus. These and other exemplary viral hemagglutinins can be employed in a combinatorial formulation (e.g., a mixture or conjugate formulation) or coordinate administration protocol with one or more of the peptide YY proteins, analogs and mimetics disclosed herein, to coordinately enhance mucosal delivery of one or more additional biologically active agent(s). Alternatively, viral hemagglutinins can be employed in a combinatorial formulation or coordinate administration protocol to directly enhance mucosal delivery of one or more of the peptide YY proteins, analogs and mimetics, with or without enhanced delivery of an additional biologically active agent.

A variety of endogenous, selective transport-mediating factors are also available for use within the invention. Mammalian cells have developed an assortment of mechanisms to facilitate the internalization of specific substrates and target these to defined compartments. Collectively, these processes of membrane deformations are termed 'endocytosis' and comprise phagocytosis, pinocytosis, receptor-mediated endocytosis (clathrin-mediated RME), and potocytosis (non-clathrin-mediated RME). RME is a highly specific cellular biologic process by which, as its name implies, various ligands bind to cell surface receptors and are subsequently internalized and trafficked within the cell. In many cells the process of endocytosis is so active that the entire membrane surface is internalized and replaced in less than a half hour.

RME is initiated when specific ligands bind externally oriented membrane receptors. Binding occurs quickly and is followed by membrane invagination until an internal vesicle forms within the cell (the early endosome, "receptosome", or CURL (compartment of uncoupling receptor and ligand). Localized membrane proteins, lipids and extracellular solutes are also internalized during this process. When the ligand binds to its specific receptor, the ligand-receptor complex accumulates in coated pits. Coated pits are areas of the membrane with high concentration of endocellular clathrin subunits. The assembly of clathrin molecules on the coated pit is believed to aid the invagination process. Specialized coat proteins called adaptins, trap specific membrane receptors that move laterally through the membrane in the coated pit area by binding to a signal sequence (Tyr-X-Arg-Phe, where X=any amino acid) at the endocellular carboxy terminus of the receptor. This process ensures that the correct receptors are concentrated in the coated pit areas and minimizes the amount of extracellular fluid that is taken up in the cell.

Following the internalization process, the clathrin coat is lost through the help of chaperone proteins, and proton pumps lower the endosomal pH to approximately 5.5, which causes dissociation of the receptor-ligand complex. CURL serves as a compartment to segregate the recycling receptor (e.g. transferrin) from receptor involved in transcytosis (e.g. transcoba-lamin). Endosomes may then move randomly or by saltatory-motion along the microtubules until they reach the trans-Golgi reticulum where they are believed to fuse with Golgi components or other membranous compartments and convert into tubulovesicular complexes and late endosomes or multivesicular bodies. The fate of the receptor and ligand are determined in these sorting vesicles. Some ligands and receptors are returned to the cell surface where the ligand is released into the extracellular milieu and the receptor is recycled. Alternatively, the ligand is directed to lysosomes for destruction while the receptor is recycled to the cell membrane. The endocytotic recycling pathways of polarized epithelial cells are generally more complex than in non-polarized cells. In these enterocytes a common recycling compartment exists that receives molecules from both apical and basolateral membranes and is able to correctly return them to the appropriate membrane or membrane recycling compartment.

Current understanding of RME receptor structure and related structure-function relationships has been significantly enhanced by the cloning of mRNA sequences coding for endocytotic receptors. Most RME receptors share principal structural features, such as an extracellular ligand binding site, a single hydrophobic transmembrane domain (unless the receptor is expressed as a dimer), and a cytoplasmic tail encoding endocytosis and other functional signals. Two classes of receptors are proposed based on their orientation in the cell membrane; the amino terminus of Type I receptors is located on the extracellular side of the membrane, whereas Type II receptors have this same protein tail in the intracellular milieu.

As noted above, potocytosis, or non-clathrin coated endocytosis, takes place through caveolae, which are uniform omega- or flask-shaped membrane invaginations 50–80 nm in diameter. This process was first described as the internalization mechanism of the vitamin folic acid. Morphological studies have implicated caveolae in i) the transcytosis of macromolecules across endothelial cells; (ii) the uptake of small molecules via potocytosis involving GPI-linked receptor molecules and an unknown anion transport protein; iii) interactions with the actin-based cytoskeleton; and (iv) the compartmentalization of certain signaling molecules involved in signal transduction, including G-protein coupled receptors. Caveolae are characterized by the presence of an integral 22-kDa membrane protein termed VIP21-caveolin, which coats the cytoplasmic surface of the membrane. From a drug delivery standpoint, the advantage of potocytosis pathways over clathrin-coated RME pathways lies in the absence of the pH lowering step, which circumvents the endosomal/lysosomal pathway. This pathway for selective transporter-mediated delivery of biologically active agents is therefore particularly effective for enhanced delivery of pH-sensitive macromolecules.

Exemplary among potocytotic transport carriers mechanisms for use within the invention is the folate carrier system, which mediates transport of the vitamin folic acid (FA) into target cells via specific binding to the folate receptor (FR). Reddy et al., *Crit. Rev. Ther. Drug Car. Syst.*, 15:587–627, 1998, incorporated herein by reference. The cellular uptake of free folic acid is mediated by the folate receptor and/or the reduced folate carrier. The folate receptor is a glycosylphosphatidylinositol (GPI)-anchored 38 kDa glycoprotein clustered in caveolae mediating cell transport by potocytosis. While the expression of the reduced folate carrier is ubiquitously distributed in eukaryotic cells, the folate receptor is principally overexpressed in human tumors. Two homologous isoforms ($\alpha$ and $\beta$) of the receptor have been identified in humans. The $\alpha$-isoform is found to be frequently overexprssed in epithelial tumors, whereas the $\beta$-form is often found in non-epithelial lineage tumors. Consequently, this receptor system has been used in drug-targeting approaches to cancer cells, but also in protein delivery, gene delivery, and targeting of antisense oligonucleotides to a variety of cell types.

Folate-drug conjugates are well suited for use within the mucosal delivery methods of the invention, because they allow penetration of target cells exclusively via FR-mediated endocytosis. When FA is covalently linked, for example, via its $\gamma$-carboxyl to a biologically active agent, FR binding affinity (KD~$10^{-10}$M) is not significantly compromised, and endocytosis proceeds relatively unhindered, promoting uptake of the attached active agent by the FR-expressing cell. Because FRs are significantly overexpressed on a large fraction of human cancer cells (e.g., ovarian, lung, breast, endometrial, renal, colon, and cancers of myeloid hematopoietic cells), this methodology allows for selective delivery of a wide range of therapeutic as well as diagnostic agents to tumors. Folate-mediated tumor targeting has been exploited to date for delivery of the following classes of molecules and molecular complexes that find use within the invention: (i) protein toxins, (ii) low-molecular-weight chemotherapeutic agents, (iii) radioimaging agents, (iv) MRI contrast agents, (v) radio-therapeutic agents, (vi) liposomes with entrapped drugs, (vii) genes, (viii) antisense oligonucleotides, (ix) ribozymes, and (x) immunotherapeutic agents. Swann, Pa., *Pharmaceutical Research*, 15:826–832, 1998, incorporated herein by reference. In virtually all cases, in vitro studies demonstrate a significant improvement in potency and/or cancer-cell specificity over the nontargeted form of the same pharmaceutical agent.

In addition to the folate receptor pathway, a variety of additional methods to stimulate transcytosis within the invention are directed to the transferrin receptor pathway, and the riboflavin receptor pathway. In one aspect, conjugation of a biologically active agent to riboflavin can effectuate RME-mediated uptake. Yet additional embodiments of the invention utilize vitamin B12 (cobalamin) as a specialized transport protein (e.g., conjugation partner) to facilitate entry of biologically active agents into target cells. Certain studies suggest that this particular system can be employed for the intestinal uptake of luteinizing hormone releasing factor (LHRH)-analogs, granulocyte colony stimulating factor (G-CSF, 18.8 kDa), erythropoietin (29.5 kDa), α-interferon, and the LHRH-antagonist ANTIDE.

Still other embodiments of the invention utilize transferrin as a carrier or stimulant of RME of mucosally delivered biologically active agents. Transferrin, an 80 kDa iron-transporting glycoprotein, is efficiently taken up into cells by RME. Transferrin receptors are found on the surface of most proliferating cells, in elevated numbers on erythroblasts and on many kinds of tumors. According to current knowledge of intestinal iron absorption, transferrin is excreted into the intestinal lumen in the form of apotransferrin and is highly stable to attacks from intestinal peptidases. In most cells, diferric transferrin binds to transferrin receptor (TfR), a dimeric transmembrane glycoprotein of 180 kDa, and the ligand-receptor complex is endocytosed within clathrin-coated vesicles. After acidification of these vesicles, iron dissociates from the transferrin/TfR complex and enters the cytoplasm, where it is bound by ferritin (Fn). Recent reports suggest that insulin covalently coupled to transferrin, is transported across Caco-2 cell monolayers by RME. Other studies suggest that oral administration of this complex to streptozotocin-induced diabetic mice significantly reduces plasma glucose levels (~28%), which is further potentiated by BFA pretreatment. The transcytosis of transferrin (Tf) and transferrin conjugates is reportedly enhanced in the presence of Brefeldin A (BFA), a fungal metabolite. In other studies, BFA treatment has been reported to rapidly increase apical endocytosis of both ricin and HRP in MDCK cells. Thus, BFA and other agents that stimulate receptor-mediated transport can be employed within the methods of the invention as combinatorially formulated (e.g., conjugated) and/or coordinately administered agents to enhance receptor-mediated transport of biologically active agents, including peptide YY proteins, analogs and mimetics.

Immunoglobulin transport mechanisms provide yet additional endogenous pathways and reagents for incorporation within the mucosal delivery methods and compositions of the invention. Receptor-mediated transcytosis of immunoglobulin G (IgG) across the neonatal small intestine serves to convey passive immunity to many newborn mammals. In rats, IgG in milk selectively binds to neonatal Fc receptors (FcRn) expressed on the surface of the proximal small intestinal enterocytes during the first three weeks after birth. FcRn binds IgG in a pH-dependent manner, with binding occurring at the luminal pH (approx. 6–6.5) of the jejunum and release at the pH of plasma (approx. 7.4). The Fc receptor resembles the major histocompatibility complex (MHC) class I antigens in that it consists of two subunits, a transmembrane glycoprotein (gp50) in association with $\beta_2$-microglobulin. In mature absorptive cells both subunits are colocalized in each of the membrane compartments that mediate transcytosis of IgG. IgG administered in situ apparently causes both subunits to concentrate within endocytic pits of the apical plasma membrane, suggesting that ligand causes redistribution of receptors at this site. These results support a model for transport in which IgG is transferred across the cell as a complex with both subunits.

Methods and compositions are described for the delivery of a therapeutic antigen conjugated to a neonatal Fc receptor (FcR) binding partner to intestinal epithelium, mucosal epithelium or epithelium of the lung. The methods and compositions are useful as antigen to neonatal FcR binding partner conjugates in an oral formulation, aerosol formulation or a nasal formulation to deliver drugs and vaccines. U.S. Pat. No. 6,485,726, incorporated herein by reference.

Within the methods and compositions of the present invention, IgG and other immune system-related carriers (including polyclonal and monoclonal antibodies and various fragments thereof) can be coordinate administered with biologically active agents to provide for targeted delivery, typically by receptor-mediated transport, of the biologically active agent. For example, the biologically active agent (including peptide YY proteins, analogs and mimetics) may be covalently linked to the IgG or other immunological active agent or, alternatively, formulated in liposomes or other carrier vehicle which is in turn modified (e.g., coated or covalently linked) to incorporate IgG or other immunological transport enhancer. In certain embodiments, polymeric IgA and/or IgM transport agents are employed, which bind to the polymeric immunoglobulin receptors (pIgRs) of target epithelial cells. Within these methods, expression of pIgR can be enhanced by cytokines.

Within more detailed aspects of the invention, antibodies and other immunological transport agents may be themselves modified for enhanced mucosal delivery, for example, as described in detail elsewhere herein, antibodies may be more effectively administered within the methods and compositions of the invention by charge modifying techniques. In one such aspect, an antibody drug delivery strategy involving antibody cationization is utilized that facilitates both trans-endothelial migration and target cell endocytosis. Pardridge, et al., *JPET,* 286:548–544, 1998, incorporated herein by reference. In one such strategy, the pI of the antibody is increased by converting surface carboxyl groups of the protein to extended primary amino groups. These cationized homologous proteins have no measurable tissue toxicity and have minimal immunogenicity. In addition, monoclonal antibodies may be cationized with retention of affinity for the target protein.

Additional selective transport-enhancing agents for use within the invention comprise whole bacteria and viruses, including genetically engineered bacteria and viruses, as well as components of such bacteria and viruses. Aside from conventional gene delivery vectors (e.g., adenovirus), this aspect of the invention includes the use of bacterial ghosts and subunit constructs, e.g., as described by Huter et al., *Journal of Controlled Release,* 61:51–63, 1999, incorporated herein by reference. Bacterial ghosts are non-denatured bacterial cell envelopes, for example as produced by the controlled expression of the plasmid-encoded lysis gene E of bacteriophage PhiX174 in gram-negative bacteria. Protein E-specific lysis does not cause any physical or chemical denaturation to bacterial surface structures, and bacterial ghosts are therefore useful in development of inactivated whole-cell vaccines. Ghosts produced from *Actinobacillus pleuropneumoniae, Pasteurella haemolytica* and *Salmonella* sp. have proved successful in vaccination experiments. Recombinant bacterial ghosts can be created by the expression of foreign genes fused to a membrane-targeting sequence, and thus can carry foreign therapeutic peptides and proteins anchored in their envelope. The fact that bacterial ghosts preserve a native cell wall, including bioadhesive structures like fimbriae of their living counterparts, makes them suitable for the attachment to specific target tissues such as mucosal surfaces. Bacterial ghosts have been shown to be readily taken up by macrophages, thus adhesion of ghosts to specific tissues can be followed by uptake through phagocytes.

In view of the foregoing, a wide variety of ligands involved in receptor-mediated transport mechanisms are known in the art and can be variously employed within the methods and compositions of the invention (e.g., as conjugate partners or coordinately administered mediators) to enhance receptor-mediated transport of biologically active agents, including peptide YY proteins, analogs and mimetics, and other biologically active agents disclosed herein. Generally, these ligands include hormones and growth factors, bacterial adhesins and toxins, lectins, metal ions and their carriers, vitamins, immunoglobulins, whole viruses and bacteria or selected components thereof. Exemplary ligands among these classes include, for example, peptide YY, neuropeptide Y, pancreatic peptide, calcitonin, prolactin, epidermal growth factor, glucagon, growth hormone, interferon-β, estrogen, lutenizing hormone, platelet derived growth factor, thyroid stimulating hormone, thyroid hormone, cholera toxin, diptheria toxin, *E. coli* heat labile toxin, Staphylococcal enterotoxins A and B, ricin, saporin, modeccin, nigrin, sarcin, concanavalin A, transcobalantin, catecholamines, transferrin, folate, riboflavin, vitamin B1, low density lipoprotein, maternal IgO, polymeric IgA, adenovirus, vesicular stomatitis virus, Rous sarcoma virus, *V. cholerae, Kiebsiella* strains, *Serratia* strains, parainfluenza virus, respiratory syncytial virus, *Varicella zoster*, and *Enterobacter* strains. Swann, P A, *Pharmaceutical Research*, 15:826–832, 1998, incorporated herein by reference.

In certain additional embodiments of the invention, membrane-permeable peptides (e.g., "arginine rich peptides") are employed to facilitate delivery of biologically active agents. While the mechanism of action of these peptides remains to be fully elucidated, they provide useful delivery enhancing adjuncts for use within the mucosal delivery compositions and methods herein. In one example, a basic peptide derived from human immunodeficiency virus (HIV)-1 Tat protein (e.g., residues 48–60) has been reported to translocate effectively through cell membranes and accumulate in the nucleus, a characteristic which can be utilized for the delivery of exogenous proteins into cells. The sequence of Tat (GRKKRRQRRRPPQ) (SEQ ID NO: 789) comprises a highly basic and hydrophilic peptide, which contains 6 arginine and 2 lysine residues in its 13 amino acid residues. Various other arginine-rich peptides have been identified which have a translocation activity very similar to Tat-(48–60). These include such peptides as the D-amino acid- and arginine-substituted Tat-(48–60), the RNA-binding peptides derived from virus proteins, such as HIV-1 Rev, and flock house virus coat proteins, and the DNA binding segments of leucine zipper proteins, such as cancer-related proteins c-Fos and c-Jun, and the yeast transcription factor GCN4. Futaki et al., *Journal Biological Chemistry,* 276: 5836–5840, 2000, incorporated herein by reference. These peptides reportedly have several arginine residues marking their only identified common structural characteristic, suggesting a common internalization mechanism ubiquitous to arginine-rich peptides, which is not explained by typical endocytosis. Using $(Arg)_n$ (n=4–16) peptides, Futaki et al. teach optimization of arginine residues (n~8) for efficient translocation. Recently, methods have been developed for the delivery of exogenous proteins into living cells with the help of arginine rich membrane-permeable carrier peptides such as HIV-1 Tat- and Antennapedia-(see, Futaki et al., supra, and references cited therein, incorporated herein by reference). By genetically or chemically hybridizing these carrier peptides with biologically active agents as described herein, additional methods and compositions are thus provided within the invention to enhance mucosal delivery.

Polymeric Delivery Vehicles and Methods

Within certain aspects of the invention, peptide YY proteins, analogs and mimetics, other biologically active agents disclosed herein, and delivery-enhancing agents as described above, are, individually or combinatorially, incorporated within a mucosally (e.g., nasally) administered formulation that includes a biocompatible polymer functioning as a carrier or base. Such polymer carriers include polymeric powders, matrices or microparticulate delivery vehicles, among other polymer forms. The polymer can be of plant, animal, or synthetic origin. Often the polymer is crosslinked. Additionally, in these delivery systems the biologically active agent (e.g., a peptide YY protein, analog or mimetic), can be functionalized in a manner where it can be covalently bound to the polymer and rendered inseparable from the polymer by simple washing. In other embodiments, the polymer is chemically modified with an inhibitor of enzymes or other agents which may degrade or inactivate the biologically active agent(s) and/or delivery enhancing agent(s). In certain formulations, the polymer is a partially or completely water insoluble but water swellable polymer, e.g., a hydrogel. Polymers useful in this aspect of the invention are desirably water interactive and/or hydrophilic in nature to absorb significant quantities of water, and they often form hydrogels when placed in contact with water or aqueous media for a period of time sufficient to reach equilibrium with water. In more detailed embodiments, the polymer is a hydrogel which, when placed in contact with excess water, absorbs at least two times its weight of water at equilibrium when exposed to water at room temperature. U.S. Pat. No. 6,004,583, incorporated herein by reference.

Drug delivery systems based on biodegradable polymers are preferred in many biomedical applications because such systems are broken down either by hydrolysis or by enzymatic reaction into non-toxic molecules. The rate of degradation is controlled by manipulating the composition of the biodegradable polymer matrix. These types of systems can therefore be employed in certain settings for long-term release of biologically active agents. Biodegradable polymers such as poly(glycolic acid) (PGA), poly-(lactic acid) (PLA), and poly(D,L-lactic-co-glycolic acid) (PLGA), have received considerable attention as possible drug delivery carriers, since the degradation products of these polymers have been found to have low toxicity. During the normal metabolic function of the body these polymers degrade into carbon dioxide and water. Mehta et al, *J. Control. Rel.,* 29:375–384, 1994. These polymers have also exhibited excellent biocompatibility.

For prolonging the biological activity of peptide YY proteins, analogs and mimetics, and other biologically active agents disclosed herein, as well as optional delivery-enhancing agents, these agents may be incorporated into polymeric matrices, e.g., polyorthoesters, polyanhydrides, or polyesters. This yields sustained activity and release of the active agent(s), e.g., as determined by the degradation of the polymer matrix. Heller, *Formulation and Delivery of Proteins and Peptides,* 292–305, Cleland et al., Eds., ACS Symposium Series 567, Washington D.C., 1994; Tabata et al., *Pharm. Res.,* 10:487–496, 1993; and Cohen et al., *Pharm. Res.,* 8:713–720, 1991, each incorporated herein by reference. Although the encapsulation of biotherapeutic molecules inside synthetic polymers may stabilize them during storage and delivery, the largest obstacle of polymer-based release technology is the activity loss of the therapeutic molecules during the formulation processes that often involve heat, sonication or organic solvents. Tabata et al., *Pharm. Res.*, 10:487–496, 1993; and Jones et al., *Drug Targeting and Delivery Series, New Delivery Systems for Recombinant Proteins—Practical Issues from Proof of Concept to Clinic*, 4: 57–67, Lee et al., Eds., Harwood Academic Publishers, 1995, each incorporated herein by reference.

Absorption-promoting polymers contemplated for use within the invention may include derivatives and chemically or physically modified versions of the foregoing types of polymers, in addition to other naturally occurring or synthetic polymers, gums, resins, and other agents, as well as blends of these materials with each other or other polymers, so long as the alterations, modifications or blending do not adversely affect the desired properties, such as water absorption, hydrogel formation, and/or chemical stability for useful application. In more detailed aspects of the invention, polymers such as nylon, acrylan and other normally hydrophobic synthetic polymers may be sufficiently modified by reaction to become water swellable and/or form stable gels in aqueous media.

Suitable polymers for use within the invention should generally be stable alone and in combination with the selected biologically active agent(s) and additional components of a mucosal formulation, and form stable hydrogels in a range of pH conditions from about pH 1 to pH 10. More typically, they should be stable and form polymers under pH conditions: ranging from about 3 to 9, without additional protective coatings. However, desired stability properties may be adapted to physiological parameters characteristic of the targeted site of delivery (e.g., nasal mucosa or secondary site of delivery such as the systemic circulation). Therefore, in certain formulations higher or lower stabilities at a particular pH and in a selected chemical or biological environment will be more desirable.

Absorption-promoting polymers of the invention may include polymers from the group of homo- and copolymers based on various combinations of the following vinyl monomers: acrylic and methacrylic acids, acrylamide, methacrylamide, hydroxyethylacrylate or methacrylate, vinylpyrrolidones, as well as polyvinylalcohol and its co- and terpolymers, polyvinylacetate, its co- and terpolymers with the above listed monomers and 2-acrylamido-2-methyl-propanesulfonic acid (AMPS®). Very useful are copolymers of the above listed monomers with copolymerizable functional monomers such as acryl or methacryl amide acrylate or methacrylate esters where the ester groups are derived from straight or branched chain alkyl, aryl having up to four aromatic rings which may contain alkyl substituents of 1 to 6 carbons; steroidal, sulfates, phosphates or cationic monomers such as N,N-dimethylaminoalkyl(meth)acrylamide, dimethylaminoalkyl(meth)acrylate, (meth)acryloxyalkyltrimethylammonium chloride, (meth)acryloxyalkyldimethylbenzyl ammonium chloride.

Additional absorption-promoting polymers for use within the invention are those classified as dextrans, dextrins, and from the class of materials classified as natural gums and resins, or from the class of natural polymers such as processed collagen, chitin, chitosan, pullalan, zooglan, alginates and modified alginates such as "Kelcoloid" (a polypropylene glycol modified alginate) gellan gums such as "Kelocogel", Xanathan gums such as "Keltrol", estastin, alpha hydroxy butyrate and its copolymers, hyaluronic acid and its derivatives, polylactic and glycolic acids.

A very useful class of polymers applicable within the instant invention are olefinically-unsaturated carboxylic acids containing at least one activated carbon-to-carbon olefinic double bond, and at least one carboxyl group; that is, an acid or functional group readily converted to an acid containing an olefinic double bond which readily functions in polymerization because of its presence in the monomer molecule, either in the alpha-beta position with respect to a carboxyl group, or as part of a terminal methylene grouping. Olefinically-unsaturated acids of this class include such materials as the acrylic acids typified by the acrylic acid itself, alpha-cyano acrylic acid, beta methylacrylic acid (crotonic acid), alpha-phenyl acrylic acid, beta-acryloxy propionic acid, cinnamic acid, p-chloro cinnamic acid, 1-carboxy-4-phenyl butadiene-1,3, itaconic acid, citraconic acid, mesaconic acid, glutaconic acid, aconitic acid, maleic acid, fumaric acid, and tricarboxy ethylene. As used herein, the term "carboxylic acid" includes the polycarboxylic acids and those acid anhydrides, such as maleic anhydride, wherein the anhydride group is formed by the elimination of one molecule of water from two carboxyl groups located on the same carboxylic acid molecule.

Representative acrylates useful as absorption-promoting agents within the invention include methyl acrylate, ethyl acrylate, propyl acrylate, isopropyl acrylate, butyl acrylate, isobutyl acrylate, methyl methacrylate, methyl ethacrylate, ethyl methacrylate, octyl acrylate, heptyl acrylate, octyl methacrylate, isopropyl methacrylate, 2-ethylhexyl methacrylate, nonyl acrylate, hexyl acrylate, n-hexyl methacrylate, and the like. Higher alkyl acrylic esters are decyl acrylate, isodecyl methacrylate, lauryl acrylate, stearyl acrylate, behenyl acrylate and melissyl acrylate and methacrylate versions thereof. Mixtures of two or three or more long chain acrylic esters may be successfully polymerized with one of the carboxylic monomers. Other comonomers include olefins, including alpha olefins, vinyl ethers, vinyl esters, and mixtures thereof.

Other vinylidene monomers, including the acrylic nitriles, may also be used as absorption-promoting agents within the methods and compositions of the invention to enhance delivery and absorption of one or more peptide YY proteins, analogs and mimetics, and other biologically active agent(s), including to enhance delivery of the active agent(s) to a target tissue or compartment in the subject (e.g., the liver, hepatic portal vein, CNS tissue or fluid, or blood plasma). Useful alpha, beta-olefinically unsaturated nitriles are preferably monoolefinically unsaturated nitriles having from 3 to 10 carbon atoms such as acrylonitrile, methacrylonitrile, and the like. Most preferred are acrylonitrile and methacrylonitrile. Acrylic amides containing from 3 to 35 carbon atoms including monoolefinically unsaturated amides also may be used. Representative amides include acrylamide, methacrylamide, N-t-butyl acrylamide, N-cyclohexyl acrylamide, higher alkyl amides, where the alkyl group on the nitrogen contains from 8 to 32 carbon atoms, acrylic amides including N-alkylol amides of alpha, beta-olefinically unsaturated carboxylic acids including those having from 4 to 10 carbon atoms such as N-methylol acrylamide, N-propanol acrylamide, N-methylol methacrylamide, N-methylol maleimide, N-methylol maleamic acid esters, N-methylol-p-vinyl benzamide, and the like.

Yet additional useful absorption promoting materials are alpha-olefins containing from 2 to 18 carbon atoms, more preferably from 2 to 8 carbon atoms; dienes containing from 4 to 10 carbon atoms; vinyl esters and allyl esters such as vinyl acetate; vinyl aromatics such as styrene, methyl styrene and chloro-styrene; vinyl and allyl ethers and ketones such as vinyl methyl ether and methyl vinyl ketone; chloroacrylates; cyanoalkyl acrylates such as alpha-cyanomethyl acrylate, and the alpha-, beta-, and gamma-cyanopropyl acrylates; alkoxyacrylates such as methoxy ethyl acrylate; haloacrylates as chloroethyl acrylate; vinyl halides and vinyl chloride, vinylidene chloride and the like; divinyls, diacrylates and other polyfunctional monomers such as divinyl ether, diethylene glycol diacrylate, ethylene glycol dimethacrylate, methylene-bis-acrylamide, allylpentaerythritol, and the like; and bis (beta-haloalkyl) alkenyl phosphonates such as bis(beta-chloroethyl) vinyl phosphonate and the like as are known to those skilled in the art. Copolymers wherein the carboxy containing monomer is a minor constituent, and the other vinylidene monomers present as major components are readily prepared in accordance with the methods disclosed herein.

When hydrogels are employed as absorption promoting agents within the invention, these may be composed of synthetic copolymers from the group of acrylic and methacrylic acids, acrylamide, methacrylamide, hydroxyethylacrylate (HEA) or methacrylate (HEMA), and vinylpyrrolidones which are water interactive and swellable. Specific illustrative examples of useful polymers, especially for the delivery of peptides or proteins, are the following types of polymers: (meth)acrylamide and 0.1 to 99 wt. % (meth) acrylic acid; (meth)acrylamides and 0.1–75 wt % (meth) acryloxyethyl trimethyammonium chloride; (meth)acrylamide and 0.1–75 wt % (meth)acrylamide; acrylic acid and 0.1–75 wt % alkyl(meth)acrylates; (meth)acrylamide and 0.1–75 wt % AMPS.RTM. (trademark of Lubrizol Corp.); (meth)acrylamide and 0 to 30 wt % alkyl(meth)acrylamides and 0.1–75 wt % AMPS.RTM.; (meth)acrylamide and 0.1–99 wt. % HEMA; (metb)acrylamide and 0.1 to 75 wt % HEMA and 0.1 to 99%(meth)acrylic acid; (meth)acrylic acid and 0.1–99 wt % HEMA; 50 mole % vinyl ether and 50 mole % maleic anhydride; (meth)acrylamide and 0.1 to 75 wt % (meth)acryloxyalky dimethyl benzylammonium chloride; (meth)acrylamide and 0.1 to 99 wt % vinyl pyrrolidone; (meth)acrylamide and 50 wt % vinyl pyrrolidone and 0.1–99.9 wt % (meth)acrylic acid; (meth)acrylic acid and 0.1 to 75 wt % AMPS.RTM. and-0.1–75 wt % alkyl(meth) acrylamide. In the above examples, alkyl means $C_1$ to $C_{30}$, preferably $C_1$ to $C_{22}$, linear and branched and $C_4$ to $C_{16}$ cyclic; where (meth) is used, it means that the monomers with and without the methyl group are included. Other very useful hydrogel polymers are swellable, but insoluble versions of poly(vinyl pyrrolidone) starch, carboxymethyl cellulose and polyvinyl alcohol.

Additional polymeric hydrogel materials useful within the invention include (poly) hydroxyalkyl (meth)acrylate: anionic and cationic hydrogels: poly(electrolyte) complexes; poly(vinyl alcohols) having a low acetate residual: a swellable mixture of crosslinked agar and crosslinked carboxymethyl cellulose: a swellable composition comprising methyl cellulose mixed with a sparingly crosslinked agar; a water swellable copolymer produced by a dispersion of finely divided copolymer of maleic anhydride with styrene, ethylene, propylene, or isobutylene; a water swellable polymer of N-vinyl lactams; swellable sodium salts of carboxymethyl cellulose; and the like.

Other gelable, fluid imbibing and retaining polymers useful for forming the hydrophilic hydrogel for mucosal delivery of biologically active agents within the invention include pectin; polysaccharides such as agar, acacia, karaya, tragacenth, algins and guar and their crosslinked versions; acrylic acid polymers, copolymers and salt derivatives, polyacrylamides; water swellable indene maleic anhydride polymers; starch graft copolymers; acrylate type polymers and copolymers with water absorbability of about 2 to 400 times its original weight; diesters of polyglucan; a mixture of crosslinked poly(vinyl alcohol) and poly(N-vinyl-2-pyrrolidone); polyoxybutylene-polyethylene block copolymer gels; carob gum; polyester gels; poly urea gels; polyether gels; polyamide gels; polyimide gels; polypeptide gels; polyamino acid gels; poly cellulosic gels; crosslinked indene-maleic anhydride acrylate polymers; and polysaccharides.

Synthetic hydrogel polymers for use within the invention may be made by an infinite combination of several monomers in several ratios. The hydrogel can be crosslinked and generally possesses the ability to imbibe and absorb fluid and swell or expand to an enlarged equilibrium state. The hydrogel typically swells or expands upon delivery to the nasal mucosal surface, absorbing about 2–5, 5–10, 10–50, up to 50–100 or more times fold its weight of water. The optimum degree of swellability for a given hydrogel will be determined for different biologically active agents depending upon such factors as molecular weight, size, solubility and diffusion characteristics of the active agent carried by or entrapped or encapsulated within the polymer, and the specific spacing and cooperative chain motion associated with each individual polymer.

Hydrophilic polymers useful within the invention are water insoluble but water swellable. Such water swollen polymers as typically referred to as hydrogels or gels. Such gels may be conveniently produced from water soluble polymer by the process of crosslinking the polymers by a suitable crosslinking agent. However, stable hydrogels may also be formed from specific polymers under defined conditions of pH, temperature and/or ionic concentration, according to know methods in the art. Typically the polymers are cross-linked, that is, cross-linked to the extent that the polymers possess good hydrophilic properties, have improved physical integrity (as compared to non cross-linked polymers of the same or similar type) and exhibit improved ability to retain within the gel network both the biologically active agent of interest and additional compounds for coadministration therewith such as a cytokine or enzyme inhibitor, while retaining the ability to release the active agent(s) at the appropriate location and time.

Generally hydrogel polymers for use within the invention are crosslinked with a difunctional cross-linking in the amount of from 0.01 to 25 weight percent, based on the weight of the monomers forming the copolymer, and more preferably from 0.1 to 20 weight percent and more often from 0.1 to 15 weight percent of the crosslinking agent. Another useful amount of a crosslinking agent is 0.1 to 10 weight percent. Tri, tetra or higher multifunctional crosslinking agents may also be employed. When such reagents are utilized, lower amounts may be required to attain equivalent crosslinking density, i.e., the degree of crosslinking, or network properties that are sufficient to contain effectively the biologically active agent(s).

The crosslinks can be covalent, ionic or hydrogen bonds with the polymer possessing the ability to swell in the presence of water containing fluids. Such crosslinkers and crosslinking reactions are known to those skilled in the art and in many cases are dependent upon the polymer system. Thus a crosslinked network may be formed by free radical copolymerization of unsaturated monomers. Polymeric hydrogels may also be formed by crosslinking preformed polymers by reacting functional groups found on the polymers such as alcohols, acids, amines with such groups as glyoxal, formaldehyde or glutaraldehyde, bis anhydrides and the like.

The polymers also may be cross-linked with any polyene, e.g. decadiene or trivinyl cyclohexane; acrylamides, such as N,N-methylene-bis (acrylamide); polyfunctional acrylates, such as trimethylol propane triacrylate; or polyfunctional vinylidene monomer containing at least 2 terminal CH.sub.2<groups, including, for example, divinyl benzene, divinyl naphthlene, allyl acrylates and the like. In certain embodiments, cross-linking monomers for use in preparing the copolymers are polyalkenyl polyethers having more than one alkenyl ether grouping per molecule, which may optionally possess alkenyl groups in which an olefinic double bond is present attached to a terminal methylene grouping (e.g., made by the etherification of a polyhydric alcohol containing at least 2 carbon atoms and at least 2 hydroxyl groups). Compounds of this class may be produced by reacting an alkenyl halide, such as allyl chloride or allyl bromide, with a strongly alkaline aqueous solution of one or more polyhydric alcohols. The product may be a complex mixture of polyethers with varying numbers of ether groups. Efficiency of the polyether cross-linking agent increases with the number of potentially polymerizable groups on the molecule. Typically, polyethers containing an average of two or more alkenyl ether groupings per molecule are used. Other cross-linking monomers include for example, diallyl esters, dimethallyl ethers, allyl or methallyl acrylates and acrylamides, tetravinyl silane, polyalkenyl methanes, diacrylates, and dimethacrylates, divinyl compounds such as divinyl benzene, polyallyl phosphate, diallyloxy compounds and phosphite esters and the like. Typical agents are allyl pentaerythritol, allyl sucrose, trimethylolpropane triacrylate, 1,6-hexanediol diacrylate, trimethylolpropane diallyl ether, pentaerythritol triacrylate, tetramethylene dimethacrylate, ethylene diacrylate, ethylene dimethacrylate, triethylene glycol dimethacrylate, and the like. Allyl pentaerythritol, trimethylolpropane diallylether and allyl sucrose provide suitable polymers. When the cross-linking agent is present, the polymeric mixtures usually contain between about 0.01 to 20 weight percent, e.g., 1%, 5%, or 10% or more by weight of cross-linking monomer based on the total of carboxylic acid monomer, plus other monomers.

In more detailed aspects of the invention, mucosal delivery of peptide YY proteins, analogs and mimetics, and other biologically active agents disclosed herein, is enhanced by retaining the active agent(s) in a slow-release or enzymatically or physiologically protective carrier or vehicle, for example a hydrogel that shields the active agent from the action of the degradative enzymes. In certain embodiments, the active agent is bound by chemical means to the carrier or vehicle, to which may also be admixed or bound additional agents such as enzyme inhibitors, cytokines, etc. The active agent may alternately be immobilized through sufficient physical entrapment within the carrier or vehicle, e.g., a polymer matrix.

Polymers such as hydrogels useful within the invention may incorporate functional linked agents such as glycosides chemically incorporated into the polymer for enhancing intranasal bioavailability of active agents formulated therewith. Examples of such glycosides are glucosides, fructosides, galactosides, arabinosides, mannosides and their alkyl substituted derivatives and natural glycosides such as arbutin, phlorizin, amygdalin, digitonin, saponin, and indican. There are several ways in which a typical glycoside may be bound to a polymer. For example, the hydrogen of the hydroxyl groups of a glycoside or other similar carbohydrate may be replaced by the alkyl group from a hydrogel polymer to form an ether. Also, the hydroxyl groups of the glycosides may be reacted to esterify the carboxyl groups of a polymeric hydrogel to form polymeric esters in situ. Another approach is to employ condensation of acetobromoglucose with cholest-5-en-3beta-ol on a copolymer of maleic acid. N-substituted polyacrylamides can be synthesized by the reaction of activated polymers with omega-aminoalkylglycosides: (1) (carbohydrate-spacer)(n)-polyacrylamide, 'pseudopolysaccharides'; (2) (carbohydrate spacer)(n)-phosphatidylethanolamine(m)-polyacrylamide, neoglycolipids, derivatives of phosphatidylethanolamine; (3) (carbohydrate-spacer)(n)-biotin(m)-polyacrylamide. These biotinylated derivatives may attach to lectins on the mucosal surface to facilitate absorption of the biologically active agent(s), e.g., a polymer-encapsulated peptide YY.

Within more detailed aspects of the invention, one or more peptide YY proteins, analogs and mimetics, and/or other biologically active agents, disclosed herein, optionally including secondary active agents such as protease inhibitor(s), cytokine(s), additional modulator(s) of intercellular junctional physiology, etc., are modified and bound to a polymeric carrier or matrix. For example, this may be accomplished by chemically binding a peptide or protein active agent and other optional agent(s) within a crosslinked polymer network. It is also possible to chemically modify the polymer separately with an interactive agent such as a glycosidal containing molecule. In certain aspects, the biologically active agent(s), and optional secondary active agent(s), may be functionalized, i.e., wherein an appropriate reactive group is identified or is chemically added to the active agent(s). Most often an ethylenic polymerizable group is added, and the functionalized active agent is then copolymerized with monomers and a crosslinking agent using a standard polymerization method such as solution polymerization (usually in water), emulsion, suspension or dispersion polymerization. Often, the functionalizing agent is provided with a high enough concentration of functional or polymerizable groups to insure that several sites on the active agent(s) are functionalized. For example, in a polypeptide comprising 16 amine sites, it is generally desired to functionalize at least 2, 4, 5, 7, and up to 8 or more of the sites.

After functionalization, the functionalized active agent(s) is/are mixed with monomers and a crosslinking agent that comprise the reagents from which the polymer of interest is formed. Polymerization is then induced in this medium to create a polymer containing the bound active agent(s). The polymer is then washed with water or other appropriate solvents and otherwise purified to remove trace unreacted impurities and, if necessary, ground or broken up by physical means such as by stirring, forcing it through a mesh, ultrasonication or other suitable means to a desired particle size. The solvent, usually water, is then removed in such a manner as to not denature or otherwise degrade the active agent(s). One desired method is lyophilization (freeze drying) but other methods are available and may be used (e.g., vacuum drying, air drying, spray drying, etc.).

To introduce polymerizable groups in peptides, proteins and other active agents within the invention, it is possible to react available amino, hydroxyl, thiol and other reactive groups with electrophiles containing unsaturated groups. For example, unsaturated monomers containing N-hydroxy succinimidyl groups, active carbonates such as p-nitrophenyl carbonate, trichlorophenyl carbonates, tresylate, oxycarbonylimidazoles, epoxide, isocyanates and aldehyde, and unsaturated carboxymethyl azides and unsaturated orthopyridyl-disulfide belong to this category of reagents. Illustrative examples of unsaturated reagents are allyl glycidyl ether, allyl chloride, allylbromide, allyl iodide, acryloyl chloride, allyl isocyanate, allylsulfonyl chloride, maleic anhydride, copolymers of maleic anhydride and allyl ether, and the like.

All of the lysine active derivatives, except aldehyde, can generally react with other amino acids such as imidazole groups of histidine and hydroxyl groups of tyrosine and the thiol groups of cystine if the local environment enhances nucleophilicity of these groups. Aldehyde containing functionalizing reagents are specific to lysine. These types of reactions with available groups from lysines, cysteines, tyrosine have been extensively documented in the literature and are known to those skilled in the art.

In the case of biologically active agents that contain amine groups, it is convenient to react such groups with an acyloyl chloride, such as acryloyl chloride, and introduce the polymerizable acrylic group onto the reacted agent. Then during preparation of the polymer, such as during the crosslinking of the copolymer of acrylamide and acrylic acid, the functionalized active agent, through the acrylic groups, is attached to the polymer and becomes bound thereto.

In additional aspects of the invention, biologically active agents, including peptides, proteins, nucleosides, and other molecules which are bioactive in vivo, are conjugation-stabilized by covalently bonding one or more active agent(s) to a polymer incorporating as an integral part thereof both a hydrophilic moiety, e.g., a linear polyalkylene glycol, a lipophilic moiety (see, e.g., U.S. Pat. No. 5,681,811, incorporated herein by reference). In one aspect, a biologically active agent is covalently coupled with a polymer comprising (i) a linear polyalkylene glycol moiety and (ii) a lipophilic moiety, wherein the active agent, linear polyalkylene glycol moiety, and the lipophilic moiety are conformationally arranged in relation to one another such that the active therapeutic agent has an enhanced in vivo resistance to enzymatic degradation (i.e., relative to its stability under similar conditions in an unconjugated form devoid of the polymer coupled thereto). In another aspect, the conjugation-stabilized formulation has a three-dimensional conformation comprising the biologically active agent covalently coupled with a polysorbate complex comprising (i) a linear polyalkylene glycol moiety and (ii) a lipophilic moiety, wherein the active agent, the linear polyalkylene glycol moiety and the lipophilic moiety are conformationally arranged in relation to one another such that (a) the lipophilic moiety is exteriorly available in the three-dimensional conformation, and (b) the active agent in the composition has an enhanced in vivo resistance to enzymatic degradation.

In a further related aspect, a multiligand conjugated complex is provided which comprises a biologically active agent covalently coupled with a triglyceride backbone moiety through a polyalkylene glycol spacer group bonded at a carbon atom of the triglyceride backbone moiety, and at least one fatty acid moiety covalently attached either directly to a carbon atom of the triglyceride backbone moiety or covalently joined through a polyalkylene glycol spacer moiety (see, e.g., U.S. Pat. No. 5,681,811, incorporated herein by reference). In such a multiligand conjugated therapeutic agent complex, the alpha' and beta carbon atoms of the triglyceride bioactive moiety may have fatty acid moieties attached by covalently bonding either directly thereto, or indirectly covalently bonded thereto through polyalkylene glycol spacer moieties. Alternatively, a fatty acid moiety may be covalently attached either directly or through a polyalkylene glycol spacer moiety to the alpha and alpha' carbons of the triglyceride backbone moiety, with the bioactive therapeutic agent being covalently coupled with the gamma-carbon of the triglyceride backbone moiety, either being directly covalently bonded thereto or indirectly bonded thereto through a polyalkylene spacer moiety. It will be recognized that a wide variety of structural, compositional, and conformational forms are possible for the multiligand conjugated therapeutic agent complex comprising the triglyceride backbone moiety, within the scope of the invention. It is further noted that in such a multiligand conjugated therapeutic agent complex, the biologically active agent(s) may advantageously be covalently coupled with the triglyceride modified backbone moiety through alkyl spacer groups, or alternatively other acceptable spacer groups, within the scope of the invention. As used in such context, acceptability of the spacer group refers to steric, compositional, and end use application specific acceptability characteristics.

In yet additional aspects of the invention, a conjugation-stabilized complex is provided which comprises a polysorbate complex comprising a polysorbate moiety including a triglyceride backbone having covalently coupled to alpha, alpha' and beta carbon atoms thereof functionalizing groups including (i) a fatty acid group; and (ii) a polyethylene glycol group having a biologically active agent or moiety covalently bonded thereto, e.g., bonded to an appropriate functionality of the polyethylene glycol group. U.S. Pat. No. 5,681,811, incorporated herein by reference. Such covalent bonding may be either direct, e.g., to a hydroxy terminal functionality of the polyethylene glycol group, or alternatively, the covalent bonding may be indirect, e.g., by reactively capping the hydroxy terminus of the polyethylene glycol group with a terminal carboxy functionality spacer group, so that the resulting capped polyethylene glycol group has a terminal carboxy functionality to which the biologically active agent or moiety may be covalently bonded.

In yet additional aspects of the invention, a stable, aqueously soluble, conjugation-stabilized complex is provided which comprises one or more peptide YY proteins, analogs and mimetics, and/or other biologically active agent(s)+ disclosed herein covalently coupled to a physiologically compatible polyethylene glycol (PEG) modified glycolipid moiety. In such complex, the biologically active agent(s) may be covalently coupled to the physiologically compatible PEG modified glycolipid moiety by a labile covalent bond at a free amino acid group of the active agent, wherein the labile covalent bond is scissionable in vivo by biochemical hydrolysis and/or proteolysis. The physiologically compatible PEG modified glycolipid moiety may advantageously comprise a polysorbate polymer, e.g., a polysorbate polymer comprising fatty acid ester groups selected from the group consisting of monopalmitate, dipalmitate, monolaurate, dilaurate, trilaurate, monoleate, dioleate, trioleate, monostearate, distearate, and tristearate. In such complex, the physiologically compatible PEG modified glycolipid moiety may suitably comprise a polymer selected from the group consisting of polyethylene glycol ethers of fatty acids, and polyethylene glycol esters of fatty acids, wherein the fatty acids for example comprise a fatty acid selected from the group consisting of lauric, palmitic, oleic, and stearic acids.

Storage of Material

In certain aspects of the invention, the combinatorial formulations and/or coordinate administration methods herein incorporate an effective amount of peptides and proteins which may adhere to charged glass thereby reducing the effective concentration in the container. Silanized containers, for example, silanized glass containers, are used to store the finished product to reduce adsorption of the polypeptide or protein to a glass container.

In yet additional aspects of the invention, a kit for treatment of a mammalian subject comprises a stable pharmaceutical composition of one or more peptide YY compound(s) formulated for mucosal delivery to the mammalian subject wherein the composition is effective to alleviate one or more symptom(s) of obesity, cancer, or malnutrition or wasting related to cancer in said subject without unacceptable adverse side effects. The kit further comprises a pharmaceutical reagent vial to contain the one or more peptide YY compounds. The pharmaceutical reagent vial is composed of pharmaceutical grade polymer, glass or other suitable material. The pharmaceutical reagent vial is, for example, a silanized glass vial. The kit further comprises an aperture for delivery of the composition to a nasal mucosal surface of the subject. The delivery aperture is composed of a pharmaceutical grade polymer, glass or other suitable material. The delivery aperture is, for example, a silanized glass.

A silanization technique combines a special cleaning technique for the surfaces to be silanized with a silanization process at low pressure. The silane is in the gas phase and at an enhanced temperature of the surfaces to be silanized. The method provides reproducible surfaces with stable, homogeneous and functional silane layers having characteristics of a monolayer. The silanized surfaces prevent binding to the glass of polypeptides or mucosal delivery enhancing agents of the present invention. See WO 83/02669 A1, incorporated herein by reference.

The procedure is useful to prepare silanized pharmaceutical reagent vials to hold peptide YY compositions of the present invention. Glass trays are cleaned by rinsing with double distilled water (ddH$_2$O) before using. The silane tray is then be rinsed with 95% EtOH, and the acetone tray is rinsed with acetone. Pharmaceutical reagent vials are sonicated in acetone for 10 minutes. After the acetone sonication, reagent vials are washed in ddH$_2$O tray at least twice. Reagent vials are sonicated in 0.1M NaOH for 10 minutes. While the reagent vials are sonicating in NaOH, the silane solution is made under a hood. (Silane solution: 800 mL of 95% ethanol; 96 L of glacial acetic acid; 25 mL of glycidoxypropyltrimethoxy silane). After the NaOH sonication, reagent vials are washed in ddH$_2$O tray at least twice. The reagent vials are sonicated in silane solution for 3 to 5 minutes. The reagent vials are washed in 100% EtOH tray. The reagent vials are dried with prepurified N$_2$ gas and stored in a 100° C. oven for at least 2 hours before using.

Bioadhesive Delivery Vehicles and Methods

In certain aspects of the invention, the combinatorial formulations and/or coordinate administration methods herein incorporate an effective amount of a nontoxic bioadhesive as an adjunct compound or carrier to enhance mucosal delivery of one or more biologically active agent(s). Bioadhesive agents in this context exhibit general or specific adhesion to one or more components or surfaces of the targeted mucosa. The bioadhesive maintains a desired concentration gradient of the biologically active agent into or across the mucosa to ensure penetration of even large molecules (e.g., peptides and proteins) into or through the mucosal epithelium. Typically, employment of a bioadhesive within the methods and compositions of the invention yields a two- to five- fold, often a five- to ten-fold increase in permeability for peptides and proteins into or through the mucosal epithelium. This enhancement of epithelial permeation often permits effective transmucosal delivery of large macromolecules, for example to the basal portion of the nasal epithelium or into the adjacent extracellular compartments or a blood plasma or CNS tissue or fluid.

This enhanced delivery provides for greatly improved effectiveness of delivery of bioactive peptides, proteins and other macromolecular therapeutic species. These results will depend in part on the hydrophilicity of the compound, whereby greater penetration will be achieved with hydrophilic species compared to water insoluble compounds. In addition to these effects, employment of bioadhesives to enhance drug persistence at the mucosal surface can elicit a reservoir mechanism for protracted drug delivery, whereby compounds not only penetrate across the mucosal tissue but also back-diffuse toward the mucosal surface once the material at the surface is depleted.

A variety of suitable bioadhesives are disclosed in the art for oral administration, U.S. Pat. Nos. 3,972,995; 4,259,314; 4,680,323; 4,740,365; 4,573,996; 4,292,299; 4,715,369; 4,876,092; 4,855,142; 4,250,163; 4,226,848; 4,948,580, U.S. Pat. No. Reissue 33,093; and Robinson, 18 Proc. Intern. Symp. Control. Rel. Bioact. Mater. 75, 1991, each incorporated herein by reference, which find use within the novel methods and compositions of the invention. The potential of various bioadhesive polymers as a mucosal, e.g., nasal, delivery platform within the methods and compositions of the invention can be readily assessed by determining their ability to retain and release a specific biologically active agent, e.g., a peptide YY, as well as by their capacity to interact with the mucosal surfaces following incorporation of the active agent therein. In addition, well known methods will be applied to determine the biocompatibility of selected polymers with the tissue at the site of mucosal administration. One aspect of polymer biocompatibility is the potential effect for the polymer to induce a cytokine response. In certain circumstances, implanted polymers have been shown to induce the release of inflammatory cytokines from adhering cells, such as monocytes and macrophages. Similar potential adverse reactions of mucosal epithelial cells in contact with candidate bioadhesive polymers will be determined using routine in vitro and in vivo assays. Since epithelial cells have the ability to secrete a number of cytokines, the induction of cytokine responses in epithelial cells will often provide an adequate measure of biocompatibility of a selected polymer delivery platform.

When the target mucosa is covered by mucus (i.e., in the absence of mucolytic or mucus-clearing treatment), it can serve as a connecting link to the underlying mucosal epithelium. Therefore, the term "bioadhesive" as used herein also covers mucoadhesive compounds useful for enhancing mucosal delivery of biologically active agents within the invention. However, adhesive contact to mucosal tissue mediated through adhesion to a mucus gel layer may be limited by incomplete or transient attachment between the mucus layer and the underlying tissue, particularly at nasal surfaces where rapid mucus clearance occurs. In this regard, mucin glycoproteins are continuously secreted and, immediately after their release from cells or glands, form a viscoelastic gel. The luminal surface of the adherent gel layer, however, is continuously eroded by mechanical, enzymatic and/or ciliary action. Where such activities are more prominent, or where longer adhesion times are desired, the coordinate administration methods and combinatorial formulation methods of the invention may further incorporate mucolytic and/or ciliostatic methods or agents as disclosed herein above.

Bioadhesive and other delivery enhancing agents within the methods and compositions of the invention can improve the effectiveness of a treatment by helping maintain the drug concentration between effective and toxic levels, by inhibiting dilution of the drug away from the delivery point, and improving targeting and localization of the drug. In this context, bioadhesion increases the intimacy and duration of contact between a drug-containing polymer and the mucosal surface. The combined effects of this enhanced, direct drug absorption, and the decrease in excretion rate that results from reduced diffusion and improved localization, significantly enhances bioavailability of the drug and allows for a smaller dosage and less frequent administration.

Typically, mucoadhesive polymers for use within the invention are natural or synthetic macromolecules which adhere to wet mucosal tissue surfaces by complex, but non-specific, mechanisms. In addition to these mucoadhesive polymers, the invention also provides methods and compositions incorporating bioadhesives that adhere directly to a cell surface, rather than to mucus, by means of specific, including receptor-mediated, interactions. One example of bioadhesives that function in this specific manner is the group of compounds known as lectins. These are glycoproteins with an ability to specifically recognize and bind to sugar molecules, e.g. glycoproteins or glycolipids, which form part of intranasal epithelial cell membranes and can be considered as "lectin receptors".

In various embodiments, the coordinate administration methods of the invention optionally incorporate bioadhesive materials that yield prolonged residence time at the mucosal surface. Alternatively, the bioadhesive material may otherwise facilitate mucosal absorption of the biologically active agent, e.g., by facilitating localization of the active agent to a selected target site of activity (e.g., the liver, CNS tissue or fluid, or blood plasma). In additional aspects, adjunct delivery or combinatorial formulation of bioadhesive agents within the methods and compositions of the invention intensify contact of the biologically active agent with the target mucosa, including by increasing epithelial permeability, (e.g., to effectively increase the drug concentration gradient). In further alternate embodiments, bioadhesives and other polymers disclosed herein serve to inhibit proteolytic or other enzymes that might degrade the biologically active agent. For a review of different approaches to bioadhesion that are useful within the coordinate administration, multi-processing and/or combinatorial formulation methods and compositions of the invention. Lehr C. M., *Eur J. Drug Metab. Pharmacokinetics,* 21:139–148, 1996, incorporated herein by reference.

In certain aspects of the invention, bioadhesive materials for enhancing intranasal delivery of biologically active agents comprise a matrix of a hydrophilic, e.g., water soluble or swellable, polymer or a mixture of polymers that can adhere to a wet mucous surface. These adhesives may be formulated as ointments, hydrogels (see above) thin films, and other application forms. Often, these adhesives have the biologically active agent mixed therewith to effectuate slow release or local delivery of the active agent. Some are formulated with additional ingredients to facilitate penetration of the active agent through the nasal mucosa, e.g., into the circulatory system of the individual.

Various polymers, both natural and synthetic ones, show significant binding to mucus and/or mucosal epithelial surfaces under physiological conditions. The strength of this interaction can readily be measured by mechanical peel or shear tests. A variety of suitable test methods and instruments to serve such purposes are known in the art. Gu et al., *Crit. Rev. Ther. Drug Carrier Syst.,* 5:21–67, 1988; Duchene et al., *Drug Dev. Ind. Pharm.* 14:283–318, 1988, incorporated herein by reference. When applied to a humid mucosal surface, many dry materials will spontaneously adhere, at least slightly. After such an initial contact, some hydrophilic materials start to attract water by adsorption, swelling or capillary forces, and if this water is absorbed from the underlying substrate or from the polymer-tissue interface, the adhesion may be sufficient to achieve the goal of enhancing mucosal absorption of biologically active agents. Al-Dujaili et al., *Int. J. Pharm.,* 34:75–79, 1986; Marvola et al., *J. Pharm. Sci.,* 72:1034–1036, 1983; Marvola et al., *J. Pharm. Sci.,* 71:975–977, 1982; and Swisher et al., *Int. J. Pharm.,* 22:219, 1984; Chen, et al., *Adhesion in Biological Systems,* 172, Manly, Ed., Academic Press, London, 1970, each incorporated herein by reference. Such 'adhesion by hydration' can be quite strong, but formulations adapted to employ this mechanism must account for swelling which continues as the dosage transforms into a hydrated mucilage. This is projected for many hydrocolloids useful within the invention, especially some cellulose-derivatives, which are generally non-adhesive when applied in pre-hydrated state. Nevertheless, bioadhesive drug delivery systems for mucosal administration are effective within the invention when such materials are applied in the form of a dry polymeric powder, microsphere, or film-type delivery form.

Other polymers adhere to mucosal surfaces not only when applied in dry, but also in fully hydrated state, and in the presence of excess amounts of water. The selection of a mucoadhesive thus requires due consideration of the conditions, physiological as well as physico-chemical, under which the contact to the tissue will be formed and maintained. In particular, the amount of water or humidity usually present at the intended site of adhesion, and the prevailing pH, are known to largely affect the mucoadhesive binding strength of different polymers.

Several polymeric bioadhesive drug delivery systems have been fabricated and studied in the past 20 years, not always with success. A variety of such carriers are, however, currently used in clinical applications involving dental, orthopedic, ophthalmological, and surgical uses. For example, acrylic-based hydrogels have been used extensively for bioadhesive devices. Acrylic-based hydrogels are well-suited for bioadhesion due to their flexibility and nonabrasive characteristics in the partially swollen state which reduce damage-causing attrition to the tissues in contact. Park et al., *J. Control. Release,* 2:47–57, 1985, incorporated herein by reference. Furthermore, their high permeability in the swollen state allows unreacted monomer, un-crosslinked polymer chains, and the initiator to be washed out of the matrix after polymerization, which is an important feature for selection of bioadhesive materials for use within the invention. Acrylic-based polymer devices exhibit very high adhesive bond strength, as determined by various known methods. Park et al., *J. Control. Release,* 2:47–57, 1985; Park et al., *Pharm. Res,* 4:457–464, 1987; and Ch'ng et al., *J. Pharm. Sci.,* 74:399–405, 1985, each incorporated herein by reference.

For controlled mucosal delivery of peptide and protein drugs, the methods and compositions of the invention optionally include the use of carriers, e.g., polymeric delivery vehicles, that function in part to shield the biologically active agent from proteolytic breakdown, while at the same time providing for enhanced penetration of the peptide or protein into or through the nasal mucosa. In this context, bioadhesive polymers have demonstrated considerable potential for enhancing oral drug delivery. As an example, the bioavailability of 9-desglycinamide, 8-arginine vasopressin (DGAVP) intraduodenally administered to rats together with a 1% (w/v) saline dispersion of the mucoadhesive poly(acrylic acid) derivative polycarbophil, was 3–5-fold increased compared to an aqueous solution of the peptide drug without this polymer. Lehr et al., *J. Pharm. Pharmacol.*, 44:402–407, 1992, incorporated herein by reference. In this study, the drug was not bound to or otherwise integrally associated with the mucoadhesive polymer in the formulation, which would therefore not be expected to yield enhanced peptide absorption via prolonged residence time or intensified contact to the mucosal surface. Thus, certain bioadhesive polymers for use within the invention will directly enhance the permeability of the epithelial absorption barrier in part by protecting the active agent, e.g., peptide or protein, from enzymatic degradation.

Recent studies have shown that mucoadhesive polymers of the poly(acrylic acid)-type are potent inhibitors of some intestinal proteases. Lueβen et al., *Pharm. Res.*, 12:1293–1298; 1995; Lueβen et al., *J. Control. Rel.*, 29:329–338, 1994; and Bai et al., *J. Pharm. Sci.*, 84:1291–1294; 1995, incorporated herein by reference. The mechanism of enzyme inhibition is explained by the strong affinity of this class of polymers for divalent cations, such as calcium or zinc, which are essential cofactors of metalloproteinases, such as trypsin and chymotrypsin. Depriving the proteases of their cofactors by poly(acrylic acid) was reported to induce irreversible structural changes of the enzyme proteins which were accompanied by a loss of enzyme activity. At the same time, other mucoadhesive polymers (e.g., some cellulose derivatives and chitosan) may not inhibit proteolytic enzymes under certain conditions. In contrast to other enzyme inhibitors contemplated for use within the invention (e.g. aprotinin, bestatin), which are relatively small molecules, the trans-nasal absorption of inhibitory polymers is likely to be minimal in light of the size of these molecules, and thereby eliminate possible adverse side effects. Thus, mucoadhesive polymers, particularly of the poly(acrylic acid)-type, may serve both as an absorption-promoting adhesive and enzyme-protective agent to enhance controlled delivery of peptide and protein drugs, especially when safety concerns are considered.

In addition,to protecting against enzymatic degradation, bioadhesives and other polymeric or non-polymeric absorption-promoting agents for use within the invention may directly increase mucosal permeability to biologically active agents. To facilitate the transport of large and hydrophilic molecules, such as peptides and proteins, across the nasal epithelial barrier, mucoadhesive polymers and other agents have been postulated to yield enhanced permeation effects beyond what is accounted for by prolonged premucosal residence time of the delivery system. For example, nasal administration of insulin to non-primate mammals in the presence of mucoadhesive starch microspheres yielded a steeply enhanced early absorption peak, followed by a continuous decline. Bjork et al., *Int. J. Pharm.*, 47:233–238, 1988; Farraj et al., *J. Control. Rel.*, 13:253–262, 1990, each incorporated herein by reference. The time course of drug plasma concentrations reportedly suggested that the bioadhesive microspheres caused an acute, but transient increase of insulin permeability across the nasal mucosa. In other studies using in vitro cultured epithelial cell monolayers, Bjork et al., *J. Drug Taraeting*, 1995, incorporated herein by reference, it was reported that dry, swellable materials such as starch microspheres induce reversible focal dilations of the tight junctions, allowing for enhanced drug transport along the paracellular route. According to this adhesion-dehydration theory, the hydrophilic polymer, applied as a dry powder, absorbs water from the mucosal tissue in such a way that the epithelial cells are dehydrated and shrink until the normally tight intercellular junctions between the cells become physically separated. Because this effect is of relatively short duration and appears to be completely reversible, it provides yet another useful tool for incorporation within the coordinate administration, multi-processing and/or combinatorial formulation methods and compositions of the invention.

Other mucoadhesive polymers for use within the invention, for example chitosan, reportedly enhance the permeability of certain mucosal epithelia even when they are applied as an aqueous solution or gel. Lehr et al., *Int. J. Pharmaceut.*, 78:43–48, 1992; Illum et al., *Pharm. Res.*, 11:1186–1189, 1994; Artursson et al., *Pharm. Res.*, 11:1358–1361, 1994; and Borchard, et al., *J. Control. Release*, 39:131–138, 1996, each incorporated herein by reference. In one study, absorption of the peptide drugs insulin and calcitonin, and the hydrophilic compound phenol red, from an aqueous gel base of poly(acrylic acid) was reported after rectal, vaginal and nasal administration. Morimoto et al., *Int. J. Pharm.*, 14:149–157, 1983; and Morimoto et al., *J. Pharmacobiodyn*, 10:85–91, 1987, each incorporated herein by reference. Another mucoadhesive polymer reported to directly affect epithelial permeability is hyaluronic acid. In particular, hyaluronic acid gel formulation reportedly enhanced nasal absorption of vasopressin and some of its analogues. Morimoto et al., *Pharm. Res.*, 8:471–474, 1991, incorporated herein by reference. Hyaluronic acid was also reported to increase the absorption of insulin from the conjunctiva in diabetic dogs. Nomura, et al., *J. Pharm. Pharmacol.*, 46:768–770, 1994, incorporated herein by reference. Ester derivatives of hyaluronic acid in the form of lyophilized microspheres were described as a nasal delivery system for insulin. Illum et al., *J. Contr. Rel.*, 29:133–141, 1994, incorporated herein by reference.

A particularly useful bioadhesive agent within the coordinate administration, and/or combinatorial formulation methods and compositions of the invention is chitosan, as well as its analogs and derivatives. Chitosan is a non-toxic, biocompatible and biodegradable polymer that is widely used for pharmaceutical and medical applications because of its favorable properties of low toxicity and good biocompatibility. Yomota, *Pharm. Tech. Japan*, 10:557–564, 1994, incorporated herein by reference. It is a natural polyaminosaccharide prepared from chitin by N-deacetylation with alkali. A wide variety of biomedical uses for chitosan have been reported over the last two decades, based for example on its reported wound healing, antimicrobial and hemostatic properties. Kas, *J. Microencapsulation*, 14:689–711, 1997, incorporated herein by reference. Chitosan has also been used as a pharmaceutical excipient in conventional dosage forms as well as in novel applications involving bioadhesion and transmucosal drug transport. Illum, *Pharm. Res.* 15:1326–1331, 1998; and Olsen et al., *Chitin and Chitosan-sources, Chemistry, Biochemistry, Physical Properties and Applications*, 813–828, Skjak-Braek et al., Eds., Elsevier, London, 1989, each incorporated herein by reference. Furthermore, chitosan has been reported to promote absorption of small polar molecules and peptide and protein drugs through nasal mucosa in animal models and human volunteers. Illum et al., *Pharm. Res.*, 11:1186–1189, 1994, incorporated herein by reference. Other studies have shown an enhancing effect on penetration of compounds across the intestinal mucosa and cultured Caco-2 cells. Schipper et al., *Pharm. res.* 14:23–29, 1997; and Kotze et al., *Int. J. Pharm.*, 159:243–253, 1997, each incorporated herein by reference. Chitosan has also been proposed as a bioadhesive polymer for use in oral mucosal drug delivery. Miyazaki et al., *Biol. Pharm. Bull.*, 17:745–747, 1994; Ikinci et al., *Advances in Chitin Science*, Vol. 4, Peter et al., Eds., University of Potsdam, in press; Senel, et al., *Int. J. Pharm.*, 193:197–203, 2000; Needleman, et al., *J. Clin. Periodontol.*, 24:394–400, 1997, each incorporated herein by reference. Initial studies showed that chitosan has an extended retention time on the oral mucosa, Needleman et al., *J. Clin. Periodontol.*, 25:74–82, 1998, incorporated herein by reference, and with its antimicrobial properties and biocompatibility is an excellent candidate for the treatment of oral mucositis. More recently, Senel et al., *Biomaterials*, 21:2067–2071, 2000, incorporated herein by reference, reported that chitosan provides an effective gel carrier for delivery of the bioactive peptide, transforming growth factor-β(TGF-β).

As used within the methods and compositions of the invention, chitosan increases the retention of peptide YY proteins, analogs and mimetics, and other biologically active agents disclosed herein at a mucosal site of application. This is may be mediated in part by a positive charge characteristic of chitosan, which may influence epithelial permeability even after physical removal of chitosan from the surface. Schipper et al., *Pharm. Res.*, 14:23–29, 1997, incorporated herein by reference. Another mechanism of action of chitosan for improving transport of biologically active agents across mucosal membranes may be attributed to transient opening of the tight junctions in the cell membrane to allow polar compounds to penetrate. Illum et al., *Pharm. Res.*, 11:1186–1189, 1994; Lueben et al., *J. Control. Rel.*, 29:329–338, 1994, each incorporated herein by reference. Chitosan may also increase the thermodynamic activity of other absorption-promoting agents used in certain formulations of the invention, resulting in enhanced penetration. Lastly, as chitosan has been reported to disrupt lipid micelles in the intestine, Muzzarelli et al., *EUCHIS'99, Third International Conference of the European Chitin Society*, Abstract Book, ORAD-PS-059, Potsdam, Germany, 1999, each incorporated herein by reference, its absorption-promoting effects may be due in part to its interference with the lipid organization in the mucosal epithelium.

As with other bioadhesive gels provided herein, the use of chitosan can reduce the frequency of application and the amount of biologically active agent administered while yielding an effective delivery amount or dose. This mode of administration can also improve patient compliance and acceptance. The occlusion and lubrication of chitosan and other bioadhesive gels is expected to reduce the discomfort of inflammatory, allergic and ulcerative conditions of the nasal mucosa. In addition, chitosan acts non-specifically on certain deleterious microorganisms, including fungi, Knapczyk, *Chitin World*, pp. 504–511, Karnicki et al., Eds., Wirtschaftverlag NW, Germany, 1994, incorporated herein by reference, and may also beneficially stimulate cell proliferation and tissue organization by acting as an inductive primer to repair and physiologically rebuild damaged tissue. Muzzarelli et al. *Biomaterials*, 10:598–603, 1989, incorporated herein by reference.

As further provided herein, the methods and compositions of the invention will optionally include a novel chitosan derivative or chemically modified form of chitosan. One such novel derivative for use within the invention is denoted as a β-[1→4]-2-guanidino-2-deoxy-D-glucose polymer (poly-GuD). Chitosan is the N-deacetylated product of chitin, a naturally occurring polymer that has been used extensively to prepare microspheres for oral and intra-nasal formulations. The chitosan polymer has also been proposed as a soluble carrier for parenteral drug delivery. Within one aspect of the invention, o-methylisourea is used to convert a chitosan amine to its guanidinium moiety. The guanidinium compound is prepared, for example, by the reaction between equi-normal solutions of chitosan and o-methylisourea at pH above 8.0, as depicted by the equation shown in FIG. 1.

The guanidinium product is -[14]-guanidino-2-deoxy-D-glucose polymer. It is abbreviated as Poly-GuD in this context (Monomer F. W. of Amine in Chitosan=161; Monomer F. W. of Guanidinium in Poly-GuD=203).

One exemplary Poly-GuD preparation method for use within the invention involves the following protocol.

Solutions:

Preparation of 0.5% Acetic Acid Solution (0.088N):

Pipette 2.5 mL glacial acetic acid into a 500 mL volumetric flask, dilute to volume with purified water.

Preparation of 2N NaOH Solution:

Transfer about 20 g NaOH pellets into a beaker with about 150 mL of purified water. Dissolve and cool to room temperature. Transfer the solution into a 250-mL volumetric flask, dilute to volume with purified water.

Preparation of O-methylisourea Sulfate (0.4N urea group equivalent):

Transfer about 493 mg of 0-methylisourea sulfate into a 10-mL volumetric flask, dissolve and dilute to volume with purified water.

The pH of the solution is 4.2

Preparation of Barium Chloride Solution (0.2M):

Transfer about 2.086 g of Barium chloride into a 50-mL volumetric flask, dissolve and dilute to volume with purified water.

Preparation of Chitosan Solution (0.06N amine equivalent):

Transfer about 100 mg Chitosan into a 50 mL beaker, add 10 mL 0.5% Acetic Acid (0.088 N). Stir to dissolve completely.

The pH of the solution is about 4.5

Preparation of O-methylisourea Chloride Solution (0.2N urea group equivalent):

Pipette 5.0 mL of O-methylisourea sulfate solution (0.4 N urea group equivalent) and 5 mL of 0.2M Barium chloride solution into a beaker. A precipitate is formed. Continue to mix the solution for additional 5 minutes. Filter the solution through 0.45 m filter and discard the precipitate. The concentration of O-methylisourea chloride in the supernatant solution is 0.2 N urea group equivalent.

The pH of the solution is 4.2.

Procedure:

Add 1.5 mL of 2 N NaOH to 10 mL of the chitosan solution (0.06N amine equivalent) prepared as described in Section 2.5. Adjust the pH of the solution with 2N NaOH to about 8.2 to 8.4. Stir the solution for additional 10 minutes. Add 3.0 mL O-methylisourea chloride solution (0.2N urea group equivalent) prepared as described above. Stir the solution overnight.

Adjust the pH of solution to 5.5 with 0.5% Acetic Acid (0.088N).

Dilute the solution to a final volume of 25 mL using purified water.

The Poly-GuD concentration in the solution is 5 mg/mL, equivalent to 0.025 N (guanidium group).

Additional compounds classified as bioadhesive agents for use within the present invention act by mediating specific interactions, typically classified as "receptor-ligand interactions" between complementary structures of the bioadhesive compound and a component of the mucosal epithelial surface. Many natural examples illustrate this form of specific binding bioadhesion, as exemplified by lectin-sugar interactions. Lectins are (glyco)proteins of non-immune origin which bind to polysaccharides or glycoconjugates. By virtue of this binding potential, lectins may bind or agglutinate cells. Goldstein et al., *Nature* 285:66, 1980, incorporated herein by reference. Lectins are commonly of plant or bacterial origin, but are also produced by higher animals (so-called 'endogenous or 'reverse' lectins), including mammals. Sharon et al., *Lectins*, Chapman and Hall, London, 1989; and Pasztai et al., *Lectins. Biomedical Perspectives*, Taylor & Francis, London, 1995, incorporated herein by reference.

Several plant lectins have been investigated as possible pharmaceutical absorption-promoting agents. One plant lectin, Phaseolus vulgaris hemagglutinin (PHA), exhibits high oral bioavailability of more than 10% after feeding to rats. Pusztai et al., *Biochem. Soc. Trans.*, 17:81–82, 1988, incorporated herein by reference. However, PHA has been reported to cause digestive disorders following oral administration, and these side effects must be determined to be minimized by any nasal therapeutic application herein. In contrast, tomato (*Lycopersicon esculeutum*) lectin (TL) appears safe for various modes of administration. This glycoprotein (approximately 70 kDa) resists digestion and binds to rat intestinal villi without inducing any deleterious effects. Kilpatrick, et al., *FEBS Lett.* 185:5–10, 1985; Woodley et al., *Int. J. Pharm.*, 110:127–136, 1994; and *Int. J. Pharm.* 107:223–230, 1994, each incorporated herein by reference. However, GI transit of this radiolabeled lectin after intragastric administration to rats was not delayed compared to controls, and other studies showed that TL has a strong cross-reactivity with gastrointestinal mucus glycoproteins. Lehr, et al., *Pharm. Res.*, 9:547–553, 1992, incorporated herein by reference. Thus, in spite of its favorable safety profile, the use of TL as a gastrointestinal bioadhesive, even though its action is "specific" (i.e., receptor-mediated) is limited by non-specific interactions with mucus—promoting rapid clearance.

Therefore, the invention provides for coordinate administration or combinatorial formulation of non-toxic lectins identified or obtained by modification of existing lectins which have a high specific affinity for mucosal, e.g., nasal epithelial, cells, but low cross reactivity with mucus. In this regard, detailed teachings regarding lectin structure-activity relationships will allow selection of non-toxic, strongly bioadhesive candidates to produce optimized lectins for therapeutic purposes, which undertaking will be further facilitated by methods of recombinant gene technology. Lehr et al., *Lectins: Biomedical Perspectives,* 117–140, Pustai et al., Eds., Taylor and Francis, London, 1995, incorporated herein by reference. In additional embodiments of the invention, mucolytic agents and/or ciliostatic agents are coordinately administered or combinatorially formulated with a biologically active agent and a lectin or other specific binding bioadhesive—in order to counter the effects of non-specific binding of the bioadhesive to mucosal mucus.

In addition to the use of lectins, certain antibodies or amino acid sequences exhibit high affinity binding to complementary elements on cell and mucosal surfaces. Thus, for example, various adhesive amino acids sequences such as Arg-Gly-Asp and others, if attached to a carrier matrix, will promote adhesion by binding with specific cell surface glycoproteins. In other embodiments, adhesive ligand components are integrated in a carrier or delivery vehicle that selectively adheres to a particular cell type, or diseased target tissue. For example, certain diseases cause changes in cell surface glycoproteins. These distinct structural alterations can be readily targeted by complementary amino acid sequences bound to a drug delivery vehicle within the invention. In exemplary aspects, well known cancer-specific markers (e.g., CEA, HER2) may be targeted by complementary antibodies or peptides for specific drug targeting to diseased cells.

In summary, the foregoing bioadhesive agents are useful in the combinatorial formulations and coordinate administration methods of the instant invention, which optionally incorporate an effective amount and form of a bioadhesive agent to prolong persistence or otherwise increase mucosal absorption of one or more peptide YY proteins, analogs and mimetics, and other biologically active agents. The bioadhesive agents may be coordinately administered as adjunct compounds or as additives within the combinatorial formulations of the invention. In certain embodiments, the bioadhesive agent acts as a 'pharmaceutical glue', whereas in other embodiments adjunct delivery or combinatorial formulation of the bioadhesive agent serves to intensify contact of the biologically active agent with the nasal mucosa, in some cases by promoting specific receptor-ligand interactions with epithelial cell "receptors", and in others by increasing epithelial permeability to significantly increase the drug concentration gradient measured at a target site of delivery (e.g., liver, blood plasma, or CNS tissue or fluid). Yet additional bioadhesive agents for use within the invention act as enzyme (e.g., protease) inhibitors to enhance the stability of mucosally administered biotherapeutic agents delivered coordinately or in a combinatorial formulation with the bioadhesive agent.

Liposomes and Micellar Delivery Vehicles

The coordinate administration methods and combinatorial formulations of the instant invention optionally incorporate effective lipid or fatty acid based carriers, processing agents, or delivery vehicles, to provide improved formulations for mucosal delivery of peptide YY proteins, analogs and mimetics, and other biologically active agents. For example, a variety of formulations and methods are provided for mucosal delivery which comprise one or more of these active agents, such as a peptide or protein, admixed or encapsulated by, or coordinately administered with, a liposome, mixed micellar carrier, or emulsion, to enhance chemical and physical stability and increase the half life of the biologically active agents (e.g., by reducing susceptibility to proteolysis, chemical modification and/or denaturation) upon mucosal delivery.

Within certain aspects of the invention, specialized delivery systems for biologically active agents comprise small lipid vesicles known as liposomes. Chonn et al., *Curr. Opin. Biotechnol.,* 6:698–708, 1995; Lasic, *Trends Biotechnol.,* 16:307–321, 1998; and Gregoriadis, *Trends Biotechnol.,* 13:527–537, 1995, each incorporated herein by reference. These are typically made from natural, biodegradable, non-toxic, and non-immunogenic lipid molecules, and can efficiently entrap or bind drug molecules, including peptides and proteins, into, or onto, their membranes. The attractiveness of liposomes as a peptide and protein delivery system within the invention is increased by the fact that the encapsulated proteins can remain in their preferred aqueous environment within the vesicles, while the liposomal membrane protects them against proteolysis and other destabilizing factors. Even though not all liposome preparation methods known are feasible in the encapsulation of peptides and proteins due to their unique physical and chemical properties, several methods allow the encapsulation of these macromolecules without substantial deactivation. Weiner, *Immunomethods*, 4:201–209, 1994, incorporated herein by reference.

A variety of methods are available for preparing liposomes for use within the invention. Szoka et al., *Ann. Rev. Biophys. Bioeng.*, 9:467, 1980; and U.S. Pat. Nos. 4,235,871, 4,501,728, and 4,837,028, each incorporated herein by reference. For use with liposome delivery, the biologically active agent is typically entrapped within the liposome, or lipid vesicle, or is bound to the outside of the vesicle. Several strategies have been devised to increase the effectiveness of liposome-mediated delivery by targeting liposomes to specific tissues and specific cell types. Liposome formulations, including those containing a cationic lipid, have been shown to be safe and well tolerated in human patients. Treat et al., *J. Natl. Cancer Instit.*, 82:1706–1710, 1990, incorporated herein by reference.

Like liposomes, unsaturated long chain fatty acids, which also have enhancing activity for mucosal absorption, can form closed vesicles with bilayer-like structures (so called "ufasomes"). These can be formed, for example, using oleic acid to entrap biologically active peptides and proteins for mucosal, e.g., intranasal, delivery within the invention.

Other delivery systems for use within the invention combine the use of polymers and liposomes to ally the advantageous properties of both vehicles. Exemplifying this type of hybrid delivery system, liposomes containing the model protein horseradish peroxidase (HRP) have been effectively encapsulated inside the natural polymer fibrin. Henschen et al., *Blood Coagulation*, 171–241, Zwaal, et al., Eds., Elsevier, Amsterdam, 1986, incorporated herein by reference. Because of its biocompatibility and biodegradability, fibrin is a useful polymer matrix for drug delivery systems in this context. Senderoff, et al., *J. Parenter. Sci. Technol.*, 45:2–6, 1991; and Jackson, *Nat. Med.*, 2:637–638, 1996, incorporated herein by reference. In addition, release of biotherapeutic compounds from this delivery system is controllable through the use of covalent crosslinking and the addition of antifibrinolytic agents to the fibrin polymer. Uchino et al., *Fibrinolysis*, 5:93–98, 1991, incorporated herein by reference.

More simplified delivery systems for use within the invention include the use of cationic lipids as delivery vehicles or carriers, which can be effectively employed to provide an electrostatic interaction between the lipid carrier and such charged biologically active agents as proteins and polyanionic nucleic acids. Hope et al., *Molecular Membrane Biology*, 15:1–14, 1998, incorporated herein by reference. This allows efficient packaging of the drugs into a form suitable for mucosal administration and/or subsequent delivery to systemic compartments. These and related systems are particularly well sLited for delivery of polymeric nucleic acids, e.g., in the form of gene constructs, antisense oligonucleotides and ribozymes. These drugs are large, usually negatively charged molecules with molecular weights on the order of $10_6$ for a gene to $10_3$ for an oligonucleotide. The targets for these drugs are intracellular, but their physical properties prevent them from crossing cell membranes by passive diffusion as with conventional drugs. Furthermore, unprotected DNA is degraded within minutes by nucleases present in normal plasma. To avoid inactivation by endogenous nucleases, antisense oligonucleotides and ribozymes can be chemically modified to be enzyme resistant by a variety of known methods, but plasmid DNA must ordinarily be protected by encapsulation in viral or non-viral envelopes, or condensation into a tightly packed particulate form by polycations such as proteins or cationic lipid vesicles. More recently, small unilamellar vesicles (SUVs) composed of a cationic lipid and dioleoylphosphatidylethanolamine (DOPE) have been successfully employed as vehicles for polynucleic acids, such as plasmid DNA, to form particles capable of transportation of the active polynucleotide across plasma membranes into the cytoplasm of a broad spectrum of cells. This process (referred to as lipofection or cytofection) is now widely employed as a means of introducing plasmid constructs into cells to study the effects of transient gene expression. Exemplary delivery vehicles of this type for use within the invention include cationic lipids (e.g., N-(2,3-(dioleyloxy)propyl)-N,N,N-trimethyl ammonium chloride (DOTMA)), quarternary ammonium salts (e.g., N,N-dioleyl-N,N-dimethylammonium chloride (DODAC)), cationic derivatives of cholesterol (e.g., 3β(N-(N',N-dimethylaminoethane-carbamoyl-cholesterol (DC-chol)), and lipids characterized by multivalent headgroups (e.g., dioctadecyldimethylammonium chloride (DOGS), commercially available as Transfectam®).

Additional delivery vehicles for use within the invention include long and medium chain fatty acids, as well as surfactant mixed micelles with fatty acids. Muranishi, *Crit. Rev. Ther. Drug Carrier Syst.*, 7:1–33, 1990, incorporated herein by reference. Most naturally occurring lipids in the form of esters have important implications with regard to their own transport across mucosal surfaces. Free fatty acids and their monoglycerides which have polar groups attached have been demonstrated in the form of mixed micelles to act on the intestinal barrier as penetration enhancers. This discovery of barrier modifying function of free fatty acids (carboxylic acids with a chain length varying from 12 to 20 carbon atoms) and their polar derivatives has stimulated extensive research on the application of these agents as mucosal absorption enhancers.

For use within the methods of the invention, long chain fatty acids, especially fusogenic lipids (unsaturated fatty acids and monoglycerides such as oleic acid, linoleic acid, linoleic acid, monoolein, etc.) provide useful carriers to enhance mucosal delivery of peptide YY proteins, analogs and mimetics, and other biologically active agents disclosed herein. Medium chain fatty acids (C6 to C12) and monoglycerides have also been shown to have enhancing activity in intestinal drug absorption and can be adapted for use within the mocosal delivery formulations and methods of the invention. In addition, sodium salts of medium and long chain fatty acids are effective delivery vehicles and absorption-enhancing agents for mucosal delivery of biologically active agents within the invention. Thus, fatty acids can be employed in soluble forms of sodium salts or by the addition of non-toxic surfactants, e.g., polyoxyethylated hydrogenated castor oil, sodium taurocholate, etc. Mixed micelles of naturally occurring unsaturated long chain fatty acids (oleic acid or linoleic acid) and their monoglycerides with bile salts have been shown to exhibit absorption-enhancing abilities which are basically harmless to the intestinal mucosa. Muranishi, *Pharm. Res.*, 2:108–118, 1985; and *Crit. Rev. Ther. drug carrier Syst.*, 7:1–33, 1990, each incorporated herein by reference. Other fatty acid and mixed micellar preparations that are useful within the invention include, but are not limited to, Na caprylate (C8), Na caprate (C10), Na laurate (C12) or Na oleate (C18), optionally combined with bile salts, such as glycocholate and taurocholate.

Pegylation

Additional methods and compositions provided within the invention involve chemical modification of biologically active peptides and proteins by covalent attachment of polymeric materials, for example dextrans, polyvinyl pyrrolidones, glycopeptides, polyethylene glycol and polyamino acids. The resulting conjugated peptides and proteins retain their biological activities and solubility for mucosal administration. In alternate embodiments, peptide YY proteins, analogs and mimetics, and other biologically active peptides and proteins, are conjugated to polyalkylene oxide polymers, particularly polyethylene glycols (PEG). U.S. Pat. No. 4,179,337, incorporated herein by reference. Numerous reports in the literature describe the potential advantages of pegylated peptides and proteins, which often exhibit increased resistance to proteolytic degradation, increased plasma half-life, increased solubility and decreased antigenicity and immunogenicity. Nucci, et al., *Advanced Drug Deliver Reviews,* 6:133–155, 1991; Lu et al., *Int. J. Peptide Protein Res.,* 43:127–138, 1994, each incorporated herein by reference. A number of proteins, including L-asparaginase, strepto-kinase, insulin, interleukin-2, adenosine deaminase, L-asparaginase, interferon alpha 2b, superoxide dismutase, streptokinase, tissue plasminogen activator (tPA), urokinase, uricase, hemoglobin, TGF-beta, EGF, and other growth factors, have been conjugated to PEG and evaluated for their altered biochemical properties as therapeutics. Ho, et al., *Drug Metabolism and Disposition* 14:349–352, 1986; Abuchowski et al., *Prep. Biochem.,* 9:205–211, 1979; and Rajagopaian et al., *J. Clin. Invest.,* 75:413–419, 1985, Nucci et al., *Adv. Drug Delivery Rev.,* 4:133–151, 1991, each incorporated herein by reference. Although the in vitro biological activities of pegylated proteins may be decreased, this loss in activity is usually offset by the increased in vivo half-life in the bloodstream. Nucci, et al., *Advanced Drug Deliver Reviews,* 6:133–155, 1991, incorporated herein by reference. Accordingly, these and other polymer-coupled peptides and proteins exhibit enhanced properties, such as extended half-life and reduced immunogenicity, when administered mucoally according to the methods and formulations herein.

Several procedures have been reported for the attachment of PEG to proteins and peptides and their subsequent purification. Abuchowski et al., *J. Biol. Chem.,* 252:3582–3586,1977; Beauchamp et al., *Anal. Biochem.,* 131:25–33, 1983, each incorporated herein by reference. In addition, Lu et al., *Int. J. Peptide Protein Res.,* 43:127–138, 1994, incorporated herein by reference, describe various technical considerations and compare PEGylation procedures for proteins versus peptides. Katre et al., *Proc. Natl. Acad. Sci. U.S.A.,* 84:1487–1491, 1987; Becker et al., *Makromol. Chem. Rapid Commun.,* 3:217–223, 1982; Mutter et al., *Makromol. Chem. Rapid Commun.,* 13:151–157, 1992; Merrifield, R. B., *J. Am. Chem. Soc.,* 85:2149–2154, 1993; Lu et al., *Peptide Res.,* 6:142–146, 1993; Lee et al., *Bioconjugate Chem.,* 10:973–981, 1999, Nucci et al., *Adv. Drug Deliv. Rev.,* 6:133–151, 1991; Francis et al., *J. Drug Targeting,* 3:321–340, 1996; Zalipsky, S., *Bioconjugate Chem.,* 6:150–165, 1995; Clark et al., *J. Biol. Chem.,* 271:21969–21977, 1996; Pettit et al., *J. Biol. Chem.,* 272: 2312–2318, 1997; Delgado et al., *Br. J. Cancer,* 73:175–182, 1996; Benhar et al., *Bioconjugate Chem.,* 5:321–326, 1994; Benhar et al., *J. Biol. Chem.,* 269:13398–13404, 1994; Wang et al., *Cancer Res.,* 53:4588–4594, 1993; Kinstler et al., *Pharm. Res.* 13:996–1002, 1996, Filpula et al., *Exp. Opin. Ther. Patents,* 9:231–245, 1999; Pelegrin et al., *Hum. Gene Ther.,* 9:2165–2175, 1998, each incorporated herein by reference.

Following these and other teachings in the art, the conjugation of biologically active peptides and proteins for with polyethyleneglycol polymers, is readily undertaken, with the expected result of prolonging circulating life and/or reducing immunogenicity while maintaining an acceptable level of activity of the PEGylated active agent. Amine-reactive PEG polymers for use within the invention include SC-PEG with molecular masses of 2000, 5000, 10000, 12000, and 20 000; U-PEG-10000; NHS-PEG-3400-biotin; T-PEG-5000; T-PEG-12000; and TPC-PEG-5000. Chemical conjugation chemistries for these polymers have been published. Zalipsky, S., *Bioconjugate Chem.,* 6:150–165, 1995; Greenwald et al., *Bioconjugate Chem.,* 7:638–641, 1996; Martinez et al., *Macromol. Chem. Phys.,* 198:2489–2498, 1997; Hermanson, G. T., *Bioconjugate Techniques,* 605–618, 1996; Whitlow et al., *Protein Eng.,* 6:989–995, 1993; Habeeb, A. F. S. A., *Anal. Biochem.,* 14:328–336, 1966; Zalipsky et al., *Poly(ethyleneglycol) Chemistry and Biological Applications,* 318–341, 1997; Harlow et al., *Antibodies: a Laboratory Manual,* 553–612, Cold Spring Harbor Laboratory, Plainview, N.Y., 1988; Milenic et al, *Cancer Res.,* 51:6363–6371, 1991; Friguet et al., *J. Immunol. Methods,* 77:305–319, 1985, each incorporated herein by reference. While phosphate buffers are commonly employed in these protocols, the choice of borate buffers may beneficially influence the PEGylation reaction rates and resulting products.

PEGylation of biologically active peptides and proteins may be achieved by modification of carboxyl sites (e.g., aspartic acid or glutamic acid groups in addition to the carboxyl terminus). The utility of PEG-hydrazide in selective modification of carbodiimide-activated protein carboxyl groups under acidic conditions has been described. Zalipsky, S., *Bioconjugate Chem.,* 6:150–165, 1995; Zalipsky et al., *Poly(ethyleneglycol) Chemistry and Biological Applications,* 318–341, American Chemical Society, Washington, D.C., 1997, incorporated herein by reference. Alternatively, bifunctional PEG modification of biologically active peptides and proteins can be employed. In some procedures, charged amino acid residues, including lysine, aspartic acid, and glutamic acid, have a marked tendency to be solvent accessible on protein surfaces. Conjugation to carboxylic acid groups of proteins is a less frequently explored approach for production of protein bioconjugates. However, the hydrazide/EDC chemistry described by Zalipsky and colleagues, Zalipsky, S., *Bioconjugate Chem.,* 6:150–165, 1995; Zalipsky et al., *Poly(ethyleneglycol) Chemistry and Biological Applications,* 318–341, American Chemical Society, Washington, D.C., 1997, each incorporated herein by reference, offers a practical method of linking PEG polymers to protein carboxylic sites. For example, this alternate conjugation chemistry has been shown to be superior to amine linkages for PEGylation of brain-derived neurotrophic factor (BDNF) while retaining biological activity. Wu et al., *Proc. Natl. Acad. Sci. U.S.A.,* 96:254–259, 1999, incorporated herein by reference. Maeda and colleagues have also found carboxyl-targeted PEGylation to be the preferred approach for bilirubin oxidase conjugations. Maeda et al., Poly(ethylene glycol) Chemistry. Biotechnical and Biomedical Applications, J. M. Harris, Ed., pp. 153–169, Plenum Press, New York, 1992, incorporated herein by reference.

Often, PEGylation of peptides and proteins for use within the invention involves activating PEG with a functional group that will react with lysine residues on the surface of the peptide or protein. Within certain alternate aspects of the invention, biologically active peptides and proteins are modified by PEGylation of other residues such as His, Trp, Cys, Asp, Glu, etc., without substantial loss of activity. If PEG modification of a selected peptide or protein proceeds to completion, the activity of the peptide or protein is often diminished. Therefore, PEG modification procedures herein are generally limited to partial PEGylation of the peptide or protein, resulting in less than about 50%, more commonly less than about 25%, loss of activity, while providing for substantially increased half-life (e.g., serum half life) and a substantially decreased effective dose requirement of the PEGylated active agent.

An unavoidable result of partial PEG modification is the production of a heterogenous mixture of PEGylated peptide or protein having a statistical distribution of the number of PEG groups bound per molecule. In addition, the usage of lysine residues within the peptide or protein is random. These two factors result in the production of a heterogeneous mixture of PEGylated proteins which differ in both the number and position of the PEG groups attached. For instance, when adenosine deaminase is optimally modified there is a loss of 50% activity when the protein has about 14 PEG per protein, with a broad distribution of the actual number of PEG moieties per individual protein and a broad distribution of the position of the actual lysine residues used. Such mixtures of diversely modified proteins are not optimally suited for pharmaceutical use. At the same time, purification and isolation of a class of PEGylated proteins (e.g., proteins containing the same number of PEG moieties) or a single type of PEGylated protein (e.g., proteins containing both the same number of moieties and having the PEG moieties at the same position) involves time-consuming and expensive procedures which result in an overall reduction in the yield of the specific PEGylated peptide or protein of interest.

Within certain alternate aspects of the invention, biologically active peptides and proteins are modified by PEGylation methods that employ activated PEG reagents that react with thio groups of the protein, resulting in covalent attachment of PEG to a cysteine residue, which residue may be inserted in place of a naturally-occurring lysine residue of the protein. As described, for example, in U.S. Pat. No. 5,166,322 (incorporated herein by reference) specific variants of IL-3 have been successfully produced which have a cysteine residue introduced at selected sites within the naturally occurring amino acid sequence. Sulfhydryl reactive compounds (e.g. activated polyethylene glycol) are then attached to these cysteines by reaction with the IL-3 variant. Additionally, U.S. Pat. No. 5,206,344 (incorporated herein by reference) describes specific IL-2 variants which contain a cysteine residue introduced at a selected sites within the naturally-occurring amino acid sequence. The IL-2 variant is subsequently reacted with an activated polyethylene glycol reagent to attach this moiety to a cysteine residue.

Yet additional methods employed within the invention for generating PEGylated peptides and proteins do not require extensive knowledge of protein structure-function (e.g., mapping amino acid residues essential for biological activity). Exemplifying these methods, U.S. Pat. No. 5,766,897, incorporated herein by reference, describes methods for production and characterization of cysteine-PEGylated proteins suitable for therapeutic applications. These are produced by attaching a polyethylene glycol to a cysteine residue within the protein. To obtain the desired result of a stable, biologically active compound the PEG is attached in a specific manner, often to a cysteine residue present at or near a site that is normally glycosylated. Typically, the specific amino acid modified by glycosylation (e.g., asparagine in N-linked glycosylation or serine or threonine in O-linked glycosylation) is replaced by a cysteine residue, which is subsequently chemically modified by attachment of PEG. It may be useful for employment of this method to generation cysteine-containing mutants of selected biologically active peptides and proteins, which can be readily accomplished by, for example, site-directed mutagenesis using methods well known in the art. Kunkel, in Nucleic Acids and Molecular Biology, Eckstein, F. Lilley, D. M. J., eds., Springer-Verlag, Berling and Heidelberg, vol. 2, p. 124, 1988, incorporated herein by reference. In addition, if the active peptide or protein is one member of a family of structurally related proteins, glycosylation sites for any other member can be matched to an amino acid on the protein of interest, and that amino acid changed to cysteine for attachment of the polyethylene glycol. Alternatively, if a crystal structure has been determined for the protein of interest or a related protein, surface residues away from the active site or binding site can be changed to cysteine for the attachment of polyethylene glycol.

These strategies for identifying useful PEG attachment sites for use within the invention are advantageous in that they are readily implemented without extensive knowledge of protein structure-function details. Moreover, these strategies also take advantage of the fact that the presence and location of glycosylation residues are often related, as a natural evolutionary consequence, to increased stability and serum half-life of the subject peptide or protein. Replacement of these glycosylation residues by cysteine, followed by cysteine-specific PEGylation, commonly yields modified peptides and proteins that retain substantial biological activity while exhibiting significantly increased stability.

If a higher degree of PEG modification is required, and/or if the peptide or protein to be chemically modified is not normally glycosylated, other solvent accessible residues can be changed to cysteine, and the resultant protein subjected to PEGylation. Appropriate residues can easily be determined by those skilled in the art. For instance, if a three-dimensional structure is available for the protein of interest, or a related protein, solvent accessible amino acids are easily identified. Also, charged amino acids such as Lys, Arg, Asp and Glu are almost exclusively found on the surface of proteins. Substitution of one, two or many of these residues with cysteine will provide additional sites for PEG attachment. In addition, amino acid sequences in the native protein that are recognized by antibodies are usually on the surface of the protein. These and other methods for determining solvent accessible amino acids are well known to those skilled in the art.

Modification of peptides and proteins with PEG can also be used to generate multimeric complexes of proteins, fragments, and/or peptides that have increased biological stability and/or potency. These multimeric peptides and proteins of the invention, e.g., dimers or tetramers of peptide YY, may be produced synthetically according to well known methods. Alternatively, other biologically active peptides and proteins may be produced in this manner that are naturally occurring dimeric or multimeric proteins. For example, dimeric peptides and proteins useful within the invention may be produced by reacting the peptide or protein with (Maleimido)$_2$-PEG, a reagent composed of PEG having two protein-reactive moieties. In the case of cysteine-pegylated peptides and proteins, the degree of multimeric cross-linking can be controlled by the number of cysteines either present and/or engineered into the peptide or protein, and by the concentration of reagents, e.g., (Maleimido)$_2$ PEG, used in the reaction mixture.

It is further contemplated to attach other groups to thio groups of cysteines present in biologically active peptides and proteins for use within the invention. For example, the peptide or protein may be biotinylated by attaching biotin to a thio group of a cysteine residue. Examples of cysteine-PEGylated proteins of the invention, as well as proteins having a group other than PEG covalently attached via a cysteine residue according to the invention, are as follows:

Other Stabilizing Modifications of Active Agents

In addition to PEGylation, biologically active agents such as peptides and proteins for use within the invention can be modified to enhance circulating half-life by shielding the active agent via conjugation to other known protecting or stabilizing compounds, for example by the creation of fusion proteins with an active peptide, protein, analog or mimetic linked to one or more carrier proteins, such as one or more immunoglobulin chains. U.S. Pat. Nos. 5,750,375; 5,843,725; 5,567,584 and 6,018,026, each incorporated herein by reference. These modifications will decrease the degradation, sequestration or clearance of the active agent and result in a longer half-life in a physiological environment (e.g., in the circulatory system, or at a mucosal surface). The active agents modified by these and other stabilizing conjugations methods are therefore useful with enhanced efficacy within the methods of the invention. In particular, the active agents thus modified maintain activity for greater periods at a target site of delivery or action compared to the unmodified active agent. Even when the active agent is thus modified, it retains substantial biological activity in comparison to a biological activity of the unmodified compound.

Thus, in certain aspects of the invention, peptide YY proteins, analogs and mimetics, and other biologically active agents, including other active peptides and proteins, for mucosal administration according to the methods of the invention are modified for enhanced activity, e.g., to increase circulating half-life, by shielding the active agent through conjugation to other known protecting or stabilizing compounds, or by the creation of fusion proteins with the peptide, protein, analog or mimetic linked to one or more carrier proteins, such as one or more immunoglobulin chains. U.S. Pat. Nos. 5,750,375; 5,843,725; 5,567,584; and 6,018,026, each incorporated herein by reference. These modifications will decrease the degradation, sequestration or clearance of the active peptide or protein and result in a longer half-life in a physiological environment (e.g., at the nasal mucosal surface or in the systemic circulation). The active peptides and proteins thus modified exhibit enhanced efficacy within the compositions and methods of the invention, for example by increased or temporally extended activity at a target site of delivery or action compared to the unmodified peptide, protein, analog or mimetic.

In other aspects of the invention, peptide and protein therapeutic compounds are conjugated for enhanced stability with relatively low molecular weight compounds, such as aminolethicin, fatty acids, vitamin $B_{12}$, and glycosides. Igarishi et al., *Proc. Int. Symp. Control. Rel. Bioact. Materials*, 17:366, 1990, incorporated herein by reference. Additional exemplary modified peptides and proteins for use within the compositions and methods of the invention will be beneficially modified for in vivo use by:

(a) chemical or recombinant DNA methods to link mammalian signal peptides, Lin et al., *J. Biol. Chem.*, 270:14255, 1995, incorporated herein by reference, or bacterial peptides, Joliot et al., *Proc. Natl. Acad. Sci. U.S.A.*, 88:1864, 1991, incorporated herein by reference, to the active peptide or protein, which serves to direct the active peptide or protein across cytoplasmic and organellar membranes and/or traffic the active peptide or protein to the a desired intracellular compartment (e.g., the endoplasmic reticulum (ER) of antigen presenting cells (APCs), such as dendritic cells for enhanced CTL induction);

(b) addition of a biotin residue to the active peptide or protein which serves to direct the active conjugate across cell membranes by virtue of its ability to bind specifically (i.e., with a binding affinity greater than about $10^6$, $10^7$, $10^8$, $10^9$, or $10^{10}$ $M^{31\ 1}$) to a translocator present on the surface of cells (Chen et al., *Analytical Biochem.*, 227:168, 1995, incorporated herein by reference);

(c) addition at either or both the amino- and carboxy-terminal ends of the active peptide or protein of a blocking agent in order to increase stability in vivo. This can be useful in situations in which the termini of the active peptide or protein tend to be degraded by proteases prior to cellular uptake or during intracellular trafficking. Such blocking agents can include, without limitation, additional related or unrelated peptide sequences that can be attached to the amino and/or carboxy terminal residues of the therapeutic polypeptide or peptide to be administered. This can be done either chemically during the synthesis of the peptide or by recombinant DNA technology. Blocking agents such as pyroglutamic acid or other molecules known to those skilled in the art can also be attached to the amino and/or carboxy terminal residues, or the amino group at the amino terminus or carboxyl group at the carboxy terminus can be replaced with a different moiety.

Biologically active agents modified by PEGylation and other stabilizing methods for use within the methods and compositions of the invention will preferably retain at least 25%, more preferably at least 50%, even more preferably between about 50% to 75%, most preferably 100% of the biological activity associated with the unmodified active agent, e.g., a native peptide or protein. Typically, the modified active agent, e.g., a conjugated peptide or protein, has a half-life ($t_{1/2}$), for example in serum following mucosal delivery, which is enhanced relative to the half-life of the unmodified active agent from which it was derived. In certain aspects, the half-life of a modified active agent (e.g., peptide YY proteins, analogs and mimetics, and other biologically active peptides and proteins disclosed herein) for use within the invention is enhanced by at least 1.5-fold to 2-fold, often by about 2-fold to 3-fold, in other cases by about 5-fold to 10-fold, and up to 100-fold or more relative to the half-life of the unmodified active agent.

Prodrug Modifications

Yet another processing and formulation strategy useful within the invention is that of prodrug modification. By transiently (i.e., bioreversibly) derivatizing such groups as carboxyl, hydroxyl, and amino groups in small organic molecules, the undesirable physicochemical characteristics (e.g., charge, hydrogen bonding potential, etc. that diminish mucosal penetration) of these molecules can be "masked" without permanently altering the pharmacological properties of the molecule. Bioreversible prodrug derivatives of therapeutic small molecule drugs have been shown to improve the physicochemical (e.g., solubility, lipophilicity) properties of numerous exemplary therapeutics, particularly those that contain hydroxyl and carboxylic acid groups.

One approach to making prodrugs of amine-containing active agents, such as the peptides and proteins of the invention, is through the acylation of the amino group. Optionally, the use of acyloxyalkoxycarbamate derivatives of amines as prodrugs has been discussed. 3-(2'-hydroxy-4',6'-dimethylphenyl)-3,3-dimethylpropionic acid has been employed to prepare linear, esterase-, phosphatase-, and dehydrogenase-sensitive prodrugs of amines (Amsberry et al., Pharm. Res. 8:455–461, 1991; Wolfe et al., J. Org. Chem. 57:6138, 1992, each incorporated herein by reference). These systems have been shown to degrade through a two-step mechanism, with the first step being the slow, rate-determining enzyme-catalyzed (esterase, phosphatase, or dehydrogenase) step, and the second step being a rapid ($t_{1/2}$=100 sec., pH 7.4, 37° C.) chemical step (Amsberry et al., J. Org. Chem. 55:5867–5877, 1990, incorporated herein by reference). Interestingly, the phosphatase-sensitive system has recently been employed to prepare a very water-soluble (greater than 10 mg/ml) prodrug of TAXOL which shows significant antitumor activity in vivo. These and other prodrug modification systems and resultant therapeutic agents are useful within the methods and compositions of the invention.

For the purpose of preparing prodrugs of peptides that are useful within the invention, U.S. Pat. No. 5,672,584 (incorporated herein by reference) further describes the preparation and use of cyclic prodrugs of biologically active peptides and peptide nucleic acids (PNAs). To produce these cyclic prodrugs, the N-terminal amino group and the C-terminal carboxyl group of a biologically active peptide or PNA is linked via a linker, or the C-terminal carboxyl group of the peptide is linked to a side chain amino group or a side chain hydroxyl group via a linker, or the N-terminal amino group of the peptide is linked to a side chain carboxyl group via a linker, or a side chain carboxyl group of the peptide is linked to a side chain amino group or a side chain hydroxyl group via a linker. Useful linkers in this context include 3-(2'-hydroxy-4',6'-dimethyl phenyl)-3,3-dimethyl propionic acid linkers and its derivatives, and acyloxyalkoxy derivatives. The incorporated disclosure provides methods useful for the production and characterization of cyclic prodrugs synthesized from linear peptides, e.g., opioid peptides that exhibit advantageous physicochemical features (e.g., reduced size, intramolecular hydrogen bond, and amphophilic characteristics) for enhanced cell membrane permeability and metabolic stability. These methods for peptide prodrug modification are also useful to prepare modified peptide therapeutic derivatives for use within the methods and compositions of the invention.

Purification and Preparation

Biologically active agents for mucosal administration according to the invention, for example peptide YY proteins, analogs and mimetics, and other biologically active agents disclosed herein, are generally provided for direct administration to subjects in a substantially purified form. The term "substantially purified" as used herein, is intended to refer to a peptide, protein, nucleic acid or other compound that is isolated in whole or in part from naturally associated proteins and other contaminants, wherein the peptide, protein, nucleic acid or other active compound is purified to a measurable degree relative to its naturally-occurring state, e.g., relative to its purity within a cell extract.

In certain embodiments, the term "substantially purified" refers to a peptide, protein, or polynucleotide composition that has been isolated from a cell, cell culture medium, or other crude preparation and subjected to fractionation to remove various components of the initial preparation, such as proteins, cellular debris, and other components. Of course, such purified preparations may include materials in covalent association with the active agent, such as glycoside residues or materials admixed or conjugated with the active agent, which may be desired to yield a modified derivative or analog of the active agent or produce a combinatorial therapeutic formulation, conjugate, fusion protein or the like. The term purified thus includes such desired products as peptide and protein analogs or mimetics or other biologically active compounds wherein additional compounds or moieties such as polyethylene glycol, biotin or other moieties are bound to the active agent in order to allow for the attachment of other compounds and/or provide for formulations useful in therapeutic treatment or diagnostic procedures.

As applied to polynucleotides, the term substantially purified denotes that the polynucleotide is free of substances normally accompanying it, but may include additional sequence at the 5' and/or 3' end of the coding sequence which might result, for example, from reverse transcription of the noncoding portions of a message when the DNA is derived from a cDNA library, or might include the reverse transcript for the signal sequence as well as the mature protein encoding sequence.

When referring to peptides, proteins and peptide analogs (including peptide fusions with other peptides and/or proteins) of the invention, the term substantially purified typically means a composition which is partially to completely free of other cellular components with which the peptides, proteins or analogs are associated in a non-purified, e.g., native state or environment. Purified peptides and proteins are generally in a homogeneous or nearly homogenous state although it can be either in a dry state or in an aqueous solution. Purity and homogeneity are typically determined using analytical chemistry techniques such as polyacrylamide gel electrophoresis or high performance liquid chromatography.

Generally, substantially purified peptides, proteins and other active compounds for use within the invention comprise more than 80% of all macromolecular species present in a preparation prior to admixture or formulation of the peptide, protein or other active agent with a pharmaceutical carrier, excipient, buffer, absorption enhancing agent, stabilizer, preservative, adjuvant or other co-ingredient in a complete pharmaceutical formulation for therapeutic administration. More typically, the peptide or other active agent is purified to represent greater than 90%, often greater than 95% of all macromolecular species present in a purified preparation prior to admixture with other formulation ingredients. In other cases, the purified preparation of active agent may be essentially homogeneous, wherein other macromolecular species are not detectable by conventional techniques.

Various techniques suitable for use in peptide and protein purification are well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and/or affinity chromatography; isoelectric focusing; gel electrophoresis; and combinations of such and other techniques.

Particularly useful purification methods include selective precipitation with such substances as ammonium sulfate; column chromatography; affinity methods, including immunopurification methods; and others. R. Scopes, *Protein Purification: Principles and Practice*, Springer-Verlag: New York, 1982, incorporated herein by reference. In general, biologically active peptides and proteins can be extracted from tissues or cell cultures that express the peptides and then immunoprecipitated, where after the peptides and proteins can be further purified by standard protein chemistry/chromatographic methods.

Formulation and Administration

Mucosal delivery formulations of the present invention comprise the biologically active agent to be administered (e.g., one or more of the peptide YY proteins, analogs and mimetics, and other biologically active agents disclosed herein), typically combined together with one or more pharmaceutically acceptable carriers and, optionally, other therapeutic ingredients. The carrier(s) must be "pharmaceutically acceptable" in the sense of being compatible with the other ingredients of the formulation and not eliciting an unacceptable deleterious effect in the subject. Such carriers are described herein above or are otherwise well known to those skilled in the art of pharmacology. Desirably, the formulation should not include substances such as enzymes or oxidizing agents with which the biologically active agent to be administered is known to be incompatible. The formulations may be prepared by any of the methods well known in the art of pharmacy.

Within the compositions and methods of the invention, the peptide YY proteins, analogs and mimetics, and other biologically active agents disclosed herein may be administered to subjects by a variety of mucosal administration modes, including by oral, rectal, vaginal, intranasal, intrapulmonary, or transdermal delivery, or by topical delivery to the eyes, ears, skin or other mucosal surfaces. Optionally, peptide YY proteins, analogs and mimetics, and other biologically active agents disclosed herein can be coordinately or adjunctively administered by non-mucosal routes, including by intramuscular, subcutaneous, intravenous, intraatrial, intra-articular, intraperitoneal, or parenteral routes. In other alternative embodiments, the biologically active agent(s) can be administered ex vivo by direct exposure to cells, tissues or organs originating from a mammalian subject, for example as a component of an ex vivo tissue or organ treatment formulation that contains the biologically active agent in a suitable, liquid or solid carrier.

Compositions according to the present invention are often administered in an aqueous solution as a nasal or pulmonary spray and may be dispensed in spray form by a variety of methods known to those skilled in the art. Preferred systems for dispensing liquids as a nasal spray are disclosed in U.S. Pat. No. 4,511,069. Such formulations may be conveniently prepared by dissolving compositions according to the present invention in water to produce an aqueous solution, and rendering the solution sterile. The formulations may be presented in multi-dose containers, for example in the sealed dispensing system disclosed in U.S. Pat. No. 4,511,069. Other suitable nasal spray delivery systems have been described in Transdermal Systemic Medication, Y. W. Chien Ed., Elsevier Publishers, New York, 1985; and in U.S. Pat. No. 4,778,810 (each incorporated herein by reference). Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or a mixture thereof.

Nasal and pulmonary spray solutions of the present invention typically comprise the drug or drug to be delivered, optionally formulated with a surface active agent, such as a nonionic surfactant (e.g., polysorbate-80), and one or more buffers. In some embodiments of the present invention, the nasal spray solution further comprises a propellant. The pH of the nasal spray solution is optionally between about pH 6.8 and 7.2, but when desired the pH is adjusted to optimize delivery of a charged macromolecular species (e.g., a therapeutic protein or peptide) in a substantially unionized state. The pharmaceutical solvents employed can also be a slightly acidic aqueous buffer (pH 4–6). Suitable buffers for use within these compositions are as described above or as otherwise known in the art. Other components may be added to enhance or maintain chemical stability, including preservatives, surfactants, dispersants, or gases. Suitable preservatives include, but are not limited to, phenol, methyl paraben, paraben, m-cresol, thiomersal, benzylalkonimum chloride, and the like. Suitable surfactants include, but are not limited to, oleic acid, sorbitan trioleate, polysorbates, lecithin, phosphotidyl cholines, and various long chain diglycerides and phospholipids. Suitable dispersants include, but are not limited to, ethylenediaminetetraacetic acid, and the like. Suitable gases include, but are not limited to, nitrogen, helium, chlorofluorocarbons (CFCs), hydrofluorocarbons (HFCs), carbon dioxide, air, and the like.

Within alternate embodiments, mucosal formulations are administered as dry powder formulations comprising the biologically active agent in a dry, usually lyophilized, form of an appropriate particle size, or within an appropriate particle size range, for intranasal delivery. Minimum particle size appropriate for deposition within the nasal or pulmonary passages is often about 0.5μ mass median equivalent aerodynamic diameter (MMEAD), commonly about 1μ MMEAD, and more typically about 2μ MMEAD. Maximum particle size appropriate for deposition within the nasal passages is often about 10μ MMEAD, commonly about 8μ MMEAD, and more typically about 4μ MMEAD. Intranasally respirable powders within these size ranges can be produced by a variety of conventional techniques, such as jet milling, spray drying, solvent precipitation, supercritical fluid condensation, and the like. These dry powders of appropriate MMEAD can be administered to a patient via a conventional dry powder inhaler (DPI) which rely on the patient's breath, upon pulmonary or nasal inhalation, to disperse the power into an aerosolized amount. Alternatively, the dry powder may be administered via air assisted devices that use an external power source to disperse the powder into an aerosolized amount, e.g., a piston pump.

Dry powder devices typically require a powder mass in the range from about 1 mg to 20 mg to produce a single aerosolized dose ("puff"). If the required or desired dose of the biologically active agent is lower than this amount, the powdered active agent will typically be combined with a pharmaceutical dry bulking powder to provide the required total powder mass. Preferred dry bulking powders include sucrose, lactose, dextrose, mannitol, glycine, trehalose, human serum albumin (HSA), and starch. Other suitable dry bulking powders include cellobiose, dextrans, maltotriose, pectin, sodium citrate, sodium ascorbate, and the like.

To formulate compositions for mucosal delivery within the present invention, the biologically active agent can be combined with various pharmaceutically acceptable additives, as well as a base or carrier for dispersion of the active agent(s). Desired additives include, but are not limited to, pH control agents, such as arginine, sodium hydroxide, glycine, hydrochloric acid, citric acid, etc. In addition, local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione) can be included. When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the nasal mucosa at the site of administration. Generally, the tonicity of the solution is adjusted to a value of about 1/3 to 3, more typically 1/2 to 2, and most often 3/4 to 1.7.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g. maleic anhydride) with other monomers (e.g. methyl (meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly (hydroxybutyric acid-glycolic acid) copolymer and mixtures thereof. Alternatively or additionally, synthetic fatty acid esters such as polyglycerin fatty acid esters, sucrose fatty acid esters, etc. can be employed as carriers. Hydrophilic polymers and other carriers can be used alone or in combination, and enhanced structural integrity can be imparted to the carrier by partial crystallization, ionic bonding, crosslinking and the like. The carrier can be provided in a variety of forms, including, fluid or viscous solutions, gels, pastes, powders, microspheres and films for direct application to the nasal mucosa. The use of a selected carrier in this context may result in promotion of absorption of the biologically active agent.

The biologically active agent can be combined with the base or carrier according to a variety of methods, and release of the active agent may be by diffusion, disintegration of the carrier, or associated formulation of water channels. In some circumstances, the active agent is dispersed in microcapsules (microspheres) or nanocapsules (nanospheres) prepared from a suitable polymer, e.g., isobutyl 2-cyanoacrylate (see, e.g., Michael et al., J. Pharmacy Pharmacol. 43: 1–5, 1991), and dispersed in a biocompatible dispersing medium applied to the nasal mucosa, which yields sustained delivery and biological activity over a protracted time.

To further enhance mucosal delivery of pharmaceutical agents within the invention, formulations comprising the active agent may also contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10000 and preferably not more than 3000. Exemplary hydrophilic low molecular weight compound include polyol compounds, such as oligo-, di- and monosaccarides such as sucrose, mannitol, lactose, L-arabinose, D-erythrose, D-ribose, D-xylose, D-mannose, D-galactose, lactulose, cellobiose, gentibiose, glycerin and polyethylene glycol. Other examples of hydrophilic low molecular weight compounds useful as carriers within the invention include N-methylpyrrolidone, and alcohols (e.g. oligovinyl alcohol, ethanol, ethylene glycol, propylene glycol, etc.) These hydrophilic low molecular weight compounds can be used alone or in combination with one another or with other active or inactive components of the intranasal formulation.

The compositions of the invention may alternatively contain as pharmaceutically acceptable carriers substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

Therapeutic compositions for administering the biologically active agent can also be formulated as a solution, microemulsion, or other ordered structure suitable for high concentration of active ingredients. The carrier can be a solvent or dispersion medium containing, for example, water, ethanol, polyol (for example, glycerol, propylene glycol, and liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols such as mannitol, sorbitol, or sodium chloride in the composition. Prolonged absorption of the biologically active agent can be brought about by including in the composition an agent which delays absorption, for example, monostearate salts and gelatin.

In certain embodiments of the invention, the biologically active agent is administered in a time release formulation, for example in a composition which includes a slow release polymer. The active agent can be prepared with carriers that will protect against rapid release, for example a controlled release vehicle such as a polymer, microencapsulated delivery system or bioadhesive gel. Prolonged delivery of the active agent, in various compositions of the invention can be brought about by including in the composition agents that delay absorption, for example, aluminum monosterate hydrogels and gelatin. When controlled release formulations of the biologically active agent is desired, controlled release binders suitable for use in accordance with the invention include any biocompatible controlled-release material which is inert to the active agent and which is capable of incorporating the biologically active agent. Numerous such materials are known in the art. Useful controlled-release binders are materials that are metabolized slowly under physiological conditions following their intranasal delivery (e.g., at the nasal mucosal surface, or in the presence of bodily fluids following transmucosal delivery). Appropriate binders include but are not limited to biocompatible polymers and copolymers previously used in the art in sustained release formulations. Such biocompatible compounds are non-toxic and inert to surrounding tissues, and do not trigger significant adverse side effects such as nasal irritation, immune response, inflammation, or the like. They are metabolized into metabolic products that are also biocompatible and easily eliminated from the body.

Exemplary polymeric materials for use in this context include, but are not limited to, polymeric matrices derived from copolymeric and homopolymeric polyesters having hydrolysable ester linkages. A number of these are known in the art to be biodegradable and to lead to degradation products having no or low toxicity. Exemplary polymers include polyglycolic acids (PGA) and polylactic acids (PLA), poly(DL-lactic acid-co-glycolic acid)(DL PLGA), poly(D-lactic acid-coglycolic acid)(D PLGA) and poly(L-lactic acid-co-glycolic acid)(L PLGA). Other useful biodegradable or bioerodable polymers include but are not limited to such polymers as poly(epsilon-caprolactone), poly(epsilon-aprolactone-CO-lactic acid), poly($\epsilon$-aprolactone-CO-glycolic acid), poly(beta-hydroxy butyric acid), poly(alkyl-2-cyanoacrilate), hydrogels such as poly(hydroxyethyl methacrylate), polyamides, poly(amino acids) (i.e., L-leucine, glutamic acid, L-aspartic acid and the like), poly (ester urea), poly (2-hydroxyethyl DL-aspartamide), polyacetal polymers, polyorthoesters, polycarbonate, polymaleamides, polysaccharides and copolymers thereof. Many methods for preparing such formulations are generally known to those skilled in the art. J. R. Robinson, ed., *Sustained and Controlled Release Drug Delivery Systems*, Marcel Dekker, Inc., New York, 1978, incorporated herein by reference. Other useful formulations include controlled-release compositions such as are known in the art for the administration of leuprolide (trade name: Lupron.RTM.), e.g., microcapsules, U.S. Pat. Nos. 4,652,441 and 4,917,893, each incorporated herein by reference, lactic acid-glycolic acid copolymers useful in making microcapsules and other formulations, U.S. Pat. Nos. 4,677,191 and 4,728,721, each incorporated herein by reference, and sustained-release compositions for water-soluble peptides, U.S. Pat. No. 4,675,189, incorporated herein by reference.

The mucosal formulations of the invention typically must be sterile and stable under all conditions of manufacture, storage and use. Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders, methods of preparation include vacuum drying and freeze-drying which yields a powder of the active ingredient plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In more detailed aspects of the invention, the biologically active agent is stabilized to extend its effective half-life following delivery to the subject, particularly for extending metabolic persistence in an active state within the physiological environment (e.g., at the nasal mucosal surface, in the bloodstream, or within a connective tissue compartment or fluid-filled body cavity). For this purpose, the biologically active agent may be modified by chemical means, e.g., chemical conjugation, N-terminal capping, PEGylation, or recombinant means, e.g., site-directed mutagenesis or construction of fusion proteins, or formulated with various stabilizing agents or carriers. Thus stabilized, the active agent administered as above retains biological activity for an extended period (e.g., 2–3, up to 5–10 fold greater stability) under physiological conditions compared to its non-stabilized form.

In accordance with the various treatment methods of the invention, the biologically active agent is delivered to a mammalian subject in a manner consistent with conventional methodologies associated with management of the disorder for which treatment or prevention is sought. In accordance with the disclosure herein, a prophylactically or therapeutically effective amount of the biologically active agent is administered to a subject in need of such treatment for a time and under conditions sufficient to prevent, inhibit, and/or ameliorate a selected disease or condition or one or more symptom(s) thereof.

The term "subject" as used herein means any mammalian patient to which the compositions of the invention may be administered. Typical subjects intended for treatment with the compositions and methods of the present invention include humans, as well as non-human primates and other animals. To identify subject patients for prophylaxis or treatment according to the methods of the invention, accepted screening methods are employed to determine risk factors associated with a targeted or suspected disease of condition as discussed above, or to determine the status of an existing disease or condition in a subject. These screening methods include, for example, conventional work-ups to determine familial, sexual, drug-use and other such risk factors that may be associated with the targeted or suspected disease or condition, as well as diagnostic methods such as various ELISA immunoassay methods, which are available and well known in the art to detect and/or characterize disease-associated markers. These and other routine methods allow the clinician to select patients in need of therapy using the mucosal methods and formulations of the invention. In accordance with these methods and principles, biologically active agents may be mucosally administered according to the teachings herein as an independent prophylaxis or treatment program, or as a follow-up, adjunct or coordinate treatment regimen to other treatments, including surgery, vaccination, immunotherapy, hormone treatment, cell, tissue, or organ transplants, and the like.

Mucosal administration according to the invention allows effective self-administration of treatment by patients, provided that sufficient safeguards are in place to control and monitor dosing and side effects. Mucosal administration also overcomes certain drawbacks of other administration forms, such as injections, that are painful and expose the patient to possible infections and may present drug bioavailability problems. For nasal and pulmonary delivery, systems for controlled aerosol dispensing of therapeutic liquids as a spray are well known. In one embodiment, metered doses of active agent are delivered by means of a specially constructed mechanical pump valve (U.S. Pat. No. 4,511,069, incorporated herein by reference). This hand-held delivery device is uniquely nonvented so that sterility of the solution in the aerosol container is maintained indefinitely.

Dosage

For prophylactic and treatment purposes, the biologically active agent(s) disclosed herein may be administered to the subject in a single bolus delivery, via continuous delivery (e.g., continuous transdermal, mucosal, or intravenous delivery) over an extended time period, or in a repeated administration protocol (e.g., by an hourly, daily or weekly, repeated administration protocol). In this context, a therapeutically effective dosage of the biologically active agent(s) may include repeated doses within a prolonged prophylaxis or treatment regimen, that will yield clinically significant results to alleviate one or more symptoms or detectable conditions associated with a targeted disease or condition as set forth above. Determination of effective dosages in this context is typically based on animal model studies followed up by human clinical trials and is guided by determining effective dosages and administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response). In alternative embodiments, an "effective amount" or "effective dose" of the biologically active agent(s) may simply inhibit or enhance one or more selected biological activity(ies) correlated with a disease or condition, as set forth above, for either therapeutic or diagnostic purposes.

The actual dosage of biologically active agents will of course vary according to factors such as the disease indication and particular status of the subject (e.g., the subject's age, size, fitness, extent of symptoms, susceptibility factors, etc), time and route of administration, other drugs or treatments being administered concurrently, as well as the specific pharmacology of the biologically active agent(s) for eliciting the desired activity or biological response in the subject. Dosage regimens may be adjusted to provide an optimum prophylactic or therapeutic response. A therapeutically effective amount is also one in which any toxic or detrimental side effects of the biologically active agent is outweighed in clinical terms by therapeutically beneficial effects. A non-limiting range for a therapeutically effective amount of a biologically active agent within the methods and formulations of the invention is 0.01 µg/kg-10 mg/kg, more typically between about 0.05 and 5 mg/kg, and in certain embodiments between about 0.2 and 2 mg/kg. Alternatively, a non-limiting range for a therapeutically effective amount of a biologically active agent within the methods and, formulations of the invention is between about 0.001 pmol to about 100 pmol per kg body weight, between about 0.01 pmol to about 10 pmol per kg body weight, between about 0.1 pmol to about 5 pmol per kg body weight, or between about 0.5 pmol to about 1.0 pmol per kg body weight. Dosages within this range can be achieved by single or multiple administrations, including, e.g., multiple administrations per day, daily or weekly administrations. Per administration, it is desirable to administer at least one microgram of the biologically active agent (e.g., one or more peptide YY proteins, analogs and mimetics, and other biologically active agents), more typically between about 10 µg and 5.0 mg, and in certain embodiments between about 100 µg and 1.0 or 2.0 mg to an average human subject. It is to be further noted that for each particular subject, specific dosage regimens should be evaluated and adjusted over time according to the individual need and professional judgment of the person administering or supervising the administration of the permeabilizing peptide(s) and other biologically active agent(s).

Dosage of biologically active agents may be varied by the attending clinician to maintain a desired concentration at the target site. For example, a selected local concentration of the biologically active agent in the bloodstream or CNS may be about 1–50 nanomoles per liter, sometimes between about 1.0 nanomole per liter and 10, 15 or 25 nanomoles per liter, depending on the subject's status and projected or measured response. In an alternative example, a selected local concentration of the biologically active agent in the bloodstream or CNS may be between about 0.1 pmol/L to about 1000 pmol/L of blood plasma or CSF, between about 1.0 pmol/L to about 100 pmol/L of blood plasma or CSF, between about 1.0 pmol/L to about 10 pmol/L of blood plasma or CSF, or between about 5.0 pmol/L to about 10 pmol/L of blood plasma or CSF. Higher or lower concentrations may be selected based on the mode of delivery, e.g., trans-epidermal, rectal, oral, or intranasal delivery versus intravenous or subcutaneous delivery. Dosage should also be adjusted based on the release rate of the administered formulation, e.g., of a nasal spray versus powder, sustained release oral versus injected particulate or transdermal delivery formulations, etc. To achieve the same serum concentration level, for example, slow-release particles with a release rate of 5 nanomolar (under standard conditions) would be administered at about twice the dosage of particles with a release rate of 10 nanomolar.

Additional guidance as to particular dosages for selected biologically active agents for use within the invention may be found widely disseminated in the literature. This is true for many of the therapeutic peptide and protein agents disclosed herein. For example, guidance for administration of human growth hormone (hGH) in the treatment of individuals intoxicated with poisonous substances may be found in U.S. Pat. Nos. 5,140,008 and 4,816,439; guidance for administration of hGH in the treatment of topical ulcers may be found in U.S. Pat. No. 5,006,509.

Kits

The instant invention also includes kits, packages and multicontainer units containing the above described pharmaceutical compositions, active ingredients, and/or means for administering the same for use in the prevention and treatment of diseases and other conditions in mammalian subjects. Briefly, these kits include a container or formulation that contains one or more peptide YY proteins, analogs or mimetics, and/or other biologically active agents in combination with mucosal delivery enhancing agents disclosed herein formulated in a pharmaceutical preparation for mucosal delivery. The biologically active agent(s) is/are optionally contained in a bulk dispensing container or unit or multi-unit dosage form. Optional dispensing means may be provided, for example a pulmonary or intranasal spray applicator. Packaging materials optionally include a label or instruction indicating that the pharmaceutical agent packaged therewith can be used mucosally, e.g., intranasally, for treating or preventing a specific disease or condition. In more detailed embodiments of the invention, kits include one or more mucosal delivery-enhancing agents selected from: (a) aggregation inhibitory agents; (b) charge modifying agents; (c) pH control agents; (d) degradative enzyme inhibitors; (e) mucolytic or mucus clearing agents; (f) ciliostatic agents; (g) membrane penetration-enhancing agents (e.g., (i) a surfactant, (ii) a bile salt, (ii) a phospholipid or fatty acid additive, mixed micelle, liposome, or carrier, (iii)

an alcohol, (iv) an enamine, (v) an NO donor compound, (vi) a long-chain amphipathic molecule (vii) a small hydrophobic penetration enhancer; (viii) sodium or a salicylic acid derivative; (ix) a glycerol ester of acetoacetic acid (x) a cyclodextrin or beta-cyclodextrin derivative, (xi) a medium-chain fatty acid, (xii) a chelating agent, (xiii) an amino acid or salt thereof, (xiv) an N-acetylamino acid or salt thereof, (xv) an enzyme degradative to a selected membrane component, (ix) an inhibitor of fatty acid synthesis, (x) an inhibitor of cholesterol synthesis; or (xi) any combination of the membrane penetration enhancing agents of (i)–(x)); (h) secondary modulatory agents of epithelial junction physiology, such as nitric oxide (NO) stimulators, chitosan, and chitosan derivatives; (i) vasodilator agents; (j) selective transport-enhancing agents; and (k) stabilizing delivery vehicles, carriers, supports or complex-forming species with which the biologically active agent is/are effectively combined, associated, contained, encapsulated or bound to stabilize the active agent for enhanced mucosal delivery.

The following examples are provided by way of illustration, not limitation.

EXAMPLE 1

An exemplary formulation for enhanced nasal mucosal delivery of peptide YY following the teachings of the instant specification was prepared and evaluated as follows:

TABLE 1

Peptide YY formulation composition

| Formulations | Peptide $YY_{3-36}$ Per 100 ml Sample | Mucosal Delivery Enhancing Agent |
|---|---|---|
| A | 60 μg | Phosphate-buffered saline (0.8%) pH 7.4 (Control 1) |
| B | 60 μg | Phosphate-buffered saline (0.8%) pH 5.0 (Control 2) |
| C | 60 μg | L-Arginine (10% w/v) |
| D | 60 μg | Poly-L-Arginine (0.5% w/v) |
| E | 60 μg | Gamma-Cyclodextrin (1% w/v) |
| F | 60 μg | α-Cyclodextrin (5% w/v) |
| G | 60 μg | Methyl-β-Cyclodextrin (3% w/v) |
| H | 60 μg | n-Capric Acid Sodium (0.075% w/v) |
| I | 60 μg | Chitosan (0.5% w/v) |
| J | 60 μg | L-α-phosphatidilcholine didecanyl (3.5% w/v) |
| K | 60 μg | S-Nitroso-N-Acetyl-Penicillamine (0.5% w/v) |
| L | 60 μg | Palmotoyl-DL-Carnitine (0.02% w/v) |
| M | 60 μg | Pluronic-127 (0.3% w/v) |
| N | 60 μg | Sodium Nitroprusside (0.3% w/v) |
| O | 60 μg | Sodium Glycocholate (1% w/v) |
| P | 60 μg | F1: Gelatin, DDPC, MBCD, EDTA |
| F 1 | | L-α-phosphatidilcholine didecanyl (0.5% w/v) Methyl β Cyclodextrin (3% w/v) EDTA (0.1% w/v, Inf. Conc. 0.5 M) Gelatin (0.5% w/v) |

EXAMPLE 2

Nasal Mucosal Delivery—Permeation Kinetics and Cytotoxicity

1. Organotypic Model

The following methods are generally useful for evaluating nasal mucosal delivery parameters, kinetics and side effects for peptide YY within the formulations and method of the invention, as well as for determining the efficacy and characteristics of the various intranasal delivery-enhancing agents disclosed herein for combinatorial formulation or coordinate administration with peptide YY.

Permeation kinetics and cytotoxicity are also useful for determining the efficacy and characteristics of the various mucosal delivery-enhancing agents disclosed herein for combinatorial formulation or coordinate administration with mucosal delivery-enhancing agents. In one exemplary protocol, permeation kinetics and lack of unacceptable cytotoxicity are demonstrated for an intranasal delivery-enhancing agents as disclosed above in combination with a biologically active therapeutic agent, exemplified by peptide YY.

The EpiAirway system was developed by MatTek Corp (Ashland, Mass.) as a model of the pseudostratified epithelium lining the respiratory tract. The epithelial cells are grown on porous membrane-bottomed cell culture inserts at an air-liquid interface, which results in differentiation of the cells to a highly polarized morphology. The apical surface is ciliated with a microvillous ultrastructure and the epithelium produces mucus (the presence of mucin has been confirmed by immunoblotting). The inserts have a diameter of 0.875 cm, providing a surface area of 0.6 cm$^2$. The cells are plated onto the inserts at the factory approximately three weeks before shipping. One "kit" consists of 24 units.

A. On arrival, the units are placed onto sterile supports in 6-well microplates. Each well receives 5 mL of proprietary culture medium. This DMEM-based medium is serum free but is supplemented with epidermal growth factor and other factors. The medium is always tested for endogenous levels of any cytokine or growth factor which is being considered for intranasal delivery, but has been free of all cytokines and factors studied to date except insulin. The 5 mL volume is just sufficient to provide contact to the bottoms of the units on their stands, but the apical surface of the epithelium is allowed to remain in direct contact with air. Sterile tweezers are used in this step and in all subsequent steps involving transfer of units to liquid-containing wells to ensure that no air is trapped between the bottoms of the units and the medium.

B. The units in their plates are maintained at 37° C. in an incubator in an atmosphere of 5% $CO_2$ in air for 24 hours. At the end of this time the medium is replaced with fresh medium and the units are returned to the incubator for another 24 hours.

2. Experimental Protocol—Permeation Kinetics

A. A "kit" of 24 EpiAirway units can routinely be employed for evaluating five different formulations, each of which is applied to quadruplicate wells. Each well is employed for determination of permeation kinetics (4 time points), transepithelial resistance, mitochondrial reductase activity as measured by MTT reduction, and cytolysis as measured by release of LDH. An additional set of wells is employed as controls, which are sham treated during determination of permeation kinetics, but are otherwise handled identically to the test sample-containing units for determinations of transepithelial resistance and viability. The determinations on the controls are routinely also made on quadruplicate units, but occasionally we have employed triplicate units for the controls and have dedicated the remaining four units in the kit to measurements of transepithelial resistance and viability on untreated units or we have frozen and thawed the units for determinations of total LDH levels to serve as a reference for 100% cytolysis.

B. In all experiments, the nasal mucosal delivery formulation to be studied is applied to the apical surface of each unit in a volume of 100 μL, which is sufficient to cover the entire apical surface. An appropriate volume of the test formulation at the concentration applied to the apical surface (no more than 100 μL is generally needed) is set aside for subsequent determination of concentration of the active material by ELISA or other designated assay.

C. The units are placed in 6 well plates without stands for the experiment: each well contains 0.9 mL of medium which is sufficient to contact the porous membrane bottom of the unit but does not generate any significant upward hydrostatic pressure on the unit.

D. In order to minimize potential sources of error and avoid any formation of concentration gradients, the units are transferred from one 0.9 mL-containing well to another at each time point in the study. These transfers are made at the following time points, based on a zero time at which the 100 μL volume of test material was applied to the apical surface: 15 minutes, 30 minutes, 60 minutes, and 120 minutes.

E. In between time points the units in their plates are kept in the 37° C. incubator. Plates containing 0.9 mL medium per well are also maintained in the incubator so that minimal change in temperature occurs during the brief periods when the plates are removed and the units are transferred from one well to another using sterile forceps.

F. At the completion of each time point, the medium is removed from the well from which each unit was transferred, and aliquotted into two tubes (one tube receives 700 μL and the other 200 μL) for determination of the concentration of permeated test material and, in the event that the test material is cytotoxic, for release of the cytosolic enzyme, lactic dehydrogenase, from the epithelium. These samples are kept in the refrigerator if the assays are to be conducted within 24 hours, or the samples are subaliquotted and kept frozen at −80° C. until thawed once for assays. Repeated freeze-thaw cycles are to be avoided.

G. In order to minimize errors, all tubes, plates, and wells are prelabeled before initiating an experiment.

H. At the end of the 120 minute time point, the units are transferred from the last of the 0.9 mL containing wells to 24-well microplates, containing 0.3 mL medium per well. This volume is again sufficient to contact the bottoms of the units, but not to exert upward hydrostatic pressure on the units. The units are returned to the incubator prior to measurement of transepithelial resistance.

3. Experimental Protocol—Transepithelial Resistance

A. Respiratory airway epithelial cells form tight junctions in vivo as well as in vitro, restricting the flow of solutes across the tissue. These junctions confer a transepithelial resistance of several hundred ohms×cm$^2$ in excised airway tissues; in the MatTek EpiAirway units, the transepithelial resistance (TER) is claimed by the manufacturer to be routinely around 1000 ohms×cm$^2$. We have found that the TER of control EpiAirway units which have been sham-exposed during the sequence of steps in the permeation study is somewhat lower (700–800 ohms×cm$^2$), but, since permeation of small molecules is proportional to the inverse of the TER, this value is still sufficiently high to provide a major barrier to permeation. The porous membrane-bottomed units without cells, conversely, provide only minimal transmembrane resistance (5–20 ohms×cm$^2$).

B. Accurate determinations of TER require that the electrodes of the ohmmeter be positioned over a significant surface area above and below the membrane, and that the distance of the electrodes from the membrane be reproducibly controlled. The method for TER determination recommended by MatTek and employed for all experiments here employs an "EVOM"™ epithelial voltohmmeter and an "ENDOHM"™ tissue resistance measurement chamber from World Precision Instruments, Inc., Sarasota, Fla.

C. The chamber is initially filled with Dulbecco's phosphate buffered saline (PBS) for at least 20 minutes prior to TER determinations in order to equilibrate the electrodes.

D. Determinations of TER are made with 1.5 mL of PBS in the chamber and 350 μL of PBS in the membrane-bottomed unit being measured. The top electrode is adjusted to a position just above the membrane of a unit containing no cells (but containing 350 μL of PBS) and then fixed to ensure reproducible positioning. The resistance of a cell-free unit is typically 5–20 ohms×cm$^2$ ("background resistance").

E. Once the chamber is prepared and the background resistance is recorded, units in a 24-well plate which had just been employed in permeation determinations are removed from the incubator and individually placed in the chamber for TER determinations.

F. Each unit is first transferred to a petri dish containing PBS to ensure that the membrane bottom is moistened. An aliquot of 350 μL PBS is added to the unit and then carefully aspirated into a labeled tube to rinse the apical surface. A second wash of 350 μL PBS is then applied to the unit and aspirated into the same collection tube.

G. The unit is gently blotted free of excess PBS on its exterior surface only before being placed into the chamber (containing a fresh 1.5 mL aliquot of PBS). An aliquot of 350 μL PBS is added to the unit before the top electrode is placed on the chamber and the TER is read on the EVOM meter.

H. After the TER of the unit is read in the ENDOHM chamber, the unit is removed, the PBS is aspirated and saved, and the unit is returned with an air interface on the apical surface to a 24-well plate containing 0.3 mL medium per well.

I. The units are read in the following sequence: all sham-treated controls, followed by all formulation-treated samples, followed by a second TER reading of each of the sham-treated controls. After all the TER determinations are complete, the units in the 24-well microplate are returned to the incubator for determination of viability by MTT reduction.

4. Experimental Protocol—Viability by MTT Reduction

MTT is a cell-permeable tetrazolium salt which is reduced by mitochondrial dehydrogenase activity to an insoluble colored formazan by viable cells with intact mitochondrial function or by nonmitochondrial NAD(P)H dehydrogenase activity from cells capable of generating a respiratory burst. Formation of formazan is a good indicator of viability of epithelial cells since these cells do not generate a significant respiratory burst. We have employed a MTT reagent kit prepared by MatTek Corp for their units in order to assess viability.

A. The MTT reagent is supplied as a concentrate and is diluted into a proprietary DMEM-based diluent on the day viability is to be assayed (typically the afternoon of the day in which permeation kinetics and TER were determined in the morning). Insoluble reagent is removed by a brief centrifugation before use. The final MTT concentration is 1 mg/mL B. The final MTT solution is added to wells of a 24-well microplate at a volume of 300 µL per well. As has been noted above, this volume is sufficient to contact the membranes of the EpiAirway units but imposes no significant positive hydrostatic pressure on the cells.

C. The units are removed from the 24-well plate in which they were placed after TER measurements, and after removing any excess liquid from the exterior surface of the units, they are transferred to the plate containing MTT reagent. The units in the plate are then placed in an incubator at 37° C. in an atmosphere of 5% $CO_2$ in air for 3 hours.

D. At the end of the 3-hour incubation, the units containing viable cells will have turned visibly purple. The insoluble formazan must be extracted from the cells in their units to quantitate the extent of MTT reduction. Extraction of the formazan is accomplished by transferring the units to a 24-well microplate containing 2 mL extractant solution per well, after removing excess liquid from the exterior surface of the units as before. This volume is sufficient to completely cover both the membrane and the apical surface of the units. Extraction is allowed to proceed overnight at room temperature in a light-tight chamber. MTT extractants traditionally contain high concentrations of detergent, and destroy the cells.

E. At the end of the extraction, the fluid from within each unit and the fluid in its surrounding well are combined and transferred to a tube for subsequent aliquotting into a 96-well microplate (200 µL aliquots are optimal) and determination of absorbance at 570 nm on a VMax multiwell microplate spectrophotometer. To ensure that turbidity from debris coming from the extracted units does not contribute to the absorbance, the absorbance at 650 nm is also determined for each well in the VMax and is automatically subtracted from the absorbance at 570 nm. The "blank" for the determination of formazan absorbance is a 200 µL aliquot of extractant to which no unit had been exposed. This absorbance value is assumed to constitute zero viability.

F. Two units from each kit of 24 EpiAirway units are left untreated during determination of permeation kinetics and TER. These units are employed as the positive control for 100% cell viability. In all the studies we have conducted, there has been no statistically significant difference in the viability of the cells in these untreated units vs cells in control units which had been sham treated for permeation kinetics and on which TER determinations had been performed. The absorbance of all units treated with test formulations is assumed to be linearly proportional to the percent viability of the cells in the units at the time of the incubation with MTT. It should be noted that this assay is carried out typically no sooner than four hours after introduction of the test material to the apical surface, and subsequent to rinsing of the apical surface of the units during TER determination.

5. Determination of Viability by LDH Release

While measurement of mitochondrial reductase activity by MTT reduction is a sensitive probe of cell viability, the assay necessarily destroys the cells and therefore can be carried out only at the end of each study. When cells undergo necrotic lysis, their cytotosolic contents are spilled into the surrounding medium, and cytosolic enzymes such as lactic dehydrogenase (LDH) can be detected in this medium. An assay for LDH in the medium can be performed on samples of medium removed at each time point of the two-hour determination of permeation kinetics. Thus, cytotoxic effects of formulations which do not develop until significant time has passed can be detected as well as effects of formulations which induce cytolysis with the first few minutes of exposure to airway epithelium.

A. The recommended LDH assay for evaluating cytolysis of the EpiAirway units is based on conversion of lactate to pyruvate with generation of NADH from NAD. The NADH is then reoxidized along with simultaneous reduction of the tetrazolium salt INT, catalyzed by a crude "diaphorase" preparation. The formazan formed from reduction of INT is soluble, so that the entire assay for LDH activity can be carried out in a homogenous aqueous medium containing lactate, NAD, diaphorase, and INT.

B. The assay for LDH activity is carried out on 50 µL aliquots from samples of "supernatant" medium surrounding an EpiAirway unit and collected at each time point. These samples were either stored for no longer than 24 h in the refrigerator or were thawed after being frozen within a few hours after collection. Each EpiAirway unit generates samples of supernatant medium collected at 15 min, 30 min, 1 h, and 2 h after application of the test material. The aliquots are all transferred to a 96 well microplate.

C. A 50 µL aliquot of medium which had not been exposed to a unit serves as a "blank" or negative control of 0% cytotoxicity. We have found that the apparent level of "endogenous" LDH present after reaction of the assay reagent mixture with the unexposed medium is the same within experimental error as the apparent level of LDH released by all the sham-treated control units over the entire time course of 2 hours required to conduct a permeation kinetics study. Thus, within experimental error, these sham-treated units show no cytolysis of the epithelial cells over the time course of the permeation kinetics measurements.

D. To prepare a sample of supernatant medium reflecting the level of LDH released after 100% of the cells in a unit have lysed, a unit which had not been subjected to any prior manipulations is added to a well of a 6-well microplate containing 0.9 mL of medium as in the protocol for determination of permeation kinetics, the plate containing the unit is frozen at −80° C., and the contents of the well are then allowed to thaw. This freeze-thaw cycle effectively lyses the cells and releases their cytosolic contents, including LDH, into the supernatant medium. A 50 µL aliquot of the medium from the frozen and thawed cells is added to the 96-well plate as a positive control reflecting 100% cytotoxicity.

E. To each well containing an aliquot of supernatant medium, a 50 µL aliquot of the LDH assay reagent is added. The plate is then incubated for 30 minutes in the dark.

F. The reactions are terminated by addition of a "stop" solution of 1 M acetic acid, and within one hour of addition of the stop solution, the absorbance of the plate is determined at 490 nm.

G. Computation of percent cytolysis is based on the assumption of a linear relationship between absorbance and cytolysis, with the absorbance obtained from the medium alone serving as a reference for 0% cytolysis and the absorbance obtained from the medium surrounding a frozen and thawed unit serving as a reference for 100% cytolysis.

6. ELISA Determinations

The procedures for determining the concentrations of biologically active agents as test materials for evaluating enhanced permeation of active agents in conjunction with coordinate administration of mucosal delivery-enhancing agents or combinatorial formulation of the invention are generally as described above and in accordance with known methods and specific manufacturer instructions of ELISA kits employed for each particular assay. Permeation kinetics of the biologically active agent is generally determined by taking measurements at multiple time points (for example 15 min., 30 min., 60 min. and 120 min) after the biologically active agent is contacted with the apical epithelial cell surface (which may be simultaneous with, or subsequent to, exposure of the apical cell surface to the mucosal delivery-enhancing agent(s)).

The procedures for determining the concentrations of peptide YY neuropeptide Y, and pancreatic peptide in blood serum, central nervous system (CNS) tissues or fluids, cerebral spinal fluid (CSF), or other tissues or fluids of a mammalian subject may be determined by immunologic assay for peptide YY neuropeptide Y, and pancreatic peptide. The procedures for determining the concentrations of peptide YY neuropeptide Y, and pancreatic peptide as test materials for evaluating enhanced permeation of active agents in conjunction with coordinate administration of mucosal delivery-enhancing agents or combinatorial formulation of the invention are generally as described above and in accordance with known methods and specific manufacturer instructions for radioimmunoassay (RIA), enzyme immunoassay (EIA), and antibody reagents for immunohistochemistry or immunofluorescence for peptide YY neuropeptide Y, and pancreatic peptide. Bachem AG (King of Prussia, Pa.).

EpiAirway™ tissue membranes are cultured in phenol red and hydrocortisone free medium (MatTek Corp., Ashland, Mass.). The tissue membranes are cultured at 37° C. for 48 hours to allow the tissues to equilibrate. Each tissue membrane is placed in an individual well of a 6-well plate containing 0.9 mL of serum free medium. 100 μL of the formulation (test sample or control) is applied to the apical surface of the membrane. Triplicate or quadruplicate samples of each test sample (mucosal delivery-enhancing agent in combination with a biologically active agent, peptide YY) and control (biologically active agent, peptide YY, alone) are evaluated in each assay. At each time point (15, 30, 60 and 120 minutes) the tissue membranes are moved to new wells containing fresh medium. The underlying 0.9 mL medium samples is harvested at each time point and stored at 4° C. for use in ELISA and lactate dehydrogenase (LDH) assays.

The ELISA kits are typically two-step sandwich ELISAs: the immunoreactive form of the agent being studied is first "captured" by an antibody immobilized on a 96-well microplate and after washing unbound material out of the wells, a "detection" antibody is allowed to react with the bound immunoreactive agent. This detection antibody is typically conjugated to an enzyme (most often horseradish peroxidase) and the amount of enzyme bound to the plate in immune complexes is then measured by assaying its activity with a chromogenic reagent. In addition to samples of supernatant medium collected at each of the time points in the permeation kinetics studies, appropriately diluted samples of the formulation (i.e., containing the subject biologically active test agent) that was applied to the apical surface of the units at the start of the kinetics study are also assayed in the ELISA plate, along with a set of manufacturer-provided standards. Each supernatant medium sample is generally assayed in duplicate wells by ELISA (it will be recalled that quadruplicate units are employed for each formulation in a permeation kinetics determination, generating a total of sixteen samples of supernatant medium collected over all four time points).

A. It is not uncommon for the apparent concentrations of active test agent in samples of supernatant medium or in diluted samples of material applied to the apical surface of the units to lie outside the range of concentrations of the standards after completion of an ELISA. No concentrations of material present in experimental samples are determined by extrapolation beyond the concentrations of the standards; rather, samples are rediluted appropriately to generate concentrations of the test material which can be more accurately determined by interpolation between the standards in a repeat ELISA.

B. The ELISA for a biologically active test agent, for example, peptide YY, is unique in its design and recommended protocol. Unlike most kits, the ELISA employs two monoclonal antibodies, one for capture and another, directed towards a nonoverlapping determinant for the biologically active test agent, e.g., peptide YY, as the detection antibody (this antibody is conjugated to horseradish peroxidase). As long as concentrations of peptide YY that lie below the upper limit of the assay are present in experimental samples, the assay protocol can be employed as per the manufacturer's instructions, which allow for incubation of the samples on the ELISA plate with both antibodies present simultaneously. When the peptide YY levels in a sample are significantly higher than this upper limit, the levels of immunoreactive peptide YY may exceed the amounts of the antibodies in the incubation mixture, and some peptide YY which has no detection antibody bound will be captured on the plate, while some peptide YY which has detection antibody bound may not be captured. This leads to serious underestimation of the peptide YY levels in the sample (it will appear that the peptide YY levels in such a sample lie significantly below the upper limit of the assay). To eliminate this possibility, the assay protocol has been modified:

B.1. The diluted samples are first incubated on the ELISA plate containing the immobilized capture antibody for one hour in the absence of any detection antibody. After the one hour incubation, the wells are washed free of unbound material.

B.2. The detection antibody is incubated with the plate for one hour to permit formation of immune complexes with all captured antigen. The concentration of detection antibody is sufficient to react with the maximum level of peptide YY which has been bound by the capture antibody. The plate is then washed again to remove any unbound detection antibody.

B.3. The peroxidase substrate is added to the plate and incubated for fifteen minutes to allow color development to take place.

B.4. The "stop" solution is added to the plate, and the absorbance is read at 450 nm as well as 490 nm in the VMax microplate spectrophotometer. The absorbance of the colored product at 490 nm is much lower than that at 450 nm, but the absorbance at each wavelength is still proportional to concentration of product. The two readings ensure that the absorbance is linearly related to the amount of bound peptide YY over the working range of the VMax instrument (we routinely restrict the range from 0 to 2.5 OD, although the instrument is reported to be accurate over a range from 0 to 3.0 OD). The amount of peptide YY in the samples is determined by interpolation between the OD values obtained for the different standards included in the ELISA. Samples with OD readings outside the range obtained for the standards are rediluted and run in a repeat ELISA.

RESULTS

Measurement of transepithelial resistance by TER Assay: After the final assay time points, membranes were placed in individual wells of a 24 well culture plate in 0.3 mL of clean medium and the trans epithelial electrical resistance (TER) was measured using the EVOM Epithelial Voltohmmeter and an Endohm chamber (World Precision Instruments, Sarasota, Fla.). The top electrode was adjusted to be close to, but not in contact with, the top surface of the membrane. Tissues were removed, one at a time, from their respective wells and basal surfaces were rinsed by dipping in clean PBS. Apical surfaces were gently rinsed twice with PBS. The tissue unit was placed in the Endohm chamber, 250 µL of PBS added to the insert, the top electrode replaced and the resistance measured and recorded. Following measurement, the PBS was decanted and the tissue insert was returned to the culture plate. All TER values are reported as a function of the surface area of the tissue.

The final numbers were calculated as:
TER of cell membrane=(Resistance (R) of Insert with membrane–R of blank Insert)×Area of membrane (0.6 cm$^2$).

The effect of pharmaceutical formulations comprising peptide YY and intranasal delivery-enhancing agents on TER measurements across the EpiAirway™ Cell Membrane (mucosal epithelial cell layer) is shown in FIG. 1. A decrease in TER value relative to the control value (control=approximately 1000 ohms-cm$^2$; normalized to 100.) indicates a decrease in cell membrane resistance and an increase in mucosal epithelial cell permeability.

Exemplary peptide YY formulation, Formulation P, showed the greatest decrease in cell membrane resistance. (Table 2). The results indicate that the exemplary formulation (e.g., Formulation P) reduces the resistance of the membrane to less than 1% of the control at the concentrations tested. The values shown are the average of three replicates of each formulation. Formulations A and B are controls prepared by reconstituting peptide YY (Bachem AG, King of Prussia, Pa.) containing 60 µg peptide $Y_{3-36}$ in 100 ml of phosphate buffered saline (PBS) at pH 7.4 or 5.0. Peptide YY without mucosal delivery enhancers did not decrease the resistance.

The results indicate that an exemplary formulation for enhanced intranasal delivery of peptide YY (e.g., Formulation P) decreases cell membrane resistance and significantly increases mucosal epithelial cells permeability. The exemplary formulations will enhance intranasal delivery of peptide YY to the blood serum or to the central nervous system tissue or fluid. The results indicate that these exemplary formulations when contacted with a mucosal epithelium yield significant increases in mucosal epithelial cell permeability to peptide YY.

TABLE 2

Influence of Pharmaceutical Formulations Comprising Peptide YY and Intranasal Delivery-Enhancing Agents on Transepithelial Resistance (TER) of EpiAirway Cell Membrane

| Formulation | Mucosal Delivery Enhancing Agent | % TER |
| --- | --- | --- |
| A | PBS pH 7.4 (Control 1) | 100 |
| B | PBS pH 5.0 (Control 2) | 100 |
| C | L-Arginine (10% w/v) | 47.88 |
| D | Poly-L-Arginine (0.5% w/v) | 3.96 |
| E | Gamma-Cyclodextrin (1% w/v) | 91.67 |
| F | Alpha-Cyclodextrin (5% w/v) | 88.91 |
| G | Methyl-β-Cyclodextrin (3% w/v) | 97.51 |
| H | n-Capric Acid Sodium (0.075% w/v) | 47.72 |
| I | Chitosan (0.5% w/v) | 4.77 |
| J | L-α-phosphatidilcholine didecanyl (3.5% w/v) | 0.49 |
| K | S-Nitroso-N-Acetyl-Penicillamine (0.5% w/v) | 44.35 |
| L | Palmotoyl-DL-Carnitine (0.02% w/v) | 1.76 |
| M | Pluronic-127 (0.3% w/v) | 97.57 |
| N | Sodium Nitroprusside (0.3% w/v) | 92.41 |
| O | Sodium Glycocholate (1%-w/v) | 14.25 |
| P | F1: Gelatin, DDPC, MBCD, EDTA | 0.65 |

Permeation kinetics as measured by ELISA Assay: The effect of pharmaceutical formulations of the present invention comprising peptide YY and intranasal delivery-enhancing agents on the permeation of peptide YY across the EpiAirway™ Cell Membrane (mucosal epithelial cell layer) is measured as described above. The results are shown in Table 3. Permeation of peptide YY across the EpiAirway™ Cell Membrane is measured by ELISA assay.

For the exemplary intranasal formulations (e.g., Formulation P) of the present invention, the greatest increase in peptide YY permeation occurred in Formulation P as shown in Table 3. The procedure uses an ELISA assay to determine the concentration of biologically active peptide YY that has permeated the epithelial cells into the surrounding medium over multiple time points. The results show increased permeation of peptide YY in Formulation P compared to Formulation A or B (peptide YY control formulation; 60 µg peptide $YY_{3-36}$ in 100 ml of phosphate buffered saline (PBS) at pH 7.4 or 5.0; Bachem AG, King of Prussia, Pa.). On average the cumulative increase in permeation at 120 minutes using Formulation P exemplary intranasal formulation is about 1195 fold greater than Formulations A or B controls.

TABLE 3

Influence of Pharmaceutical Formulations Comprising Peptide YY and Intranasal Delivery-Enhancing Agents on Permeation of Peptide YY through EpiAirway Cell Membrane by ELISA Assay.

| | Formulation | % Permeation at Time Points (min) | | | | | Total % | Fold Increase |
|---|---|---|---|---|---|---|---|---|
| | Peptide YY$_{3-36}$ (60 µg/100 ml) | 0 | 15 | 30 | 60 | 120 | Permeation | in Permeability |
| A | PBS pH 7.4 (Control 1) | 0 | 0.00171 | 0.00096 | 0.00451 | 0.00327 | 0.01 | 1 |
| B | PBS pH 5.0 (Control 2) | 0 | 0.00093 | 0.00048 | 0.00042 | 0.00367 | 0.01 | 1 |
| C | L-Arginine (10% w/v) | 0 | 0.00119 | 0.00277 | 0.00685 | 0.00566 | 0.02 | 2 |
| D | Poly-L-Arginine (0.5% w/v) | 0 | 0.00324 | 0.01587 | 0.10395 | 0.49656 | 0.62 | 62 |
| E | Gamma-Cyclodextrin (1% w/v) | 0 | 0.00017 | 0.00042 | 0.00028 | 0.0035 | 0 | 1 |
| F | α-Cyclodextrin (5% w/v) | 0 | 0.00031 | 0.000745 | 0.00147 | 0.0031 | 0.01 | 1 |
| G | Methyl-β-Cyclodextrin (3% w/v) | 0 | 0.00028 | 0.00038 | 0.00059 | 0.01028 | 0.01 | 1 |
| H | n-Capric Acid Sodium (0.075% w/v) | 0 | 0.0004 | 0.00131 | 0.00448 | 0.00821 | 0.01 | 1 |
| I | Chitosan (0.5% w/v) | 0 | 0.00086 | 0.01098 | 0.09749 | 0.82126 | 0.93 | 93 |
| J | L-α-phosphatidilcholine didecanyl (3.5% w/v) | 0 | 0.00934 | 0.02 | 0.08507 | 1.9642 | 2.08 | 208 |
| K | S-Nitroso-N-Acetyl-Penicillamine (0.5% w/v) | 0 | 0.00074 | 0.0032 | 0.0688 | 0.90432 | 0.98 | 98 |
| L | Palmotoyl-DL-Carnitine (0.02% w/v) | 0 | 0.00378 | 0.03422 | 0.15141 | 1.31011 | 1.5 | 150 |
| M | Pluronic-127 (0.3% w/v) | 0 | 0.00025 | 0.00027 | 0.00066 | 0.00395 | 0.01 | 1 |
| N | Sodium Nitroprusside (0.3% w/v) | 0 | 0.00171 | 0.00114 | 0.00079 | 0.05492 | 0.05 | 5 |
| O | Sodium Glycocholate (1% w/v) | 0 | 0.00325 | 0.00313 | 0.09023 | 0.70214 | 0.8 | 80 |
| P | F1 Gelatin, DDPC, MBCD, EDTA | 0 | 0.05864 | 1.3972 | 2.9799 | 7.519 | 11.95 | 1195 |

MTT Assay: The MTT assays were performed using MTT-100, MatTek kits. 300 mL of the MTT solution was added into each well. Tissue inserts were gently rinsed with clean PBS and placed in the MTT solution. The samples were incubated at 37° C. for 3 hours. After incubation the cell culture inserts were then immersed with 2.0 mL of the extractant solution per well to completely cover each insert. The extraction plate was covered and sealed to reduce evaporation. Extraction proceeds overnight at RT in the dark. After the extraction period was complete, the extractant solution was mixed and pipetted into a 96-well microtiter plate. Triplicates of each sample were loaded, as well as extractant blanks. The optical density of the samples was then measured at 550 nm on a plate reader (Molecular Devices).

The MTT assay on an exemplary formulation for enhanced nasal mucosal delivery of peptide YY following the teachings of the instant specification (e.g., Formulation P) compared to control formulation (Formulations A or B) are shown in Table 4. The results for formulations comprising peptide YY and one or more intransal delivery enhancing agents, for example, Formulation P (experiment performed in three replicates) indicate that there is minimal toxic effect of this exemplary embodiment on viability of the mucosal epithelial tissue.

TABLE 4

Influence of Pharmaceutical Formulations Comprising Peptide YY and Intranasal Delivery-Enhancing Agents on the Viability of EpiAirway Cell Membrane as shown by % MTT

| Formulations | Treatment | % MTT |
|---|---|---|
| A | PBS pH .4 (Control 1) | 100 |
| B | PBS pH 5.0 (Control 2) | 100 |
| C | L-Arginine (10% w/v) | 91.54 |
| D | Poly-L-Arginine (0.5% w/v) | 79.39 |
| E | Gamma-Cyclodextrin (1% w/v) | 100 |
| F | α-Cyclodextrin (5% w/v) | 96.63 |
| G | Methyl-β-Cyclodextrin (3% w/v) | 100 |
| H | n-Capric Acid Sodium (0.075% w/v) | 100 |
| I | Chitosan (0.5% w/v) | 100 |
| J | L-α-phosphatidilcholine didecanyl (3.5% w/v) | 94.25 |
| K | S-Nitroso-N-Acetyl-Penicillamine (0.5% w/v) | 97.64 |
| L | Palmotoyl-DL-Carnitine (0.02% w/v) | 91.77 |
| M | Pluronic-127 (0.3% w/v) | 100 |
| N | Sodium Nitroprusside (0.3% w/v) | 100 |
| O | Sodium Glycocholate (1% w/v) | 100 |
| P | F1: Gelatin, DDPC, MBCD, EDTA | 88.75 |

LDH Assay: The LDH assay on an exemplary formulation for enhanced nasal mucosal delivery of peptide YY following the teachings of the instant specification (e.g., Formulation P) are shown in Table 5. The results for three replicates of Formulation P indicate that there is minimal toxic effect of this exemplary embodiment on viability of the mucosal epithelial tissue.

TABLE 5

Influence of Pharmaceutical Formulations Comprising Peptide YY and Intranasal Delivery-Enhancing Agents on the Viability of EpiAirway Cell Membrane as shown by % Dead Cells (LDH Assay)

| Formulations | Treatment | % dead cells |
|---|---|---|
| A | PBS pH .4 (Control1) | 1.0 |
| B | PBS pH 5.0 (Control 2) | 1.1 |
| C | L-Arginine (10% w/v) | 0.8 |
| D | Poly-L-Arginine (0.5% w/v) | 1.4 |
| E | Gamma-Cyclodextrin (1% w/v) | 0.8 |
| F | α-Cyclodextrin (5% w/v) | 0.7 |
| G | Methyl-β-Cyclodextrin (3% w/v) | 0.8 |
| H | n-Capric Acid Sodium (0.075% w/v) | 1.3 |
| I | Chitosan (0.5% w/v) | 0.7 |
| J | L-α-phosphatidilcholine didecanyl (3.5% w/v) | 1.2 |

TABLE 5-continued

Influence of Pharmaceutical Formulations Comprising Peptide YY and Intranasal Delivery-Enhancing Agents on the Viability of EpiAirway Cell Membrane as shown by % Dead Cells (LDH Assay)

| Formulations | Treatment | % dead cells |
| --- | --- | --- |
| K | S-Nitroso-N-Acetyl-Penicillamine (0.5% w/v) | 0.7 |
| L | Palmotoyl-DL-Carnitine (0.02% w/v) | 0.8 |
| M | Pluronic-127 (0.3% w/v) | 1.0 |
| N | Sodium Nitroprusside (0.3% w/v) | 0.6 |
| O | Sodium Glycocholate (1% w/v) | 0.8 |
| P | F1: Gelatin, DDPC, MBCD, EDTA | 2.0 |

EXAMPLE 3

Formulation P (Peptide YY) of the Present Invention In Combination With Triamcinolone Acetonide Corticosteroid Improves Cell Viability The present example provides an in vitro study to determine the permeability and reduction in epithelial mucosal inflammation of an intranasally administered peptide YY, for example, human peptide YY, in combination with a steroid composition, for example, triamcinolone acetonide, and further in combination with one or more intranasal delivery-enhancing agents. The study involves determination of epithelial cell permeability by TER assay and reduction in epithelial mucosal inflammation as measured by cell viability in an MTT assay by application of an embodiment comprising peptide YY and triamcinolone acetonide.

Formulation P (see Table 1 above) is combined in a formulation with triamcinolone acetonide at a dosage of 0.5, 2.0, 5.0, or 50 µg. Normal dose of triamcinolone acetonide, (Nasacort®, Aventis Pharmaceuticals) for seasonal allergic rhinitis, is 55 µg per spray. Formulation P in combination with triamcinolone acetonide corticosteroid improves cell viability as measured by the MTT assay, while maintaining epithelial cell permeability as measured by TER and ELISA assays.

According to the methods and formulations of the invention, measurement of permeability of Formulation P in the presence or absence of triamcinolone acetonide is performed by transepithelial electrical resistance (TER) assays in an EpiAirway™ cell membrane. TER assays of Formulation P plus triamcinolone acetonide at a concentration of 0.5, 2.0, 5.0, or 50 µg per spray indicate that peptide YY permeability did not decrease and was equal to permeability of Formulation P alone. Formulation P plus triamcinolone acetonide at a triamcinolone acetonide concentration between 0 and 50 µg per spray is typically, at least 10-fold to 100-fold greater than permeability of Formulations A or B (peptide YY control).

According to the methods and formulations of the invention, measurement of permeability of Formulation P in the presence or absence of triamcinolone acetonide is performed by ELISA assay in an EpiAirway™ cell membrane. Similar to the TER assay above, ELISA assay of Formulation P plus triamcinolone acetonide at a concentration of 0.5, 2.0, 5.0, or 50 µg per spray indicate that peptide YY permeability did not decrease and was equal to permeability of Formulation P alone. Formulation P plus triamcinolone acetonide at a triamcinolone acetonide concentration between 0 and 50 µg per spray is typically greater than permeability of Formulations A or B (peptide YY control).

According to the methods and formulations of the invention, MTT assay measured cell viability of Formulation P in the presence or absence of triamcinolone acetonide. Typically, addition of triamcinolone acetonide (at a concentration of 0.5, 2.0, 5.0, or 50 µg per spray) to Formulation P improves cell viability compared to Formulation P in the absence of triamcinolone acetonide.

Addition of triamcinolone acetonide to Formulation P increases cell viability and maintains epithelial permeability as measured by TER assay comparable to Formulation P in the absence of triamcinolone acetonide.

Reduction in epithelial mucosal inflammation of an intranasally administered peptide YY is accomplished with an intranasal formulation of peptide YY in combination with one or more steroid or corticosteroid compound(s) typically high potency compounds or formulations, but also in certain cases medium potency, or low potency compounds or formulations. Overall potency (equivalent dosages) of high, medium, and low potency steroids are given. Typically, an intranasal formulation of peptide YY in combination with a high potency steroid composition includes, but is not limited to, betamethasone (0.6 to 0.75 mg dosage), or dexamethasone (0.75 mg dosage). In an alternative formulation, an intranasal formulation of peptide YY in combination with a medium potency steroid composition includes, but is not limited to, methylprednisolone (4 mg dosage), triamcinolone (4 mg dosage), or prednisolone (5 mg dosage). In a further alternative formulation, an intranasal formulation of peptide YY in combination with a low potency steroid composition includes, but is not limited to hydrocortisone (20 mg dosage) or cortisone (25 mg dosage).

EXAMPLE 4

Bioavailability and Bioactivity of Three Different Doses of Peptide YY (PYY) Via Nasal Mucosal Administration to Healthy Subjects to Measure Appetite Control STUDY SYNOPSIS. The present example provides a non-blinded study to determine the uptake of intranasally administered peptide YY into the blood serum in healthy male volunteers. The study involves administration of peptide YY nasal formulation, as described above to evaluate the absorption and tolerance of the peptide YY nasal formulation Twelve healthy male subjects, age 18–50, are enrolled in the study. Each receives one intranasal dose of the test formulation. Each subject visits the clinical site three times in a 3-week period. These visits consist of a screening visit, one dosing visit, and a final visit. Demographic data, subject initials, gender, age, race and statement of non-smoking status is recorded at the time of screening. A complete medical history and physical examination including electrocardiogram, vital signs, height and weight, and clinical laboratory evaluations is conducted at screening and when the subject completes the study.

The proposed study involves administration of one reformulated product of intranasal formulation of peptide YY as follows:

Control Product/Formulation B: Nasal spray=40 pmol $PYY_{3-36}$/0.1 ml spray (one 0.1 ml spray in each nostril each day; in PBS, pH 5.0). Formulation $PYY_{3-36}$ (Bachem AG, King of Prussia, Pa.) One 0.1 ml spray to one nostril every day, alternating from left nostril to right Test Formulation P Product: Nasal spray=2.6 mg/0.1 ml spray. (Formulation P: $PYY_{3-36}$, 60 µg per 100 ml;

Gelatin, DDPC, MBCD, EDTA as described in Table 1). One 0.1 ml spray in each nostril each day; or one 0.1 ml spray to one nostril every day, alternating from left nostril to right. The absorption and tolerance results of all test products tested will be tabulated and analyzed for $C_{max}$, $t_{max}$ and AUC. Data resulting form the study will be compared to the pharmacokinetic parameters in the available literature and to the data from the peptide YY studies using Formulation B control and Formulation P.

For each preparation, 7 mL blood samples will be drawn at 0 (prior to dose), 10, 20, 30, 45, 60, 75, 90, 120, 180 and 240 minutes post dosing into appropriate vacutainers.

Serum anti-human peptide YY antibodies will be measured at the screening and final visits.

On the day of dosing, subjects' vital signs (blood pressure, pulse, respiration rate and body temperature) will be monitored before dosing and post dosing at 15, 30, 45, 60, 75, 90, 120 and 240 minutes post dosing and prior to discharge.

The nasal examination will be performed by qualified personnel at pre-dosing, 15, 30, 45, 60, 75, 90, 120 and 240 minutes and prior to discharge from the visit.

The results of the study will be evaluated for each test dose for safety and absorption. If administration of the dose results in a grading scale of 3 (based on the Common Toxicity Criteria [CTC]) for any of the parameters observed, the study arm will be discontinued.

The intent of the study, the study protocol, and the Informed Consent Form to be used in the study is approved in writing by the IRB prior to initiation of the study.

Subject Inclusion Criteria. The following inclusion criteria are used:

Healthy male subjects.

Age 18–50.

Non-smokers (greater than 6 months).

For whom administration of peptide YY is not contraindicated (such as known hypersensitivity to the product or any of the constituents).

The male subjects have a normal nasal mucosa. Demographic data, subject initials, gender, age, race and statement of non-smoking status are recorded at screening. A complete medical history and physical examination including electrocardiogram, vital signs, height and weight, and the following laboratory tests are conducted at screening and when the subject completes the study: Blood Chemistry, Thyroid Function Tests, Hematology, Urinalysis, Drug Screens.

Subject Exclusion Criteria. The following exclusion criteria are used:

Subjects with a history of hypersensitivity to natural or recombinant peptide YY or any other component of the Formulation P (Gelatin, DDPC, MBCD, EDTA as described in Table 1).

Subjects with active neoplasia.

Subjects with glucose intolerance, diabetes mellitus or a family history of diabetes.

Subjects with thyroid hormone abnormalities.

Subjects currently taking glucocorticoids.

Subjects with clinically significant nasal abnormalities.

Subjects with history of nosebleeds or allergic rhinitis.

Subject with history of alcoholism or drug abuse.

Subject with psychiatric disorders.

Subjects with acute critical illness due to complications following open heart or abdominal surgery, multiple accidental trauma or patients having acute respiratory failure.

DOSING. Before dosing, all subjects will be given an orientation of the proper dosing technique and general conduct of the study.

Physical Activity: Avoid vigorous exertion for 3 hours after dose.

Confinement: Subjects will be confined immediately prior to the first draw and at least until the last blood draw is completed. Subjects may be confined longer at the discretion of the Principal Investigator.

Fasting: Volunteers are not required to fast before the study. However, during the study they may not eat until after the 90-minute blood draw time point.

Meals: Meals may be provided after the 90-minute blood sample.

Fluid Intake: Hot and cold carbonated liquids are prohibited for 90 minutes before and 90 minutes after dosing (water allowed).

Environmental Conditions: Subjects will be in a smoke-free environment at time of dosing and/or during study confinement. Full resuscitative facilities will be immediately available.

Concurrent Medication: Subjects will be instructed to take no antibiotics for at least 2 days and no medications including alcohol, monoamine oxidase (MAO) inhibitors, sedatives, antihistamines, psychotropic drugs and any OTC products for at least three days prior to the start of the study. They will also be informed to take no intranasal medications (including intranasal OTC) for three days prior to or during the study except those administered as per the study protocol.

The intranasal formulation is manufactured by Nastech Pharmaceutical Clinical Supply department under GMP compliance. The intranasal formulation is either Formulation B (control) or Formulation P, as described above. The dosage comprises one 0.1 ml spray in each nostril each day; or one 0.1 ml spray to one nostril every day, alternating from left nostril to right.

When receiving the nasal spray, the subject is seated and instructed to gently blow his nose before dosing. During dosing, the other nostril must be closed with the forefinger. Subjects are instructed to tilt their heads slightly back for dosing and to return their heads to an upright position while sniffing in gently immediately following dosing. Subjects must avoid additional sniffing and must remain in a seated position with head upright for 5 minutes after dosing. Subjects must inform the staff if they sneeze or if the product drips out of their nose.

The blood samples are collected in 7 mL vacutainers and centrifuged at room temperature for not less than 8 minutes at 1,500 rpm after at least 30 minutes have elapsed from the time of blood draw. At least 1.2 mL of serum is pipetted into the first of two prelabeled polypropylene tubes, with the remainder pipetted into the second tube. Both tubes are frozen promptly and stored at −10° C. for no more than 30 days until analysis.

The second sample is retained by the Investigator until the study monitor notifies him/her of the appropriate disposition.

All subjects are monitored throughout the confinement portion of the study. Blood pressure, respiration rate, pulse, and body temperature are obtained prior to dosing and as scheduled following dosing. Dosing proceeds as authorized by the medical investigator who will be available on-site and/or by pager throughout the study.

Serum drug concentrations are measured using a validated ELISA method. The concentration at each sampling time and the appropriate pharmacokinetic parameters are reported.

On the day of dosing, subjects' vital signs (blood pressure, pulse, respiration rate and body temperature are monitored before dosing and post dosing at 15, 30, 45, 60, 75, 90, 120 and 240 minutes post dosing and prior to discharge.

NASAL MUCOSAL EXAMINATIONS. The investigator, or a medically qualified designee (Sub-Investigator/Nurse Practitioner), visually examines the nasal mucosa of all subjects. On the day of dosing these examinations are performed immediately before the intranasal dosing and at 15, 30, 45, 60, 75, 90, 120, and 240 minutes after dosing and prior to discharge from the visit.

Observations are made upon examination of the nasal mucosa which covers the septum and turbinates. The investigator notes upon examination the color (redness) and swelling, bleeding or exudates. If exudates are present, they are noted for character, clear, mucopusulent or pusulent. The nasal septum is examined for any deviation, inflammation or perforation of the septum. The septum is observed for epistaxis. Any abnormalities such as ulcers or polyps is also be documented.

All observations are recorded in the adverse event forms in the Case Report Forms. Each subject completes a nasal tolerance questionnaire on the formulations administered.

ABSORPTION DATA EVALUATION. All absorption data will be plotted for individual subjects as well as for the averaged data. The $C_{max}$, $t_{max}$ and the bioavailability (measured as area under the individual serum peptide YY time curves, AUC) of the test products are evaluated with the goal of comparing the aforementioned pharmacokinetic parameters for intransal formulations, Formulation B control or Formulation P, as described above.

STATISTICS: Determination of AUC. The areas under the individual serum GH concentration vs. time curves (AUC) were calculated according to the linear trapezoidal rule and with addition of the residual areas. A decrease of 23% or an increase of 30% between two dosages would be detected with a probability of 90% (type II error$\beta$=10%). The rate of absorption was estimated by comparison of the time ($t_{max}$) to reach the maximum concentration ($C_{max}$). Both $C_{max}$ and $t_{max}$ were analyzed using non-parametric methods. Comparisons of the pharmacokinetics of subcutaneous, intravenous, and intranasal peptide YY administration were performed by analysis of variance (ANOVA). For pairwise comparisons a Bonferroni-Holmes sequential procedure was used to evaluate significance. The dose-response relationship between the three nasal doses was estimated by regression analysis. $P<0.05$ was considered significant. Results are given as mean values +/−SEM. Laursen et al., *Eur. J. Endocrinology*, 135: 309–315, 1996, incorporated herein by reference.

Results: Due to its unique characteristics, the intranasal administration of pharmaceutical formulations of the present invention comprising peptide YY and one or more intranasal delivery-enhancing agents offers many advantages in terms of providing absorption of macromolecular drugs which are either not absorbed or variably absorbed after oral administration or absorbed more slowly following intramuscular or subcutaneous injection. No non-injectable products of peptide YY are currently available. Pulmonary administration has achieved some success but has disadvantages including patient inconvenience and questionable pulmonary safety.

According to the methods and formulations of the invention, pharmacokinetic data for intranasal delivery of peptide YY in a pharmaceutical formulation of the present invention (e.g., Formulation P) is compared to subcutaneous delivery of a control formulation of peptide YY (Formulation B).

The results exemplify bioavailability of peptide YY achieved by the methods and formulations herein, e.g., as measured by area under the concentration curve (AUC) in blood serum, CNS, CSF or in another selected physiological compartment or target tissue. According to the methods and formulations of the invention, bioavailability of peptide YY will be, typically, $AUC_{0-8\ hr}$ for peptide YY of approximately 100 pmol·hr/L of blood plasma or CSF, $AUC_{0-8\ hr}$ for peptide YY of approximately 200 pmol·hr/L of blood plasma or CSF, or $AUC_{0-8\ hr}$ for peptide YY up to approximately 400 pmol·hr/L of blood plasma or CSF.

According to the methods and formulations of the invention, relative bioavailability as measured by area under the concentration curve (AUC) for an exemplary intranasal formulation (Formulation P) of peptide YY of the present invention is typically 5% to 6% relative to subcutaneous administration under comparable experimental conditions. This result is compared to relative bioavailability of a control formulation (human peptide YY; Formulation B) is typically 1% to 3% for intranasal delivery of a prior art formulation of peptide YY relative to subcutaneous administration under comparable experimental conditions. According to the methods and formulations of the invention, the exemplary formulation administered intranasally provides time to maximal plasma concentration of peptide YY typically between 0.3 to 1.0 hours. These results are fully consistent with the foregoing disclosure.

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation.

What is claimed is:

1. A PYY composition comprised of a solubilizing agent, a chelating agent, L-α-phosphatidylcholine didecanoyl (DDPC) and a PYY peptide wherein the PYY peptide is comprised of the amino acid sequence of SEQ ID NO: 2.

2. The PYY composition of claim 1 wherein the chelating agent is ethylene diamine tetraacetic acid (EDTA) or ethylene glycol tetraacetic acid (EGTA).

3. The PYY composition of claim 2 wherein the chelating agent is EDTA.

4. The PYY composition of claim 1 wherein the solubilizing agent is selected from the group consisting of a cyclodextrin, hydroxypropyl-β-cyclodextrin, sulfobutylether-β-cyclodextrin and methyl-β-cyclodextrin.

5. The PYY composition of claim 4 wherein the solubilizing agent is a methyl-β-cyclodextrin.

6. The PYY composition of claim 1 wherein the composition is an aqueous PYY composition.

7. The PYY composition of claim 6 wherein the aqueous PYY composition has a pH of about from about 3 to about 6.

8. The PYY composition of claim 7 wherein the pH of the aqueous PYY composition is from about 4.0 to about 5.0.

9. A PYY composition comprised of methyl-β-cyclodextrin, EDTA, L-α-phosphatidylcholine didecanoyl (DDPC) and a PYY peptide wherein the PYY peptide is comprised of the amino acid sequence of SEQ ID NO: 2.

10. A PYY composition comprised of water, a buffer, methyl-β-cyclodextrin, EDTA, L-α-phosphatidylcholine didecanoyl (DDPC) and PYY(3-36) (SEQ ID NO: 2), wherein the formulation has a pH from about 4.0 to about 5.0.

11. The PYY composition of claim 10 wherein the buffer is selected from a group consisting of lysine, arginine, histidine, lactate, and citrate.

12. The PYY composition of claim 10 further comprised of a preservative selected from the group consisting of chlorobutanol and benzalkonium chloride.

13. The composition of claim 12 wherein the preservative is chlorobutanol.

14. A PYY composition comprised of water, chlorobutanol, a buffer, methyl-β-cyclodextrin, EDTA, L-α-phosphatidylcholine didecanoyl (DDPC) and PYY(3-36) (SEQ ID NO: 2), wherein the formulation has a pH from about 4.0 to about 5.0.

15. A PYY composition comprised of water, benzalkonium chloride, a buffer, methyl-β-cyclodextrin, EDTA, L-α-phosphatidylcholine didecanoyl (DDPC) and PYY(3-36) (SEQ ID NO: 2), wherein the formulation has a pH from about 4.0 to about 5.0.

16. A PYY composition comprised of water, chlorobutanol at a concentration of 5 mg/ml, a buffer, methyl-β-cyclodextrin at a concentration of about 45 mg/ml, EDTA at a concentration of about 1 mg/ml, L-α-phosphatidylcholine didecanoyl (DDPC) at a concentration of about 1 mg/ml and PYY(3-36) (SEQ ID NO: 2) at a concentration of about 1 mg/ml, wherein the formulation has a pH from about 4.0 to about 5.0.

17. A PYY composition comprised of water, chlorobutanol at a concentration of 5 mg/ml, a buffer, methyl-β-cyclodextrin at a concentration of about 45 mg/ml, EDTA at a concentration of about 1 mg/ml, L-α-phosphatidylcholine didecanoyl (DDPC) at a concentration of about 1 mg/ml and PYY(3-36) (SEQ ID NO: 2) at a concentration of about 15 mg/ml, wherein the formulation has a pH from about 4.0 to about 5.0.

18. A kit for treatment of a mammalian subject comprising a stable pharmaceutical composition comprised of PYY(3-36) (SEQ ID NO: 2), L-α-phosphatidylcholine didecanoyl and a solubilizing agent selected from the group consisting of a cyclodextrin, hydroxypropyl-β-cyclodextrin, sulfobutylether-β-cyclodextrin and methyl-β-cyclodextrin.

19. A kit for treatment of a mammalian subject comprising a stable pharmaceutical composition comprised of PYY(3-36) (SEQ ID NO: 2), a solubilizing agent, and an L-α-phosphatidylcholine didecanoyl.

* * * * *